US010723698B2

(12) United States Patent
Baiocchi et al.

(10) Patent No.: US 10,723,698 B2
(45) Date of Patent: *Jul. 28, 2020

(54) INHIBITORS OF PRMT5 AND METHODS OF THEIR USE

(71) Applicant: Ohio State Innovation Foundation, Columbus, OH (US)

(72) Inventors: Robert A. Baiocchi, Dublin, OH (US); Chenglong Li, Dublin, OH (US); Hongshan Lai, Columbus, OH (US); Said Sif, Dublin, OH (US)

(73) Assignee: The Ohio State University, Columbus, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/039,365

(22) Filed: Jul. 19, 2018

(65) Prior Publication Data

US 2019/0270707 A1 Sep. 5, 2019

Related U.S. Application Data

(63) Continuation of application No. 15/822,549, filed on Nov. 27, 2017, now abandoned, which is a continuation of application No. 14/776,685, filed as application No. PCT/US2014/029936 on Mar. 15, 2014, now Pat. No. 9,856,218.

(60) Provisional application No. 61/788,461, filed on Mar. 15, 2013.

(51) Int. Cl.
*C07D 209/82* (2006.01)
*C07D 209/86* (2006.01)
*C07D 209/88* (2006.01)

(52) U.S. Cl.
CPC ......... *C07D 209/82* (2013.01); *C07D 209/86* (2013.01); *C07D 209/88* (2013.01)

(58) Field of Classification Search
CPC .................................................. C07D 209/82
See application file for complete search history.

(56) References Cited

U.S. PATENT DOCUMENTS

| | | |
|---|---|---|
| 6,800,656 B2 | 10/2004 | Booth et al. |
| 2003/0229073 A1 | 12/2003 | Booth et al. |
| 2012/0277402 A1 | 11/2012 | Liaw |

FOREIGN PATENT DOCUMENTS

| | | |
|---|---|---|
| EP | 1253141 | 10/2002 |
| JP | 2001-526276 | 12/2001 |
| JP | 2003-519693 | 6/2003 |
| WO | 9932463 | 7/1999 |
| WO | 2011079236 | 6/2011 |
| WO | 2014145214 | 9/2014 |

OTHER PUBLICATIONS

Cancer [online], [retrieved on Jul. 6, 2007]. Retrieved from the internet, URL http://www.nlm.nih.gov/medlineplus/cancer.html>.
Peeyush K. Lala et al. "Role of nitric oxide in tumor progressions: Lessons from experimental tumors." Cancer and Metastasis Reviews. (1998), 17(1), 91-106.
Golub, T. R. et al. "Molecular classification of cancer: class discovery and class prediction by gene expression monitoring." Science (1999), vol. 286, 531-537.
International Search Report (ISA/US) for International Application No. PCT/US2014/029936, dated Nov. 7, 2014, 5 pages.
Communication Pursuant to Article 94(3) EPC issued for European Application No. 14765093.1, dated Jul. 9, 2018.
Extended European Search Report issued for European Application No. 14765093.1, dated Jan. 13, 2017.
Office Action received in Japanese counter-part Application No. 2016-503285, dated Sep. 21, 2018. Machine Translation included.
Decision of Grant received in Japanese counter-part Application No. 2016-503285, dated, March 12, 2019. Machine Translation included.

*Primary Examiner* — Shawquia Jackson
(74) *Attorney, Agent, or Firm* — Meunier Carlin & Curfman LLC

(57) ABSTRACT

The disclosure relates to PRMT5 inhibitors, including optionally substituted N-alkyl-9H-carbazole analogs, derivatives thereof, and related compounds; synthesis methods for making the compounds; pharmaceutical compositions comprising the compounds; and methods of treating disorders of uncontrolled cellular proliferation and benign hematologic diseases using the compounds and compositions.

13 Claims, 74 Drawing Sheets

Specification includes a Sequence Listing.

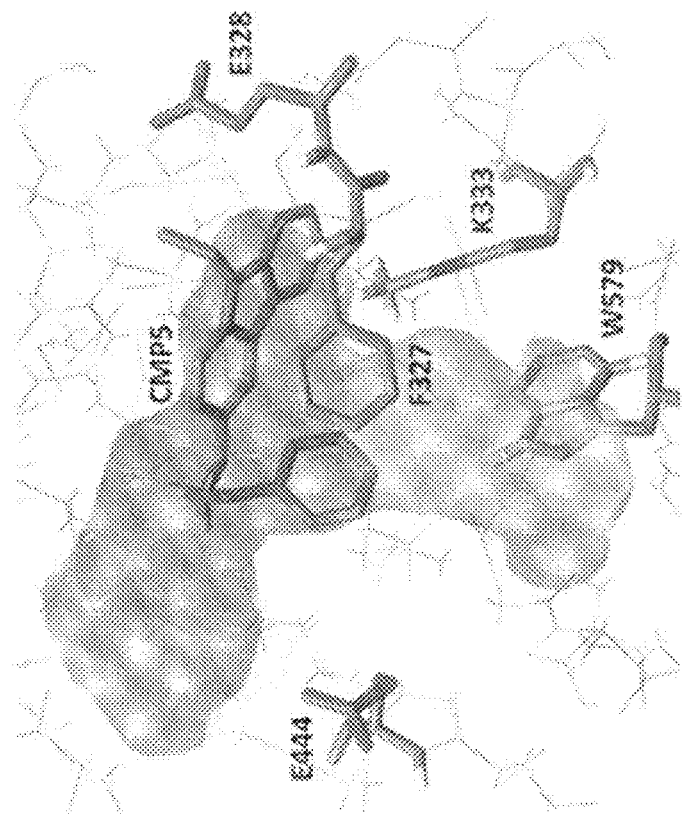
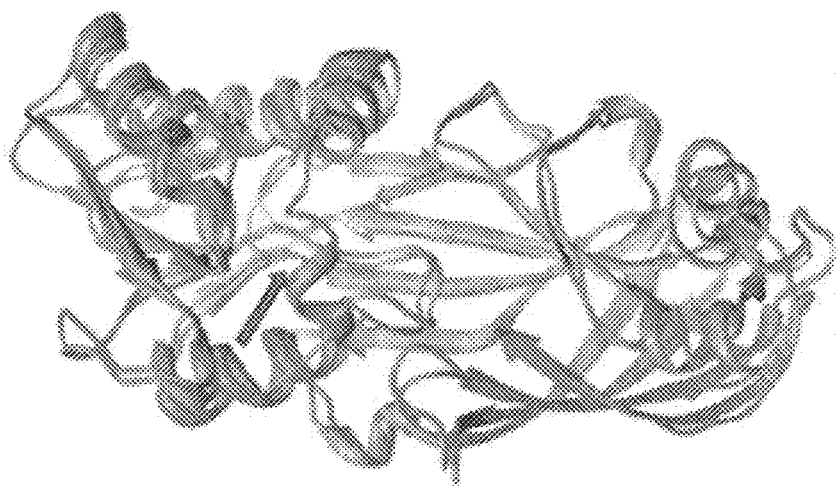
FIG. 2B
FIG. 2A

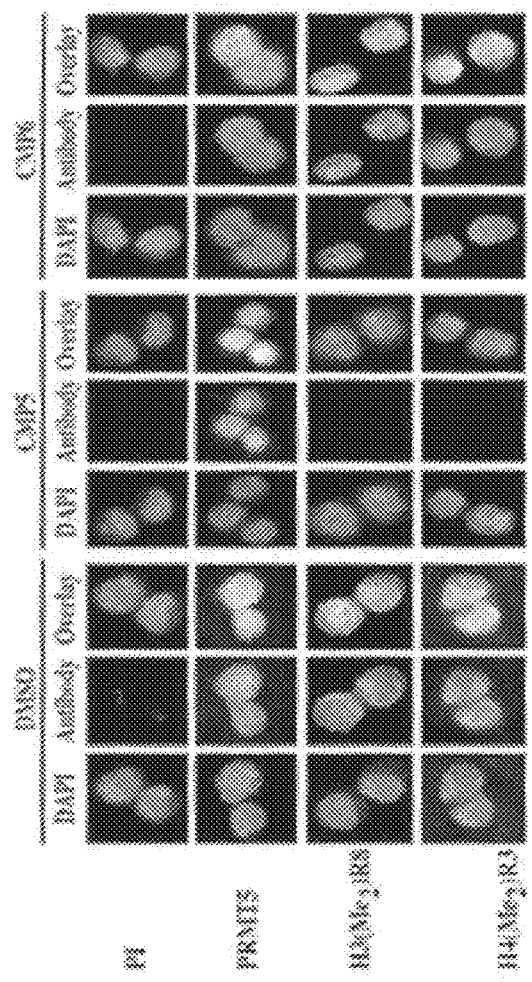
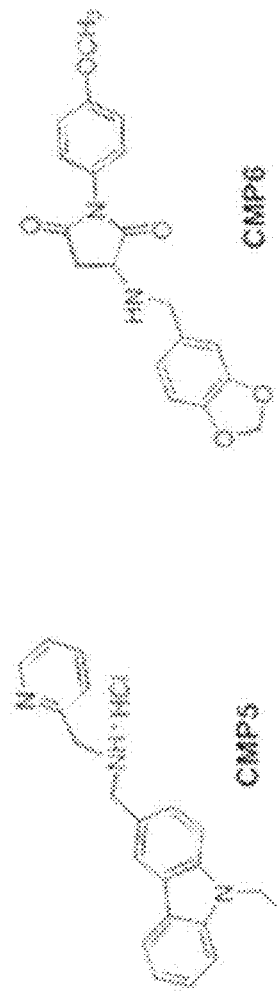
FIG. 2F
FIG. 2G

PRMT5 nuclear
staining intensity
- Greater intensity
  =worse survival
- Hazard ratio: 1.545
  (p=0.0121)

PRMT5 cytoplasmic
staining intensity was
not significant (p=0.2598)

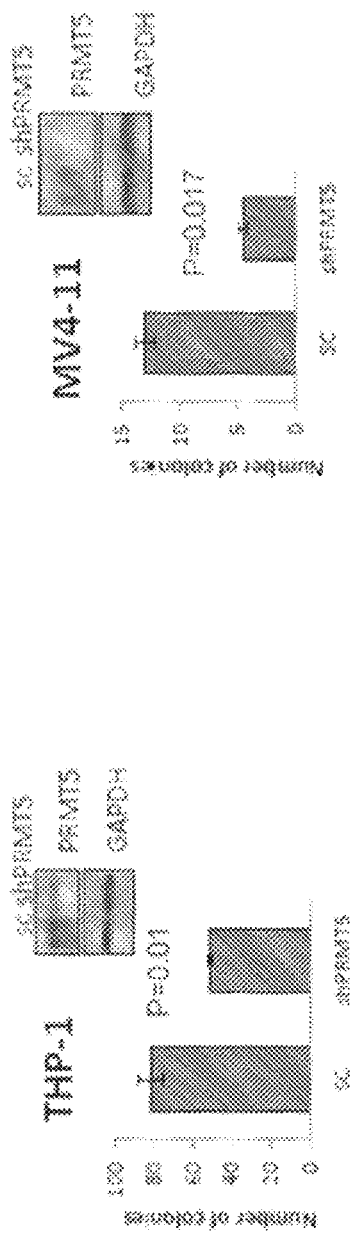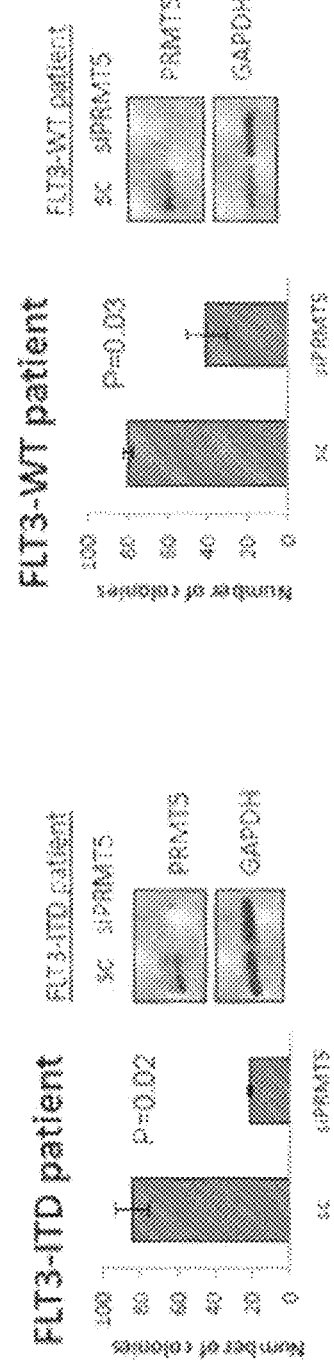
FIG. 29A  FIG. 29B  FIG. 29C  FIG. 29D

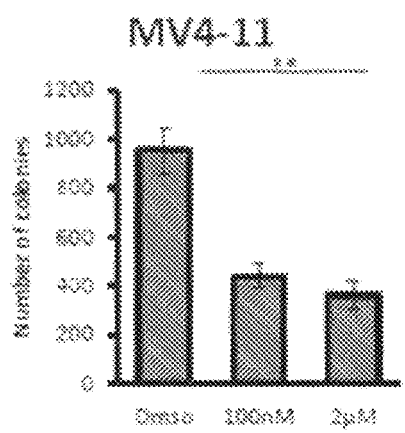
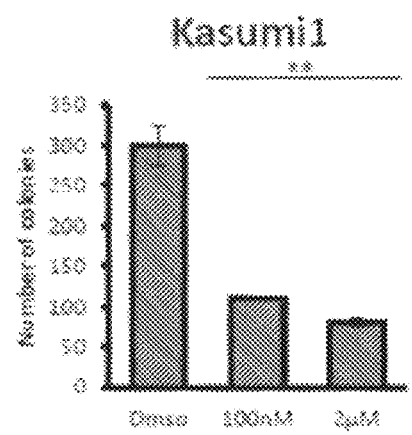
FIG. 35A          FIG. 35B
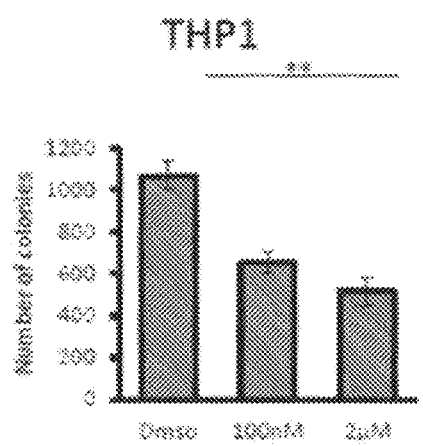
FIG. 35C

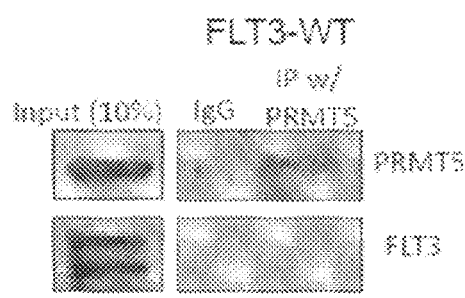
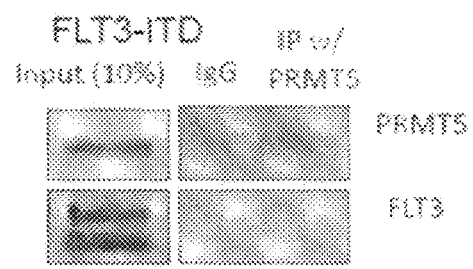
FIG. 38A   FIG. 38B
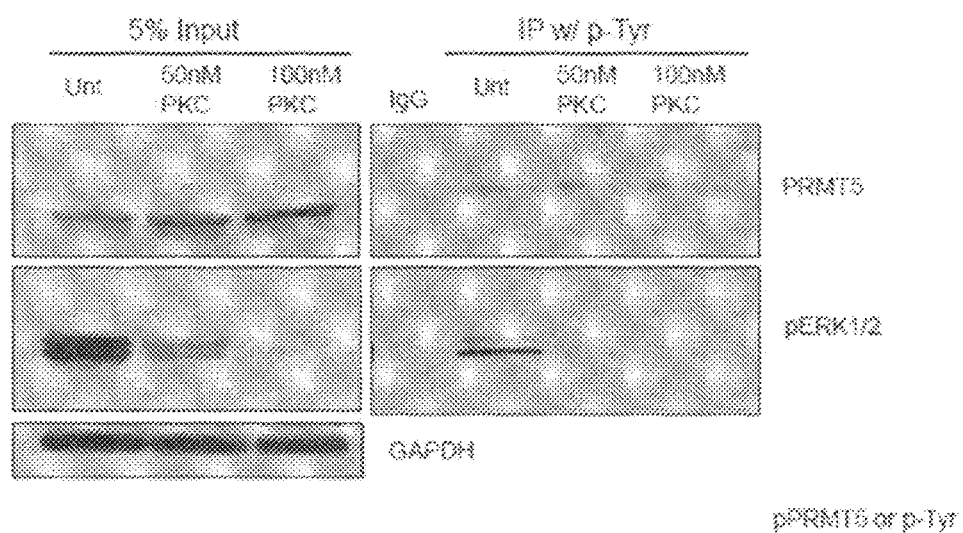
FIG. 38C

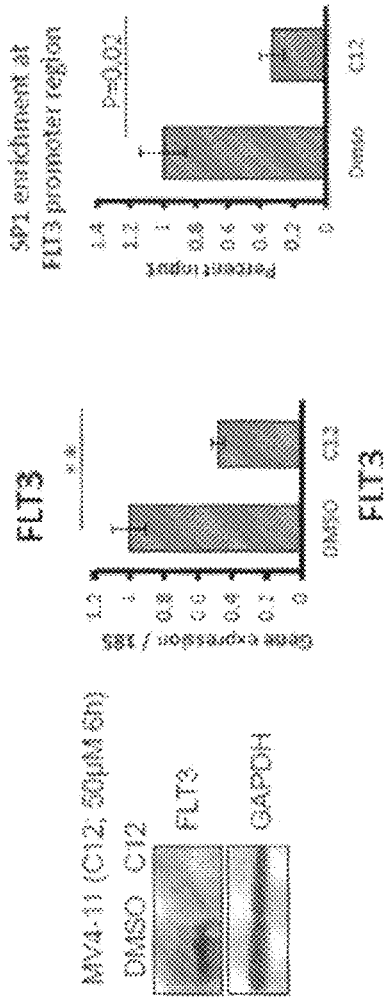
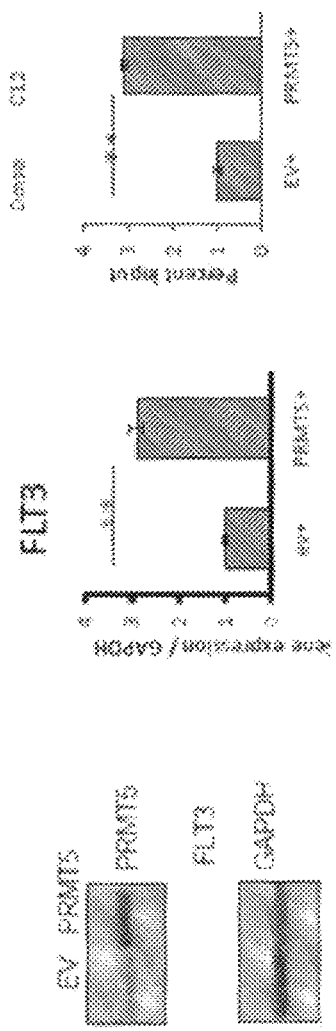
FIG. 42A
FIG. 42B

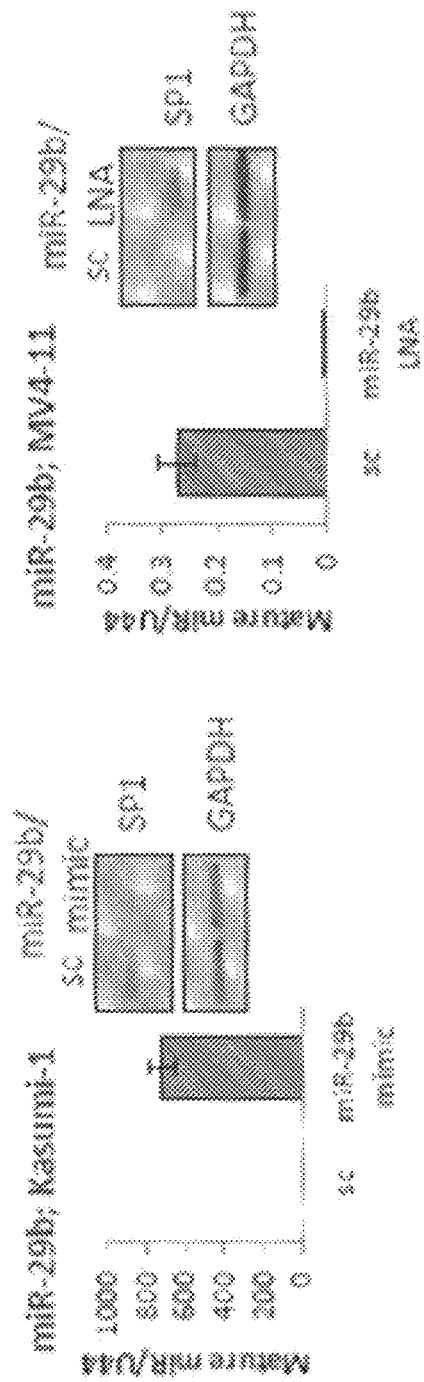

INHIBITORS OF PRMT5 AND METHODS OF THEIR USE

CROSS-REFERENCE TO RELATED APPLICATIONS

This Application is a continuation of U.S. application Ser. No. 15/822,549, filed on Nov. 27, 2017, which is a continuation of U.S. application Ser. No. 14/776,685, filed on Sep. 14, 2015, and patented as U.S. Pat. No. 9,856,218 on Jan. 2, 2018, which is a § 371 National Phase of PCT/US2014/29936, filed on Mar. 15, 2014, which claims the benefit of U.S. Provisional Application No. 61/788,461, filed on Mar. 15, 2013, the contents of each are incorporated herein by reference in its entirety.

BACKGROUND

Protein arginine N-methyltransferase 5 (PRMT5) is an enzyme encoded by the PRMT5 gene. Up-regulation of PRMT5 is believed to be involved in tumorigenesis. Thus, PRMT5 is a target with cancer and non-cancer clinical potential.

Despite advances in PRMT5 research, there is still a scarcity of compounds that are both potent, efficacious, and selective PRMT5 inhibitors and also effective in the treatment of cancer and of other diseases in which the PRMT5 receptor is involved. These needs and other needs are satisfied by the present invention.

SUMMARY

In accordance with the purpose(s) of the invention, as embodied and broadly described herein, the invention, in one aspect, relates to compounds useful as PRMT5 inhibitors, methods of making same, pharmaceutical compositions comprising same, and methods of treating disorders of uncontrolled cellular proliferation and benign hematologic diseases using same.

Disclosed are compounds, or pharmaceutically acceptable salts thereof, having a structure represented by a formula:

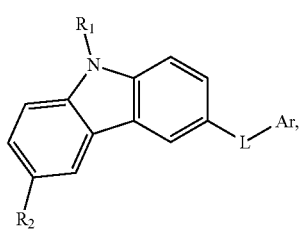

wherein $R^1$ is C1-C4 alkyl; wherein $R^2$ is selected from hydrogen, fluoro, chloro, and bromo; wherein $R^3$ is selected from C1-C4 alkyl, $-NH_3$, $-NHCH_3$, and $-N(CH_3)_2$; and wherein:

(a) L is

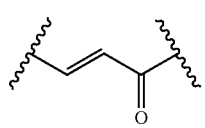 [SMILES: */C=C/C(*)=O]

and Ar is

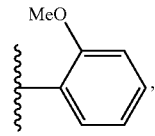 [SMILES: *c1ccccc1OC]

provided that $R^2$ is fluoro, chloro, or bromo, or Ar is

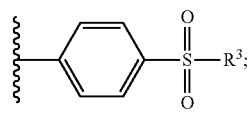

or (b) L is

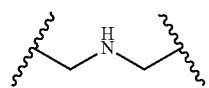

and Ar is

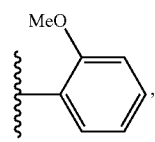 [SMILES: *c1ccccc1OC]

provided that $R^2$ is fluoro, chloro, or bromo, or Ar is

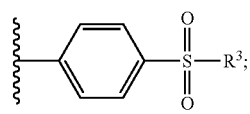

or (c) L is

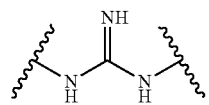

and Ar is

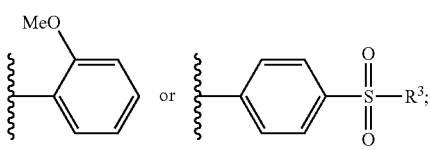

or
(d) L is

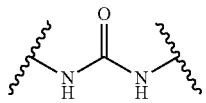

and Ar is

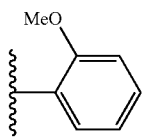 [SMILES: *c1ccccc1OC]

or Ar is

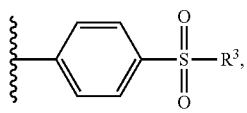

provided that $R^3$ is C1-C4 alkyl; or
(e) L is

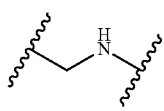

and Ar is

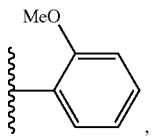

provided that $R^2$ is fluoro, chloro, or bromo, or Ar is

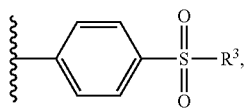

provided that $R^3$ is C1-C4 alkyl.

Also disclosed are compounds, or pharmaceutically acceptable salts thereof, capable of interaction with subregion 1 of PRMT5 with hydrophobic interaction with Y324, or F327, or K333, or Y334, or V363, or G365, or G367, or P370, or L371; or aromatic interactions with Y324, or F327, or Y334; and none, one, two; or three additional interactions selected from: interaction with hydrogen bonding to E392 or E435 or E444; interaction with subregion 2 of PRMT5 through aromatic interaction or hydrogen bonding; and interaction with subregion 3 of PRMT5 through aromatic interaction and/or hydrogen bonding to E435 or E444; wherein the compound has a molecular weight of less than 1000 Daltons.

Also disclosed are pharmaceutical compositions comprising a pharmaceutically acceptable carrier and one or more disclosed compounds, or pharmaceutically acceptable salts thereof.

Also disclosed are methods for treating a disorder of uncontrolled cellular proliferation in a mammal, the method comprising administering to the mammal a therapeutically effective amount of one or more disclosed compounds, or pharmaceutically acceptable salts thereof:

Also disclosed are methods for screening tissue for increased risk of a disorder of uncontrolled cellular proliferation, the method comprising detecting overexpression of PRMT5 within cellular nuclei or cytoplasm of the tissue.

Also disclosed are methods for treating a disorder of uncontrolled cellular proliferation, the method comprising the steps of identifying tissue having cells with increased expression of PRMT5 within the cellular nuclei or cytoplasm; and administering therapy to the tissue.

Also disclosed are methods for treating a disorder of uncontrolled cellular proliferation, the method comprising administering therapy to tissue identified as having cells with increased expression of PRMT5 within the cellular nuclei or cytoplasm.

Also disclosed are methods for treating a benign hematologic disease in a mammal, the method comprising administering to the mammal a therapeutically effective amount of a small-molecule PRMT5 inhibitor.

Also disclosed are methods for inhibition of PRMT5 in a mammal, the method comprising administering to the mammal a therapeutically effective amount of one or more disclosed compounds, or pharmaceutically acceptable salts thereof.

Also disclosed are methods for making the disclosed compounds and/or compositions.

Also disclosed are products of the disclosed methods of making.

Also disclosed are kits comprising the disclosed compounds and/or compositions.

Also disclosed are uses of a disclosed compound or a disclosed product of making, including use in the manufacture of a medicament for the treatment of a disorder.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE FIGURES

The accompanying figures, which are incorporated in and constitute a part of this specification, illustrate several aspects and together with the description serve to explain the principles of the invention.

FIG. 2A shows representative data pertaining to the crystal structure of rPRMT1 (aa 41-353, PDB ID 1GR8 GREEN) superimposed on the C-terminal domain (aa 310-637) of model hPRMT5 (YELLOW ribbon structure). Grey and magenta arrows indicate SAH and arginine binding sites, respectively. Comparative modeling using Crystal rat PRMT1 as a guide to build an in silico model of human PRMT5.

FIG. 2B shows representative data pertaining to the docked conformation of first generation PRMT5 inhibitor CMP5 (orange) within the active site of model hPRMT5. Amino acid residues within 5 angstroms of CMP5 are shown in grey, and interacting residues are depicted in yellow stick format. Grey shaded area represents the SAH cofactor binding region and pink shaded area represents the arginine binding pocket.

FIG. 2F shows representative immunofluorescence staining of JeKo cells treated with DMSO, CMP5 (PRMT5 inhibitor), or CMP6 (non-reactive compound) using antibodies against symmetrically (Sym) or asymmetrically (Asym) methylated $H4(Me_2)R3$ or $H3(Me_2)R8$. DAPI was used to stain nuclei. CMP5 interferes with PRMT5 driven epigenetic marks.

FIG. 2G shows the chemical structure of selective PRMT5 inhibitor CMP5 and non-reactive control CMP6.

FIG. 8 shows representative photomicrographs from primary brain astrocytoma study. Specifically.

FIG. 9A shows Kaplan Meier plots of survival by glioma grade. FIG. 9B shows the distribution of PRMT5 expression index by glioma grade. FIG. 9C shows Kaplan Meier plots of overall survival as a function of PRMT5 expression index. In patients with GBM there was a statistically significant association of PRMT5 level and overall survival (Log rank p<0.0001). FIG. 9D shows the time to death and PRMT5 level in patients who died with GBM. PRMT5 level is continuously associated with time to death (Spearman's rho=-0.57, p=0.0001).

FIG. 29 shows representative data pertaining to the proliferation rate in AML cell lines and patient primary blasts.

FIG. 33 shows representative data pertaining to the antileukemic activity of PRMT5 inhibition in AML samples. Specifically.

FIG. 35A-E shows representative data pertaining to the effect of sub-lethal doses of CMPD 12 on the proliferation potential of AML cell lines and primary tumor cells.

FIG. 38A-C shows representative data pertaining to the up-regulation of PLT3 mRNA and protein levels in AML cells by PRMT5. Specifically, FIGS. 38A and 38B show data from an immunoprecipitation assay demonstrating no apparent physical association between PRMT5 and FLT3. FIG. 38C shows that overall phosphorylated PRMT5 levels were not influenced by inhibition of FLT3 kinase activity.

FIGS. 42A and 42B show representative data pertaining to localization of SP1 following PRMT5 inhibition. Specifically, FIG. 42A shows representative data from a chromatin immunoprecipitation (ChIP) assay demonstrating localization of SP1 to the promoter region of FLT3 following PRMT5 inhibition. FIG. 42B shows representative data from a ChIP assay in cells which ectopically over-expressed PRMT5 demonstrating enhanced localization of SP1 to the promoter region of FLT3.

FIG. 43A shows that transient transfection of AML cells with siRNA specific to SP1 resulted in sufficient knockdown of SP1, and as a result down-regulation of FLT3. FIG. 43B shows representative data confirming the regulatory functions of the promoter region of FLT3.

FIG. 49 shows representative data pertaining to regulation of SP1 by over-expression and suppression of miR-29b.

FIG. 62A shows representative data demonstrating that controlled expression of PRMT5 shRNA leads to 100% survival of mice engrafted with primary DLBCL tumor cells. FIG. 62B shows representative data pertaining to pharmacokinetic results obtained in vivo with HLCL-65.

FIG. 62C shows representative data demonstrating improved survival in mice treated with HLCL-65 compared to control.

Figures 1A, 1B:
FIG. 1A shows representative data pertaining to the 3 dimensional structure of the PRMT5 enzyme as depicted in a computational model. The enzyme cofactor SAH (shown in yellow) and Fragments (shown in blue) are docked in the model to identify critical structures capable of interfering with SAH and substrate arginine.
FIG. 1B shows the fragments (shown in blue) and linked molecule (HLCL-61, shown in yellow).
Figure 2D:
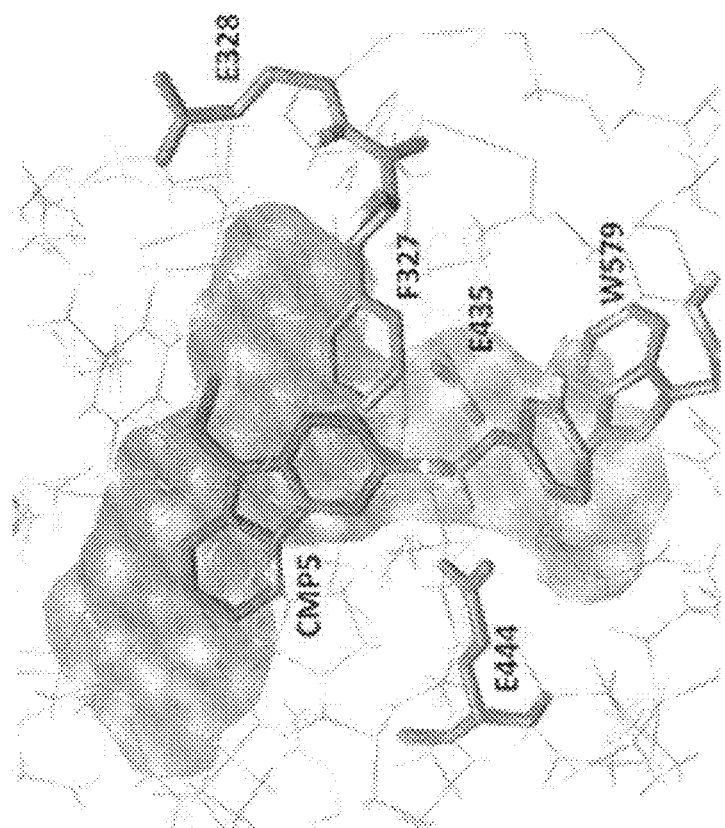
FIG. 2D shows representative data pertaining to the docked conformation of CMP5 (green) within the active site of the optimized hPRMT5 crystal structure. Interacting a residues are shown in cyan stick format CMP5 binds in a fashion that interacts with F327, E435 and E444 and likely exerts its PRMT5 inhibitory activities by interfering with SAH cofactor docking and/or transfer of methyl group to SAH/Arginine substrate pocket.
Figure 2C:
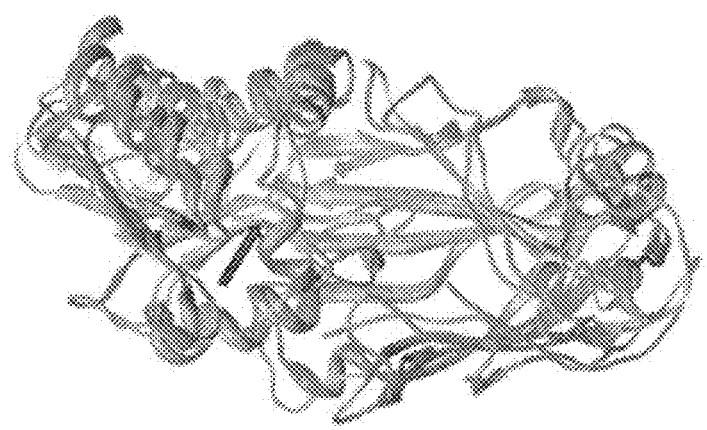
FIG. 2C shows representative data pertaining to crystal structure (BLUE ribbon) of the C-terminal domain of hPRMT5 (aa 310-637, PDB ID 4GQB) superimposed on model hPRMT5 (YELLOW ribbon). The crystal structure became available in 2012 and is now publically available. Superimposed structure of our model is identical to that of crystal structure hPRMT5.
Figure 2E:
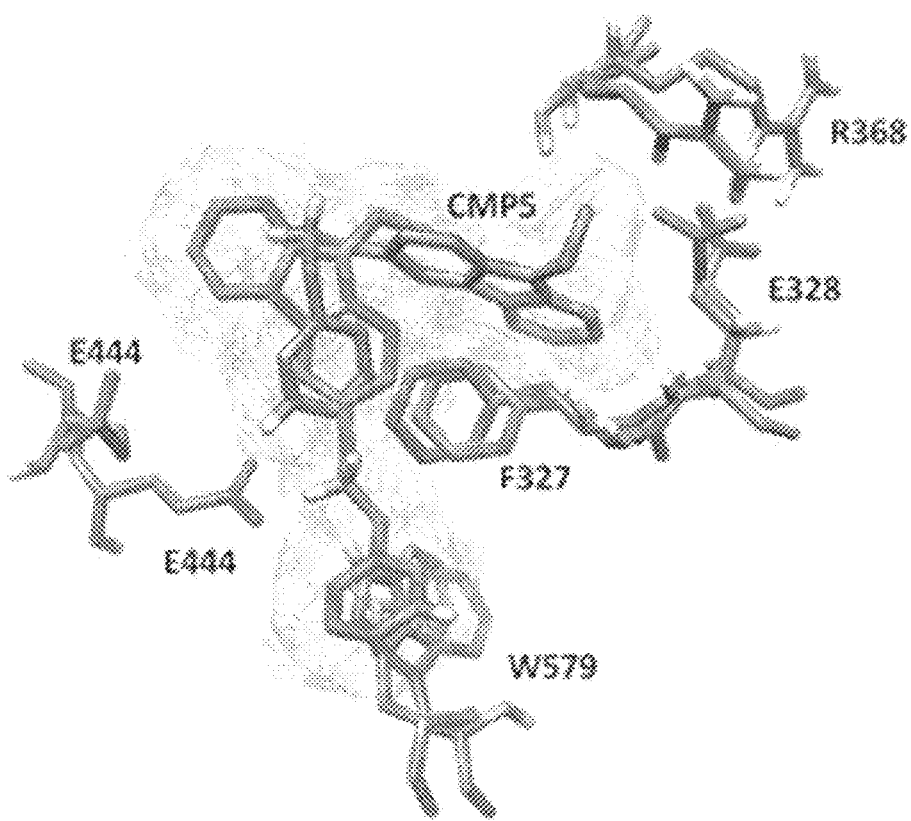
FIG. 2E shows representative data pertaining to an overlay of the docked conformation of CMP5 (orange) with model hPRMT5 and that of CMP5 (green) with the resolved hPRMT5 crystal structure. Model AA are shown in yellow and crystal AA are shown in blue.
Figure 2I:
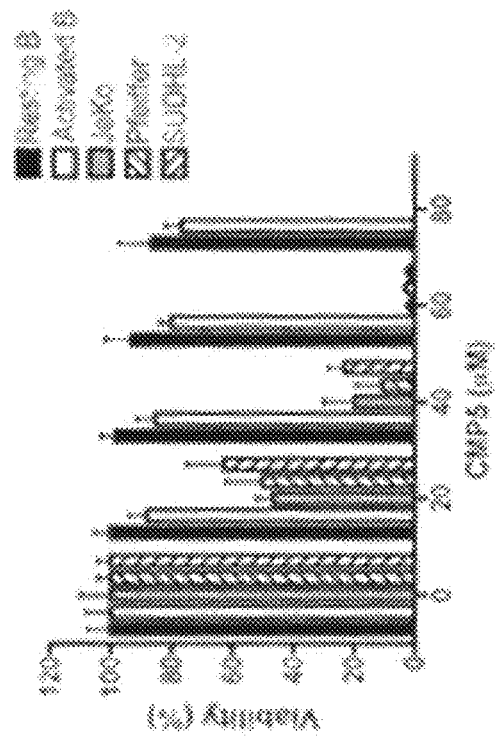
FIG. 2I shows representative data pertaining to cell viability. An equal number ($2 \times 10^5$) of normal B cells (resting or activated) or the indicated NHL cell lines was treated with increasing amounts of CMP5, and cell viability was determined by trypan blue staining after 48 h. Data in each graph represents the average of two experiments in triplicate, and are plotted as mean±SD.
Figure 2H:
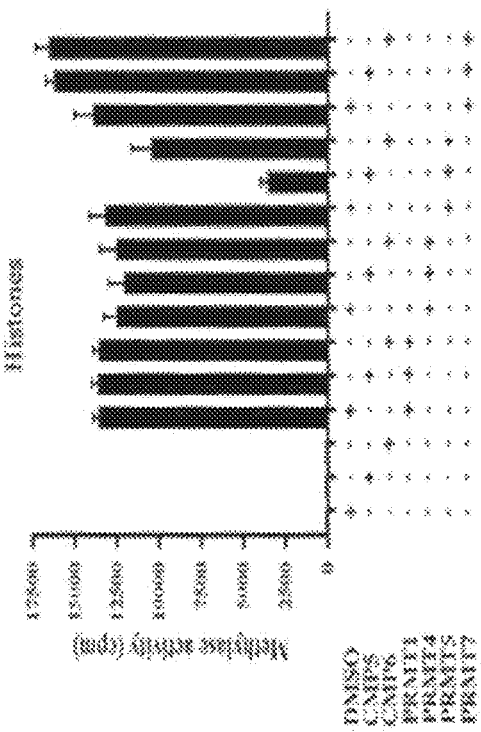
FIG. 2H shows representative data pertaining to histone methyltransferase assays, which were performed as described in experimental procedures in the presence of DMSO, CMP5 (100 μM), or CMP6 (100 μM). These methyltransferase assays are capable of demonstrating selectivity for PRMT5 as enzymatic activity of PRMT1, PRMT4 (both type I PRMTs) is compared to PRMT5 and PRMT7 (both type II PRMTs).

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

A. Definitions

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a functional group," "an alkyl," or "a residue" includes mixtures of two or more such functional groups, alkyls, or residues, and the like.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

References in the specification and concluding claims to parts by weight of a particular element or component in a composition denotes the weight relationship between the element or component and any other elements or components in the composition or article for which apart by weight is expressed. Thus, in a compound containing 2 parts by weight of component X and 5 parts by weight component Y, X and Y are present at a weight ratio of 2:5, and are present in such ratio regardless of whether additional components are contained in the compound.

A weight percent (wt. %) of a component, unless specifically stated to the contrary, is based on the total weight of the formulation or composition in which the component is included.

As used herein, the terms "optional" or "optionally" means that the subsequently described event or circumstance can or cannot occur, and that the description includes instances where said event or circumstance occurs and instances where it does not.

As used herein, the term "ligand" refers to a natural or synthetic molecular entity that is capable of associating or binding to a receptor to form a complex and mediate, prevent or modify a biological effect. Thus, the term "ligand" encompasses allosteric modulators, inhibitors, activators, agonists, antagonists, natural substrates and analogs of natural substrates.

As used herein, the terms "natural ligand" and "endogenous lipand" are used interchangeably, and refer to a naturally occurring ligand, found in nature, which binds to a receptor.

As used herein, the term "orthosteric site" refers to the primary binding site on a receptor that is recognized by the endogenous ligand or agonist for that receptor.

As used herein, the term "allosteric site" refers to a ligand binding site that is topographically distinct from the orthosteric binding site.

As used herein, the term "modulator" refers to a molecular entity (e.g., but not limited to, a ligand ad a disclosed compound) that modulates the activity of the target receptor protein.

As used herein, the term "inhibitor" refers to a substance (e.g., a compound) that slows down or prevents a particular chemical reaction or other process (e.g., receptor activity).

As used herein, the term "subject" can be a vertebrate, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder. The term "patient" includes human and veterinary subjects. In some aspects of the disclosed methods, the subject has been diagnosed with a need for treatment prior to the administering step. In some aspects of the disclosed methods, the subject has been identified with a need for treatment prior to the administering step.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder, and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In one aspect, the subject is a mammal such as a primate, and, in a further aspect, the subject is a human. The term "subject" also includes domesticated animals (e.g., cats, dogs, etc.), livestock (e.g., cattle, horses, pigs, sheep, goats, etc.), and laboratory animals (e.g., mouse, rabbit, rat, guinea pig, fruit fly, etc.).

As used herein, the term "prevent" or "preventing" refers to precluding, averting, obviating, forestalling, stopping, or hindering something from happening, especially by advance action. It is understood that where reduce, inhibit or prevent are used herein, unless specifically indicated otherwise, the use of the other two words is also expressly disclosed.

As used herein, the term "diagnosed" means having been subjected to a physical examination by a person of skill, for example, a physician, and found to have a condition that can be diagnosed or treated by the compounds, compositions, or methods disclosed herein.

As used herein, the phrase "identified to be in need of treatment for a disorder," or the like, refers to selection of a subject based upon need for treatment of the disorder. For example, a subject can be identified as having a need for treatment of a disorder based upon an earlier diagnosis by a person of skill and thereafter subjected to treatment for the disorder. It is contemplated that the identification can, in one aspect, be performed by a person different from the person making the diagnosis. It is also contemplated, in a further aspect, that the administration can be performed by one who subsequently performed the administration.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed compound and a cell, a target receptor, or other biological entity together in such a manner that the compound can affect the activity of the target, either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder, the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. For example, it is well within the skill of the art to start doses of a compound at levels lower than those required to achieve the desired therapeutic effect and to gradually increase the dosage until the desired effect is achieved. If desired, the effective daily dose can be divided into multiple doses for purposes of administration. Consequently, single dose compositions can contain such amounts or submultiples thereof to make up the daily dose. The dosage can be adjusted by the individual physician in the event of any contraindications. Dosage can vary, and can be administered in one or more dose administrations daily, for one or several days. Guidance can be found in the literature for appropriate dosages for given classes of pharmaceutical products. In further various aspects, a preparation can be administered in a "prophylactically effective amount"; that is, an amount effective for prevention of a disease or condition.

As used herein, "kit" means a collection of at least two components constituting the kit. Together, the components constitute a functional unit for a given purpose. Individual member components may be physically packaged together or separately. For example, a kit comprising an instruction for using the kit may or may not physically include the instruction with other individual member components. Instead, the instruction can be supplied as a separate member component, either in a paper form or an electronic form which may be supplied on computer readable memory device or downloaded from an internet website, or as recorded presentation.

As used herein, "instruction(s)" means documents describing relevant materials or methodologies pertaining to a kit. These materials may include any combination of the following: background information, list of components and their availability information (purchase information, etc.), brief or detailed protocols for using the kit, trouble-shooting, references, technical support, and any other related documents. Instructions can be supplied with the kit or as a separate member component, either as a paper form or an electronic form which may be supplied on computer readable memory device or downloaded from an internet website, or as recorded presentation. Instructions can comprise one or multiple documents, and are meant to include future updates.

As used herein, the terms "therapeutic agent" include any synthetic or naturally occurring biologically active compound or composition of matter which, when administered to an organism (human or nonhuman animal), induces a desired pharmacologic, immunogenic, and/or physiologic effect by local and/or systemic action. The term therefore encompasses those compounds or chemicals traditionally regarded as drugs, vaccines, and biopharmaceuticals including molecules such as proteins, peptides, hormones, nucleic acids, gene constructs and the like. Examples of therapeutic agents are described in well-known literature references such as the Merck Index (14th edition), the Physicians' Desk Reference (64th edition), and The Pharmacological Basis of Therapeutics (12th edition), and they include, without limitation, medicaments vitamins; mineral supplements; substances used for the treatment, prevention, diagnosis, cure or mitigation of a disease or illness; substances that affect the structure or function of the body, or pro-drugs, which become biologically active or more active after they have been placed in a physiological environment. For example, the term "therapeutic agent" includes compounds or compositions for use in all of the major therapeutic areas including, but not limited to, adjuvants; anti-infectives such as antibiotics and antiviral agents; analgesics and analgesic combinations, anorexics, anti-inflammatory agents, anti-epileptics, local and general anesthetics, hypnotics, sedatives, antipsychotic agents, neuroleptic agents, antidepressants, anxiolytics, antagonists, neuron blocking agents, anticholinergic and cholinomimetic agents, antimuscarinic and muscarinic agents, antiadrenergics, antiarrhythmics, antihypertensive agents, hormones, and nutrients, antiarthritics, antiesthmatic agents, anticonvulsants, antihistamines, antinauseants, antincoplastics, antipruritics, antipyrctics; antispasmodics, cardiovascular preparations (including calcium channel blockers, beta-blockers, beta-agonists and antiarrhythmics), antihypertensives, diuretics, vasodilators; central nervous system stimulants; cough and cold preparations; decongestants; diagnostics; hormones; bone growth stimulants and bone resorption inhibitors; immunosuppressives; muscle relaxants; psychostimulants; sedatives; tranquilizers; proteins, peptides, and fragments thereof (whether naturally occurring, chemically synthesized or recombinantly produced); and nucleic acid molecules (polymeric forms of two or more nucleotides, either ribonucleotides (RNA) or deoxyribonucleotides (DNA) including both double- and single-stranded molecules, gene constructs, expression vectors, antisense molecules and the like), small molecules (e.g., doxorubicin) and other biologically active macromolecules such as, for example, proteins and enzymes. The agent may be a biologically active agent used in medical, including veterinary, applications and in agriculture, such as with plants, as well as other areas. The term therapeutic agent also includes without limitation, medicaments; vitamins; mincral supplements; substances used for the treatment, prevention, diagnosis, cure or mitigation of disease or illness; or substances which affect the structure or function of the body; or pro-drugs, which become biologically active or more active after they have been placed in a predetermined physiological environment.

As used herein, "$EC_{50}$," is intended to refer to the concentration of a substance (e.g., a compound or a drug) that is required for 50% activation or enhancement of a biological process, or component of a process. For example, $EC_{50}$ can refer to the concentration of agonist that provokes a response halfway between the baseline and maximum response in an appropriate assay of the target activity.

As used herein, "$IC_{50}$," is intended to refer to the concentration of a substance (e.g., a compound or a drug) that is required for 50% inhibition of a biological process, or component of a process. For example, $IC_{50}$ refers to the half maximal (50%) inhibitory concentration (IC) of a substance as determined in a suitable assay.

The term "pharmaceutically acceptable" describes a material that is not biologically or otherwise undesirable, i.e., without causing an unacceptable level of undesirable biological effects or interacting in a deleterious manner.

As used herein, the term "derivative" refers to a compound-having a structure derived from the structure of a parent compound (e.g., a compound disclosed herein) and whose structure is sufficiently similar to those disclosed herein and based upon that similarity, would be expected by one skilled in the art to exhibit the same or similar activities and utilities as the claimed compounds, or to induce, as a precursor, the same or similar activities and utilities as the claimed compounds. Exemplary derivatives include salts, esters, amides, salts of esters or amides, and N-oxides of a parent compound.

As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

A residue of a chemical species, as used in the specification and concluding claims, refers to the moiety that is the resulting product of the chemical species in a particular reaction scheme or subsequent formulation or chemical product, regardless of whether the moiety is actually obtained from the chemical species. Thus, an ethylene glycol residue in a polyester refers to one or more —$OCH_2CH_2O$— units in the polyester, regardless of whether ethylene glycol was used to prepare the polyester. Similarly, a sebacic acid residue in a polyester refers to one or more —$CO(CH_2)_8CO$— moieties in the polyester, regardless of whether the residue is obtained by reacting sebacic acid or an ester thereof to obtain the polyester.

As used herein, the term "substituted" is contemplated to include all permissible substituents of organic compounds. In a broad aspect, the permissible substituents include acyclic and cyclic, branched and unbranched, carbocyclic and hetrocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc. It is also contemplated that, in certain aspects, unless expressly indicated to the contrary, individual substituents can be further optionally substituted (i.e., further substituted or unsubstituted).

In defining various terms, "$A^1$," "$A^2$," "$A^3$," and "$A^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" or "aliphatic group," as used herein, denotes a hydrocarbon moiety that may be straight-chain (i.e., unbranched), branched, or cyclic (including fused, bridging, and spirofused polycyclic) and may be completely saturated or may contain one or more units of unsaturation, but which is not aromatic. Unless otherwise specified, aliphatic groups contain 1-20 carbon atoms. Aliphatic groups include, but are not limited to, linear or branched, alkyl, alkenyl, and alkynyl groups, and hybrids thereof such as (cycloalkyl)alkyl, (cycloalkenyl)alkyl or (cycloalkyl)alkanyl.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also be substituted or unsubstituted. For example, the alkyl group can be substituted with one or more groups including, but not limited to, alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms. The term alkyl group can also be a C1 alkyl, C1-C2 alkyl, C1-C3 alkyl, C1-C4 alkyl, C1-C5 alkyl, C1-C6 alkyl, C1-C7 alkyl, C1-C8 alkyl, C1-C9 alkyl, C1-C10 alkyl, and the like up to and including a C1-C24 alkyl.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" or "haloalkyl" specifically refers to an alkyl group that is substituted with one or more halide, e.g., fluorine, chlorine, bromine, or iodine. Alternatively, the term "monohaloalkyl" specifically refers to an alkyl group that is substituted with a single halide, e.g. fluorine, chlorine, bromine, or iodine. The term "polyhaloalkyl" specifically refers to an alkyl group that is independently substituted with two or more halides, i.e. each halide substituent need not be the same halide as another halide substituent, nor do the multiple instances of a halide substituent need to be on the same carbon. The term "alkoxyalkyl" specifically refers to an alkyl group that is substituted with one or more alkoxy groups, as described below. The term "aminoalkyl" specifically refers to an alkyl group that is substituted with one or more amino groups. The term "hydroxyalkyl" specifically refers to an alkyl group that is substituted with one or more hydroxy groups. When "alkyl" is used in one instance and a specific term such as "hydroxyalkyl" is used in another, it is not meant to imply that the term "alkyl" does not also refer to specific terms such as "hydroxyalkyl" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, norbornyl, and the like. The term "heterocycloalkyl" is a type of cycloalkyl group as defined above, and is included within the meaning of the term "cycloalkyl," where at least one of the carbon atoms of the ring is replaced with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, cycloalkyl, alkoxy, amino, ether, halide, hydroxy, nitro, silyl, sulfo-oxo, or thiol as described herein.

The term "polyalkylene group" as used herein is a group having two or more $CH_2$ groups linked to one another. The polyalkylene group can be represented by the formula —$(CH_2)_a$—, where "a" is an integer of from 2 to 500.

The terms "alkoxy" and "alkoxyl" as used herein to refer to an alkyl or cycloalkyl group bonded through an ether linkage; that is, an "alkoxy" group can be defined as —$OA^1$ where $A^1$ is alkyl or cycloalkyl as defined above. "Alkoxy" also includes polymers of alkoxy groups as just described; that is, an alkoxy can be a polyether such as —$OA^1$-$OA^2$ or —$OA^1$-$(OA^2)_a$-$OA^3$, where "a" is an integer of from 1 to 200 and $A^1$, $A^2$, and $A^3$ are alkyl and/or cycloalkyl groups.

The term "alkenyl" as used herein is a hydrocarbon group of from 2 to 24 carbon atoms with a structural formula containing at least one carbon-carbon double bond. Asymmetric structures such as $(A^1A^2)C=C(A^3A^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkenyl" as used herein is a non-aromatic carbon-based ring composed of at least three carbon atoms and containing at least one carbon-carbon double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, norbornenyl, and the like. The term "heterocycloalkenyl" is a type of cycloalkenyl group as defined above, and is included within the meaning of the term "cycloalkenyl," where at least one of the carbon atoms of the ring is replaced with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "alkynyl" as used herein is a hydrocarbon group of 2 to 24 carbon atoms with a structural formula containing at least one carbon-carbon triple bond. The alkynyl group can be unsubstituted or substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol, as described herein.

The term "cycloalkynyl" as used herein is a non-aromatic carbon-based ring composed of at least seven carbon atoms and containing at least one carbon-carbon triple bound. Examples of cycloalkynyl groups include, but are not limited to, cycloheptynyl, cyclooctynyl, cyclononynyl, and the like. The term "heterocycloalkynyl" is a type of cycloalkenyl group as defined above, and is included within the meaning of the term "cycloalkynyl," where at least one of the carbon atoms of the ring is replaced with a heteroatom such as, but not limited to, nitrogen, oxygen, sulfur, or phosphorus. The cycloalkynyl group and heterocycloalkynyl group can be substituted or unsubstituted. The cycloalkynyl group and heterocycloalkynyl group can be substituted with one or more groups including, but not limited to, alkyl, cycloalkyl, alkoxy, alkenyl, cycloalkenyl, alkynyl, cycloalkynyl, aryl, heteroaryl, aldehyde, amino, carboxylic acid, ester, ether, halide, hydroxy, ketone, azide, nitro, silyl, sulfo-oxo, or thiol as described herein.

The term "aromatic group" as used herein refers to a ring structure having cyclic clouds of delocalized π electrons above and below the plane of the molecule, where the π clouds contain (4n+2) π electrons. A further discussion of aromaticity is found in Morrison and Boyd. Organic Chemistry, (5th Ed., 1987), Chapter 13, entitled "Aromaticity," pages 477-497, incorporated herein by reference. The term "aromatic group" is inclusive of both aryl and heteroaryl groups.

The term "aryl" as used herein is a group that contains any carbon-based aromatic group including, but not limited to, benzene, naphthalene, phenyl, biphenyl, anthracene, and the like. The aryl group can be substituted or unsubstituted. The aryl group can be substituted with one or more groups including, but not limited to, alkyl, cycloalkyl, alkoxy, alkenyl, cycloalkenyl, alkynyl, cycloalkynyl, aryl, heteroaryl, aldehyde, —$NH_2$, carboxylic acid, ester, ether, halide, hydroxy, ketone, azide, nitro, silyl, sulfo-oxo, or thiol as described herein. The term "biaryl" is a specific type of aryl group and is included in the definition of "aryl." In addition, the aryl group can be a single ring structure or comprise multiple ring structures that are either fused ring structures or attached via one or more bridging groups such as a carbon-carbon bond. For example, biaryl to two aryl groups that are bound together via a fused ring structure, as in naphthalene, or are attached via one or more carbon-carbon bonds, as in biphenyl.

The term "aldehyde" as used herein is represented by the formula —C(O)H. Throughout this specification "C(O)" is a short hand notation for a carbonyl group, i.e., C=O.

The terms "amine" or "amino" as used herein are represented by the formula —$NA^1A^2$, where $A^1$ and $A^2$ can be, independently, hydrogen or alkyl, cycloalkyl, alkenyl, cycloalkenyl, alkynyl, cycloalkynyl, aryl, or heteroaryl group as described herein. A specific example of amino is —$NH_2$.

The term "alkylamino" as used herein is represented by the formula —NH(-alkyl) where alkyl is a described herein. Representative examples include, but are not limited to, methylamino group, ethylamino group, propylamino group, isopropylamino group, butylamino group, isobutylamino group, (sec-butyl)amino group, (tert-butyl)amino group, pentylamino group, isopentylamino group, (tert-pentyl) amino group, hexylamino group, and the like.

The term "dialkylamino" as used herein is represented by the formula —N(-alkyl)$_2$ where alkyl is a described herein. Representative examples include, but are not limited to, dimethylamino group, diethylamino group, dipropylamino group, diisopropylamino group, dibutylamino group, diisobutylamino group, di(sec-butyl)amino group, di(tert-butyl)amino group, dipentylamino group, diisopentylamino group, di(tert-pentyl)amino group, dihexylamino group, N-ethyl-N-methylamino group, N-methyl-N-propylamino group, N-ethyl-N-propylamino group and the like.

The term "carboxylic acid" as used herein is represented by the formula —C(O)OH.

The term "ester" as used herein is represented by the formula —OC(O)A$^1$ or —C(O)OA$^1$, where A$^1$ can be alkyl, cycloalkyl, alkenyl, cycloalkenyl, alkynyl, cycloalkynyl, aryl, or heteroaryl group as described herein. The term "polyester" as used herein is represented by the formula —(A$^1$O(O)C-A$^2$-C(O)O)$_a$— or —(A$^1$O(O)C-A$^2$-OC(O))$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer from 1 to 500. "Polyester" is as the term used, to describe a group that is produced by the reaction between a compound having at least two carboxylic acid groups with a compound having at least two hydroxyl groups.

The term "ether" as used herein is represented by the formula A$^1$OA$^2$, where A$^1$ and A$^2$ can be, independently, an alkyl, cycloalkyl, alkenyl, cycloalkenyl, alkynyl, cycloalkynyl, aryl, or heteroaryl group described herein. The term "polyether" as used herein is represented by the formula —(A$^1$O-A$^2$O)$_a$—, where A$^1$ and A$^2$ can be, independently, an alkyl, cycloalkyl, alkenyl, cycloalkenyl, alkynyl, cycloalkynyl, aryl, or heteroaryl group described herein and "a" is an integer of from 1 to 500. Examples of polyester groups include polyethylene oxide, polypropylene oxide, and polybutylene oxide.

The terms "halo," "halogen" or "halide", as used hebtin can be used interchangeably and refer to F, Cl, Br, or I.

The terms "pseudohalide," "pseudohalogen" or "pseudohalo," as used herein can be used interchangeably and refer to functional groups that behave substantially similar to halides. Such functional groups include, by way of example, cyano, thiocyanato, azido, trifluoromethyl, trifluoromethoxy, perfluoroalkyl, and perfluoralkoxy groups.

The term "heteroalkyl," as used herein refers to an alkyl group containing at least one heteroatom. Suitable heteroatoms include, but are not limited to, O, N, Si, P and S, wherein the nitrogen, phosphorous and sulfur atoms are optionally oxidized, and the nitrogen heteroatom is optionally quaternized. Heteroalkyls can be substituted as defined above for alkyl groups.

The term "heteroaryl," as used herein refers to an aromatic group that has at least one heteroatom incorporated within the ring of the aromatic group. Examples of heteroatoms include, but not limited to, nitrogen, oxygen, sulfur, and phosphorus, where N-oxides, sulfur oxides, and dioxides are permissible heteroatom substitutions. The heteroaryl group can be substituted or unsubstituted. The heteroaryl group can be substituted with one or more groups including, but not limited to, alkyl, cycloalkyl, alkoxy, amino, ether, halide, hydroxy, nitro, silyl, sulfo-oxo, or thiol as described herein. Heteroaryl groups can be monocyclic, or alternatively fused ring systems. Heteroaryl groups include, but am not limited to, furyl, imidazolyl, pyrimidinyl, tetrazolyl, thienyl, pyridinyl, pyrrolyl, N-methylpyrrolyl, quinolinyl, isoquinolinyl, pyrazolyl, triazolyl, thiazolyl, oxazolyl, isoxazolyl, oxadiazolyl, thiadiazolyl, isothiazolyl, pyridazinyl, pyrazinyl, benzofuranyl, benzodioxolyl, benzothiophenyl, indolyl, indazolyl, benzimidazolyl, imidazopyridinyl, pyrazolopyridinyl, and pyrazolopyrimidinyl. Further not limiting examples of heteroaryl groups include, but are not limited to, pyridinyl, pyridazinyl, pyrimidinyl, pyrazinyl, thiophenyl, pyrazolyl, imidazolyl, benzo[d]oxazolyl, benzo[d]thiazolyl, quinolinyl, quinazolinyl, indazolyl, imidazo[1,2-b]pyridazinyl, imidazo[1,2-a]pyrazinyl, benzo[c][1,2,5]thiadiazolyl, benzo[c][1,2,5]oxadiazolyl, and pyrido[2,3-b]pyrazinyl.

The terms "heterocycle" or "heterocyclyl," as used herein can be used interchangeably and refer to single and multi-cyclic aromatic or non-aromatic ring systems in which at least one of the ring members is other than carbon. Thus, the term is inclusive of, but not limited to, "heterocycloalkyl", "heteroaryl", "bicyclic heterocycle" and "polycyclic heterocycle." Heterocycle includes pyridine, pyrimidine, furan, thiophene, pyrrole, isoxazole, isothiazole, pyrazole, oxazole, thiazolo, imidazole, oxazole, including, 1,2,3-oxadiazole, 1,2,5-oxadiazolo and 1,3,4-oxadiazole, thiadiazole, including 1,2,3-thiadiazolo, 1,2,5-thiadiazole, and 1,3,4-thiadiazole, triazole, including, 1,2,3-triazole, 1,3,4-triazole, tetrazole, including 1,2,3,4-tetrazole and 1,2,4,5-tetrazole, pyridazine, pyrazine, triazine, including 1,2,4-triazine and 1,3,5-triazine, tetrazine, including 1,2,4,5-tetramine, pyrrolidine, piperidine, piperazine, morpholine, azetidine, tetrahydropyran, tetrahydrofuran, dioxane, and the like. The term heterocyclyl group can also be a C2 heterocyclyl, C2-C3 heterocyclyl, C2-C4 heterocyclyl, C2-C5 heterocyclyl, C2-C6 heterocyclyl, C2-C7 heterocyclyl, C2-C8 heterocyclyl, C2-C9 heterocyclyl, C2-C10 heterocyclyl, C2-C11 heterocycyl, and the like up to and including a C2-C18 heterocyclyl. For example, a C2 heterocyclyl comprises a group which has two carbon atoms and at least one heteroatom, including, but not limited to, aziridinyl, diazetidinyl, dihydrodiazetyl, oxitanyl, thiiranyl, and the like. Alternatively for example, a C5 heterocyclyl comprises a group which has five carbon atoms and at least one heteroatom, including, but not limited to, piperidinyl, tetrahydropyranyl, tetrahydrothiopyranyl, diazepanyl, pyridinyl, and the like. It is understood that a heterocyclyl group may be bound either through a heteroatom in the ring, where chemically possible, or one of carbons comprising the heterocyclyl ring.

The term "bicyclic heterocycle" or "bicyclic heterocyclyl," as used herein refers to a ring system in which at least one of the ring members is other than carbon. Bicyclic heterocyclyl encompasses ring systems wherein an aromatic ring is fused with another aromatic ring, or wherein an aromatic ring is fused with a non-aromatic ring. Bicyclic heterocyclyl encompasses ring systems wherein a benzene ring is fused to a 5- or a 6-membered ring containing 1, 2 or 3 ring heteroatoms or wherein a pyridine ring is fused to a 5- or a 6-membered ring containing 1, 2 or 3 ring heteroatoms. Bicyclic heterocyclic groups include, but are not limited to, indolyl, indazolyl, pyrazolo[1,5-a]pyridinyl, benzofuranyl, quinolinyl, quinoxalinyl, 1,3-benzodioxolyl, 2,3-dihydro-1,4-benzodioxinyl, 3,4-dihydro-2H-chromenyl, 1H-pyrazolo[4,3-c]pyridin-3-yl; 1H-pyrrolo[3,2-b]pyridin-3-yl; and 1H-pyrazolo[3,2-b]pyridin-3-yl.

The term "heterocycloalkyl" as used herein refers to an aliphatic, partially unsaturated or fully saturated, 3- to 14-membered ring system, including single rings of 3 to 8 atoms and bi- and tricyclic ring systems. The heterocycloalkyl ring-systems include one to four heteroatoms independently selected from oxygen, nitrogen, and sulfur, wherein a nitrogen and sulfur heteroatom optionally can be oxidized and a nitrogen heteroatom optionally can be substituted. Representative heterocycloalkyl groups include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "hydroxyl" or "hydroxy" as used herein is represented by the formula —OH.

The term "ketone" as used herein is represented by the formula $A^1C(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "azido" or "azido" as used herein is represented by the formula $-N_3$.

The term "nitro" as used herein is represented by the formula $-NO_2$.

The term "nitrile" or "cyano" as used herein is represented by the formula —CN.

The term "silyl" as used herein is represented by the formula $-SiA^1A^2A^3$, where $A^1$, $A^2$, and $A^3$ can be, independently, hydrogen or an alkyl, cycloalkyl, alkoxy, alkenyl, cycloalkenyl, alkynyl, cycloalkynyl, aryl, or heteroaryl group as described herein.

The term "sulfo-oxo" as used herein is represented by the formulas $-S(O)A^1$, $-S(O)_2A^1$, $-OS(O)_2A^1$, or $-OS(O)_2OA^1$, where $A^1$ can be hydrogen or an alkyl, cycloalkyl, alkenyl, cycloalkenyl, alkynyl, cycloalkynyl, aryl, or heteroaryl group as described herein. Throughout this specification "S(O)" is a short hand notation for S=O. The term "sulfonyl" is used herein to refer to the sulfo-oxo group represented by the formula $-S(O)_2A^1$, where $A^1$ can be hydrogen or an alkyl, cycloalkyl, alkenyl, cycloalkenyl, alkynyl, cycloalkynyl, aryl, or heteroaryl group as described herein. The term "sulfone" as used herein is represented by the formula $A^1S(O)_2A^2$, where $A^1$ and $A^2$ can be, independently an alkyl, cycloalkyl, alkenyl, cycloalkenyl, alkynyl, cycloalkynyl, aryl, or heteroaryl group as described herein. The term "sulfoxide" as used herein is represented by the formula $A^1S(O)A^2$, where $A^1$ and $A^2$ can be, independently, an alkyl, cycloalkyl, alkenyl, cycloalkenyl, alkynyl, cycloalkynyl, aryl, or heteroaryl group as described herein.

The term "thiol" as used herein is represented by the formula —SH.

"$R^1$," "$R^2$," "$R^3$," "$R^n$," where n is an integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. In is also contemplated that, in certain aspects, unless expressly indicated to the contrary, individual substituents can be further optionally substituted (i.e., further substituted or unsubstituted).

The term "stable," as used herein, refers to compounds that are not substantially altered when subjected to conditions to allow for their production, detection, and, in certain aspects, their recovery, purification, and use for one or more of the purposes disclosed herein.

Suitable monovalent substituents on a substitutable carbon atom of an "optionally substituted" group are independently halogen; $-(CH_2)_{0-4}R°$; $-(CH_2)_{0-4}OR°$; $-O(CH_2)_{0-4}R°$, $-O-(CH_2)_{0-4}C(O)OR°$; $-(CH_2)_{0-4}CH(OR°)_2$; $-(CH_2)_{0-4}SR°$; $-(CH_2)_{0-4}Ph$, which may be substituted with $R°$; $-(CH_2)_{0-4}O(CH_2)_{0-1}Ph$ which may be substituted with $R°$; —CH=CHPh, which may be substituted with $R°$; $-(CH_2)_{0-4}O(CH_2)_{0-1}$-pyridyl which may be substituted with $R°$; $-NO_2$; —CN; $-N_3$; $-(CH_2)_{0-4}N(R°)_2$; $-(CH_2)_{0-4}N(R°)C(O)R°$; $-N(R°)C(S)R°$; $-(CH_2)_{0-4}N(R°)C(O)NR°_2$; $-N(R°)C(S)NR°_2$; $-(CH_2)_{0-4}N(R°)C(O)OR°$; $-N(R°)N(R°)C(O)R°$; $-N(R°)N(R°)C(O)NR°_2$; $-N(R°)N(R°)C(O)OR°$; $-(C_2)_{0-4}C(O)R°$; $-C(S)R°$; $-(CH_2)_{0-4}C(O)OR°$; $-(CH_2)_{0-4}C(O)SR°$; $-(CH_2)_{0-4}C(O)OSiR°_3$; $-(CH_2)_{0-4}OC(O)R°$; $-OC(O)(CH_2)_{0-4}SR-$, $SC(S)SR°$; $-(CH_2)_{0-4}SC(O)R°$; $-(CH_2)_{0-4}C(O)NR°_2$; $-C(S)NR°_2$; $-C(S)SR°$; $-(CH_2)_{0-4}OC(O)NR°_2$; $-C(O)N(OR°)R°$; $-C(O)C(O)R°$; $-C(O)CH_2C(O)R°$; $-C(NOR)R°$; $-(CH_2)_{0-4}SSR°$; $-(CH_2)_{0-4}S(O)_2R°$; $-(CH_2)_{0-4}S(O)_2OR°$; $-(CH_2)_{0-4}S(O)_2R°$; $-S(O)_2NR°_2$; $-(CH_2)_{0-4}S(O)R°$; $-N(R°)S(O)_2NR°_2$; $-N(R°)S(O)_2R°$; $-N(OR°)R°$; $-C(NH)NR°_2$; $-P(O)_2R°$; $-P(O)R°_2$; $-OP(O)R°_2$; $-OP(O)(OR°)_2$; $SiR°_3$; $-(C_{1-4}$ straight or branched alkylene)O—N(R°); or $-(C_{1-4}$ straight or branched alkylene)C(O)O—N(R°)_2$, wherein each R° may be substituted as defined below and is independently hydrogen, $C_{1-6}$ aliphatic, $-CH_2Ph$, $-O(CH_2)_{0-1}Ph$, $-CH_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, $-(CH_2)_{0-2}R^•$, $-(haloR^•)$, $-(CH_2)_{0-2}OH$, $-(CH_2)_{0-2}OR^•$, $-(CH_2)_{0-2}CH(OR^•)$; $-O(haloR^•)$, —CN, $-N_3$, $-(CH_2)_{0-2}C(O)R^•$, $-(CH_2)_{0-2}C(O)OH$, $-(CH_2)_{0-2}C(O)OR^•$, $-(CH_2)_{0-2}SR^•$, $-(CH_2)_{0-2}SH$, $-(CH_2)_{0-2}NH_2$, $-(CH_2)_{0-2}NHR^•$, $-(CH_3)_{0-2}NR^•_2$, $-NO_2$, $-SiR^•_3$, $-OSiR^•_3$, $-C(O)SR^•$, $-(C_{1-4}$ straight or branched alkylene)C(O)OR$^•$, or $-SSR^•$ wherein each $R^•$ is unsubstituted or where preceded by "halo" is substituted only with one or more halogens, and is independently selected from $C_{1-4}$ aliphatic, $-CH_2Ph$, $O(CH_2)_{0-1}Ph$, Or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*₂, —NNHC(O)R*, —NNHC(O)OR*, =NNHS(O)₂R*, =NR*, =NOR*, —O(C(R*₂))₂₋₃O—, or —S(C(R*₂))₂₋₃S—, wherein each independent occurrence of R* is selected from hydrogen, C₁₋₆ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*₂)₂₋₃O—, wherein each independent occurrence of R° is selected from hydrogen, C₁₋₆ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R° include halogen, —R●, —(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, —NR†₂, —C(O)R†, —C(O)OR†, C(O)C(O)R†, —C(O)CH₂C(O)R†, —S(O)₂R†, —S(O)₂NR†₂, —C(S)NR†₂. —C(NH)NR†₂, or —N(R†)S(O)₂R†; wherein each R† is independently hydrogen, C₁₋₆ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, —(haloR●), —OH, —OR●, —O(haloR●), —CN, —C(O)OH, —C(O)OR●, —NH₂, —NHR●, —NR●₂, or —NO₂, wherein each R● is unsubstituted or where preceded by "halo" is substituted only with one or more halogens, and is independently C₁₋₄ aliphatic, —CH₂Ph, —O(CH₂)₀₋₁Ph, or a 5-6-membered saturated, partially unsaturated, or aryl ring having 0-4 heteroatoms independently selected from nitrogen, oxygen, or sulfur.

The term "leaving group" refers to an atom (or a group of atoms) with electron withdrawing ability that can be displaced as a stable species, taking with it the bonding electrons. Examples of suitable leaving groups include halides and sulfonate esters, including but not limited to, triflate, mesylate, tosylate, and brosylate.

The terms "hydrolysable group" and "hydrolysable moiety" refer to a functional group capable of undergoing hydrolysis, e.g., under basic or acidic conditions. Examples of hydrolysable residues include, without limitation, acid halides, activated carboxylic acids, and various protecting groups known in the art (ace, for example, "Protective Groups in Organic Synthesis," T. W. Greene, P. G. M. Wuts, Wiley-Interscience, 1999).

The term "organic residue" defines a carbon containing residue, i.e., a residue comprising at least one carbon atom, and includes but is not limited to the carbon-containing groups, residues, or radicals defined hereinabove. Organic residues can contain various heteroatoms, or be bonded to another molecule through a heteroatom, including oxygen, nitrogen, sulfur, phosphorus, or the like. Examples of organic residues include but are not limited alkyl or substituted alkyls, alkoxy or substituted alkoxy, mono or di-substituted amino, amide groups, etc. Organic residues can preferably comprise 1 to 18 carbon atoms, 1 to 15, carbon atoms, 1 to 12 carbon atoms, 1 to 8 carbon atoms, 1 to 6 carbon atoms, or 1 to 4 carbon atoms. In a further aspect, an organic residue can comprise 2 to 18 carbon atoms, 2 to 15, carbon atoms, 2 to 12 carbon atoms, 2 to 8 carbon atoms, 2 to 4 carbon atoms, or 2 to 4 carbon atoms.

A very close synonym of the term "residue" is the term "radical," which as used in the specification and concluding claims, refers to a fragment, group, or substructure of a molecule described herein, regardless of how the molecule is prepared. For example, a 2,4-thiazolidinedione radical in a particular compound has the structure:

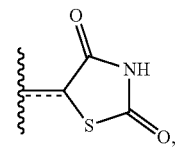

regardless of whether thiazolidinedione is used to prepare the compound. In some embodiments the radical (for example an alkyl) can be further modified (Le, substituted alkyl) by having bonded thereto one or more "substituent radicals." The number of atoms in a given radical is not critical to the present invention unless it is indicated to the contrary elsewhere herein.

"Organic radicals," a the term is defined and used herein, contain one Or more carbon atoms. An organic radical can have, for example, 1-26 carbon atoms, 1-18 carbon atoms, 1-12 carbon atoms, 1-8 carbon atoms, 1-6 carbon atoms, or 1-4 carbon atoms. In a further aspect, an organic radical can have 2-26 carbon atoms, 2-18 carbon atoms, 2-12 carbon atoms, 2-8 carbon atoms, 2-6 carbon atoms, or 2-4 carbon atoms. Organic radicals often have hydrogen bound to at least some of the carbon atoms of the organic radical. One example, of an organic radical that comprises no inorganic atoms is a 5,6,7,8-tetrahydro-2-naphthyl radical. In some embodiments, an organic radical can contain 1-10 inorganic heteroatoms bound thereto or therein, including halogens, oxygen, sulfur, nitrogen, phosphorus, and the like. Examples of organic radicals include but are not limited to an alkyl, substituted alkyl, cycloalkyl, substituted cycloalkyl, mono-substituted amino, di-substituted amino, acyloxy, cyano, carboxy, carboalkoxy, alkylcarboxamide, substituted alkylcarboxamide, dialkylcarboxamide, substituted dialkylcarboxamide, alkylsulfonyl, alkylsulfinyl, thioalkyl, thiohaloalkyl, alkoxy, substituted alkoxy, haloalkyl, haloalkoxy, aryl, substituted aryl, heteroaryl, heterocyclic, or substituted heterocyclic radicals, wherein the terms are defined elsewhere herein. A few non-limiting examples of organic radicals that include heteroatoms include alkoxy radicals, trifluoromethoxy radicals, acetoxy radicals, dimethylamino radicals and the like.

"Inorganic radicals," as the term is defined and used herein, contain no carbon atoms and therefore comprise only atoms other than carbon. Inorganic radicals comprise bonded combinations of atoms selected from hydrogen, nitrogen, oxygen, silicon, phosphorus, sulfur, selenium, and halogens such as fluorine, chlorine, bromine, and iodine, which can be present individually or bonded together in their chemically stable combinations. Inorganic radicals have 10 or fewer, or preferably one to six or one to four inorganic atoms as listed above bonded together. Examples of inorganic radicals include, but not limited to, amino, hydroxy, halogens, nitro, thiol, sulfite, phosphate, and like commonly known inorganic radicals. The inorganic radicals do not have bonded therein the metallic elements of the periodic table (such as the alkali metals, alkaline earth metals, transition metals, lanthanide metals, or actinide metals), although such metal ions can sometimes serve as a pharmaceutically acceptable cation for anionic inorganic radicals such as sulfate, phosphate, or like anionic inorganic radical. Inorganic radicals do not comprise metalloids elements such as boron, aluminum, gallium, germanium, arsenic, tin, lead, or tellurium, or the noble gas elements, unless otherwise specifically indicated elsewhere herein.

Compounds described herein can contain one or more double bonds and, thus, potentially give rise to cis/trans(E/Z) isomers, as well as other conformational isomers. Unless stated to the contrary, the invention includes all such possible isomers, as well as mixtures of such isomers.

Unless stated to the contrary, a formula with chemical bonds shown only as solid lines and not as wedges or dashed lines contemplates each possible isomer, e.g., each enantiomer and diastereomer, and a mixture of isomers, such as a racemic or scalemic mixture. Compounds described herein can contain one or more asymmetric centers and, thus, potentially give rise to diastereomers and optical isomers. Unless stated to the contrary, the present invention includes all such possible diastereomer as well as their racemic mixtures, their substantially pure resolved enantiomers, all possible geometric isomers, and pharmaceutically acceptable salts thereof. Mixtures of stereoisomers, as well as isolated specific stereoisomers, are also included. During the course of the synthetic procedures used to prepare such compounds, or in using racemization or epimerization procedures known to those skilled in the art, the products of such procedures can be a mixture of stereoisomers.

Many organic compounds exist in optically active forms having the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or meaning that the compound is levorotatory. A compound prefixed with (+) or d is dextrorotatory. For a given chemical structure, these compounds, called stereoisomers, are identical except that they are non-superimposable mirror images of one another. A specific stereoisomer can also be referred to as an enantiomer, and a mixture of such isomers is often called an enantiomeric mixture. A 50:50 mixture of enantiomers is referred to as a racemic mixture. Many of the compounds described herein can have one or more chiral centers and therefore can exist in different enantiomeric forms. If desired, a chiral carbon can be designated with an asterisk (*). When bonds to the chiral carbon are depicted as straight lines in the disclosed formulas, it is understood that both the (R) and (S) configurations of the chiral carbon, and hence both enantiomers and mixtures thereof, are embraced within the formula. As is used in the art, when it is desired to specify the absolute configuration about a chiral carbon, one of the bonds to the chiral carbon can be depicted as a wedge (bonds to atoms above the plane) and the other can be depicted as a series or wedge of short parallel lines (bonds to atoms below the plane). The Cahn-Inglod-Prelog system can be used to assign the (R) or (S) configuration to a chiral carbon.

Compounds described herein comprise atoms in both their natural isotopic abundance and in non-natural abundance. The disclosed compounds can be isotopically-labeled or isotopically-substituted compounds identical to those-described, but for the fact that one or more atoms are replaced by an atom having an atomic mass or mass number different from the atomic mass or mass number typically found in nature. Examples of isotopes that can be incorporated into compounds of the invention include isotopes of hydrogen, carbon, nitrogen, oxygen, sulfur, fluorine and chlorine, such as $^2H$, $^3H$, $^{13}C$, $^{14}C$, $^{15}N$, $^{18}O$, $^{17}O$, $^{35}S$, $^{18}F$ and $^{36}Cl$, respectively. Compounds further comprise prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3H$ and $^{14}C$ are incorporated, are useful in drug and/or substrate tissue distribution assays. Tritiated, i.e., $^3H$, and carbon-14, i.e., 14C, isotopes are particularly preferred for their ease of preparation and detectability. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labeled compounds of the present invention and prodrugs thereof can generally be prepared by carrying out the procedures below, by substituting a readily available isotopically labeled reagent for a non-isotopically labeled reagent.

The compounds described in the invention can be present as a solvate. In some cases, the solvent used to prepare the solvate is an aqueous solution, and the solvate is then often referred to as a hydrate. The compounds can be present as a hydrate, which can be obtained, for example, by crystallization from a solvent or from aqueous solution. In this connection, one, two, three or any arbitrary number of solvent or water molecules can combine with the compounds according to the invention to form solvates and hydrates. Unless stated to the contrary, the invention includes all such possible solvates.

The term "co-crystal" means a physical association of two or more molecules which owe their stability through non-covalent interaction. One or more components of this molecular complex provide a stable framework in the crystalline lattice. In certain instances, the guest molecules are incorporated in the crystalline lattice as anhydrates or solvates, see e.g. "Crystal Engineering of the Composition of Pharmaceutical Phases. Do Pharmaceutical Co-crystals Represent a New Path to Improved Medicines?" Almrasson, O., et. al., The Royal Society of Chemistry, 1889-1896, 2004. Examples of co-crystals include p-toluenesulfonic acid, and benzenesulfonic acid.

It is known that chemical substances form solids which are present in different states of order which are termed polymorphic forms or modifications. The different modifications of a polymorphic substance can differ greatly in their physical properties. The compounds according to the invention can be present in different polymorphic forms, with it being possible for particular modifications to be metastable. Unless stated to the contrary, the invention includes all such possible polymorphic forms.

In some aspects, a structure of a compound can be represented by a formula:

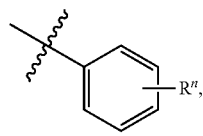

which is understood to be equivalent to a formula:

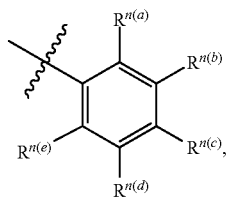

wherein n is typically an integer. That is, $R''$ is understood to represent five independent substituents, $R^{n(a)}$, $R^{n(b)}$, $R^{n(c)}$, $R^{n(d)}$, $R^{n(e)}$. By "independent substituents," it is meant that each R substituent can be independently defined. For example, if in one instance $R^{n(a)}$ is halogen, then $R^{n(b)}$ is not necessarily halogen in that instance.

Certain materials, compounds, compositions, and components disclosed herein can be obtained commercially or readily synthesized using techniques generally known to those of skill in the art. For example, the starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989).

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, ii is no way intended that an order be inferred, in any respect. This holds for any possible non-express basis for interpretation, including: matters of logic with respect to arrangement of steps or operational flow; plain meaning derived from grammatical organization or punctuation; and the number type of embodiments described in the specification.

Disclosed are the components to be used to prepare the compositions of the invention as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds cannot be explicitly disclosed, each is specifically contemplated and described herein. For example, if a particular compound is disclosed and discussed and a number of modifications that can be made to a number of molecules including the compounds are discussed, specifically contemplated is each and every combination and permutation of the compound and the modifications that are possible unless specifically indicated to the contrary. Thus, if a class of molecules A, B, and C are disclosed a well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the compositions of the invention. Thus, if there are a variety of additional steps that can be performed it is understood that each of these additional steps can be performed with any specific embodiment or combination of embodiments of the methods of the invention.

It is understood that the compositions disclosed herein have certain functions. Disclosed herein are certain structural requirements for performing the disclosed functions, and it is understood that there are a variety of structures that can perform the same function that are related to the disclosed structures, and that these structures will typically achieve the same result.

B. Compounds

In one aspect, the invention relates to compounds useful as PRMT5 inhibitors.

It is contemplated that each disclosed derivative can be optionally further substituted. It is also contemplated that any one or more derivative can be optionally omitted from the invention. It is understood that a disclosed compound can be provided by the disclosed methods. It is also understood that the disclosed compounds can be employed in the disclosed methods of using.

1. Binding

In the PRMT5 binding domain, there are three binding subregions, defined as subregion 1 (key residues Y324, F327, K333, Y334, V363, G365, G367, P370, L371), binding subregion 2 (key residues K393, D419, M420, R421) and binding subregion 3 (key residues F327, E435, E444). Interactions with these binding regions can uniquely define specificity to type II PRMTs, such PRMT5.

Thus, in one aspect, the invention relates to a compound, or pharmaceutically acceptable salt thereof, capable of: interaction with subregion 1 of PRMT5 with hydrophobic interaction with Y324, or F327, or K333, or Y334, or V363, or G365, or G367, or P370, or L371; or aromatic interactions with Y324, or F327, or Y334; and none, one, two, or three additional interactions selected from: interaction with hydrogen bonding to E392 or E435 or E444; interaction with subregion 2 of PRMT5 through aromatic interaction or hydrogen bonding; and interaction with subregion 3 of PRMT5 through aromatic interaction and/or hydrogen bonding to E435 or E444; wherein the compound has a molecular weight of less than 1000 Daltons.

In a further aspect, the compound comprises a bicyclic or tricyclic heteroaromatic moiety capable of hydrophobic interaction with Y324, or F327, do K333, or Y334, or V363, or G365, or G367, or P370, or L371; and/or capable of aromatic interactions with Y324, or F327, or Y334; a linker moiety between 3A and 7A in length having at least one electron-donating group capable of hydrogen bonding to E392 or E435 or E444; and a monocyclic or bicyclic aromatic moiety, substituted with electron-donating and/or electron-accepting group(s), capable of aromatic interaction and/or hydrogen bonding to W579. In a yet further aspect, the compound has at least one carbazole moiety. In a further aspect, the carbazole moiety is capable of binding to the SAM Adenine region of PRMT5. In a further aspect, a linker moiety can be selected from:

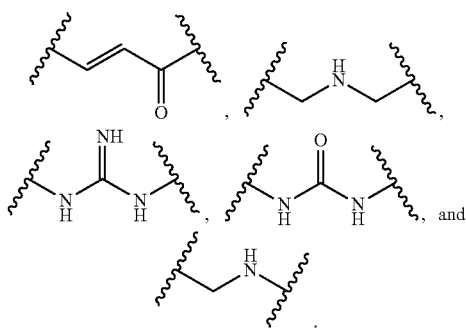

In a further aspect, the linker moiety is capable of binding to the SAM/ARG region of PRMT5.

2. Structure

In one aspect, the invention relates to a compound, or pharmaceutically acceptable salt thereof, having a structure represented by a formula:

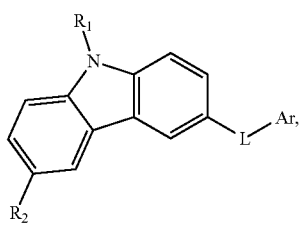

wherein $R^1$ is C1-C4 alkyl; wherein $R^2$ is selected from hydrogen, fluoro, chloro, and bromo; wherein $R^3$ is selected from C1-C4 alkyl, —NH$_2$, —NHCH$_3$, and —N(CH$_3$)$_2$; and wherein:

(a) L is

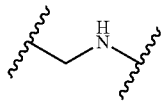 [SMILES: *CN*]

and Ar is

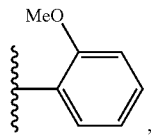 [SMILES: *c1ccccc1OC]

provided that $R^2$ is fluoro, chloro, or bromo, or Ar is

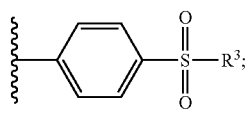

or (b) L is

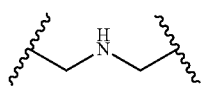

and Ar is

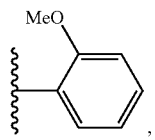 [SMILES: *c1ccccc1OC]

provided that $R^2$ is fluoro, chloro, or bromo, or Ar is

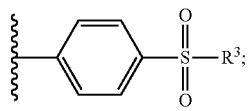

or (c) L is

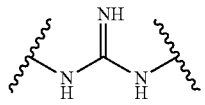 [SMILES: *NC(=N)N*]

and Ar is

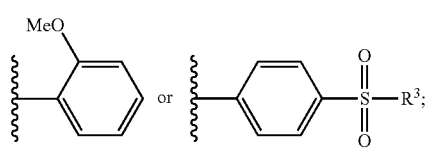

or (d) L is

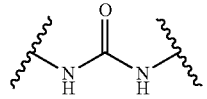

and Ar is

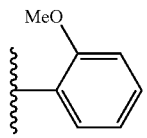 [SMILES: *c1ccccc1OC]

or Ar is

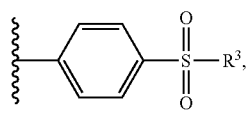

provided that $R^3$ is C1-C4 alkyl; or (e) L is

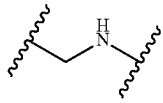 [SMILES: *CN*]

and Ar is

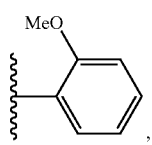, provided that $R^2$ is fluoro, chloro, or bromo, or Ar is

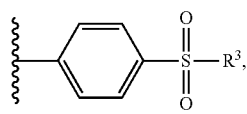

provided that $R^3$ is C1-C4 alkyl.

In a further aspect, the compound has a structure represented by a formula:

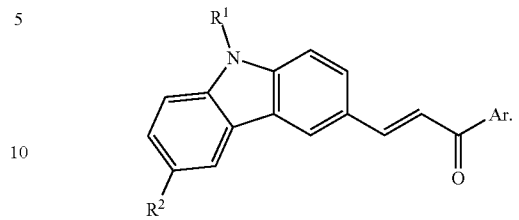

In a further aspect, the compound has a structure represented by a formula:

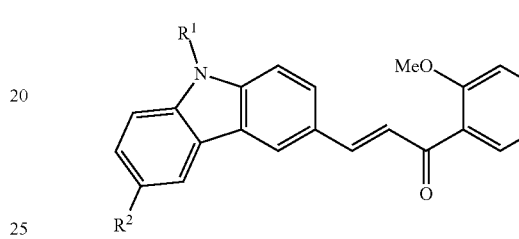

In a further aspect, the compound has a structure represented by a formula:

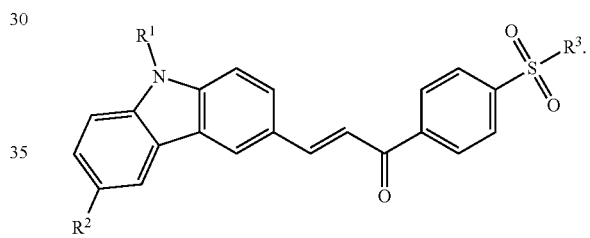

In a further aspect, the compound has a structure represented by a formula:

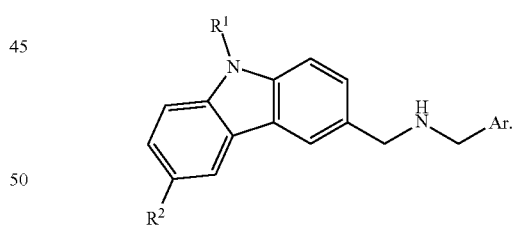

In a further aspect, the compound has a structure represented by a formula:

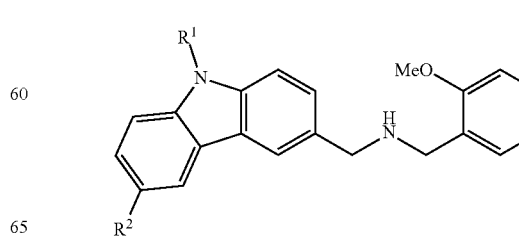

In a further aspect, the compound has a structure represented by a formula:

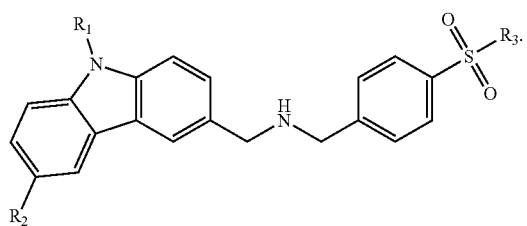

In a further aspect, the compound has a structure represented by a formula:

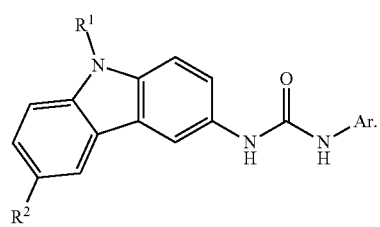

In a further aspect, the compound has a structure represented by a formula:

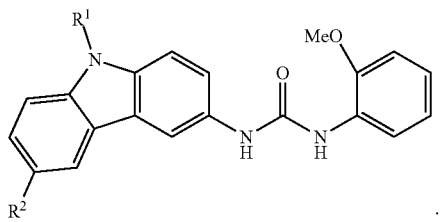

In a further aspect, the compound has a structure represented by a formula:

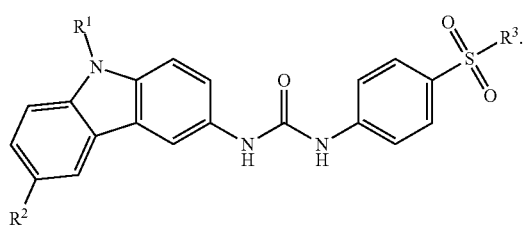

In a further aspect, the compound has a structure represented by a formula:

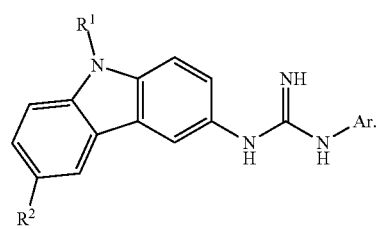

In a further aspect, the compound has a structure represented by a formula:

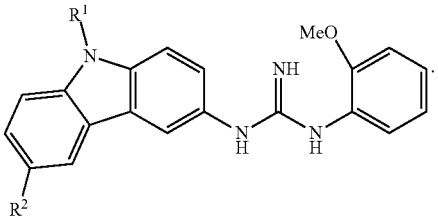

In a further aspect, the compound has a structure represented by a formula:

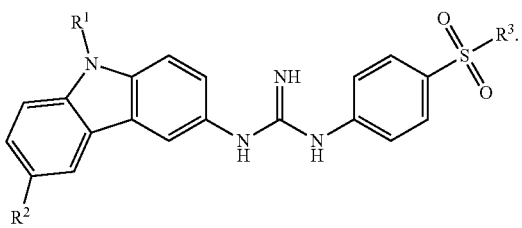

In a further aspect, the compound has a structure represented by a formula:

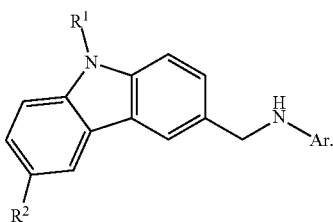

In a further aspect, the compound has a structure represented by a formula:

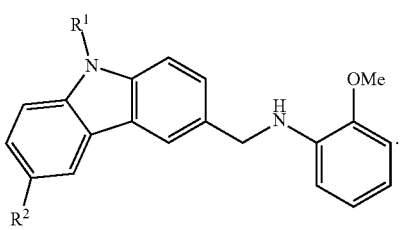

In a further aspect, the compound has a structure represented by a formula:

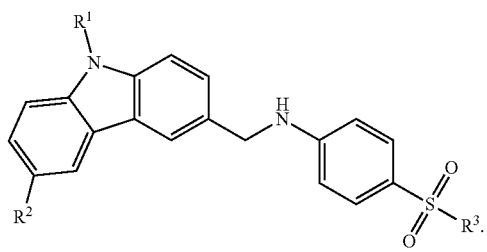

Suitable substituents are described below.

a. $R^1$ Groups

In one aspect, $R^1$ is C1-C4 alkyl. In a further aspect, $R^1$ is C2-C4 alkyl. In a further aspect, $R^1$ is C3-C4 alkyl. In a further aspect, $R^1$ is C1-C2 alkyl. In a further aspect, $R^1$ is C1-C3 alkyl. In a further aspect, $R^1$ is selected from methyl, ethyl, propyl, and butyl. In a further aspect, $R^1$ is selected from ethyl, propyl, and butyl. In a further aspect, $R^1$ is selected from methyl, propyl, and butyl. In a further aspect, $R^1$ is selected from methyl, ethyl, and butyl. In a further aspect, $R^1$ is selected from methyl, ethyl, and propyl. In a further aspect, $R^1$ is ethyl. In a further aspect, $R^1$ is n-propyl, i-propyl, or cyclopropyl. In a further aspect, $R^1$ is n-butyl, i-butyl, s-butyl, t-butyl, or cyclobutyl.

b. $R^2$ Groups

In one aspect, $R^2$ is selected from hydrogen, fluoro, chloro, and bromo. In a further aspect, $R^2$ is hydrogen. In a further aspect, $R^2$ is fluoro, chloro, or bromo. In a further aspect, $R^2$ is hydrogen, chloro, or bromo. In a further aspect, $R^2$ is hydrogen, fluoro, or bromo. In a further aspect, $R^2$ is hydrogen, fluoro, or chloro. In a further aspect, $R^2$ is fluoro. In a further aspect, $R^2$ is chloro. In a further aspect, $R^2$ is bromo.

c. $R^3$ Groups

In one aspect, $R^3$ is selected from C1-C4 alkyl, —$NH_2$, —$NHCH_3$, and —$N(CH_3)$. In a further aspect, $R^3$ is —$NH_2$, —$NHCH_3$, or —$N(CH_3)_3$. In a further aspect, $R^3$ is C1-C4 alkyl, —$NHCH_3$, or —$N(CH_3)_2$. In a further aspect, $R^3$ is C1-C4 alkyl, —$NH_2$, or —$N(CH_3)_2$. In a further aspect, $R^3$ is C1-C4 alkyl, —$NH_2$, or —$NHCH_3$. In a further aspect, $R^3$ is —$NHCH_3$ or —$N(CH_3)_2$. In a further aspect, $R^3$ is —$NH_2$ or —$N(CH_3)_2$. In a further aspect, $R^3$ is —$NH_2$ or —$NHCH_3$.

In one aspect, $R^3$ is C1-C4 alkyl. In a further aspect, $R^3$ is C2-C4 alkyl. In a further aspect, $R^3$ is C3-C4 alkyl. In a further aspect, $R^3$ is C1-C2 alkyl. In a further aspect, $R^3$ is C1-C3 alkyl. In a further aspect, $R^3$ is selected from methyl, ethyl, propyl, and butyl. In further aspect, $R^3$ is selected from ethyl, propyl, and butyl. In a further aspect, $R^3$ is selected from methyl, propyl, and butyl. In a further aspect, $R^3$ is selected from methyl, ethyl, and butyl. In a further aspect, $R^3$ is selected from methyl, ethyl, and propyl. In a further aspect, $R^3$ is ethyl. In a further aspect, $R^3$ is n-propyl, i-propyl, or cyclopropyl. In a further aspect, $R^3$ is n-butyl, i-butyl, s-butyl, t-butyl, or cyclobutyl.

a. AR Groups

In one aspect, Ar is selected from:

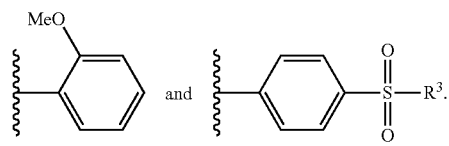

and

In a further-aspect, Ar is

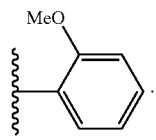 [SMILES: *c1ccccc1OC]

In a further-aspect, Ar is

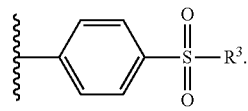

b. L Groups

In one aspect, L is selected from:

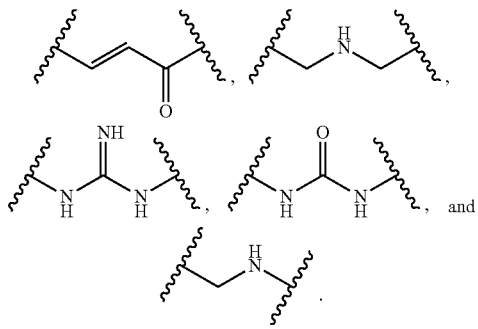

In a further aspect, L is selected from:

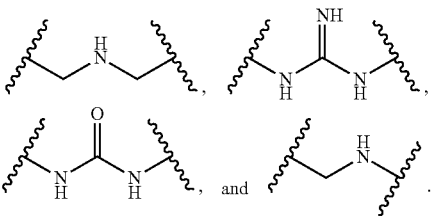

In a further aspect, L is selected from:

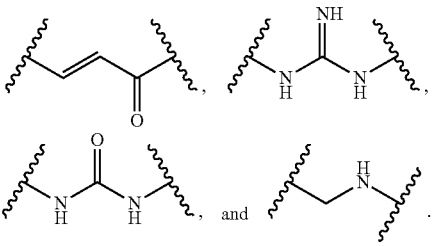

In a further aspect, L is selected from:

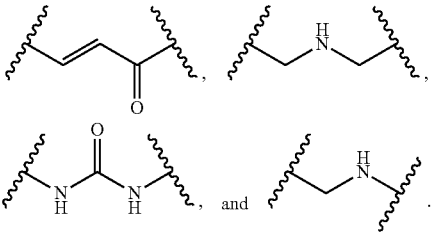

In a further aspect, L is selected from:
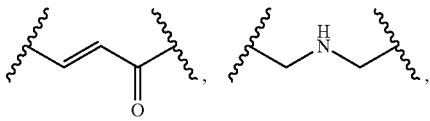
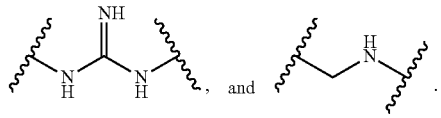
In a further aspect, L is selected from:
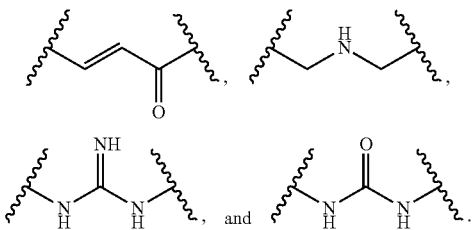 [SMILES: */C=C/C(*)=O ; *CNC* ; *NC(=N)N* ; *NC(=O)N*]
In a further aspect, L is
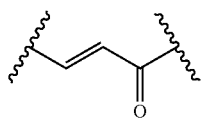
and Ar is
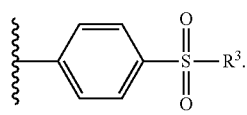
provided that $R^2$ is fluoro, chloro, or bromo, or Ar is
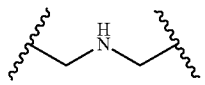 [SMILES: *CNC*]
In a further aspect, L is
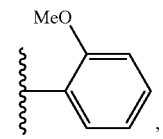 [SMILES: *c1ccccc1OC]
and Ar is
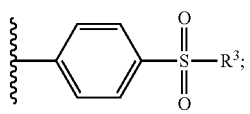
,
provided that $R^2$ is fluoro, chloro, or bromo, or A is
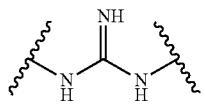 [SMILES: *NC(=N)N*]
or
In a further aspect, L is
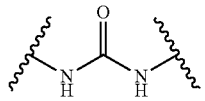
and Ar is
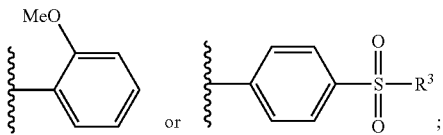
or
In a further aspect, L is
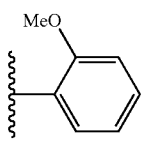
and Ar is
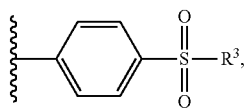
or Ar is
provided that $R^3$ is C1-C4 alkyl; or In a further aspect, L is

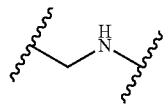 [SMILES: *CN*]

and Ar is

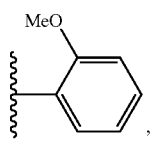 [SMILES: *c1ccccc1OC]

provided that R² is fluoro, chloro, or bromo, or Ar is

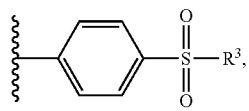

provided that R³ is C1-C4 alkyl.

In a further aspect, L is

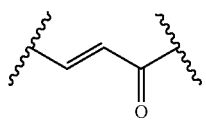 [SMILES: */C=C/C(*)=O]

and Ar is

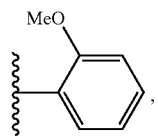

R² is fluoro, chloro, or bromo.

3. Example Compounds

In one aspect, a compound can b present as one or more of the following structures:

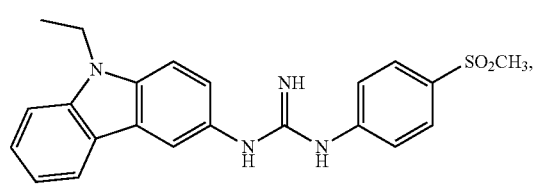

-continued

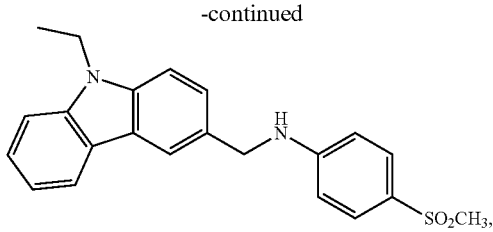

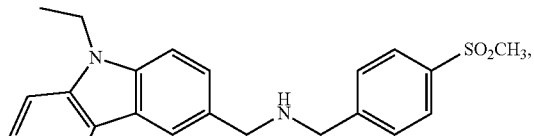

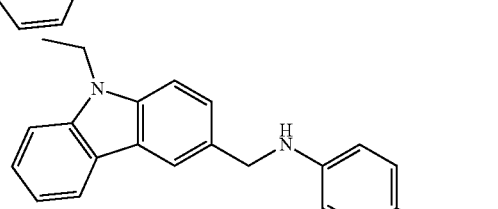

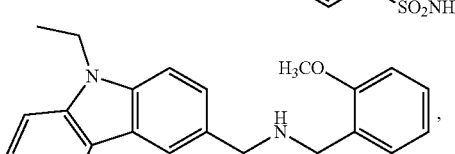

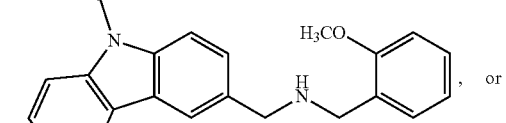

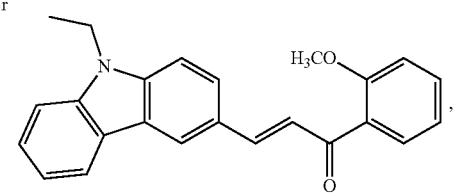

or a subgroup thereof.

In a further aspect, a compound can be present as one or more of the following structures:

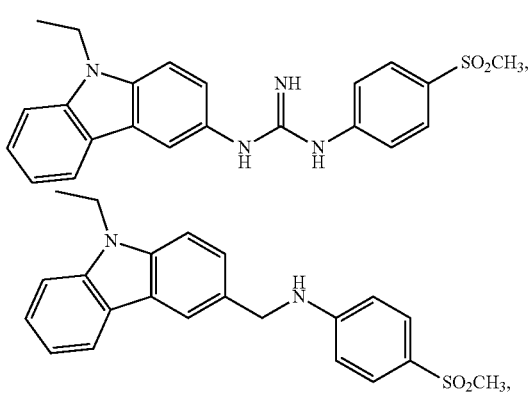

-continued

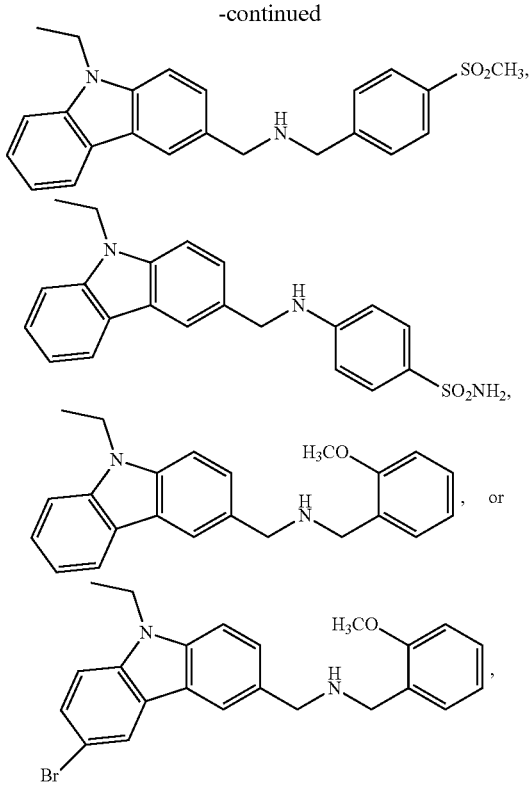

or a subgroup thereof.

In a further aspect, a compound can be present as one or more of the following structures:

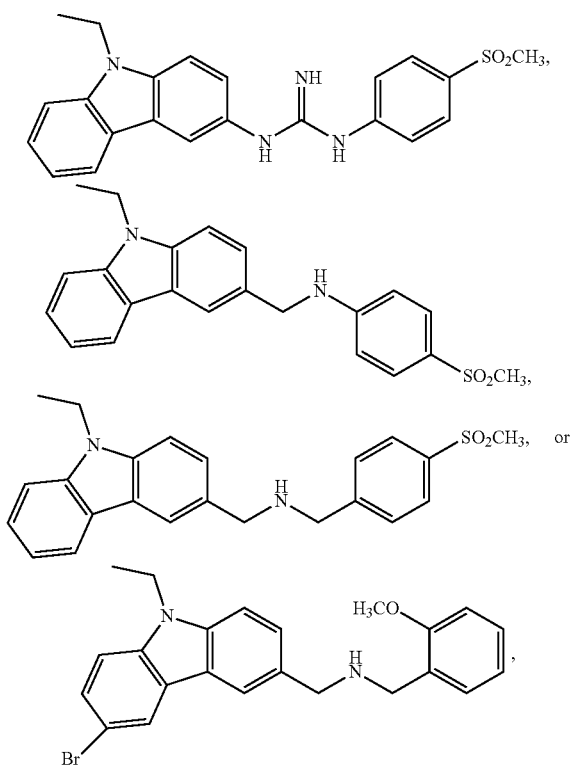

or a subgroup thereof.

In a further aspect, a compound can be present as one or more of the following structures:

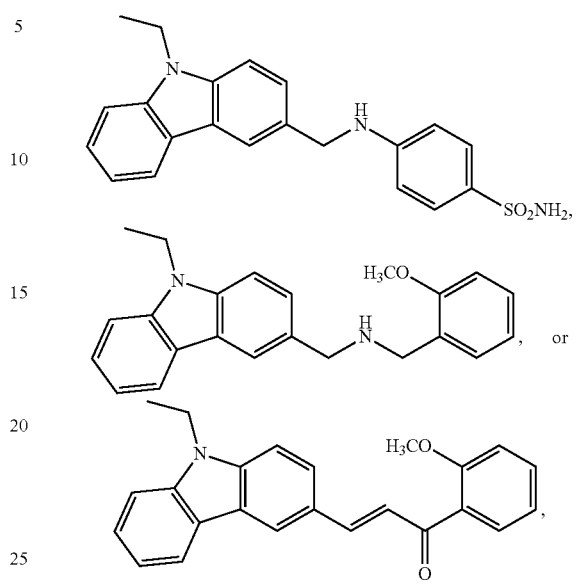

or a subgroup thereof.

In a further aspect, a compound can be present as one or more of the following structures:

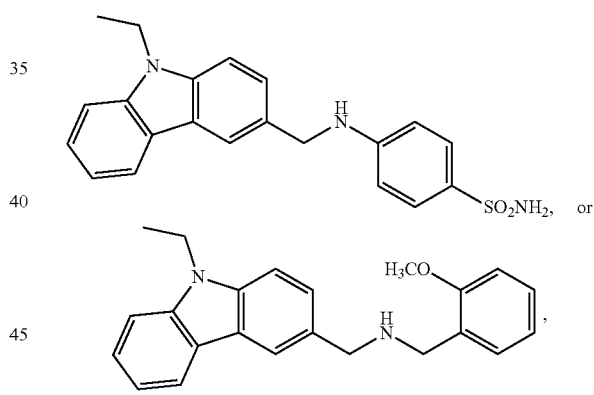

or a subgroup thereof.

It is understood that the disclosed compounds can be used in connection with the disclosed methods, compositions, kits, and uses.

4. Activity

In one aspect, a compound has an $IC_{50}$ in the anti-proliferation assay of no more than about 100 µM, about 50 µM, about 25 µM, about 10 µM, about 5 µM, about 2 µM, about 1 µM, or about 0.5 µM.

In a further aspect, a compound has an $EC_{50}$ in the induction of apoptosis assay of no more than about 100 µM, about 50 µM, about 25 µM, about 10 µM, about 5 µM, about 2 µM, about 1 µM, or about 0.5 µM.

In a further aspect, a compound has an $IC_{50}$ in the inhibition of PRMT5 mediated H4R3 methylation assay of no more than about 100 µM, about 50 µM, about 25 µM, about 10 µM, about 5 µM, about 2 µM, about 1 µM, or about 0.5 µM.

C. Methods of Making the Compounds

In one aspect, the invention relates to methods of making compounds (e.g., carbazole derivatives) useful as PRMT5 inhibitors, which can be useful in the treatment of disorders of uncontrolled cellular proliferation. In one aspect, the invention relates to the disclosed synthetic manipulations. In a further aspect, the disclosed compounds comprise the products of the synthetic methods described herein. In a further aspect, the disclosed compounds comprise a compound produced by a synthetic method described herein. In a still further aspect, the invention comprises a pharmaceutical composition comprising a therapeutically effective amount of the product of the disclosed methods and a pharmaceutically acceptable carrier. In a still further aspect, the invention comprises a method for manufacturing a medicament comprising combining at least one compound of any of disclosed compounds or at least one product of the disclosed methods with a pharmaceutically acceptable carrier or diluent.

The compounds of this invention can be prepared by employing reactions as shown in the disclosed schemes, in addition to other standard manipulations that are known in the literature, exemplified in the experimental sections or clear to one skilled in the art. The following examples are provided so that the invention might be more fully understood, are illustrative only, and should not be construed as limiting. For clarity, examples having a fewer substituent can be shown where multiple substituents are allowed under the definitions disclosed herein.

It is contemplated that each disclosed method can further comprise additional steps, manipulations, and/or components. It is also contemplated that any one or more step, manipulation, and/or component can be optionally omitted from the invention. It is understood that a disclosed method can be used to provide the disclosed compounds. It is also understood that the products of the disclosed methods can be employed in the disclosed compositions, kits, and uses.

1. Route I

In one aspect, carbazole analogs of the present invention can be prepared generically by the synthetic scheme as shown below.

SCHEME 1A

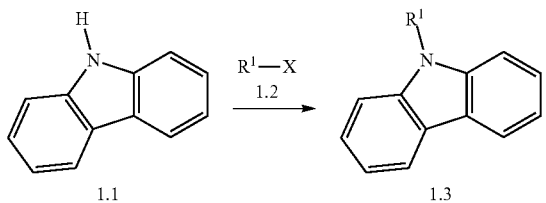

Compounds are represented in generic form, with substituents as noted in compound descriptions elsewhere herein. A more specific example is set forth below.

SCHEME 1B

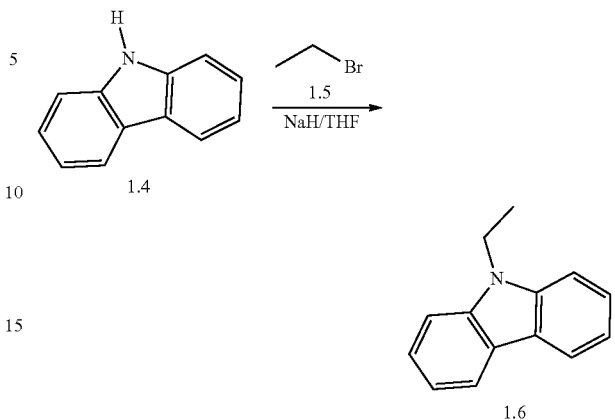

In one aspect, compounds of type 1.3; and similar compounds, can be prepared according to reaction Scheme 1B above. Thus, compounds of type 1.6 can be prepared by an alkylation reaction of an appropriate carbazole; e.g., 9H-carbazole (1.4) as shown above. Appropriate carbazoles are commercially available or prepared by methods known to one skilled in the art. The alkylation reaction is carried out in the presence of an appropriate alkyl halide, e.g., ethyl bromide (1.5) as shown above, which is commercially available or prepared by methods known to one skilled in the art, and an appropriate base, e.g., sodium hydride, in an appropriate aprotic solvent. e.g., tetrahydrofuran as shown above. As can be appreciated by one skilled in the art, the above reaction provides an example of a generalized approach wherein compounds similar in structure to the specific reactants above (compounds similar to compounds of type 1.1 and 1.2), can be substituted in the reaction to provide carbazole analogs similar to Formula 1.3.

2. Route II

In one aspect, carbazole analogs of the present invention can be prepared generically by the synthetic scheme as shown below.

SCHEME 2A

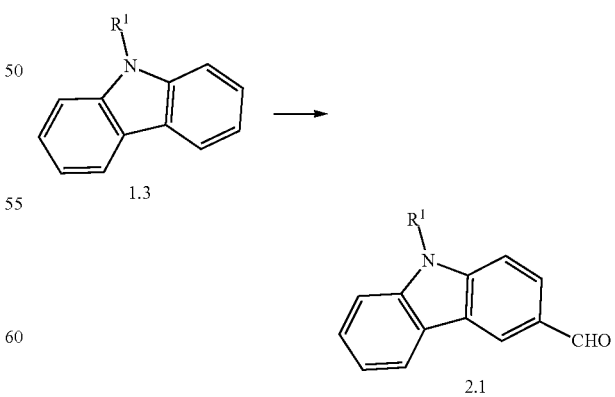

Compounds are represented in generic form, with substituents as noted in compound descriptions elsewhere herein. A more specific example is set forth below.

SCHEME 2B

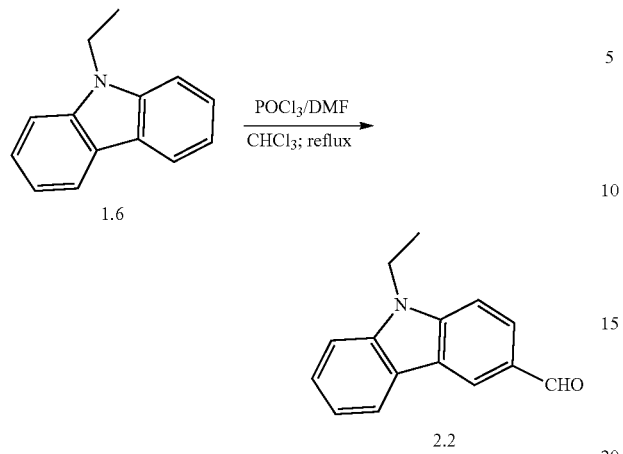

In one aspect, compounds of typo 2.1, and similar compounds, can be prepared according to reaction Scheme 2B above. Thus, compounds of type 2.2 can be prepared by a formylation reaction (i.e., Vilsmeier-Haack formylation) of an appropriate carbazole, e.g., 9-ethyl-9H-carbazole (1.6) as shown above. Appropriate carbazoles are commercially available or prepared by methods known to one skilled in the art. The alkylation reaction is carried out in the presence of an appropriate formylating reagent, e.g., phosphorous oxychloride and dimethylformamide as shown above, in an appropriate aprotic solvent, e.g., chloroform, at an appropriate temperature, e.g., refluxing conditions. As can be appreciated by one skilled in the art, the above reaction provides an example of a generalized approach wherein compounds similar in structure to the specific reactants above (compounds similar to compounds of type 13), can be substituted in the reaction to provide substituted carbazole analogs similar to Formula 2.1.

3. Route III

In one aspect, carbazole analogs of the present invention can be prepared generically by the synthetic scheme as shown below.

SCHEME 3A

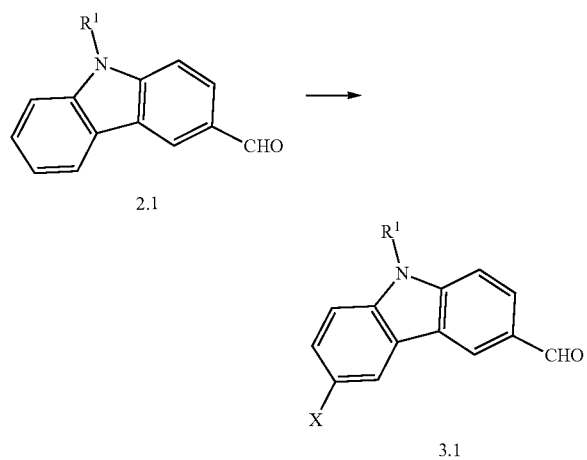

Compounds are represented in generic form, with substituents as noted in compound descriptions elsewhere herein. A more specific example is set forth below.

SCHEME 3B

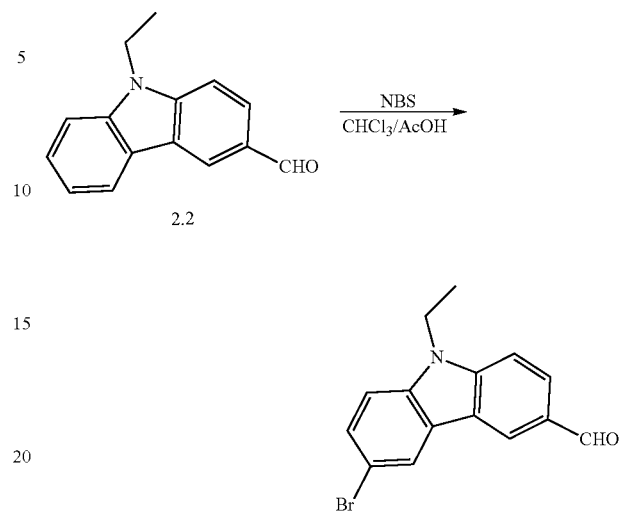

In one aspect, compounds of type 3.1, and similar compounds, can be prepared according to reaction Scheme 3B above. Thus, compounds of type 3.2 can be prepared by a halogenation (i.e., bromination) reaction of an appropriate carbazole, e.g., 9-ethyl-9H-carbazole-3-carbaldehyde (2.2) a shown above. Appropriate carbazoles are commercially available or prepared by methods known to one skilled in the art. The halogenation reaction is carried out in the presence of an appropriate halogenating reagent, e.g., N-bromosuccinimide as shown above, in an appropriate aprotic solvent, e.g., chloroform and acetic acid. As can be appreciated by one skilled in the art, the above reaction provides an example of a generalized approach wherein compounds similar in structure to the specific reactants above (compounds similar to compounds of type 2.1), can be substituted in the reaction to provide substituted carbazole analogs similar to Formula 3.1. It is appreciated that the halogenation reaction can be performed before the formylation reaction, if desired.

4. Route IV

In one aspect, carbazole analogs of the present invention can be prepared generically by the synthetic scheme as shown below.

SCHEME 4A

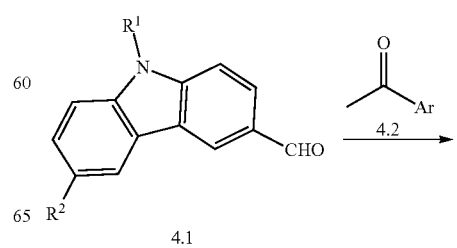

-continued

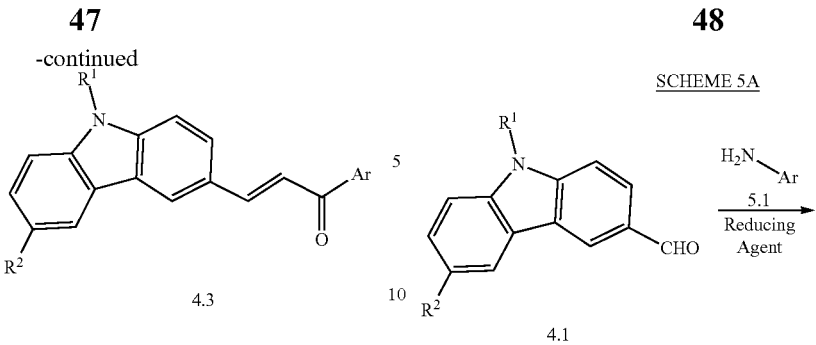

Compounds are represented in generic form, with substituents as noted in compound descriptions elsewhere herein. A more specific example is set forth below.

SCHEME 4B

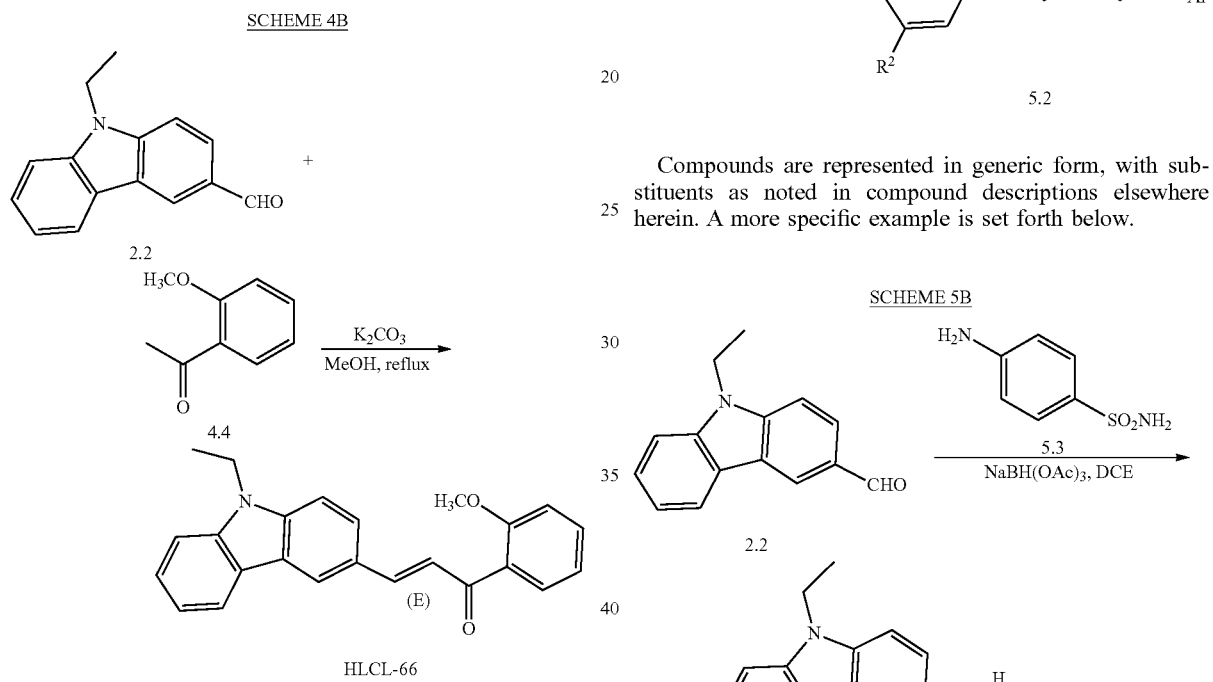

HLCL-66

In one aspect, compounds of type 4.3, and similar compounds, can be prepared according to reaction Scheme 4B above. Thus, compounds of type HLCL-66 can be prepared by an aldol condensation of an appropriate carbazole, e.g., 9-ethyl-9H-carbazole-3-carbaldehyde (2.2) as shown above. Appropriate carbazoles are commercially available or prepared by methods known to one skilled in the art. The aldol condensation is carried out in the presence of an appropriate methyl ketone e.g., 1-(2-methoxyphenyl)ethanone (4.4) as shown above, in the presence of an appropriate base, e.g., potassium carbonate as shown above, in an appropriate protic solvent, e.g., methanol, at a suitable temperature, e.g., refluxing conditions. As can be appreciated by one skilled in the art, the above reaction provides an example of a generalized approach wherein compounds similar in structure to the specific reactants above (compounds similar to compounds of type 4.1 and 4.3), can be substituted in the reaction to provide substituted carbazole analogs similar to Formula 4.3.

5. Route V

In one aspect, carbazole analogs of the present invention can be prepared generically by the synthetic scheme as shown below.

SCHEME 5A

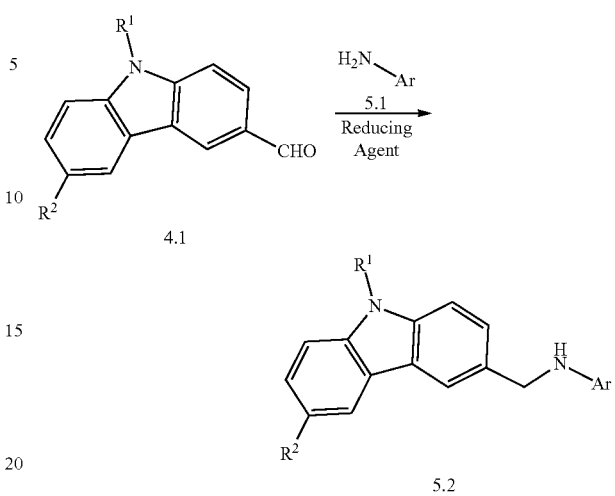

Compounds are represented in generic form, with substituents as noted in compound descriptions elsewhere herein. A more specific example is set forth below.

SCHEME 5B

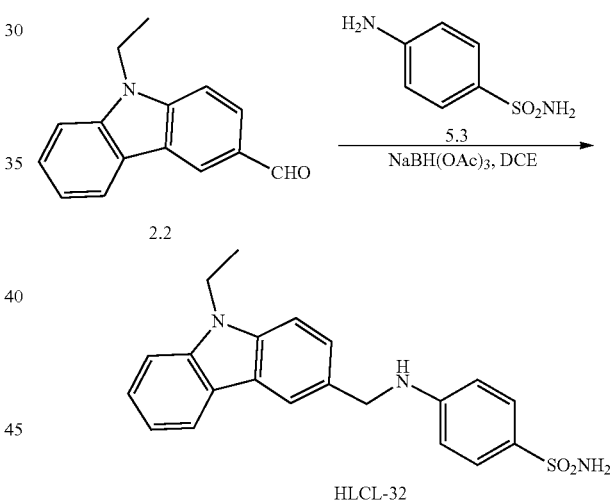

HLCL-32

In one aspect, compounds of type 5.2, and similar compounds, can be prepared according to reaction Scheme SB above. Thus, compounds of type HLCL-32 can be prepared by reductive amination of an appropriate aniline, e.g., 4-aminobenzenesulfonamide (5.3) as shown above. Appropriate anilines are commercially available or prepared by methods known to one skilled in the art. The reductive amination is carried out in the presence of an appropriate aldehyde, e.g., 9-ethyl-91-carbazole-3-carbaldehyde (2.2) as shown above, in the presence of an appropriate reducing agent, e.g., sodium triacetoxyborohydride, in an appropriate protic solvent, e.g., dichloroethane. As can be appreciated by one skilled in the art, the above reaction provides an example of a generalized approach wherein compounds similar in structure to the specific reactants above (compounds similar to compounds of type 4.1 and 5.1), can be substituted in the reaction to provide substituted carbazole analogs similar to Formula 5.2.

6. Route VI

In one aspect, carbazole analogs of the present invention can be prepared generically by the synthetic scheme as shown below.

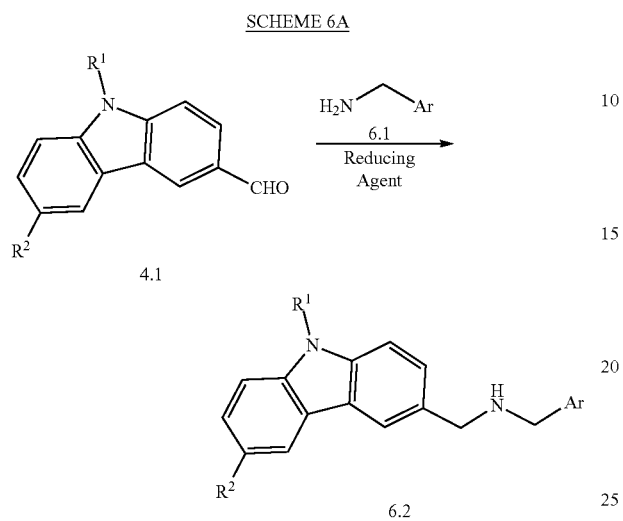

Compounds are represented in generic form, with substituents as noted in compound descriptions elsewhere herein. A more specific example is set forth below.

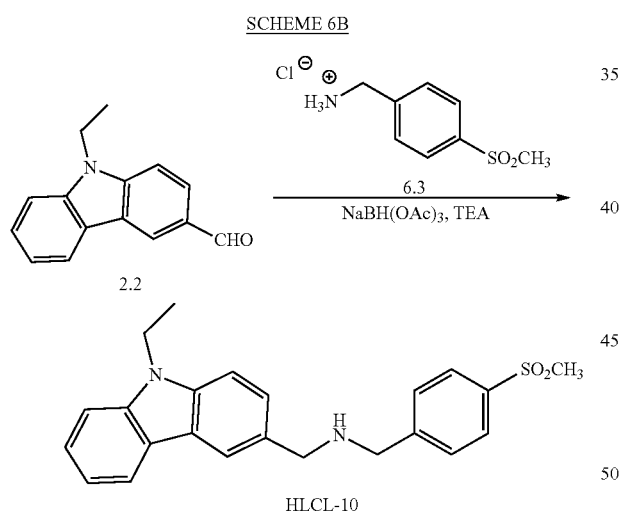

In one aspect, compounds of type 5.2, and similar compounds, can be prepared according to reaction Scheme 6B above. Thus, compounds of type HLCL-10 can be prepared by reductive amination of an appropriate benzylic amine, e.g., (4-(methylsulfonyl)phenyl)methanamine hydrochloride (6.3) as shown above. Appropriate benzylic amines are commercially available or prepared by methods known to one skilled in the art. The reductive amination is carried out in the presence of an appropriate aldehyde, e.g., 9-ethyl-9H-carbazolo-3-carbaldehyde (2.2) as shown above, in the presence of an appropriate reducing agent, e.g., sodium triacetoxyborohydride, in the presence of an appropriate base, e.g., triethylamine. As can be appreciated by one skilled in the art, the above reaction provides an example of a generalized approach wherein compounds-similar in structure to the specific reactants above (compounds similar to compounds of type 4.1 and 6.1), can be substituted in the reaction to provide substituted carbazole analogs similar to Formula 6.2.

7. Route VII

In one aspect, carbazole analogs of the present invention can be prepared generically by the synthetic scheme as shown below.

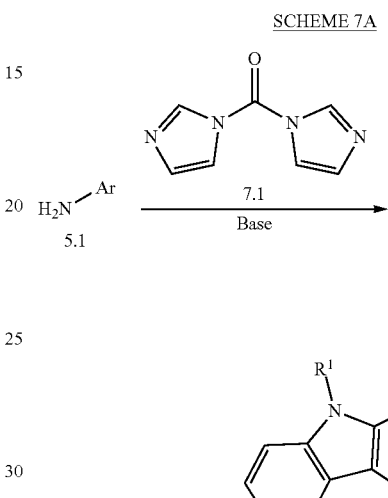

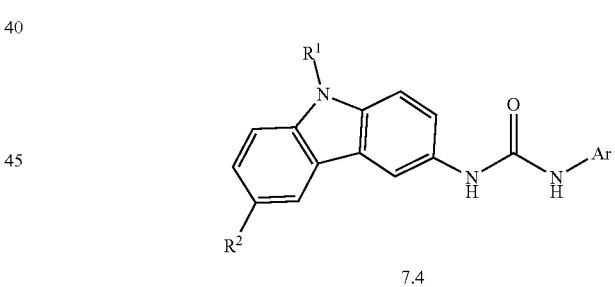

Compounds a represented in generic form, with substituents as noted in compound descriptions elsewhere herein. A more specific example is set forth below.

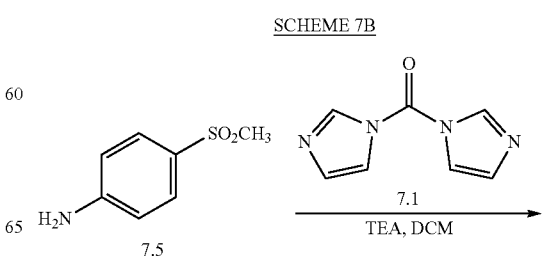

-continued

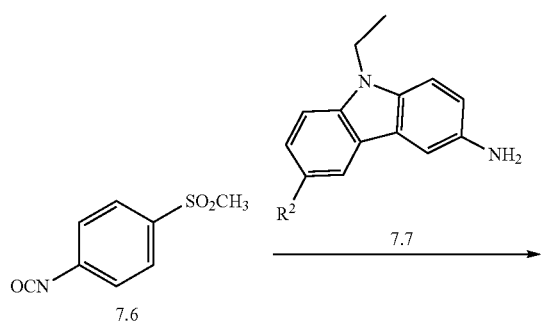

7.6

7.8

In one aspect, compounds of type 7.4, and similar compounds, can be prepared according to reaction Scheme 7B above. Thus, compounds of type 7.6 can be prepared by activation of an appropriate aniline, e.g., 4-(methylsulfonyl) aniline (7.5) as shown above. Appropriate anilines are commercially available or prepared by methods known to one skilled in the art. The activation is carried out in the presence of an appropriate activating reagent, e.g., 1,1'-carbonyldiimidazole (7.1) as shown above, in the presence of an appropriate base, e.g., triethylamine, in n appropriate solvent, e.g., dichloromethane Compounds of type 7.8 can be prepared by a coupling reaction of an appropriate isocyanate, e.g., 7.6 as shown above. The coupling is carried out in the presence of an appropriate amine, e.g., 7.7 as shown above. As can be appreciated by one skilled in the art, the above reaction provides an example of a generalized approach wherein compounds similar in structure to the specific reactants above (compounds similar to compounds of type 7.1, 7.5, 7.6, and 7.7), can be substituted in the reaction to provide substituted carbamate analogs similar to Formula 7.8.

8. Route VIII

In one aspect, carbazole analogs of the present invention can be prepared generically by the synthetic scheme as shown below.

SCHEME 8A

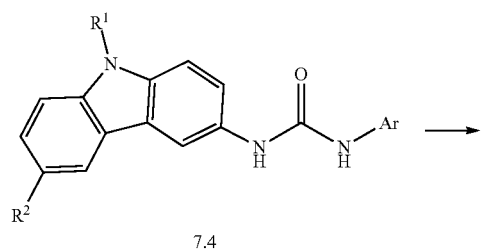

7.4

-continued

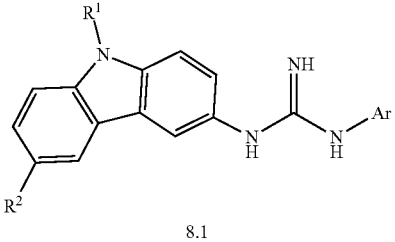

8.1

Compounds are represented in generic form, with substituents as noted in compound descriptions elsewhere herein. A more specific example is set forth below.

SCHEME 8B

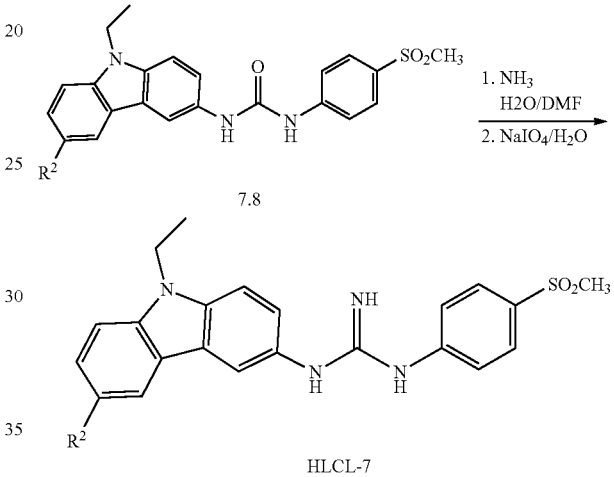

7.8

HLCL-7

In one aspect, compounds of type 8.1, and similar compounds, can be prepared according to reaction Scheme 8B above. Thus, compounds of type HLCL-7 can be prepared by conversion of an appropriate urea, e.g., 7.8 as shown above. Appropriate ureas are commercially available or prepared by methods known to one skilled in the art. The conversion is carried out in the presence of an appropriate nucleophile, e.g., aqueous ammonia, in an appropriate solvent, e.g., dimethylformamide, followed by reaction with an appropriate oxidizing agent, e.g., sodium periodate as shown above. As can be appreciated by one skilled in the art, the above reaction provides an example of a generalized approach wherein compounds similar in structure to the specific reactants above (compounds similar to compounds of type 7.8), can be substituted in the reaction to provide substituted carbazole analogs similar to Formula 78. It is understood that the disclosed methods of making can be used in connection with the disclosed compounds, kits, compositions, and methods of using.

D. Pharmaceutical Compounds

In one aspect, the invention relates to pharmaceutical compositions comprising the disclosed compounds and products of disclosed methods. That is, a pharmaceutical composition can be provided comprising an effective amount of at least one disclosed compound, at least one product of a disclosed method, or a pharmaceutically acceptable salt, solvate, hydrate, or polymorph thereof ad a pharmaceutically acceptable carrier. In one aspect, the invention relates to pharmaceutical compositions comprising a pharmaceutically acceptable carrier and an effective amount of at least one disclosed compound; or a pharmaceutically acceptable salt thereof.

In a further aspect, the effective amount is a therapeutically effective amount. In a still further aspect, the effective amount is a prophylactically effective amount. In a still further aspect, the pharmaceutical composition comprises a compound that is a product of a disclosed method of making.

In a further aspect, the pharmaceutical composition comprises disclosed compound. In a yet further aspect, the pharmaceutical composition comprises a product of a disclosed method of making.

In certain aspects, the disclosed pharmaceutical compositions comprise the disclosed compounds (including pharmaceutically acceptable salt(s) thereof) as an active ingredient, a pharmaceutically acceptable carrier, and, optionally, other therapeutic ingredients or adjuvants. The instant compositions include those suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

As used herein, the term "pharmaceutically acceptable salts" refers to salts prepared from pharmaceutically acceptable nontoxic bases or acids. When the compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (-ic and -ous), ferric, ferrous, lithium, magnesium, manganese (-ic and -ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

As used herein, the term "pharmaceutically acceptable non-toxic acids", includes inorganic acids, organic acids, and salts prepared therefrom, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, hydrochloric, maleic, phosphoric, sulfuric, and tartaric acids.

In practice, the compounds of the invention, or pharmaceutically acceptable salts thereof of this invention can be combined as the active ingredient in intimate admixture with a pharmaceutical carrier according to conventional pharmaceutical compounding techniques. The carrier can take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, and/or pharmaceutically acceptable salt(s) thereof, can also be administered by controlled release means and/or delivery devices. The compositions can be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention can include a pharmaceutically acceptable carrier and a compound or a pharmaceutically acceptable salt of the compounds of the invention. The compounds of the invention, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media can be employed. For example, water, glycols, oils, alcohols, flavoring agents, preservatives, coloring agents and the like can be used to form oral liquid preparations such as suspensions, elixirs and solutions; while carriers such as starches, sugars, microcrystalline cellulose, diluents, granulating agents, lubricants, binders, disintegrating agents, and the like can be used to form oral solid preparations such a powders, capsules and tablets. Because of their ease of administration, tablets and capsules are the preferred oral dosage units whereby solid pharmaceutical caries are employed. Optionally, tablets can be coated by standard aqueous or nonaqueous techniques A tablet containing the composition of this invention can be prepared by compression or molding, optionally with one or more accessory ingredients or adjuvants. Compressed tablets can be prepared by compressing, in a suitable machine, the active ingredient in a free-flowing form such as powder or granules, optionally mixed with a binder, lubricant, inert diluent, surface active or dispersing agent Molded tablets can be made by molding in a suitable machine, a mixture of the powdered compound moistened with an inert liquid diluent.

The pharmaceutical compositions of the present invention comprise a compound of the invention (or pharmaceutically acceptable salts thereof) as an active ingredient, a pharmaceutically acceptable carrier, and optionally one or more additional therapeutic agents or adjuvants. The instant compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions can be conveniently presented in unit dosage form and prepared by any of the methods well known in the art of pharmacy.

Pharmaceutical compositions of the present invention suitable for parenteral administration can be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, mouth washes, gargles, and the like. Further, the compositions can be in a form suitable for use in transdermal devices. These formulations can be prepared, utilizing a compound of the invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories can be conveniently formed by first admixing the composition with the softened or melted carrier(s) followed by chilling and shaping in molds.

In addition to the aforementioned carrier ingredients, the pharmaceutical formulations described above can include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient Compositions containing a compound of the invention, and/or pharmaceutically acceptable salts thereof, can also be prepared in powder or liquid concentrate form.

It is understood, however, that the specific dose level for any particular patient will depend upon a variety of factors. Such factors include the age, body weight, general health, sex, and diet of the patient Other factors include the time and route of administration, rate of excretion, drug combination, and the type and severity of the particular disease undergoing therapy.

Thus, in one aspect, the invention relates to a pharmaceutical composition comprising a pharmaceutically acceptable carrier and a compound, or pharmaceutically acceptable salt thereof, capable of: interaction with subregion 1 of PRMT5 with hydrophobic interaction with Y324, or F327, or K333, or Y334, or V363, or G365, or G367, or P370, or L371; or aromatic interactions with Y324. Or F327, or Y334; and none, one, two, or three additional interactions selected from: interaction with hydrogen bonding to E392 or E435 or E444; interaction with subregion 2 of PRMT5 through aromatic interaction or hydrogen bonding; and interaction with subregion 3 of PRMT5 through aromatic interaction and/or hydrogen bonding to E435 or E444; wherein the compound has a molecular weight of less than 1000 Daltons.

In a further aspect, the compound comprises a bicyclic or tricyclic heteroaromatic moiety capable of hydrophobic interaction with Y324, or F327, or K333, or Y334, or V363, or G365, or G367, or P370, or 1371; and/or capable of aromatic interactions with Y324, or P327, or Y334; a linker moiety between 3A and 7A in length having at least one electron-donating group capable of hydrogen bonding to E392 or E435 or E444; and a monocyclic or bicyclic aromatic moiety, substituted with electron-donating and/or electron-accepting group(s), capable of aromatic interaction and/or hydrogen bonding to W579. In a yet further aspect, the compound has at least one carbazole moiety. In a farther aspect, the carbazole moiety is capable of binding to the SAM Adenine region of PRMT5. In a further aspect, a linker moiety can be selected from:

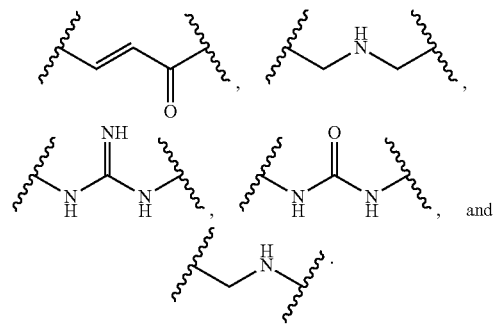

In a further aspect, the linker moiety is capable of binding to the SAM/ARG region of PRMT5.

In one aspect the invention relates to a pharmaceutical composition comprising a pharmaceutically acceptable carrier and a compound, or pharmaceutically acceptable salt thereof having a structure represented by a formula:

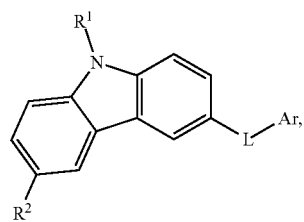

wherein R¹ is C1-C4 alkyl; wherein R² is selected from hydrogen, fluoro, chloro, and bromo; wherein R³ is selected from C1-C4 alkyl, —NH₂, —NHCH₃, and —N(CH₃)₂; wherein L is selected from:

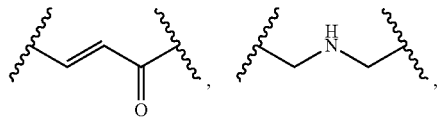

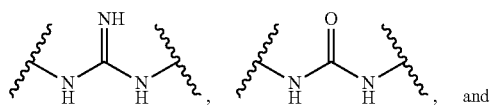, and

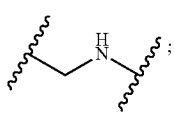

and wherein Ar is selected from:

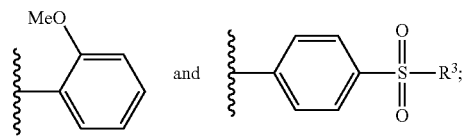

provided that, when L is

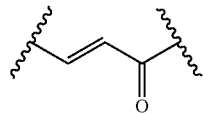

and Ar is

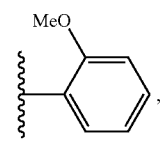

R² is fluoro, chloro, or bromo.
In a further aspect,
(a) L is

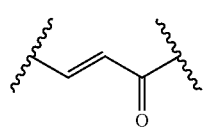 [SMILES: */C=C/C(*)=O]

and Ar is

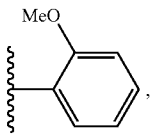

provided that R² is fluoro, chloro, or bromo, or Ar is

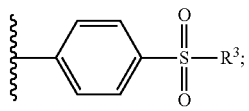

(b) L is

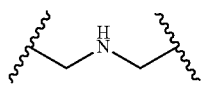

and Ar is

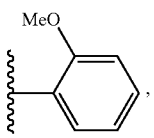 [SMILES: *c1ccccc1OC]

provided that R² is fluoro, chloro, or bromo, or Ar is

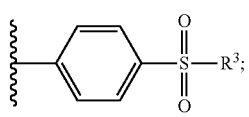

or
(c) L is

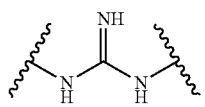

and Ar is
or

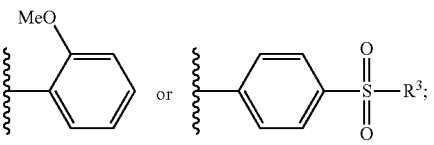

(d) L is

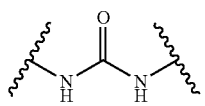 [SMILES: *NC(=O)N*]

and Ar is

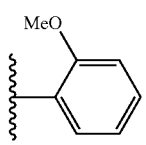 [SMILES: *c1ccccc1OC]

or Ar is

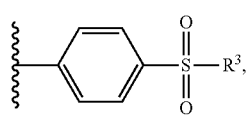

provided that $R^3$ is C1-C4 alkyl; or
(e) L is

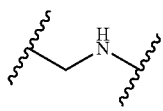

and Ar is

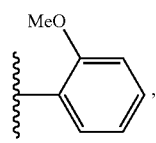 [SMILES: *c1ccccc1OC]

provided that $R^2$ is fluoro, chloro, or bromo, or Ar is

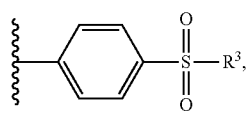

provided that $R^3$ is C1-C4 alkyl.

It is understood that the disclosed compositions can be prepared from the disclosed compounds. It is also understood that the disclosed compositions can be employed in the disclosed methods of using.

E. Methods of Using the Compounds and Compositions

Also provided is a method of use of a disclosed compound, composition, or medicament. In one aspect, the method of use is directed to the treatment of a disorder. In a further aspect, the disclosed compounds can be used as single agents or in combination with one or more other drugs in the treatment, prevention, control, amelioration or reduction of risk of the aforementioned diseases, disorders and conditions for which the compound or the other drugs have utility, where the combination of drugs together are safer or more effective than either drug alone. The other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

The pharmaceutical compositions and methods of the present invention can further comprise other therapeutically active compounds as noted herein which are usually applied in the treatment of the above mentioned pathological conditions.

1. Screening Methods

In one aspect, the invention relates to a method for screening tissue for increased risk of a disorder of uncontrolled cellular proliferation, the method comprising detecting overexpression of PRMT5 within cellular nuclei or cytoplasm of the tissue. In a further aspect, detecting comprises the steps of: obtaining tissue from a subject; extracting biological material from the nuclei or cytoplasm of cells within the tissue; measuring the levels of PRMT5 within the extract; and comparing the extract PRMT5 levels to levels of PRMT5 from a control, wherein greater levels of PRMT5 in the extract than in the control indicates an increased risk of a disorder of uncontrolled cellular proliferation.

In a further aspect, overexpression of PRMT5 is detected within cellular nuclei of the tissue, and the disorder is selected from squamous-cell carcinoma, head & neck cancer, glioma, lung cancer, and lymphoma. In a further aspect, overexpression of PRMT is detected within cytoplasm of the tissue, and the disorder is melanoma.

2. Selective PRMT5 Inhibition

In one aspect, the invention relates to a method for inhibition of PRMT5 in a mammal, the method comprising administering to the mammal a therapeutically effective amount of a compound, or pharmaceutically acceptable salt thereof, capable of interaction with subregion 1 of PRMT5 with hydrophobic interaction with Y324, or F327, or K333, or Y334, or V363, or G365, or G367, or P370, or L371; or aromatic interactions with Y324, or F327, or Y334; and none, one, two, or three additional interactions selected from: interaction with hydrogen bonding to E392 or E435 or E444; interaction with subregion 2 of PRMT5 through aromatic interaction or hydrogen bonding; and interaction with subregion 3 of PRMT5 through aromatic interaction and/or hydrogen bonding to E435 or E444; wherein the compound has a molecular weight of less than 1000 Daltons.

In a further aspect, the compound comprises: a bicyclic or tricyclic heteroaromatic moiety capable of hydrophobic interaction with Y324, or F327, or K333, or Y334, or V363, or C365, or G367, or P370, or L371; and/or capable of aromatic interactions with Y324, or F327, or Y334; a linker moiety between 3A and 7A in length having at least one electron-donating group capable of hydrogen bonding to E392 or E435 or F444; and a monocyclic or bicyclic aromatic moiety, substituted with electron-donating and/or electron-accepting group(s), capable of aromatic interaction and/or hydrogen bonding to W579. In a further aspect, the compound has at least one carbazole moiety.

In a further aspect, the method comprises administering to the mammal a therapeutically effective amount of a compound, or pharmaceutically acceptable salt thereof, having a structure represented by a formula:

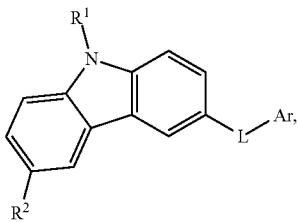

wherein R¹ is C1-C4 alkyl; wherein R² is selected from hydrogen, fluoro, chloro, and bromo; wherein R³ is selected from C1-C4 alkyl, —NH₂, —NHCH₃, and —N(CH₃)₂; wherein L is selected from:

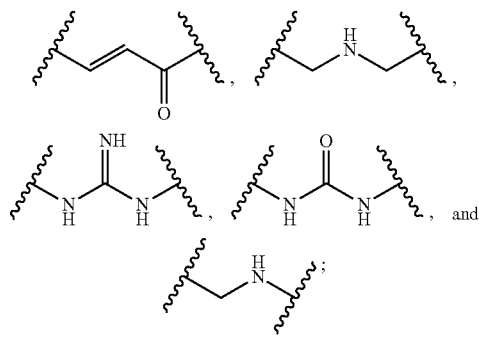

and wherein Ar is selected from:

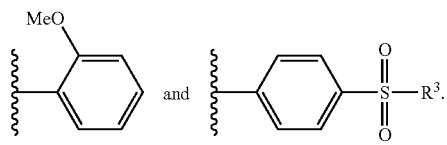

In a further aspect, L is

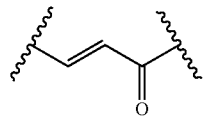

and Ar is

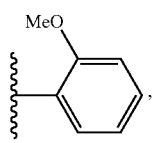

R² is fluoro, chloro, or bromo.

In a further aspect, (a) L is

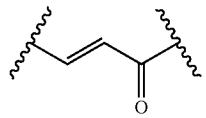 [SMILES: */C=C/C(*)=O]

and Ar is

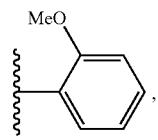

provided that R² is fluoro, chloro, or bromo, or Ar is

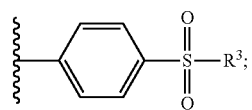

or (b) L is

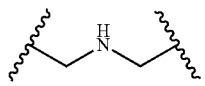

and Ar is

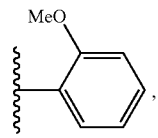

provided that R² is fluoro, chloro, or bromo, or Ar is

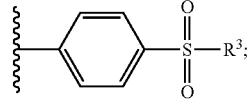

or (c) L is

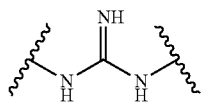

and Ar is

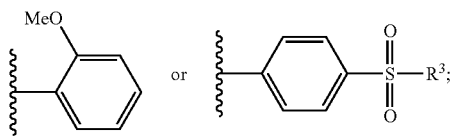

or
(d) L is

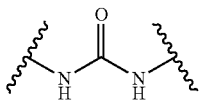

and Ar is

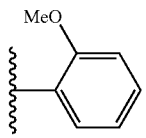 [SMILES: *c1ccccc1OC]

or Ar is

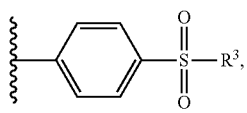

provided that $R^3$ is C1-C4 alkyl; or
(e) L is

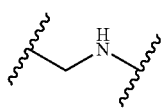 [SMILES: *CN*]

and Ar is

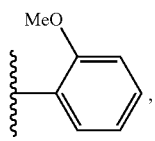

provided that $R^2$ is fluoro, chloro, or bromo, or Ar is

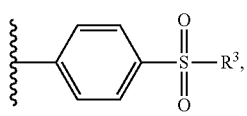

provided that $R^3$ is C1-C4 alkyl.

In a further aspect, inhibition is selective inhibition. In a further aspect, the IC50 for the compound against PRMT5 is at least 2-fold lower than the IC50 for the compound against a type I arginine N-methyl transferase (PRMT). In a further aspect, the IC50 is at least 3-fold lower. In a further aspect, the IC50 is at least 5-fold lower. In a further aspect, the IC50 for the compound against PRMT5 is at least 2-fold lower than the IC50 for the compound against a type III arginine N-methyl transferase (PRMT). In a further aspect, the IC50 is at least 3-fold lower. In a further aspect, the IC50 is at least 5-fold lower.

3. Treatment Methods

The compounds disclosed herein are useful for treating, preventing, ameliorating, controlling or reducing the risk of a variety of disorders associated with PRMT5 activity.

a. Treating Disorders of Uncontrolled Cellular Proliferation

In one aspect, the invention relates to a method for the treatment of disorders of uncontrolled cellular proliferation. In a further aspect, the compound administered is a product of a disclosed method of making. In a still further aspect, an effective amount is a therapeutically effective amount. In a yet further aspect, an effective amount is a prophylactically effective amount.

In one aspect, the mammal is a human. In a further aspect, the mammal has been diagnosed with a need for treatment of the disorder prior to the administering step. In a further aspect, the method further comprises the step of identifying a mammal in need of treatment of the disorder.

Thus, in one aspect, the invention relates to a method for treating a disorder of uncontrolled cellular proliferation in a mammal, the method comprising administering to the mammal a therapeutically effective amount of a compound, or pharmaceutically acceptable salt thereof, having a structure represented by a formula:

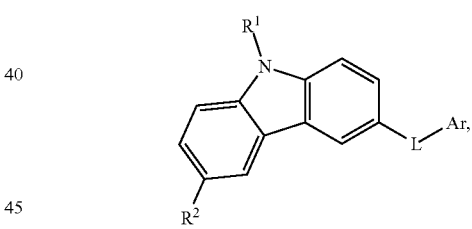

wherein $R^1$ is C1-C4 alkyl; wherein $R^2$ is selected from hydrogen, fluoro, chloro, and bromo; wherein $R^3$ is selected from C1-C4 alkyl, $-NH_2$, $-NHCH_3$, and $-N(CH_3)_2$; wherein L is selected from:

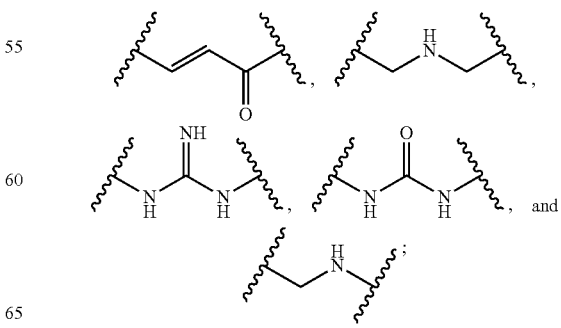

and wherein Ar is selected from:
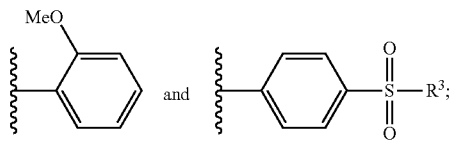
provided that, when L is
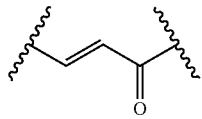 [SMILES: */C=C/C(*)=O]
and Ar is
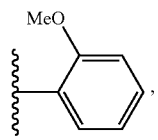 [SMILES: *c1ccccc1OC]
$R^2$ is fluoro, chloro, or bromo.
In a further aspect,
(a) L is
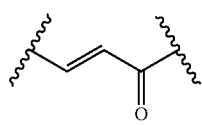 [SMILES: */C=C/C(*)=O]
and Ar is
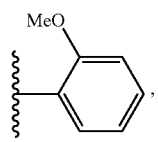
provided that $R^2$ is fluoro, chloro, or bromo, or Ar is
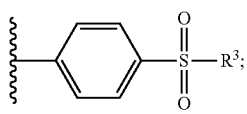
or
(b) L is
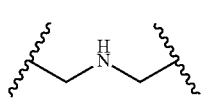
and Ar is
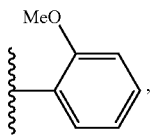 [SMILES: *c1ccccc1OC]
provided that $R^2$ is fluoro, chloro, or bromo, or Ar is
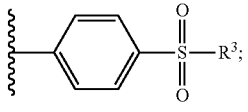
or
(c) L is
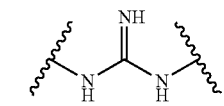
and Ar is
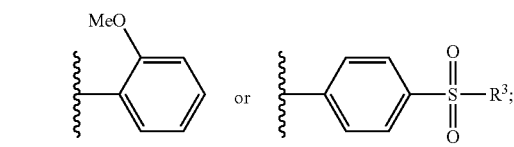
or
(d) L is
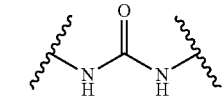
and Ar is
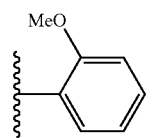 [SMILES: *c1ccccc1OC]
or Ar is
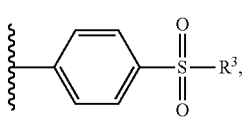
provided that $R^3$ is C1-C4 alkyl; or (e) L is

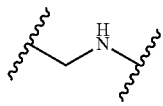 [SMILES: *CN*]

and Ar is

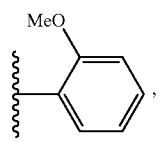

provided that $R^2$ is fluoro, chloro, or bromo, or Ar is

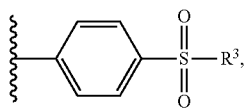

provided that $R^3$ is C1-C4 alkyl.

In one aspect, the invention relates to a method for treating a disorder of uncontrolled cellular proliferation in a mammal, the method comprising administering to the mammal a therapeutically effective amount of a compound, or pharmaceutically acceptable salt thereof, capable of interaction with subregion 1 of PRMT5 with hydrophobic interaction with Y324, or F327, or K333, or Y334, or V363, or G365, or G367, or P370, or L371; or aromatic interactions with Y324, or F327, or Y334; and none, one, two, or three additional interactions selected from: interaction with hydrogen bonding to E392 or E435 or E444; interaction with subregion 2 of PRMT5, through aromatic interaction or hydrogen bonding; and interaction with subregion 3 of PRMT5 through aromatic interaction and/or hydrogen bonding to E435 or E444; wherein the compound has a molecular weight of less than 1000 Daltons.

In a further aspect, the compound comprises a bicyclic or tricyclic heteroaromatic moiety capable of hydrophobic interactiotr with Y324, or F327, or K333, or Y334, or V363, or G365, or G367, or P370, or L371; and/or capable of aromatic interactions with Y324, or F327, or Y334; a linker moiety between 3A and 7A in length having at least one electron-donating group capable of hydrogen bonding to E392 or E435 or E444; and a monocyclic or bicyclic aromatic moiety, substituted with electron-donating and/or electron-acepting group(s), capable 9f aromatic interaction and/or hydrogen bonding to W579. In a further aspect, the compound has at least one carbazole moiety.

In one aspect, the invention relates to a method for treatinga disorder of uncontrolled cellular proliferation, the methiod comprising the steps of identifying tissue having cells with increased expression of PRMT5 within the cellular nuclei or cytoplasm; and administering therapy to the tissue. In a further aspect, the method comprise administering therapy to tissue identified as having cells with increased expression of PRMT5 within the cellular nuclei or cytoplasm.

In a further aspect, the therapy is aggressive. In a further aspect, the therapy is selected from chemotherapy, radiation therapy, biologic therapy, surgery, and administration of targeted small molecule agents. In a further aspect, therapy comprises administration of at least one PRMT5 inhibitor. In a further aspect, therapy comprises administration of at least one BTK inhibitor.

In a further aspect, increased expression of PRMT5 is within cellular nuclei of the tissue, and the disorder is selected from squamous-cell carcinoma, head & neck cancer, glioma, lung cancer, and lymphoma. In a further aspect, increased expression of PRMT5 is within cytoplasm of the tissue, and the disorder is melanoma.

In certain aspects, the disorder of uncontrolled cellular proliferation is cancer. In a further aspect, the cancer is selected from prostate cancer, lung cancer, colon cancer, pancreatic cancer, head & neck cancer, skin cancer, brain cancer, breast cancer, testicular cancer, and ovarian cancer. In a further aspect, the cancer is selected from melanoma, glioma, lymphoma, and leukemia.

b. Methods for Treating Benign Hematologic Diseases

In one aspect, the invention relates to a method for treating a benign hematologic disease in a mammal, the method comprising administering to the mammal a therapeutically effective amount of a small-molecule PRMT5 inhibitor. In a further aspect, the benign hematologic disease is selected from post-transplant lymphoproliferative disease, castlemans (unicentric/multicentric), X-linked lymphoproliferative disease, chronic active EBV infection, infectious mononucleosis, HHV8 and EBV-driven B cell lymphoproliferative diseases, and lymphadenitis (kikuchis). In a further aspect, the benign hematologic disease is a myeloid disorder selected from myeloproliferativo disorders (Chronic myclomonocytic leukomia/CMML, polycythemia vera, essential thrombocytosis), and histocytic disorders (histiocytosis X, langerhans cell histiocytosis, erdheim chester disease, rosai dorfnman). In a further aspect, the benign hematologic disease is sickle cell disease. In a further aspect; the benign hematologic disease is beta thalassemia.

In a further aspect, the PRMT5 inhibitor is a compound, or pharmaceutically acceptable salt thereof, capable of: interaction with subregion 1 of PRMT5 with hydrophobic interaction with Y324, or F327, or K333, or Y334, or V363, or G365, or G367, or P370, or L371; or aromatic interactions with Y324, or F327, or Y334; and none, one, two, or three additional interactions selected from: interaction with hydrogen bonding to E392 or E435 or E444; interaction with subregion 2 of PRMT5 through aromatic interaction or hydrogen bonding; and interaction with subregion 3 of PRMT5 through aromatic interaction and/or hydrogen bonding to E435 or E444; wherein the compound has a molecular weight of less than 1000. Daltons.

In a further aspect, the PRMT5 inhibitor comprises: a bicyclic or tricyclic heteroaromatic moiety capable of hydrophobic interaction with Y324, or F327, or K333, or Y334, or V363, or G365, or G367, or P370, or L371; and/or capable of aromatic interactions with Y324, or F327, or Y334; a linker moiety between 3A and 7A in length having at least one electron-donating group capable of hydrogen bonding to E392 or E435 or E444; and a monocyclic or bicyclic aromatic moiety, substituted with electron-donating and/or electron-accepting group(s), capable of aromatic interaction and/or hydrogen bonding to W579. In a further aspect, the PRMT5 inhibitor comprises at least one carbazole moiety.

In a further aspect, the PRMT5 inhibitor comprises a compound, or pharmaceutically acceptable salt thereof, having a structure represented by a formula:

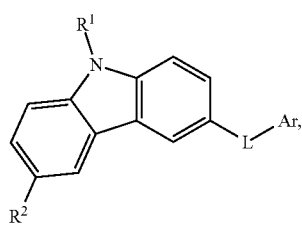

wherein R¹ is C1-C4 alkyl; wherein R² is selected from hydrogen, fluoro, chloro, and bromo; wherein R³ is selected from C1-C4 alkyl, —NH₂, —NHCH₃, and —N(CH₃)₂; wherein L is selected from:

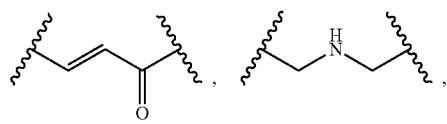

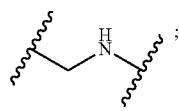

and wherein Ar is selected from:

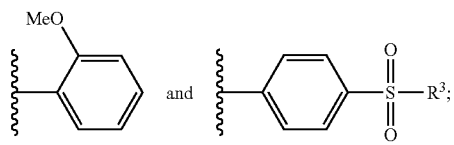

In a further aspect, L is

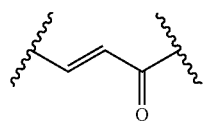 [SMILES: */C=C/C(*)=O]

and Ar is

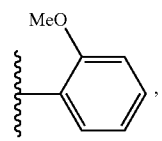

R² is fluoro, chloro, or bromo.

In a further aspect, (a) L is

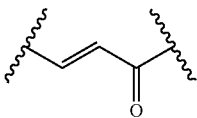 [SMILES: */C=C/C(*)=O]

and Ar is

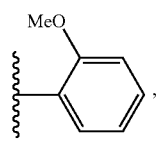

provided that R² is fluoro, chloro, or bromo, or Ar is

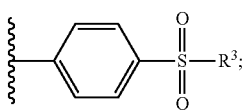

(b) L is

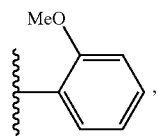

and Ar is

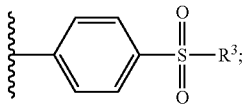

provided that R² is fluoro, chloro, or bromo, or Ar is

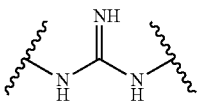 [SMILES: *NC(=N)N*]

or (c) L is and Ar is

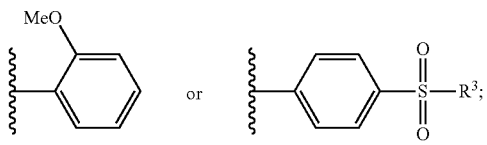

or
(d) L is

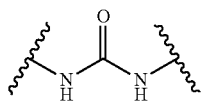

and Ar is

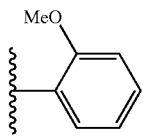 [SMILES: *c1ccccc1OC]

or Ar is

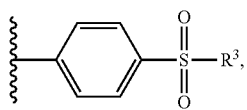

provided that R³ is C1-C4 alkyl; or
(e) L is

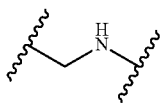 [SMILES: *CN*]

and Ar is

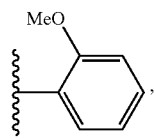

provided that R² is fluoro, chloro, or bromo, or Ar is

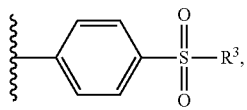

provided that R³ is C1-C4 alkyl.

1. Cotherapeutic Methods

Agents that can be co-administered with PRMT5 inhibitors include the following: chemotherapeutic agents (including but not limited to antimetabolites, alkylators, anthracyclines etc.); monoclonal/polyclonal antibodies (and associated drug conjugates), small molecule inhibitors targeting epigenetic processes (including but not limited to; hypomethylating agents, histone deacetylase inhibitors, histone methyltransferase inhibitors that target EZH2, bromodomain inhibitors etc.), kinases (BTK, BCR/ABL), proteasome, autophagosome (chloroquine/rapamycin), pro-survival proteins (BCL2 family), BRAF, MEK, JAK/STAT inhibitors, EGFR, PDGF, KIT, immune modulating agents (cytokines, inhibitors of negative regulating receptors like anti KIR), nucleic acid therapies (including but not limited to non-coding RNAs, micro RNA, anti-sense, shRNA, gene therapy etc.). Other methods of treatment that can be combined with PRMT5 inhibition include radiation and surgery.

Thus, in one aspect, the invention relates to a pharmaceutical composition comprising one or more disclosed compound and one or more additional agents. In a further aspect, the invention relates to a method for treating a disorder related to PRMT5 activity, the methods comprising administration of a therapeutically effective amount of one or more disclosed compound and an effective amount of one or more additional agents.

It is understood that the disclosed cotherapeutic methods can be used in connection with the disclosed compounds, compositions, kits, and uses.

2. Manufacture of a Medicament

In one aspect, the invention relates to a method for preparing a medicament comprising one or more disclosed compounds, or a pharmaceutically acceptable salt thereof or a product of a disclosed method of making. In a further aspect, the one or more compounds is a product of a disclosed method of making.

In a further aspect, the invention relates to a medicament comprising one or more disclosed compounds; or a pharmaceutically acceptable salt thereof. In a further aspect, the one or more compounds is a product of a disclosed method of making.

It is understood that the disclosed methods can be performed with the disclosed compounds, products, and pharmaceutical compositions. It is also understood that the disclosed methods can be employed in connection with the disclosed methods of using.

3. Use of Compounds

Also provided are the uses of the disclosed compounds and products. In one aspect, the invention relates to use of at least one disclosed compound; or a pharmaceutically acceptable salt thereof. In a further aspect, the compound used is a product of a disclosed method of making.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, for use as a medicament.

In a further aspect, the use relates to a process for preparing a pharmaceutical composition comprising a therapeutically effective amount of a disclosed compound or a product of a disclosed method of making, or a pharmaceutically acceptable salt, solvate, or polymorph thereof, wherein a pharmaceutically acceptable carrier is intimately mixed with a therapeutically effective amount of the compound or the product of a disclosed method of making.

It is understood that the disclosed uses can be employed in connection with the disclosed compounds, products of disclosed methods of making, methods, compositions, and kits.

F. Kits

In one aspect, the invention relates to kits comprising at least one disclosed compound; or a pharmaceutically acceptable salt thereof, and one or more of:
(a) at least one agent known to increase PRMT5 activity;
(b) at least one agent known to decrease PRMT5 activity,
(c) at least one agent known to treat a disorder of uncontrolled cellular proliferation;
(d) at least one agent known to increase risk for a disorder of uncontrolled cellular proliferation;
(e) at least one agent known to treat a benign hematologic disease;
(f) at least one agent known to increase risk for a benign hematologic disease;
(g) instructions for treating a disorder associated with PRMT5 activity;
(h) instructions for treating a disorder of uncontrolled cellular proliferation; or
(i) instructions for treating a benign hematologic disease; or
(j) instructions for administering the compound in connection with treatment of cancer.

In a further aspect, the kit comprises a disclosed compound or a product of a disclosed method of making. In a further aspect, the at least one compound and the at least one agent are co-formulated. In a still further aspect the at least one compound and the at least one agent are co-packaged.

The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

It is understood that the disclosed kits can be prepared from the disclosed compounds, products, and pharmaceutical compositions. It is also understood that the disclosed kits can be employed in connection with the disclosed methods of using.

G. Examples

The following examples are put forth so a to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are part by weight, temperature is in ° C. or is at ambient temperature, and pressure is at or near atmospheric.

Several methods for preparing the compounds of this invention are illustrated in the following Examples. Starting materials and the requisite intermediates are in some cases commercially available, or can be prepared according to literature procedures as illustrated herein. The Examples are provided herein to illustrate the invention, and should not be construed as limiting the invention in any way. The Examples are typically depicted in free base form, according to the IUPAC naming convention. Examples are provided herein to illustrate the invention, and should not be construed as limiting the invention in any way.

1. Experimental Methods a. Cell Lines and Primary Blasts

MV4-11 and THP-1 cells (ATCC, Manassas, Va.) were maintained in RPMI 1640 medium supplemented with 10% calf serum and Kasumi-1 cells were cultured in 20% RPMI. Blasts from AML patients were maintained in RPMI 1640 medium supplemented with 20% fetal bovine serum, 1% HEPES buffer, and 1× StemSpan cytokine cocktail CC100 (StemCell Technologies, Vancouver, BC, Canada) containing IL-3, IL-6, and SCF. All cells were incubated at 37° C. with 5% $CO_2$. Primary blasts from AML patients were obtained from apheresis blood samples collected from patients treated at the Ohio State University (OSU) and stored in the OSU Leukemia Tissue Bank. Informed consent to use cells for investigational studies was obtained from each patient under an OSU Institutional Review Board-approved protocol, according to the Declaration of Helsinki.

b. Plasmids and Transient Transpections

PRMT5 cDNA and shRNA were cloned, respectively, into pCDH1-MSCV-green-puro-cDNA and pGreenPuro shRNA cloning lentivector (SBI system biosciences). On-target plus siRNA-SMART pool specific for PRMT5, SP1 and off-target scrambled control were obtained from Dharmacon (Lafayette, Colo.). A locked nucleic acid (LNA)-antimiR-29b inhibitor (hsa-miR-29b mercury LNA microRNA Power inhibitor, Exiqon, Woburn, Mass.) was used to knockdown miR-29b and synthetic Pre-miR™ miRNA Precursor (Ambion) was used to overexpress miR-29b. MicroRNA tmnsfections were carried out by siPORT NeoFX transfection reagent (Life technologies) including proper scrambled negative control for each treatment. Gene knockdown and overexpression was carried out either by electroporation using Nucleofector Kit (Amaxa, Walkersville, Md.) or infection by lentivirus (SBI system biosciences reagents and methods). Commercially available PKC412 (Sigma-Aldrich, St Louis, Mo., # M1323) and FLT3 inhibitor (CALBIOCHEM #343020) was purchased while HLCL-61 (C12) compound was prepared/synthesized by Hongshan Lai, College of Pharmacy, Ohio State University.

c. Western Immunoblot and Immuprecipitation (IP) Analyses

Whole cell lysates were prepared by suspending cell pellets in RIPA buffer for 20 min (1% NP-40, 0.1% SDS, 150 mM NaCl, 50 mM Tris, pH 8.0), then supplemented with IX complete EDTA free protease inhibitor (Roche) and IX PhosStop (Roche). Lysates were separated by 4-20% SDS-PAGE and transferred to PVDF membrane (GE Healthcare, Piscataway, N.J.). Membranes were blocked with 5% milk or BSA in 1×TBS with 0.1% Tween 20 for 1 hour at room temperature with shaking. Primary antibodies for ACTIN, GAPDH and FLT3 (Santa Cruz Biotechnology, Santa Cruz Calif.), P65 (Cell signaling), PRMT5 and SP1 (Millipore), H4R3, H3R8, H3 and H4 (Abeam), were diluted 1:1000 or 1:2000 in 5% milk or BSA and incubated for 1-2 hr at room temperature. Membranes were washed using Ix TBS-T, incubated with HRP-conjugated secondary antibodies diluted in 1×TBS-T with 5% milk or BSA, washed, and developed using SuperSignal West Dura Chemiluminescent Substrate (Thermo Scientific). Whole cell lysate (at least 500 µg) was used to pull down protein complexes using Catch and Release v2.0 Reversible Immunoprecipitation System (Millipore) and ~4 µg antibodies against PRMT5, SP1, p65 and 1 µg normal IgG as negative control (Millipore). Denatured pull down samples were subjected to regular western blotting with exception of using TrueBlot IP secondary antibody (Rockland) for immunodetection.

d. Colony Formation Assay and Cell Viability Analysis

Clonogenic assays were set up by plating $1\times10^3$ cell/mL in semi-solid methylcellulose medium (MethoCult, Stem Cell Technologies). Colonies were counted after 10-14 days using an inverted microscope. Growth inhibition assays were measured using a colorimetric MTS assay: $5\times10^4$ cells were plated in 100 L final volume in a 96-well plate in the presence of different concentrations of C12 for 24, 48 and 72 hours at 37° C. Afterwards, 20 µL of the CellTiter 96W AQueous One Solution Reagent, which contains tetrazolium compound [3-(4,5-dimethyl-2-yl)-5(3-carboxymethoxyphenyl)-2-(4-sulfophenyl)-2H-tetrazolium, inner salt; MTS] and an electron coupling reagent (phenazine ethosulfate; PES) (Promega, Madison Wis.), was added to each well. Within 1-4 hours of incubation at 37° C., the optical density at 490 and 690 nm was measured. Cell viability was calculated with respect to the control samples and reference background wavelength at 690 nm. At least three independent experiments were performed. Growth curve assays were done by counting live cells using Trypan blue exclusion and inverted microscope for >12 days after plating the cells in $1\times10^5$ concentrations.

e. Flow Cytometry and Fluorescence Activated Cell Sorting (FACS)

Cells ($1\times10^6$) were washed and passed through a 40 µM filter (BD), then re-suspended in 200 µL binding buffer with or without 5 µL AnnexinV (for apoptosis detection) or CD11b (for maturation detection) antibody (BD Biosciences, Billeria, Mass.). After 15 min. of incubation cells were washed with PBS, re-suspended in 500 µL flow buffer and analyzed on a FACSCalibur cytometr (BD Biosciences). For apoptosis detection, 5 µL propidium iodide (P1) (BD Biosciences) was added to cell before running flow cytometry. Sorting for OFP-positive cells was carried out on BD FACS Aria instrument after filtering and washing cells 2× with ice cold PBS supplemented with 2% calf bovine serum and re-suspending in FACS buffer.

f. Chromatin Immunoprecipitation (CHIP)

Cross-linked chromatin was prepared by incubating cells in 1% formaldehyde for 10 min at room temperature and quenching with ice cold IM Glycine. Cells were sonicated in 1% SDS lysis buffer and sheared chromatin was used to pull down protein/DNA complexes using antibodies against SP1, p65 (ChIP-grade Millipore), H4R3me2, H3R8me2 (Abcam) and RNA Pol II as positive control and normal IgG (Millipore) as negative control. Reverse cross-linked DNA was purified using QIAquick PCR Purification kit (Qiagen) and quantitative real-time PCR was carried out using SYBER green incorporation and primers designed for either FLT3 promoter region (sequenceF:R:) or miR-29b enhancer region (sequenceF:R:). DNA signals were calculated relative to input DNA amount and in comparison to expression values of negative control IgG.

g. RNA Isolation and Real-Time PCR

Total RNA was extracted using TriZol reagent (Invitrogen) and subjected to Reverse Transcription using SuperScript III reagents (Invitrogen). Quantitative Real-Time PCR was performed on resulting cDNA using commercially available TaqMan Gene Expression Assay primers and probes, and the 7900HT Fast Real-Time PCR System (Applied Biosystems). Mature microRNA levels were quantified using reverse transcription product made with TaqMan MicroRNA Reverse Transcription Kit (Life Technologies).

h. Luciferase Reporter Assay

Promoter region of FLT3 (SEQ ID NO. 1: CTTATTGCAAAGAAAATAATAATAATTTTCAACTCGAAAAA A-TTATGCGATGAAGAACAAGAACTATTGAGCGGATG ATTCGCAACATCCTCTGGGATGTATTTCTGTGTTTT-GTGTGAAGGCTGTTTG TTAACCTCCCTAATTGCCT-TGGTTGACATTGAAACCCTGCCTGTTTTTCTTGAT-CCCGCCCTGATGAGGGTCCTGAGCATCCTAGAGA-TGGAGGCAGAGACGAGAGAAAAGGAAA TCAGTC-CACAATTAAGAATGGAATGGTFCTTAATGGAATGC-TCGCCTGTGCGCTGGCGGGAGTTGCCAGCGTGCC-GAGCGGATTCAGGCCTTTCTCAGGGCCTCAAAG A-TCCCAGCTAGGAGGCTGGGTFGTGGCTCCCTGCA-GTCCCCACGCCCCGGA TCCAAACGACAGAGTTCG-GGGACTCACAGGGCAGCAAGGCGGCAGAGCCGCG GAGCCAGTGAACTCTCCGGCGGGACCGCCCAAT-CTTCCCCOCCGCAGTCGG GGAGCCCCGGGGGCC-GCCGAGCACAGGCTGCGGACCOCGGCGGGCACG-TOGGCT CGGCTGCAGCGCTGCGCCAGGCACCGGC-TGCTCGGCTCTGCCCAACCTCTCCGCT CCCGCCTC-GGTCCCTGCCTCTGGcGAGAGGGGTTCCTCCCCC-CTTCCACTTTGCACC AGTCCGAGGGAATTTGCGG-CTCGTGACGCGCATCCTTAAGAGAGCCACCTGCAG CGCGAGGCGCGCCGCTCCAGGCGGCATCGCAGG-GCTCGGCCGCGCGCCTGG GGACCCCGGGCTC-CGGAGCCCATCGCCGCGTTGGCGCGCGACGGCG-GCCAGCTGCCGCTGCTCGGTAAGGCCCCGCTCGC-TCGCTCGCAGCCCCTCOCGGTCCCTCAGC CCCCA-CCCCGCAGTGTOGACGCGGGCGCGCGCCTCCTC-CGGCCCAGCCGCCTCGC TCCTCCCGCOCTCGCTC-CTTCCATTGCCTCCCGCGCCCCCCCCTCFTCGCGCC CTCCGGACTCGCCCACTACTTGCCTGCGGCCCCG-GCGTTTCCCACCCCGCGTCCTC TTCCCTCTTCTC-CGAAGTCTCTCC) was cloned into pGLA.11[luc2P] vector. THP-1 cells were transfected with empty vector or FLT3-promoter luciferase plasmid and Renilla in presence or absence of C12. Firefly luciferase and Renilla luciferase activity was measured using Dual-Luciferase Reporter Assay System (Promega).

i. THP-1 Xenograft Murine Model

To generate PRMT5 overexpressing AML xenograft mouse model, THP-1 cells were transduced with PRMT5 overexpressing lentivirus marked with GFP. Positively infected cells ($1\times10^6$) were injected via tail vain into 4-66 week-old non-obese diabetic severe combined immunodeficient gamma (NSG) mice (NOD.Cg-Prkdcscid Il2rgtm1Wjl/SzJ, The Jackson Laboratory, Bar Harbor, Me.). After 10 weeks, animals were sacrificed and blood, bone marrow, spleen, liver, and sternum were processed for RNA, protein isolation, Wright-Giemsa staining and pathology. Mouse survival assays were carried out similarly, but by injecting $2\times10^6$ THP-1 cells, and sick mice were scored and sacrificed upon manifestation of AML signs.

j. Immunofluorescence Assays

Immunofluorescence assays for screening for presence of type II PRMT epigenetic marks (H4(SMe2)R3) compared to type I mark (H4(AMe2)R3). Cell lines were incubated for 24 hours with all the 14 compounds. After 24 hours, cells were fixed, blocked and treated with mAbs specific for symmetric dimethylation and asymmetric dimethylation of histone H4R3 respectively. Alexa Fluor 488 conjugated $2^{nd}$ Ab was used for the staining of histone marks (green). Draq5 was used to stain nuclei (blue).

k. Anti-Proliferation Assay

MTS proliferation assays were performed according the CellTiter 96™ Aqueous Cell Proliferation Assay Technical Bulletin (Promega, Madison, Wis.). $5 \times 10^5$ cells were plated in each well of a 96-well plate at 37° C. and assayed for proliferation at 24, 48, and 72 hr. Proliferation signal at 50% of control was used as IC50 for growth.

l. Induction of Apoptosis Assay

Analysis by flow cytometry. Cell viability was also measured by flow cytometry at 24 and 48 hr using annexin-V-FITC and propidium iodide (P1) according to the manufacturer's instructions (BD Biosciences).

m. Inhibition of PRMT5 Mediated H4R3 Methylation

Histone methylation was performed in the presence of DMSO, and 1-40 µM inhibitor compounds. The first assay that was carried out explored activity on PRMT5 alone in order to calculate an $IC_{50}$ by using 2 µg of HeLa S3 core histones and 500 ng of recombinant PRMT1 (Millipore Cat #14-474), 500 ng of recombinant PRMT4 (Millipore Cat #14-575), 5 µL of affinity-purified hSWI/SNF associated PRMT5, or 15 µA of affinity-purified hSWI/SNF associated FI-PRMT7 in a 25 µL reaction mixture containing 15 mM HEPES (pH 7.9), 100 mM KCl, 5 mM MgCl2, 20% glycerol, 1 mM EDTA, 0.25 mM dithiothreitol, 0.5 mM phenylmethylsulfonyl fluoride, and 2.75 µCi of S-[3H]adenosylmethionine (SAM) (Amersham Pharmacia Biotech., Inc.). After 1.5 h incubation at 30° C., reaction mixtures were spotted on Whatman P-81 filter paper, washed five times with 10 mL of 0.1 mM sodium carbonate buffer (pH 9.0) to remove unincorporated [3H]SAM, and methylated peptides were detected by scintillation counting.

n. In Vivo Evaluation of PRMT5 Inhibitors in OPSCC

PRMT5 and Cyclin D1 expression was assessed in 223 surgically treated oropharyngeal head and neck squamous cell carcinoma (HNSCC) samples obtained from patients treated at the Ohio State University James Cancer Hospital and Solove Research Institute from 2002-2008. Cores from paraggin embedded tumors were arrayed on tissue microarrays. Sections of the arrays were stained for PRMT5 and Cyclin D1. The expression of these biomarkers was correlated with survival, p16 status (a surrogate marker for human papillomavirus), and other clinical and pathological variables.

Overall survival was defined as time from the date of surgery to the date of death. Patients alive at the date of last observation were censored for survival analysis. Univariate Cox regression models were used to calculate hazard ratios and 95% confidence intervals (CI) and to explore the relationship between overall survival and PRMT5, Cyclin D1, and p16. Associations between categorical variables were assessed by Chi-Square tests. Analyses were conducted in SAS version 9.2 (SAS Institute, Cary, N.C.).

o. General Procedures for the Synthesis of the Disclosed Compounds

The carbazole-aldehyde (5.5 mmol) and the corresponding amine (5 mmol) were mixed in 1,2-dichloroethane (15 mL). If the hydrochloride salt of amine was used, equal amount of triethylamine was added to the reaction mixture and neutralize the salt. The reaction mixture was then treated with sodium triacetoxyborohydride (7 mmol) and stirred at room temperature under $N_2$ atmosphere until the reaction was completed (determined by TLC). Aqueous saturated $NaHCO_3$ was used to quench the reaction. The reaction product was extracted with EtOAc. The extraction was then dried ($MgSO_4$), concentrated, and purified by column chromatography (EtOAc/MeOH) to afford the pure product (yield: 52-70%). (1) Synthesis of HLCL-1

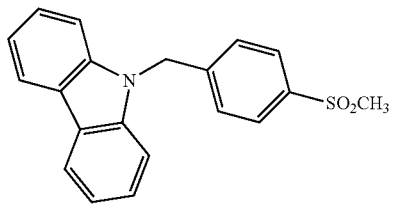 [SMILES: CS(=O)(=O)c1ccc(Cn2c3ccccc3c3ccccc32)cc1]

Sodium hydride (1.2 mmol) was firstly suspended in DMF under stirring. DMF solution of carbazole (0.6 mmol) was then added dropwise to the suspension of sodium hydride at rt. After 1 hour, 4-(Methanesulfonyl)benzyl bromide (0.6 mmol) was added to the reaction mixture. The reaction was monitored by TLC and quenched by water. EtOAc was used to extract the product. The combined organic layer was washed by water, dried ($MgSO_4$), concentrated, and purified by column chromatography (Hexane/EtOAc=2:1) to afford HLCL-1 (yield: 82%).

(2) Synthesis of HLCL-6 and HLCL-7

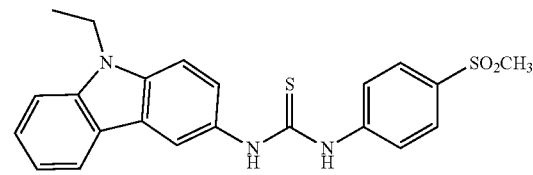

HLCL-6

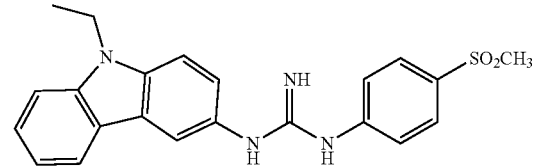

HLCL-7

4-Methylsulfonylaniline hydrochloride (5 mmol) was suspended in $CH_2Cl_2$ under stirring. Triethylamine (5 mmol) was added to the suspension and the resulted reaction mixture was stirred at r.t. for 30 min. The reaction was cooled in an ice-water bath. N,N$_0$-thiocarbonyldiimidazole (5 mmol) in $CH_2Cl_2$ was added dropwise to the reaction mixture. The reaction mixture was then allowed to stir at r.t. for 12 hours (TLC was used to monitor the reaction). The solvent was removed under reduced pressure and the crude product was purified by column chromatography (Hexane/EtOAc-2:1) to afford 4-Methylsulfonyl isothiocyanate (yield: 70%). 3-amino-9-ethylcarbazole (3.85 mmol) was used to react with 4-Methylsulfonyl isothiocyanate (3.5 mmol) in MeOH (10 mL) under reflux. After 1 hour, the reaction was complete and the thiourea product—HLCL-6 was obtained by vacuum filtration (yield: 81%). HLCL-6 was further oxidized to afford HLCL-7. Aqueous sodium metaperiodate (2.75 mmol) was added dropwise to stirred mixture of HLCL-6 (2.5 mmol), DMF (2 mL), water (2 mL), and ammonium hydroxide solution (3.75 mmol). The reaction mixture was heated to 60° C. After 1 hour, the reaction was complete and 10% aqueous NaOH (1 mL) was added. Stirring continued at room temperature for another 20 min. The crude product was filtered, washed with water and dried. Column chromatography (CH$_2$Cl$_2$/MeOH/NH$_4$OH=140:7:1) was applied to afford the pure guanidine—HLCL-7.

(3) Synthesis of HLCL-12

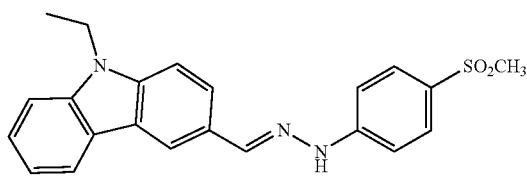 [SMILES: CCn1c2ccccc2c2cc(/C=N/Nc3ccc(S(C)(=O)=O)cc3)ccc21]

Condensation of 3-carboxaldehyde-9-ethylcarbazole and p-(Methylsulfonyl)phenylhydrazine affords HLCL-12. Procedures are the same as the general procedures for the synthesis of compounds in formula 1.

(4) Synthesis of HLCL-17 & 20

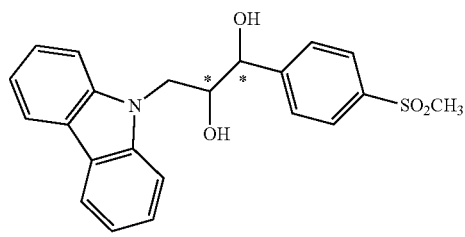 [SMILES: CS(=O)(=O)c1ccc(C(O)C(O)Cn2c3ccccc3c3ccccc32)cc1]

To a mixture of osmium tetroxide (0.06 mmol), N-methylmorpholine N-oxide (0.66 mmol), THF (5 mL) and water (2.5 mL) was added HLCL-64 (0.6 mmol) at room temperature. The reaction mixture was then heated to 85° C. and stirred overnight under N$_2$ atmosphere. The resulting mixture was filtered through a pad of celite. The filter cake was washed with EtOAc. The filtrate was concentrated and purified by column chromatography (CH$_2$Cl$_2$/MeOH=20:1) to afford HLCL-17&20.

(5) Synthesis of HLCL-23

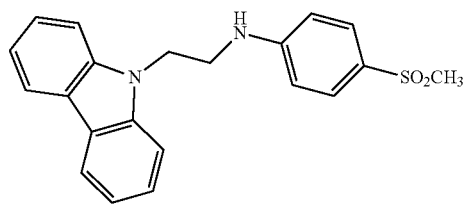 [SMILES: CS(=O)(=O)c1ccc(NCCn2c3ccccc3c3ccccc32)cc1]

The aldehyde precursor of HLCL-23 was synthesized through the formation of arylaminoacetaldehyde diethylacetal followed by hydrolysis. A stirred suspension of sodium hydride (100 mmol) in dry dioxane (50 mL) was treated with carbazole (25 mmol) at room temperature. The reaction mixture was then heated to reflux. After 4 hours, 2-bromoacetalaldehyde diethylacetal (52.5 mmol) was added dropwise to the reaction mixture under maintained reflux. The reaction was continued for another 36 hours. The excess sodium hydride was carefully destroyed by ethanol. The resulted reaction mixture was poured to water and extracted by hexane. Combined organic layers were dried (MgSO$_4$), concentrated, and purified by column chromatography (Hexane/EtOAc=1:1) to afford the pure diethylacetal product as light yellow oil (yield: 92%). Pure diethylacetal (23 mmol) was dissolved in acetone/water (30 mL:6 mL) under stirring. p-Toluenesulfonic acid (9 mmol) was added to the reaction mixture which was then heated up to reflux. After 4 hours, the reaction mixture was cooled down and extracted by EtOAc; The extraction was then dried (MgSO$_4$), concentrated, and purified by column chromatography (Hexane:EtOAc=6:1) to afford HLCL-23 (yield: 73%).

(6) Synthesis HLCL-3 and HLCL-64

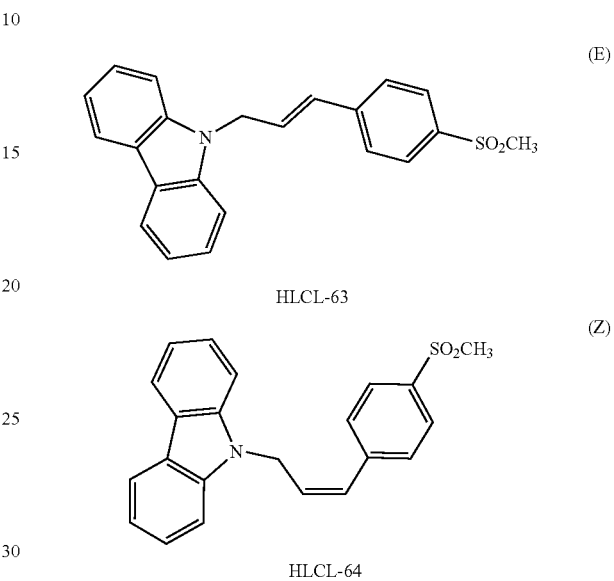

Triphenylphosphine (5 mmol) and 4-(Methanesulfonyl) benzyl bromide (5 mmol) were mixed and stirred in 10 mL chloroform. The reaction mixture was heated to reflux under a N$_2$ atmosphere. After 4 hours of reflux, the reaction mixture was poured to cold ethyl ether. White precipitate was filtered, washed with ether and dried in vacuo to afford ylide (yield: 80%). The synthesized ylide (4 mmol) was then mixed with Potassium tert-butoxide (4 mmol) in dry THF (15 mL) and heated to reflux under N$_2$ atmosphere. After 3 hours, Carbazole-9-acetaldehyde (4 mmol, its synthetic method was described above) in dry THF was added to the reaction mixture and the reaction was continued for another 2 hours. TLC showed the reaction was complete. The reaction mixture was filtered under vacuum and the concentrated filtrate was purified by flash chromatography (Hexane/EtOAc=3:1). HLCL-63 and HLCL-64 were separated by flash chromatography. The yields of HLCL-63 and HLCL-64 are 48% and 40% respectively.

(7) Synthesis of HLCL-65

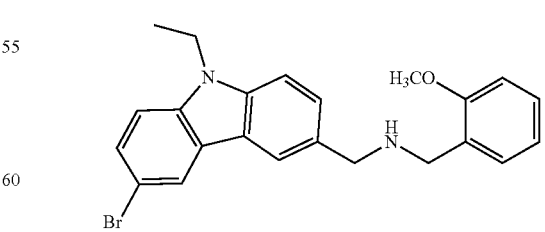

The aldehyde precursor of HLCL-65 was synthesized through bromination of 3-carboxaldehyde 9-ethylcarbazole. N-Bromosuccinimide (11 mmol) was reacted with 3-carboxaldehyde-9-ethylcarbazole (10 mmol) at r.t. in chloroform/

AcOH (30 mL/30 mL). After 18 hours of stirring, the reaction was quenched with water. CH₂Cl₂ was used for extraction. The combined organic layer was washed with water and saturated brine. The resulted organic solution was then dried (MgSO₄), concentrated, and purified by column chromatography (Hexane/EtOAc=10:1) to afford the pure product (yield: 82%).

(8) Synthesis of HLCL-66

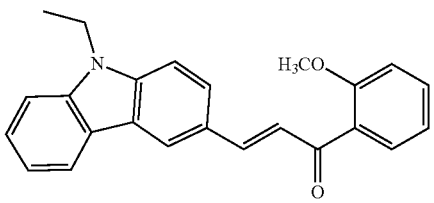 [SMILES: CCn1c2ccccc2c2cc(/C=C/C(=O)c3ccccc3OC)ccc21]

To a stirred solution of 2'-methoxyacetophenone (1.1 mmol) and 3-carboxaldehyde-9-ethylcarbazole (1 mmol) in MeOH (10 mL) was added K₂CO₃ (2.2 mmol). The reaction mixture was heated to reflux. After 12 hours, the reaction was complete and MeOH was evaporated. The residue was dissolved in EtOAc/H₂O (4:1). The organic layer was washed with brine, dried (MgSO₄), concentrated and purified by column chromatography (Hexane/EtOAc-6:1) to afford the product (yield 95%).

2. Generation of Small Molecule Inhibitors of PRMT5 Activity

Chromatin remodeling complexes and associated co-repressors such as histone deacetylases (HDAC), DNA methyltransferases and protein arginine methyltransferase 5 (PRMT5), are involved in silencing tumor suppressor (TSG) gene expression and contribute to lymphoid cellular transformation. PRMT5 over expression in mantle ell (MCL) and EBV-driven lymphomas has been observed and shown to work concertedly with histone deacetylase 2 (HDAC2), methyl-CpG binding domain protein 2 (MBD2) and DNA methyltransferase 3a (DNMT3a) to silence genes with anticancer activity. Such epigenetic dysregulation has been approached with drugs that inhibit HDAC enzymes (HDAC-I) or prevent DNA methylation, strategies currently being examined in clinical trials treating patients with hematologic malignancies. As single agents, these compounds have limited activity; thus, it can be important to discover and develop novel combination approaches to target the epigenome.

PRMT5 is a type II PRMT enzyme that silences the transcription of key regulatory genes by symmetric di-methylation (S2Mc) of arginine (R) residues on histone proteins (H4R3 & H3R5) and works more efficiently when associated with the activity of other co-repressor enzymes such as HDAC and methyl binding domain proteins (Karkhanis, V., et al. (2011) *Trends in Biochemical Sciences.* 3, 633-441). ChIP-seq work found S2Me-H4R3 to be the most globally repressive epigenetic mark among the 20 histone methylation sites studied. PRMT5 is also involved in a wide variety of cellular processes, including RNA processing, transcriptional regulation and signal transduction pathways that are highly relevant to lymphomagenesis. PRMT5 over expression is relevant to the pathogenesis of MCL and represents an important event occurring during B cell transformation driven by Epstein-Barr virus. PRMT5 is not over-expressed in normal resting or activated B cells and therefore represents an attractive therapeutic target for this disease.

PRMT5 has been identified as a therapeutic target in both hematologic and solid tumors, most of which comprise a group of diseases that are presently incurable and in need of new treatment approaches. Promising compounds have been rigorously evaluated on both in vitro and in vivo development platforms and are enhancing our ability to develop this new class of drug that selectively inhibits a promising therapeutic target in cancer. Based on this work, it has been learned that PRMT5 over expression is an oncogenic process associated with more aggressive clinical behavior and poor overall survival of patients, with cancer. While work using siRNA molecules to block PRMT5 expression supports the experimental therapeutic approach to inhibit PRMT5 in cancer, the use of RNA-based therapeutics is at early stages of development and presently impractical. It is believed that PRMT5 over expression and hypermethylation of its epigenetic marks trigger genome wide chromatin and gene expression changes, which promote transformed B cell growth, and that inhibition of PRMT5 activity will result in reactivation of growth regulatory networks that can arrest cancer. Generation of small molecule inhibitors of PRMT5 activity allows for rapid development of a novel, "first in class" drug capable of targeting a newly discovered oncogenic pathway and lead to improved strategies to treat patients with cancer. Current work addresses optimizing the selectivity and the potency of candidate compounds, characterizing the anti-tumor activity and mechanisms of these drugs in both blood and solid tumors, and evaluating PRMT5 inhibitors alone and in combination with other FDA-approved drugs that target epigenetic processes in preclinical models of cancer.

PRMT5 small molecule inhibitors represent a new class of drug capable of selectively targeting type II PRMT enzymes and synergizing with other drugs that target epigenetic processes in cancer. Without wishing to be bound by theory, the significance of this class of drug may have a profound effect on the outcome of patients diagnosed with cancer.

Fragment based drug design (FBDD) has been recognized recently as an effective approach to develop high-affinity drugs Repurposing existing drugs has resulted in a decreased risk of failure in drug development. Therefore, utilizing drug fragments and linking them together provided an attractive strategy to develop PRMT5 inhibitions. This was approached in a step-wise fashion. (A) First, a fragment library was constructed from an FDA-approved drug database. This library was further categorized according to different properties of the compound fragments. (B) The carbazole fragment was identified in our previous lead compound (Baiocchi, R.; Li, C.; Li, P.; Yan, F. WO 2011079236 A1 2011). Interestingly, a simple carbazole derivative Phikan083 (Boeckler, F. M., et al. (2008) *Proc. Nat. Acad. Sci. U.S.A.* 105, 10360-10365) was discovered to stabilize p53 carrying Y220 mutation. Phikan083 was thus selected as fragment 1 and the other aromatic fragment in the compound library as fragment 2 followed by docking these two fragment together to the computational model of human PRMT5 catalytic domain (FIGS. 1A and 1B; surface transparency is allowed to show catalytic residues; for clarity, protein surface is generated omitting the residues which cover the catalytic site face).

The docking strategy, referred to as Multiple Ligand Simultaneous Docking (MLSD), was implemented on the AutoDock4 platform. Hybrid PSO algorithm was used to search for the increased degrees of freedom for multi-ligand translation and rotation. (C) Fragments which showed similar docking position to the natural ligand (SAH) and high ranking in docking score were selected out (FIG. 1A). Multiple linkers were designed to link the two fragments and the linked molecules were re-docked in the model. (D) Finally, the linked molecules which reproduce the fragments' binding position and show high-ranking binding energy were chosen as synthetic candidates (FIG. 1B). Among them, 14 compounds were synthesized (Table 1).

TABLE 1

| Compound No. | Structure |
|---|---|
| HLCL-1 | 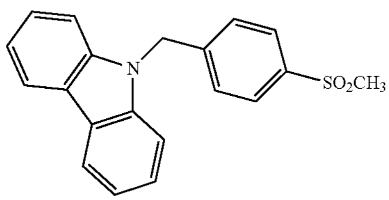 [SMILES: CS(=O)(=O)c1ccc(Cn2c3ccccc3c3ccccc32)cc1] |
| HLCL-6 | 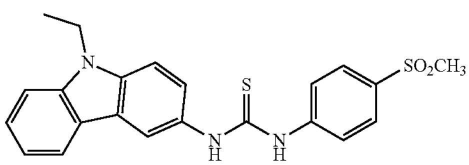 [SMILES: CCn1c2ccccc2c2cc(NC(=S)Nc3ccc(S(C)(=O)=O)cc3)ccc21] |
| HLCL-7 | 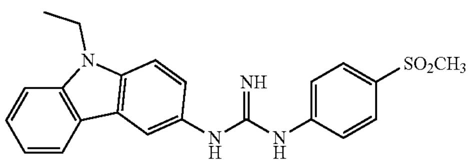 [SMILES: CCn1c2ccccc2c2cc(NC(=N)Nc3ccc(S(C)(=O)=O)cc3)ccc21] |
| HLCL-9 | 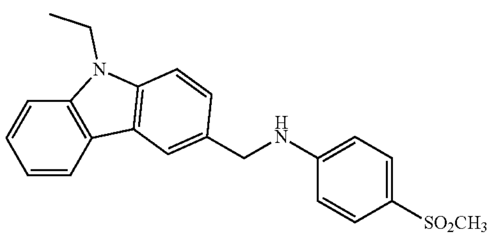 [SMILES: CCn1c2ccccc2c2cc(CNc3ccc(S(C)(=O)=O)cc3)ccc21] |
| HLCL-10 | 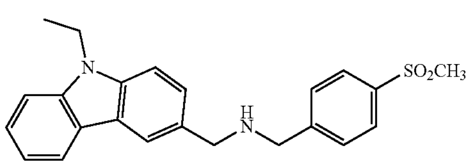 [SMILES: CCn1c2ccccc2c2cc(CNCc3ccc(S(C)(=O)=O)cc3)ccc21] |
| HLCL-12 | 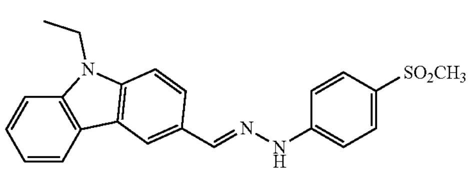 [SMILES: CCn1c2ccccc2c2cc(/C=N/Nc3ccc(S(C)(=O)=O)cc3)ccc21] |

TABLE 1-continued

| Compound No. | Structure |
|---|---|
| HLCL-17&20 | 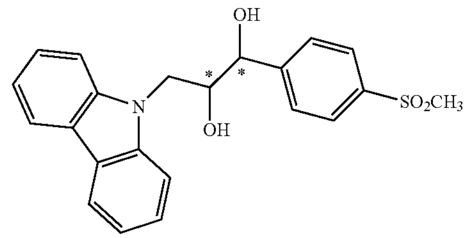 [SMILES: CS(=O)(=O)c1ccc(C(O)C(O)Cn2c3ccccc3c3ccccc32)cc1] |
| HLCL-23 | 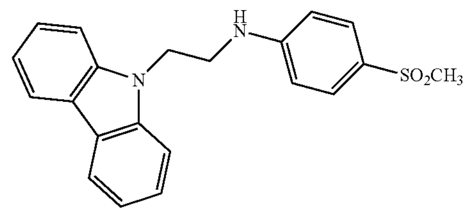 [SMILES: CS(=O)(=O)c1ccc(NCCn2c3ccccc3c3ccccc32)cc1] |
| HLCL-32 | 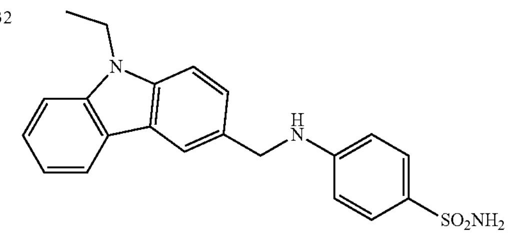 |
| HLCL-61 | 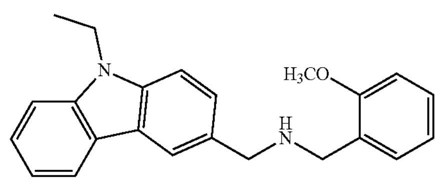 [SMILES: CCn1c2ccccc2c2cc(CNCc3ccccc3OC)ccc21] |
| HLCL-63 | 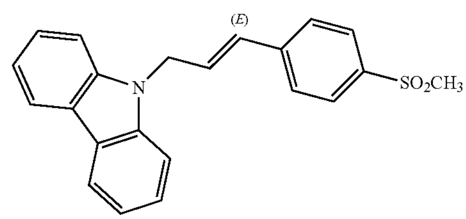 [SMILES: CS(=O)(=O)c1ccc(/C=C/Cn2c3ccccc3c3ccccc32)cc1] |
| HLCL-64 | 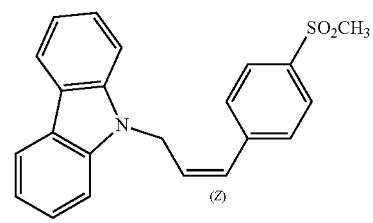 [SMILES: CS(=O)(=O)c1ccc(/C=C\Cn2c3ccccc3c3ccccc32)cc1] |
| HLCL-65 | 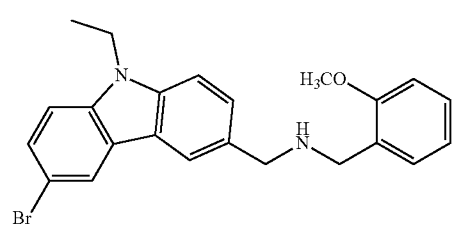 [SMILES: CCn1c2ccc(Br)cc2c2cc(CNCc3ccccc3OC)ccc21] |

TABLE 1-continued

| Compound No. | Structure |
|---|---|
| HLCL-66 | (structure: N-ethyl carbazole linked via vinyl group to 2-methoxyphenyl ketone) |

Based upon the model, functional inhibitors occupy the Adenine region within the SAM/SAH binding pocket, the methionine region within the SAM/SAH pocket, the groove linking SAM/SAH pocket with the arginine pocket, and/or the arginine pocket of PRMT5. This strategy is unique to Type II PRMT enzymes. This model is explained in FIG. 2A-I.

Figure 3:
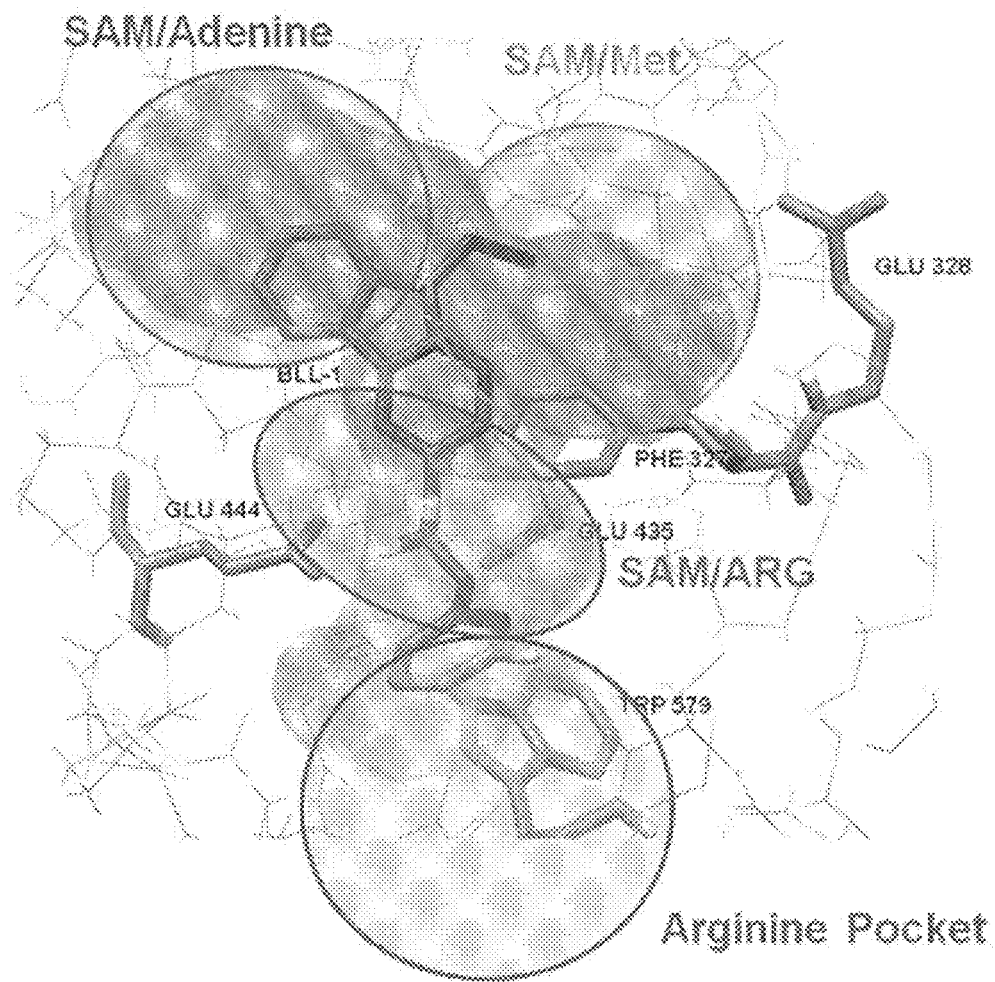
FIG. 3 illustrates the PRMT5 binding model based on crystal structure information.

Without wishing to be bound by theory, it is believed that substituents on selective PRMT5 inhibitors can interact with one or more of: Cofactor binding pocket SAM Adenine region; Cofactor binding pocket: SAM Met region (PHE327); Connecting Pocket: (GLU444/GLU435, PHE327); and/or Arginine substrate pocket (Interaction with TRP579). These regions and such interaction are illustrated in FIG. 3. It has been observed that effective and potent inhibitors can occupy the proximal SAM (RED) docking site, the tunnel connecting SAM and ARG binding pockets and a portion of the ARG binding pocket.

3. Evaluation of Using PRMT5 Nuclear Expression as a Biomarker

PRMT5 is expressed in B cells infected by the oncogenic virus, EBV, and is required for EBV-driven B cell transformation. Upon infection of B cells (negative for PRMT5) with the oncogenic virus, EBV, PRMT5 becomes overexpressed as early as 4 days after infection. By day 8, PRMT5 levels in nucleus increase and PRMT5 epigenetic marks S2MeH4R3 and S2MeH3R8 become globally distributed on nuclear chromatin. Blockage of PRMT5 expression or activity prevents EBV-driven immortalization of the B lymphocyte, suggesting that PRMT5 is required for B cell transformation. Biologic activity of PRMT5 relates to transcriptional repression of tumor suppressor genes that regulate the tonic signaling of the B cell receptor. In other examples, PRMT5 is weakly/not expressed in most CLL patients circulating CLL cells. It is, however, expressed in CLL patient circulating B cells of patients who eventually experience Richter's transformation (RT), a complication where CLL transforms to aggressive diffuse large B cell lymphoma. PRMT5 can be found months or years before patients undergo RT indicating that, like PRMT5 induced with EBV infection of B cells. PRMT5 is a required RT driver event Without wishing to be bound by theory, this work, along with GBM, head/neck squamous and lung cancer biomarker data indicates that PRMT5 detection (in tumor or blood as circulating gene/gene product) could serve as a sensitive and specific biomarker for cancer.

Figure 4:
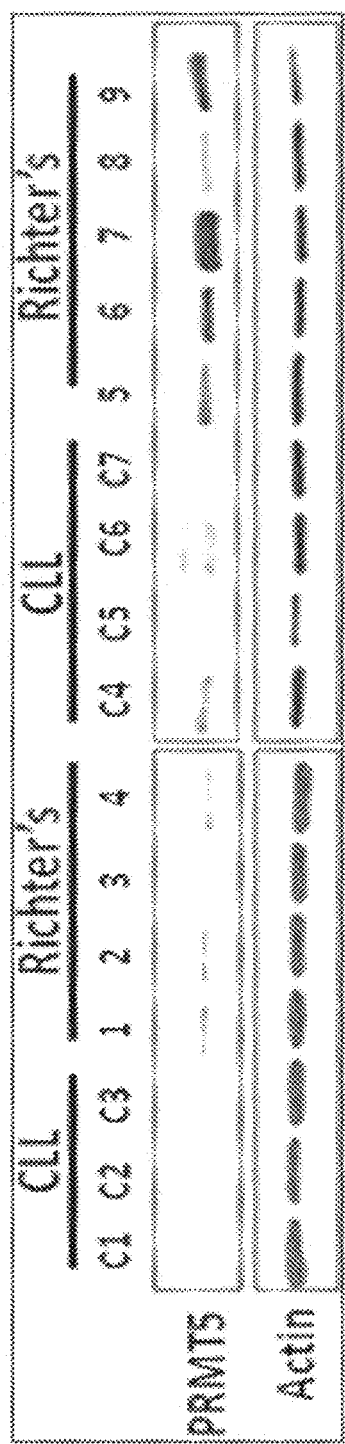
FIG. 4 shows representative data pertaining to the use of PRMT5 as a biomarker for more aggressive malignant behavior. expression of PRMT5 in whole cell lysates derived from primary CLL cells and Richter's transformation patients' samples (months to years prior transformation). CLL cells express little to no PRMT5, however, in patients who go on to transform from CLL to aggressive diffuse large B cell lymphoma (Richter's transformation), PRMT5 becomes detectable in circulating CLL months to years prior to this transformation event.
Figure 5:
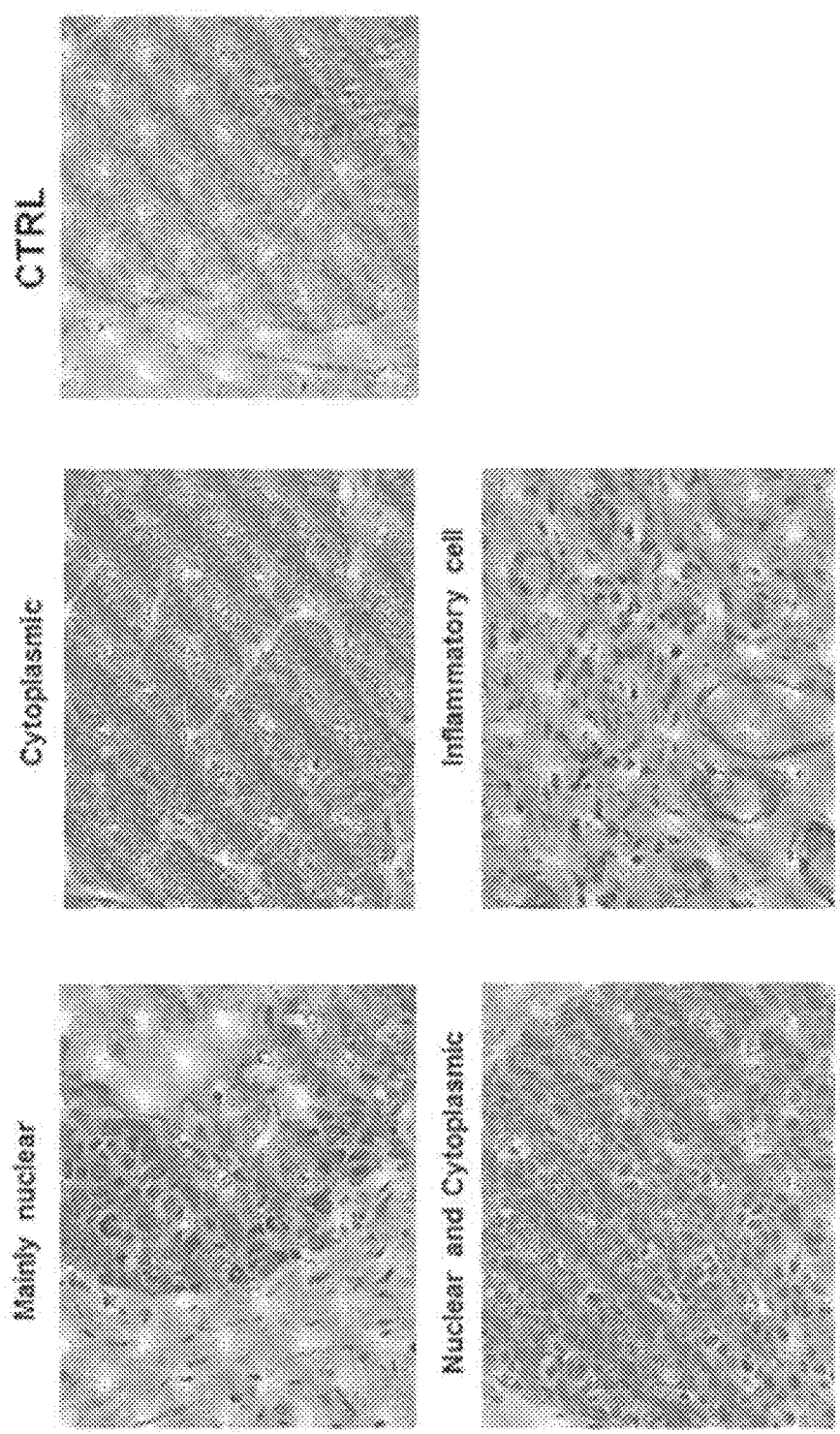
FIG. 5 shows representative staining patterns of PRMT5 expression in squamous cell carcinomas of the head and neck.

PRMT5 is variably expressed in CLL primary cells and cell lines while absent in resting (RB) or activated (AB) B cells (data not shown). Preliminary analysis of 10 CLL patients B cells prior to RT demonstrated elevated levels of PRMT5 suggesting that PRMT5 dysregulation may be relevant to lymphomagenesis in this setting (FIG. 4). PRMT5 expression can occur in both nucleus and cytoplasm. It has been shown that the degree of nuclear PRMT5 expression is inversely proportional to overall survival in patients with high grade gliomas (GBM). A similar study was performed in head & neck cancers with similar results. Staining patterns are shown in FIG. 5.

Figure 6:
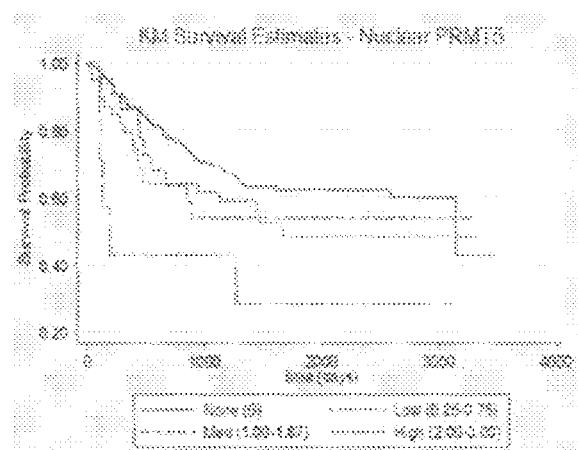
FIG. 6 shows representative data pertaining to a Cox regression model correlating nuclear PRMT5 and survival of patients with squamous cell carcinoma. Levels of nuclear expression of PRMT5 are inversely proportional to survival in these patients.
Figure 7:
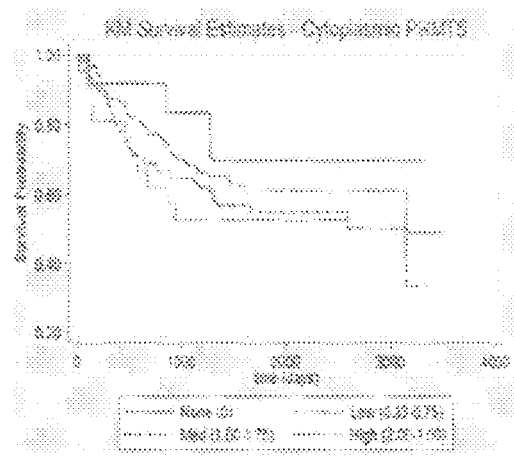
FIG. 7 shows representative data pertaining to a Cox regression model correlating cytoplasmic PRMT5 and survival for squamous cell carcinoma.

In a study of squamous cell carcinoma (48 females, 189 males; median age 58 years (range 31-82); median follow up of 3 years; disease staging ranged from stage I-IV), it was demonstrated that staining intensity strongly inversely correlates with patient survival (FIG. 6 and Table 2). On the other hand, cytoplasmic PRMT5 staining intensity was not significant for squamous cell carcinoma (FIG. 7).

TABLE 2

| Characteristic | Grade I-II (N = 10) | Grade III (N = 7) | Grade IV (GBM) (N = 43) |
|---|---|---|---|
| Age in years (Median, $25^{th}$-$75^{th}$ percentile) | 29 (20-45) | 51 (44-59) | 64 (52-71) |
| Male | 6/10 (60%) | 5/7 (71.4%) | 24/43 (56%) |
| Caucasian | 8/10 (80%) | 6/7 (86%) | 40/43 (93%) |
| Previous tumor history | 4/10 (40%) | 0/7 (0%) | 11/43 (26%) |
| Overall mortality over follow-up | 2/10 (20%) | 4/7 (57%) | 39/43 (91%) |
| Follow-up in days (Median, $25^{th}$-$75^{th}$ percentile) | 648 (409-1,272) | 619 (387-1,177) | 259 (108-604) |
| Ki67 proliferation index (Median, $25^{th}$-$75^{th}$ percentile) | 1.5% (1.3-1.8%) | 10% (4.6-15.5%) | 20% (12.5-30%) |
| PRMT-5 nuclear staining level (Median, $25^{th}$-$75^{th}$ percentile) | 0 | 0.15 (0.11-0.25) | 0.53-0.19-0.78) |

PRMT5 expression can occur in both nucleus and cytoplasm. The degree of nuclear PRMT5 expression has been shown to be inversely proportional to overall survival in patients with high grade gliomas (GBM) (Table 3).

TABLE 3

| Survival | Frequency | Percent |
|---|---|---|
| Alive | 139 | 58.65 |
| Dead | 98 | 41.35 |

Figures 8A, 8B:
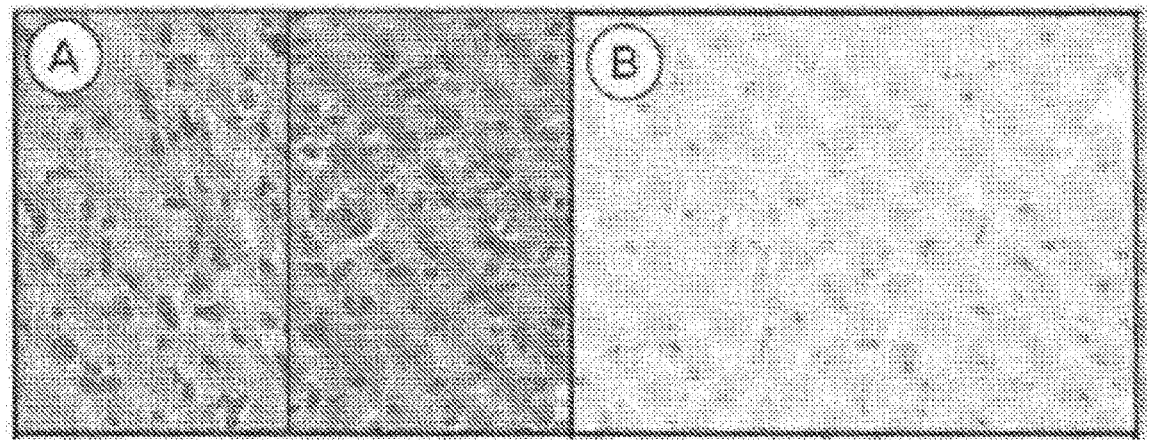
FIG. 8A shows an H&E stain of normal brain and astrocytoma.
FIG. 8B-F are immunohistochemistry staining for PRMT5 in normal brain (SB), grade I astrocytoma (SC), grade II astrocytoma (SD), grade I astrocytoma (BE), and grade IV astrocytoma or glioblastoma multiform (SF). Nuclear staining intensifies with grade.
Figures 8C, 8D:
Figures 8E, 8F:
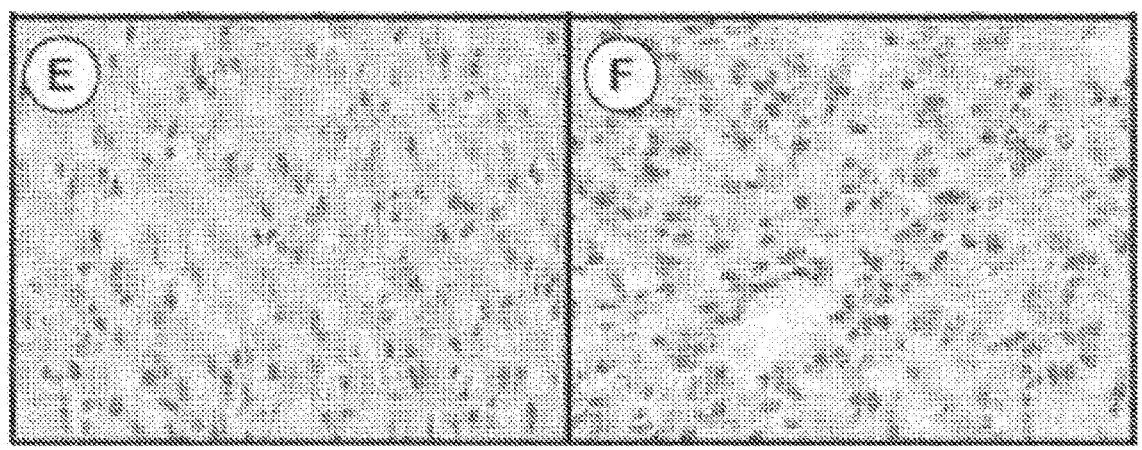
Figure 9A:
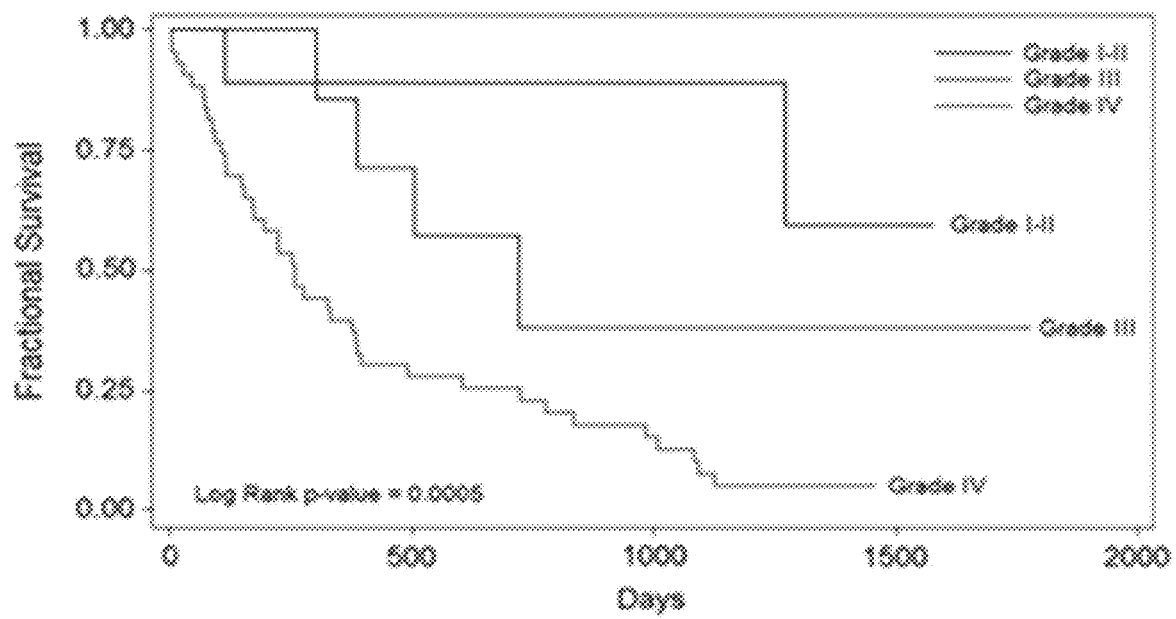
FIG. 9A-D shows representative data pertaining to PRMT5 levels and survival. Specifically.
Figure 9B:
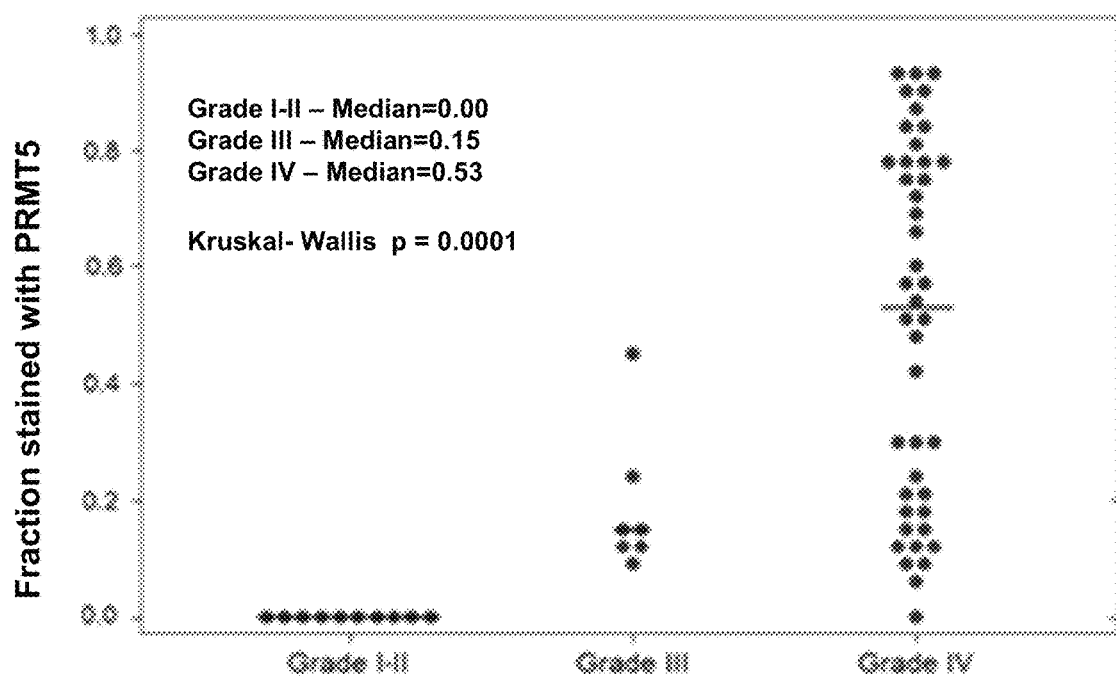
Figure 9C:
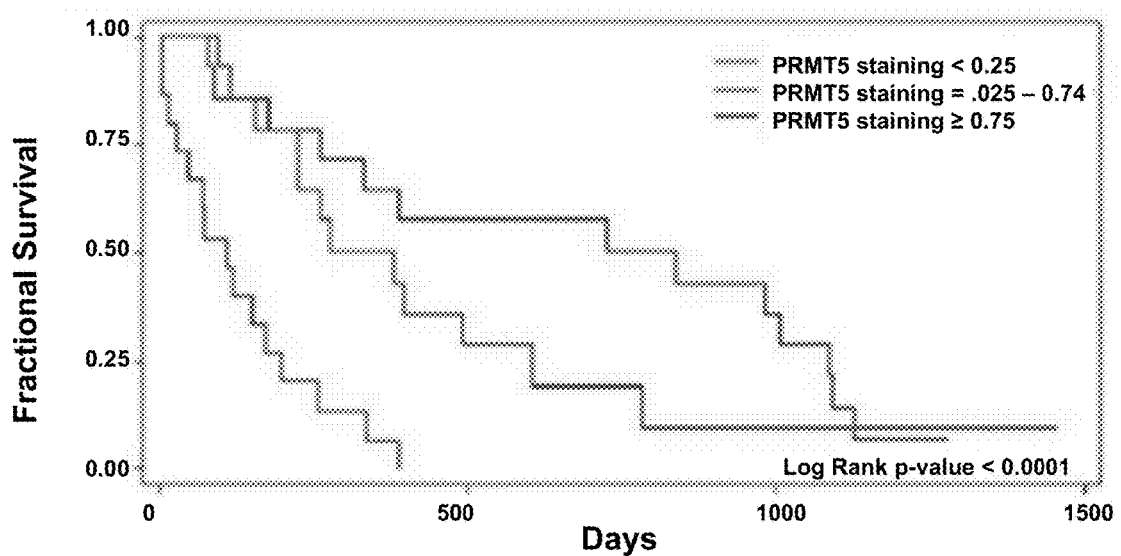
Figure 9D:
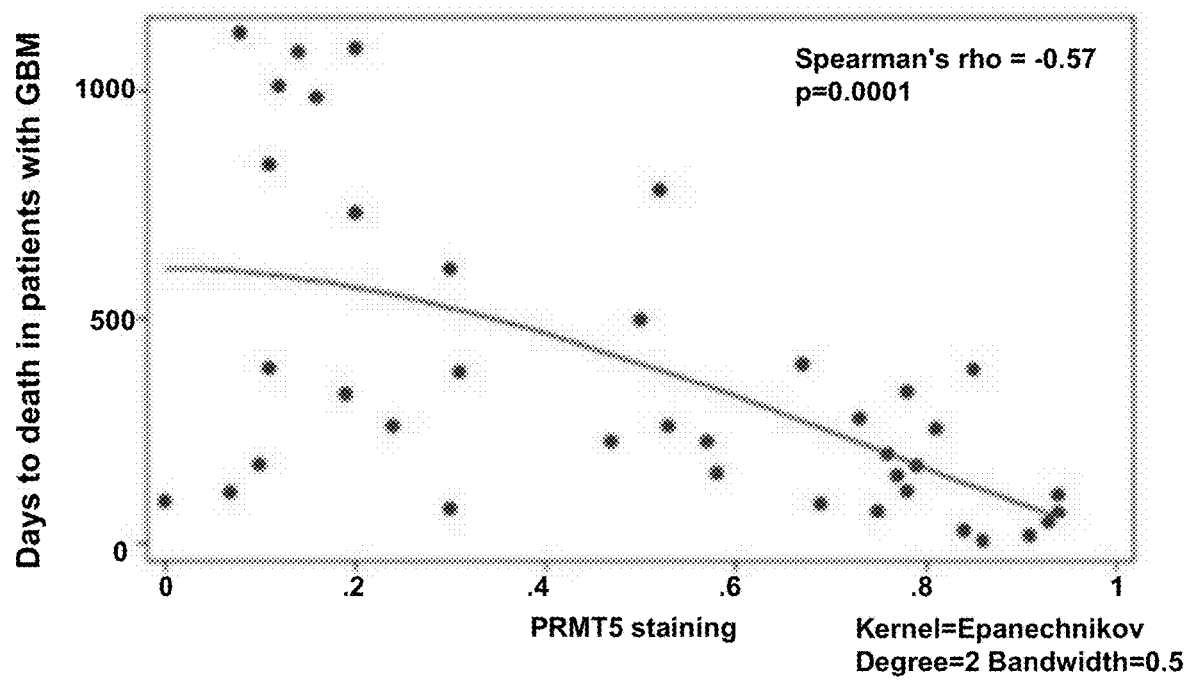

FIG. 8A shows photomicrographs (H&E staining) of normal brain and glioma; FIG. 8BB shows PRMT5 expression in normal brain; FIG. 8C shows PRMT5 expression in Grade I glioma; FIG. 8D shows PRMT5 expression in Grade II glioma; FIG. 8E shows PRMT5 expression in Grade III glioma; and FIG. 8F shows PRMT5 expression in Grade IV glioma. Thus, PRMT5 is over-expressed in primary astrocytoma tumors and inversely correlated with patient survival (see also FIG. 9).

Figure 10:
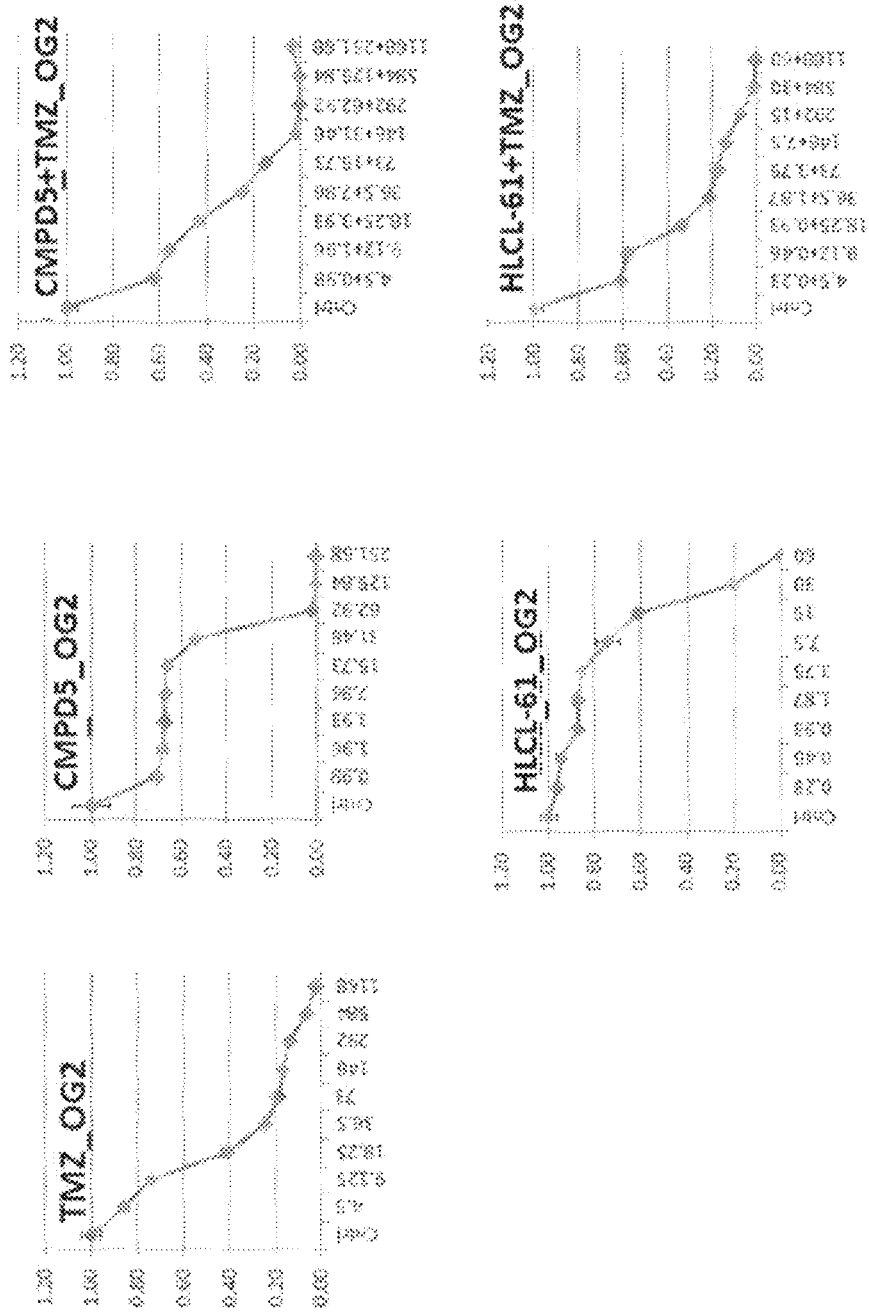
FIG. 10 shows representative data pertaining to a viability assay for CMPD 5 and HLCL-61 alone and in combination with temozolomide (TMZ).
Figure 11:
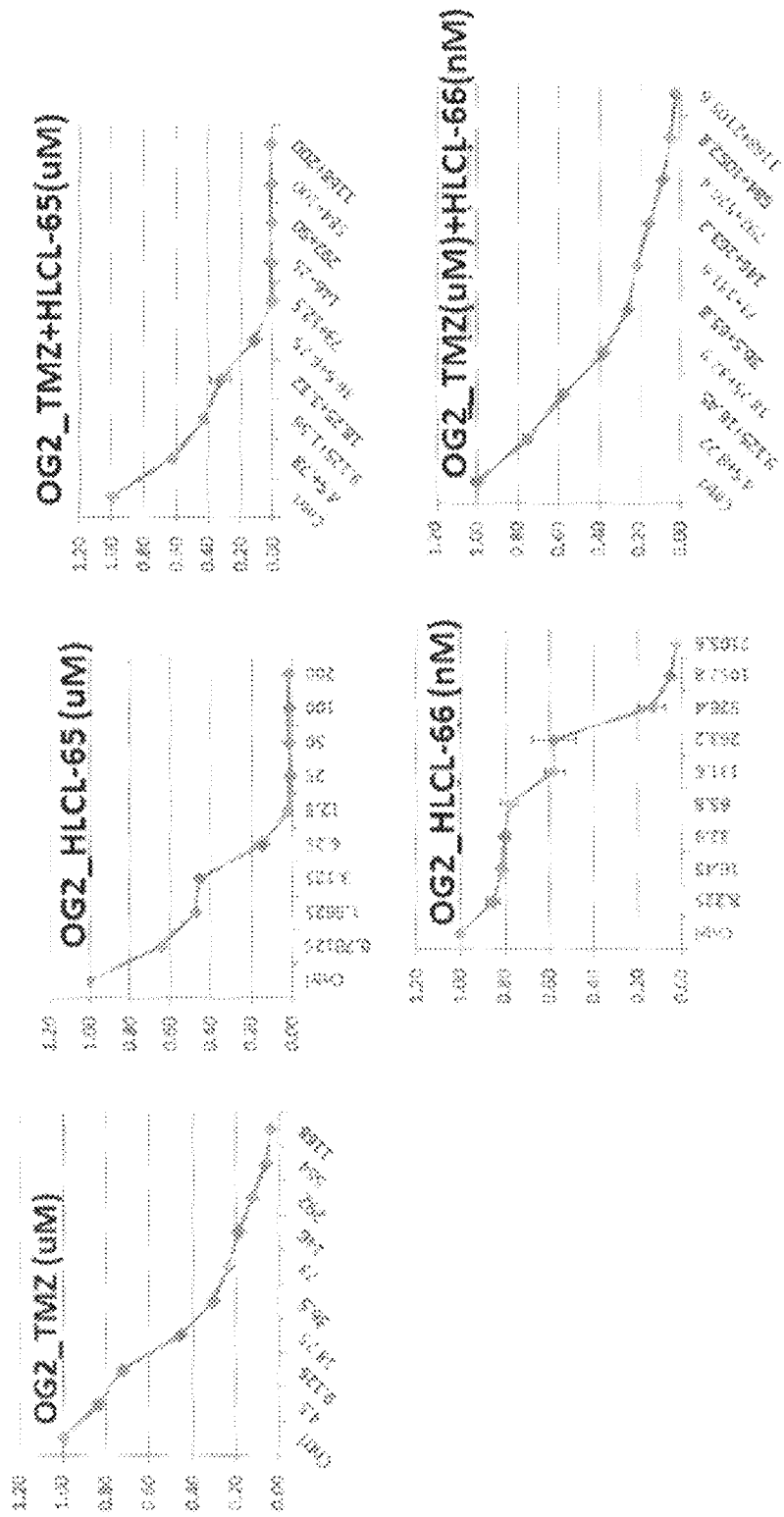
FIG. 11 shows representative data pertaining to a viability assay for HLCL-65 and HLCL-66 alone and in combination with TMZ.
Figure 12:
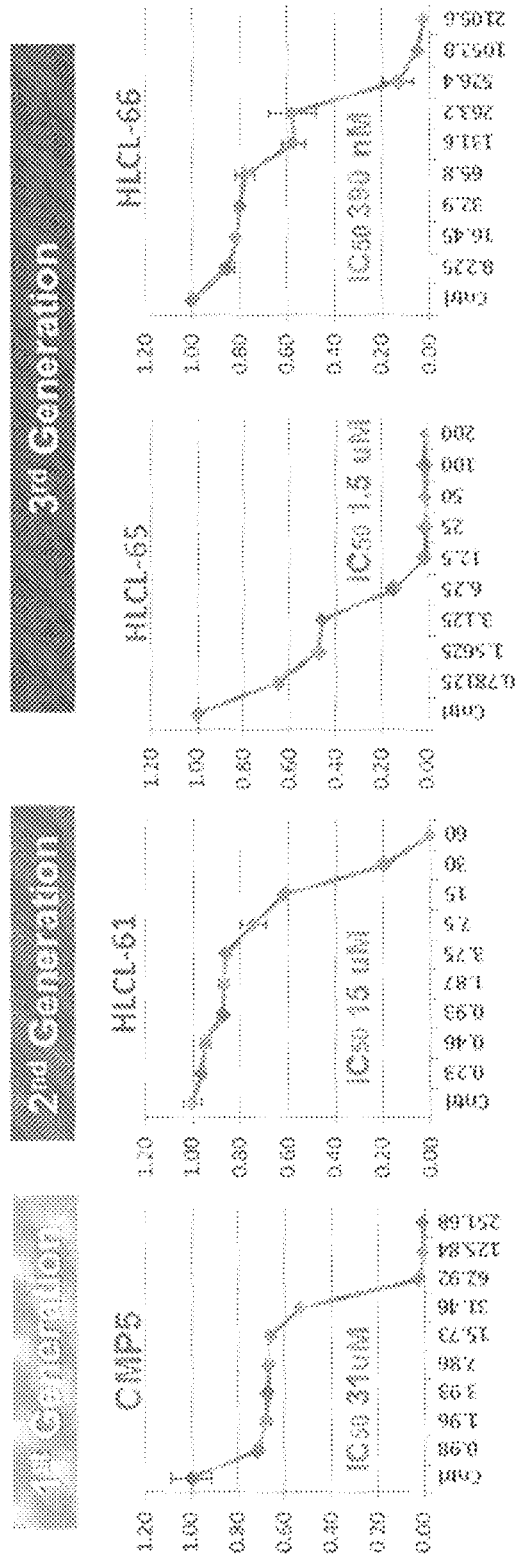
FIG. 12 shows representative data pertaining to the inhibitory activity of first, second, and third generation PRMT5 inhibitors.
Figure 13:
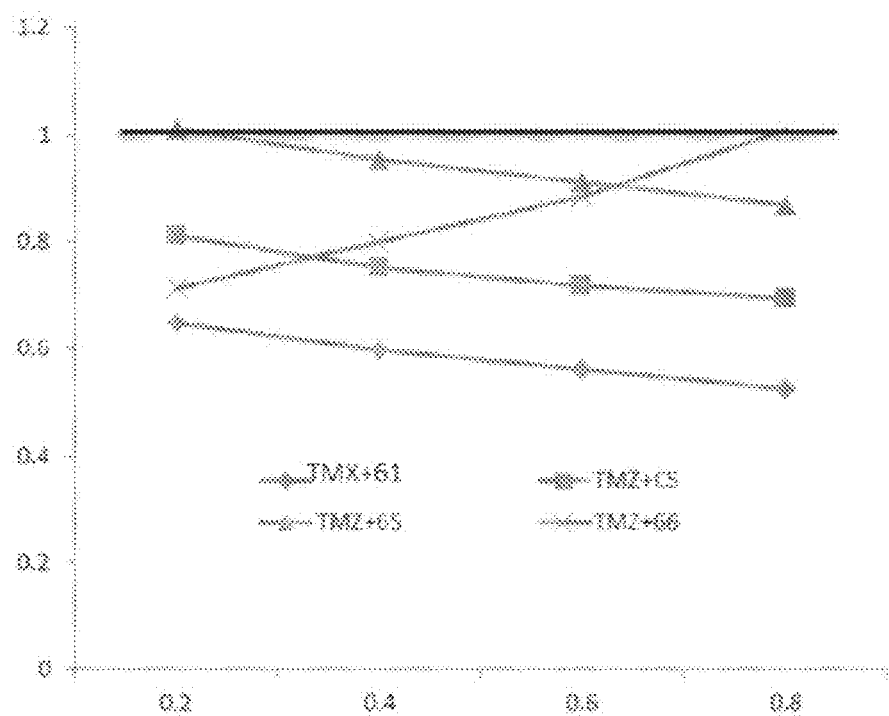
FIG. 13 shows representative data pertaining to the synergistic effect of TMZ and either CMPD 5, HLCL-61, HLCL-65, or HLCL-66.

A viability assay was conducted for CMPD 5, HLCL-61, HLCL-65, and HLCL-55 alone and in combination with temozolomide (TMZ), an FDA-approved drug for glioblastoma (GBM), on OG2 cells (FIGS. 10 and 11; see FIG. 12 for a comparison of the potency of $1^{st}$, $2^{nd}$, and $3^{rd}$ generation PRMT5 inhibitors). OG2 cells are tumor cells derived from glioblastoma primary tumors. TMZ and HLCL-66 were shown to induce apoptosis in a synergistic fashion (FIG. 13).

4. Evaluation of Compound Activity

Following the synthesis of 14 compounds, the anti-proliferation and pro-apoptotic activities of those compounds was evaluated in Mantle cell lymphoma cell line Jcko. Replicate cultures of Jeko were incubated in DMSO and the compounds for 24, 48 and 72 hours. FITC-Annexin V-PI stained flow cytometry was used to detect the apoptotic population of cells (Table 4).

TABLE 4

| | Activity | | |
|---|---|---|---|
| Compound No. | Anti-proliferation ($IC_{50}$, µM)* | Induction of apoptosis ($EC_{50}$, µM) | Inhibition of PRMT5 mediated H4R3 methylation ($IC_{50}$, µM) |
| HLCL-1 | >50 | N/A | >50 |
| HLCL-6 | >50 | N/A | >50 |
| HLCL-7 | 32 (24 h); 26 (48 h); 13 (72 h) | 32 (24 h); 26 (48 h) | 7 |
| HLCL-9 | >50 | N/A | >50 |
| HLCL-10 | 84 (24 h); 47 (48 h); 60 (72 h) | 40 (24 h); 35 (48 h) | >50 |
| HLCL-12 | >50 | N/A | >50 |
| HLCL-17&20 | >50 | N/A | >50 |
| HLCL-23 | >50 | N/A | >50 |
| HLCL-32 | 51 (24 h); 29 (48 h); 29 (72 h) | 30 (24 h); 20 (48 h) | >50 |
| HLCL-61 | 44 (24 h); 29 (48 h); 28 (72 h) | 15 (24 h); 11 (48 h) | 12 |
| HLCL-63 | >50 | N/A | >50 |
| HLCL-64 | >50 | N/A | >50 |
| HLCL-65 | 9 (24 h); 8 (48 h); 6 (72 h) | 4 (24 h); 5 (48 h) | 30 |
| HLCL-66 | 1.9 (24 h); 0.4 (48 h); 0.2 (72 h) | 1.4 (24 h); 0.5 (48 h) | 26 |

*24, 48, and 72 h are the incubation times of drug with mantle cell lymphoma cell line Jeko.

Figure 14:
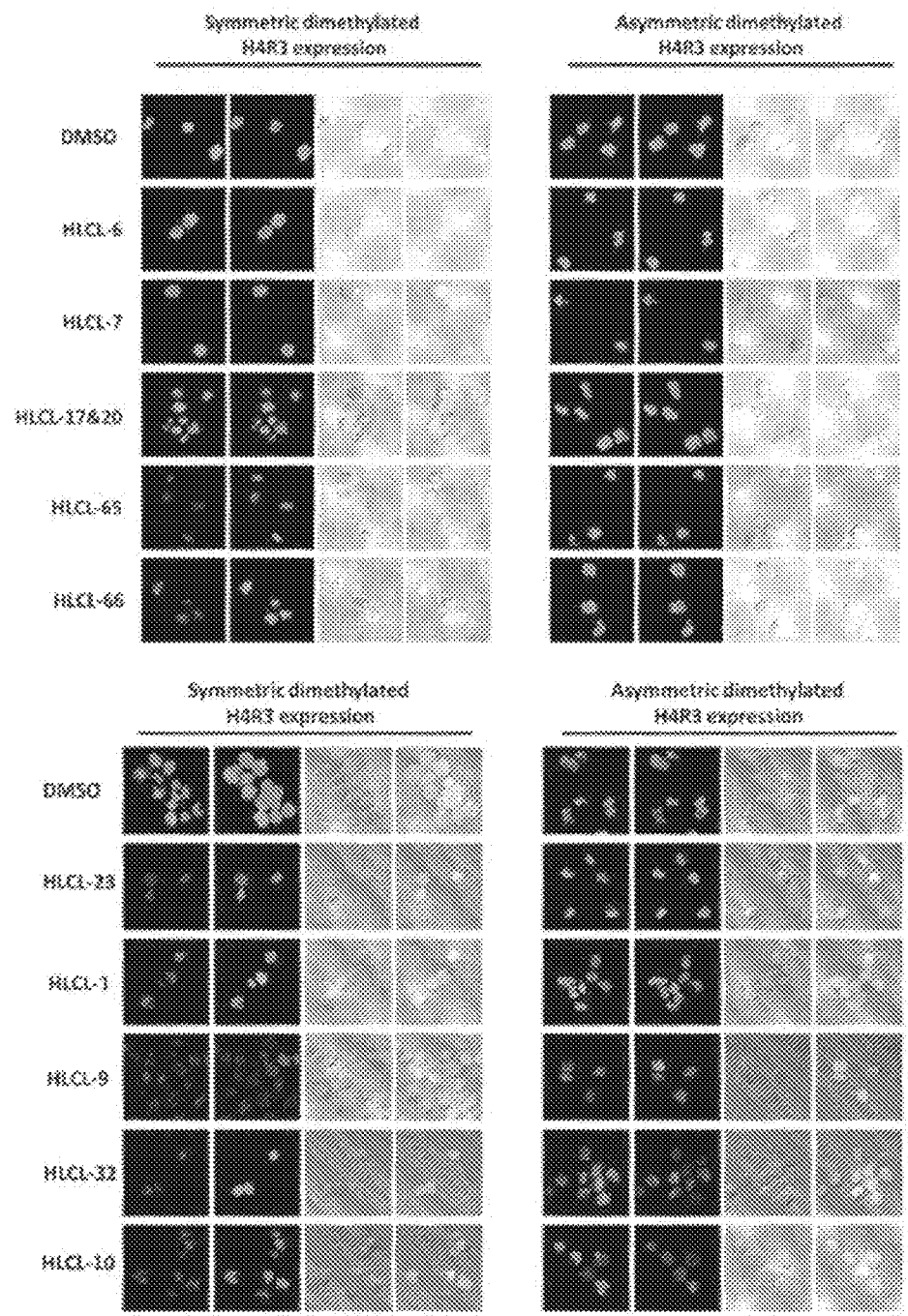
FIG. 14 shows representative data pertaining to immunofluorescence screening for presence of type II PRMT epigenetic marks (H4(SMe2)R3) compared to type I mark (H4(AMe2)R3).
Figure 14:
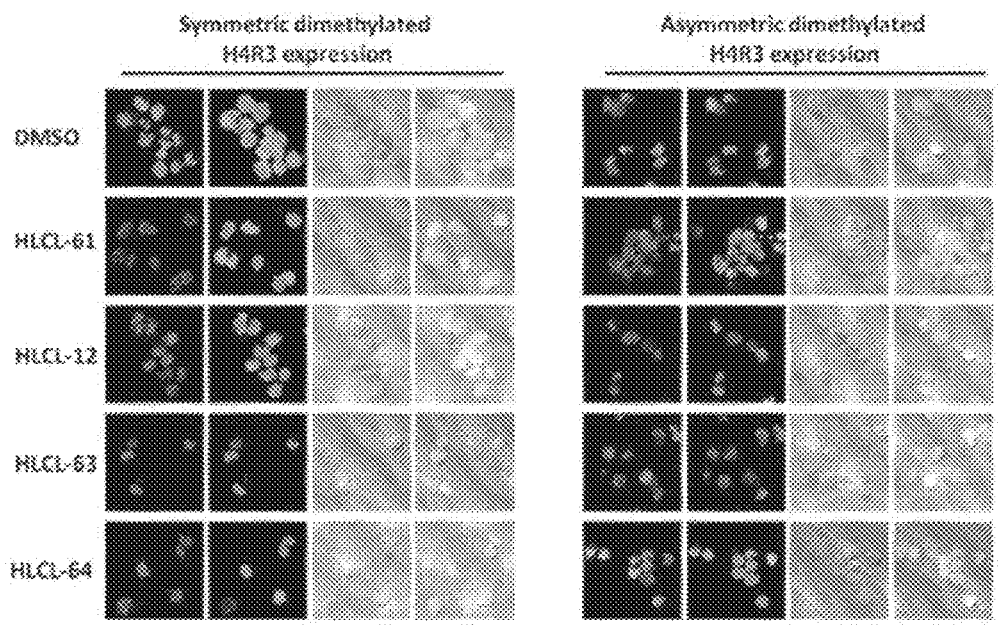

The inhibition of PRMT5 mediated H4R3 methylation result was obtained with Epigenase™ PRMT methyltransferase (type II-specific) activity/inhibition assay kit. 25 g. recombinant human PRMT5/MEP50 enzyme (purchased from BPS Bioscience) was used in each reaction. FIG. 14 shows that immunofluorescence screening for presence of type II PRMT epigenetic marks (H4(SMe2)R3) compared to type I mark (H4(AMe2)R3).

Figure 15:
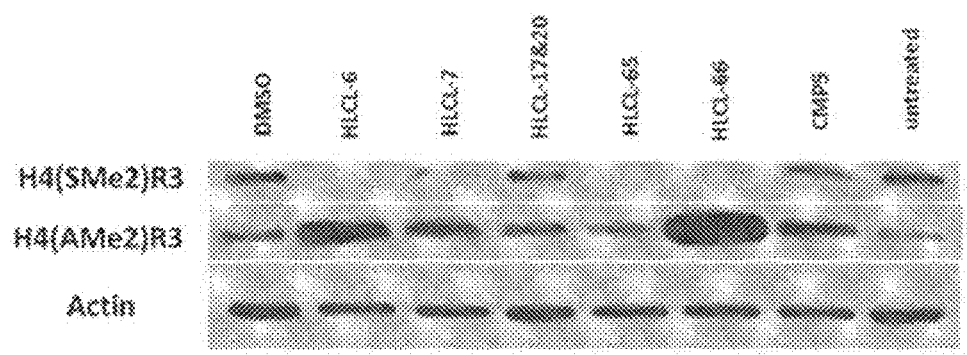
FIG. 15 shows representative data pertaining to western blot analysis for presence of type II PRMT epigenetic marks (H4(SMc2)R3) compared to type I mark (H4(AMc2)R3).

Jeko cell line was incubated for 24 hours with all the 14 compounds. After 24 hours, cells were fixed, blocked and treated with mAbs specific for symmetric dimethylation and asymmetric dimethylation of histone H4R3 respectively. Alexa Fluor 488 conjugated $2^{nd}$ Ab was used for the staining of histone marks (green). Draq5 was used to stain nuclei (blue). FIG. 15 shows that the immunoblotting study in the presence of presence of type II PRMT epigenetic marks (H4(SMe2)R3) compared to type I mark (H4(AMe2)R3).

Given these results, HLCL-23, HLCL-10, HLCL-61, HLCL-64 were chosen to evaluate in an enzyme inhibition assay which are capable of determining whether the compounds can directly target at PRMT5 enzyme and selectively inhibit type II PRMT enzymes. Type II PRMT enzymes repress gene transcription and symmetrically dimethylate H3R8 and H4R3, while type I PRMT enzymes activate gene transcription and asymmetrically dimethylate H4R3. Purified PRMT5, PRMT1, PRMT4 and PRMT7 were obtained to perform the assay.

Figure 16:
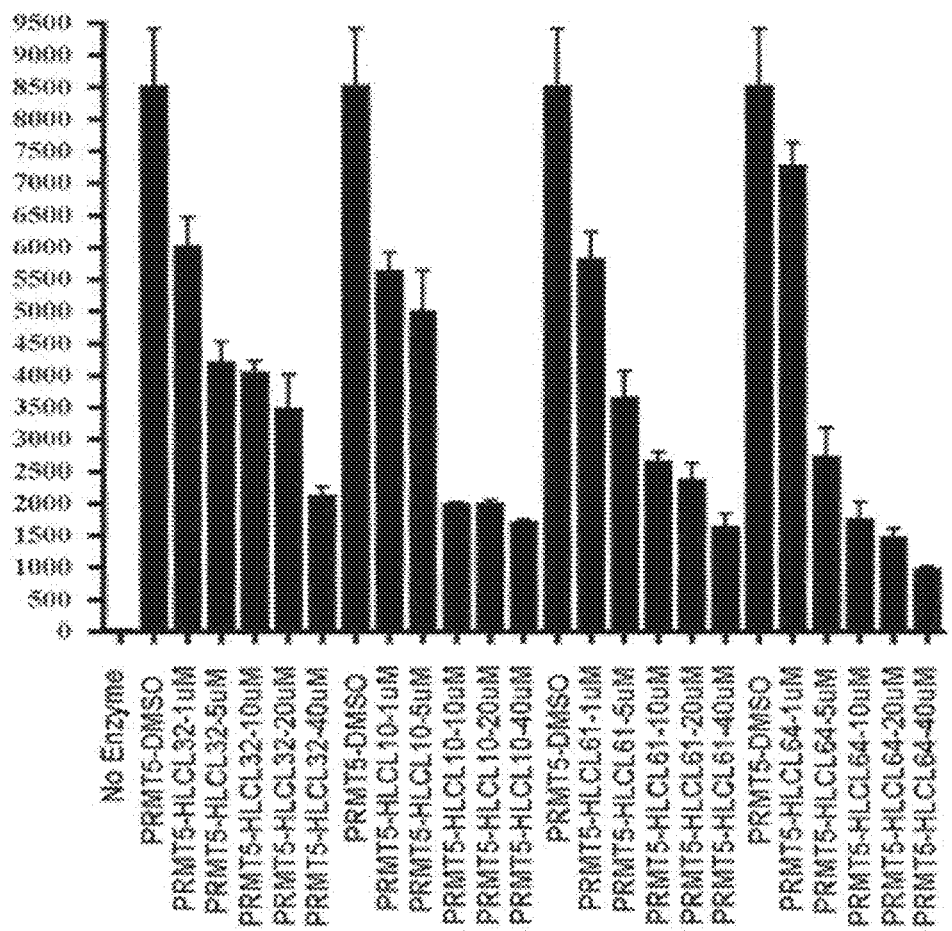
FIG. 16 shows representative data pertaining to histone methyltransferase assays using purified PMRT5. Third generation PRMT5 inhibitors show improved potency compared to earlier generation drugs.

Histone methylation was performed in the presence of DMSO, and 1-40 µM HLCL-32, HLCL-10, HLCL-61 and HLCL-64. The first assay that was carried out explored activity on PRMT5 alone in order to calculate an $IC_{50}$ by using 2 µg of HeLa S3 core histones and 500 ng of recombinant PRMT1 (Millipore Cat #14-474), 500 ng of recombinant PRMT4 (Millipore Cat #14-575), 5 µL of affinity-purified hSWI/SNF associated PRMT5, or 15 µL of affinity-purified hSWI/SNF associated FI-PRMT7 in a 25 µL reaction mixture containing 15 mM HEPES (pH 7.9), 100 mM KCl, 5 mM $MgCl_2$, 20% glycerol, 1 mM EDTA, 0.25 mM dithiothreitol, 0.5 mM phenylmethylsulfonyl fluoride, and 2.75 µCi of S-[$^3$H]adenosylmethionine (SAM) (Amersham Pharmacia Biotech., Inc.). After a 1.5 h incubation at 30° C. reaction mixtures were spotted on Whatman P-81 filter paper, washed five times with 10 mL of 0.1 mM sodium carbonate buffer (pH 9.0) to remove unincorporated [$^3$H] SAM, and methylated peptides were detected by scintillation counting. FIG. 16 shows that all four compounds inhibit PRMT5 methylation activity at $IC_{50}$ values around 5 µM.

Figure 17:
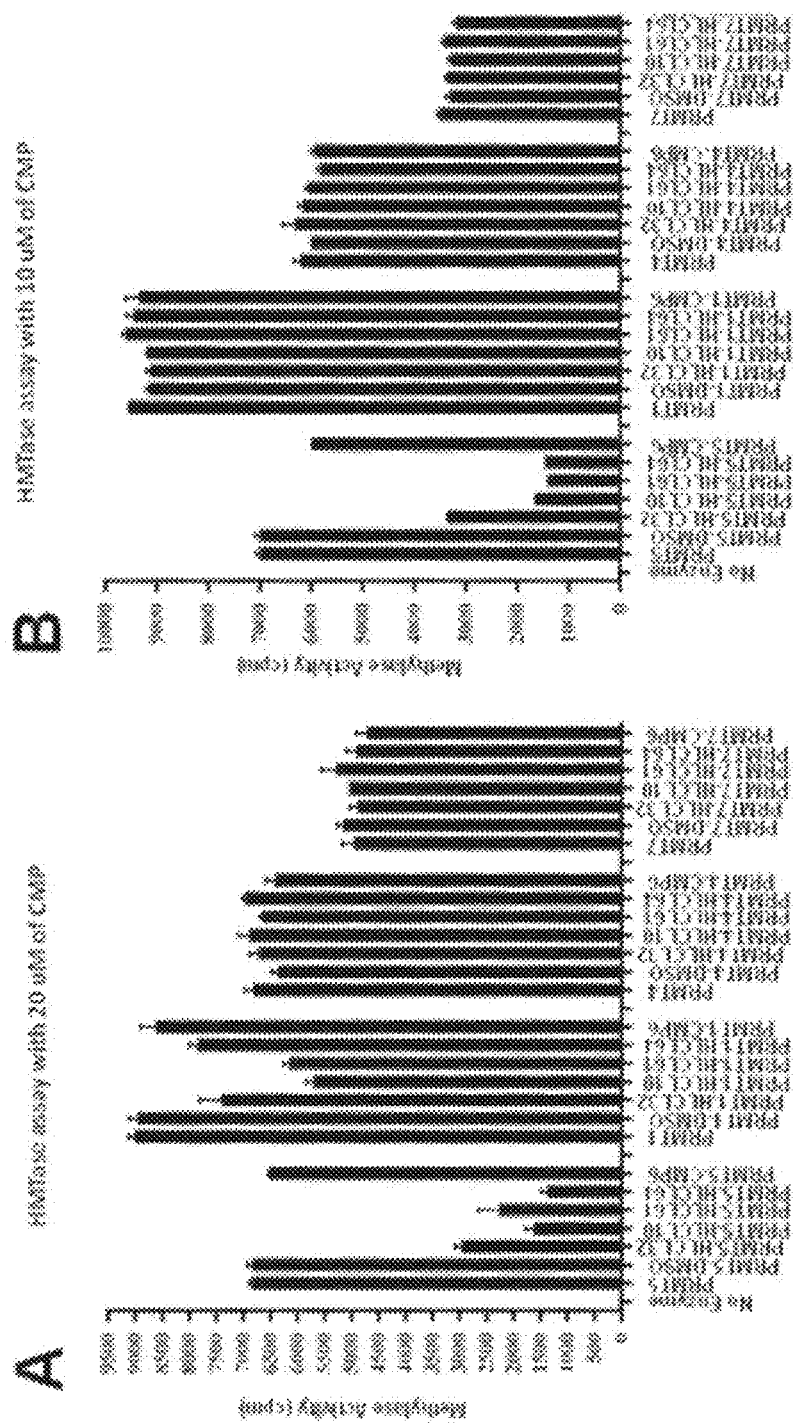
FIG. 17 shows representative data pertaining to the potency and selectivity of PRMT5 inhibitor compounds. Comparisons are made to PRMT1, PRMT4 and PRMT7.

Referring to FIG. 17, all of the compounds selectively inhibit PRMT5 enzyme but not PRMT1, PRMT4, PRMT7. At concentrations of 20 µM and above, compounds HLCL32, 10, 61 and 64 show non-specific inhibition of PRMT1 enzyme (FIG. 17A); however, at 10 µM concentrations, this non-specific activity is lost and the only enzyme that is affected is PRMT5 (FIG. 17B).

a. Biologic Activity of PRMT5 Inhibition

Figure 18:
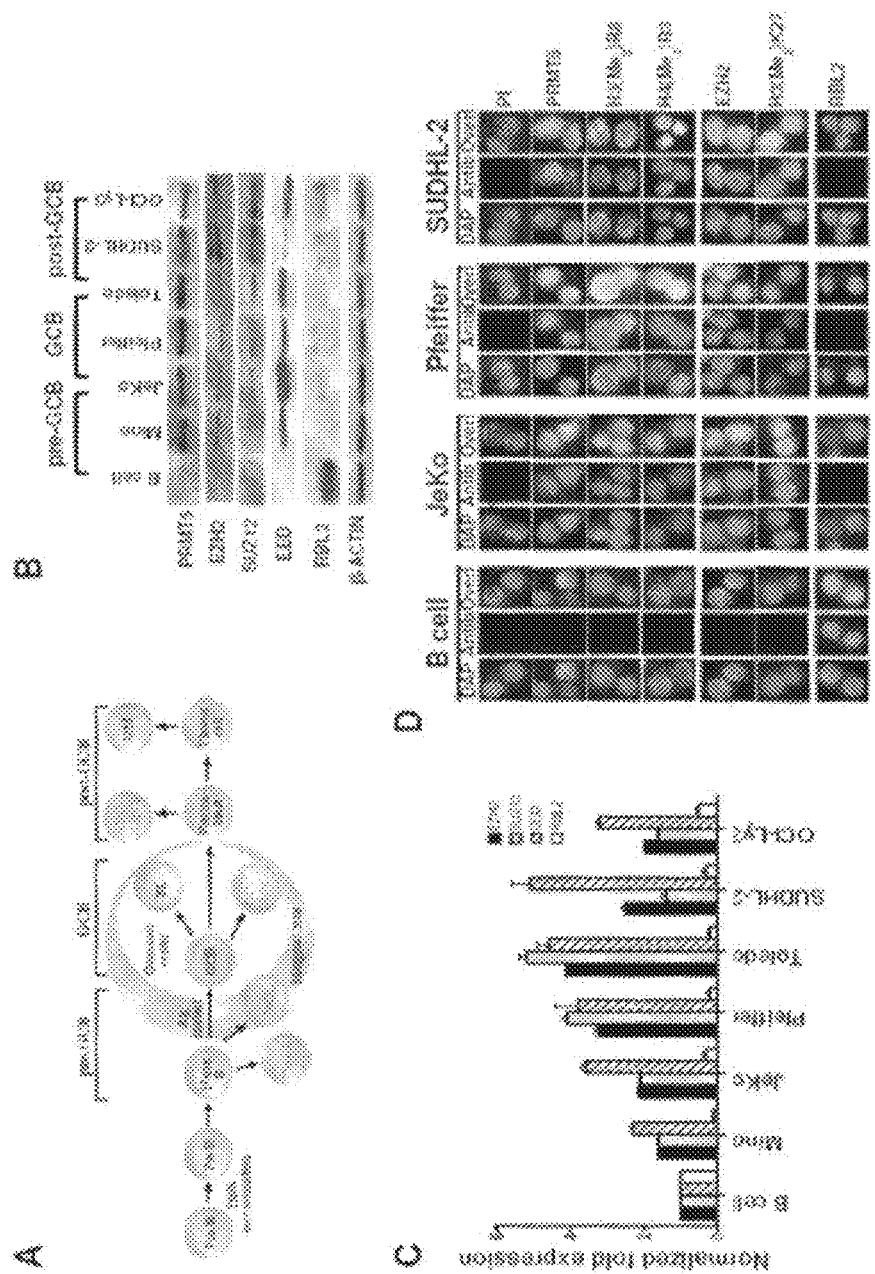
FIG. 18 shows representative data indicating that PRMT5 and PRC2 enzymes are over-expressed, while RBL2 levels are suppressed in different types of NHL cell lines. PRMT5 over-expression silences RB/E2F pathway and promotes over-expression of the PRC2 family of lysine methyltransferase enzymes.

Effects on other epigenetic pathways in cancer cells. PRMT55 and PRC2 proteins (EZH2, SUZ12, and EED) are over-expressed in pre germinal center (GC), GC, and post GC lymphomas FIG. 18A-D). RBL2, a known PRMT5 target, is silenced in pre GC. GC and post GC lymphomas (FIG. 18B and FIG. 18D) at the transcriptional level (FIG. 18C).

Figure 19:
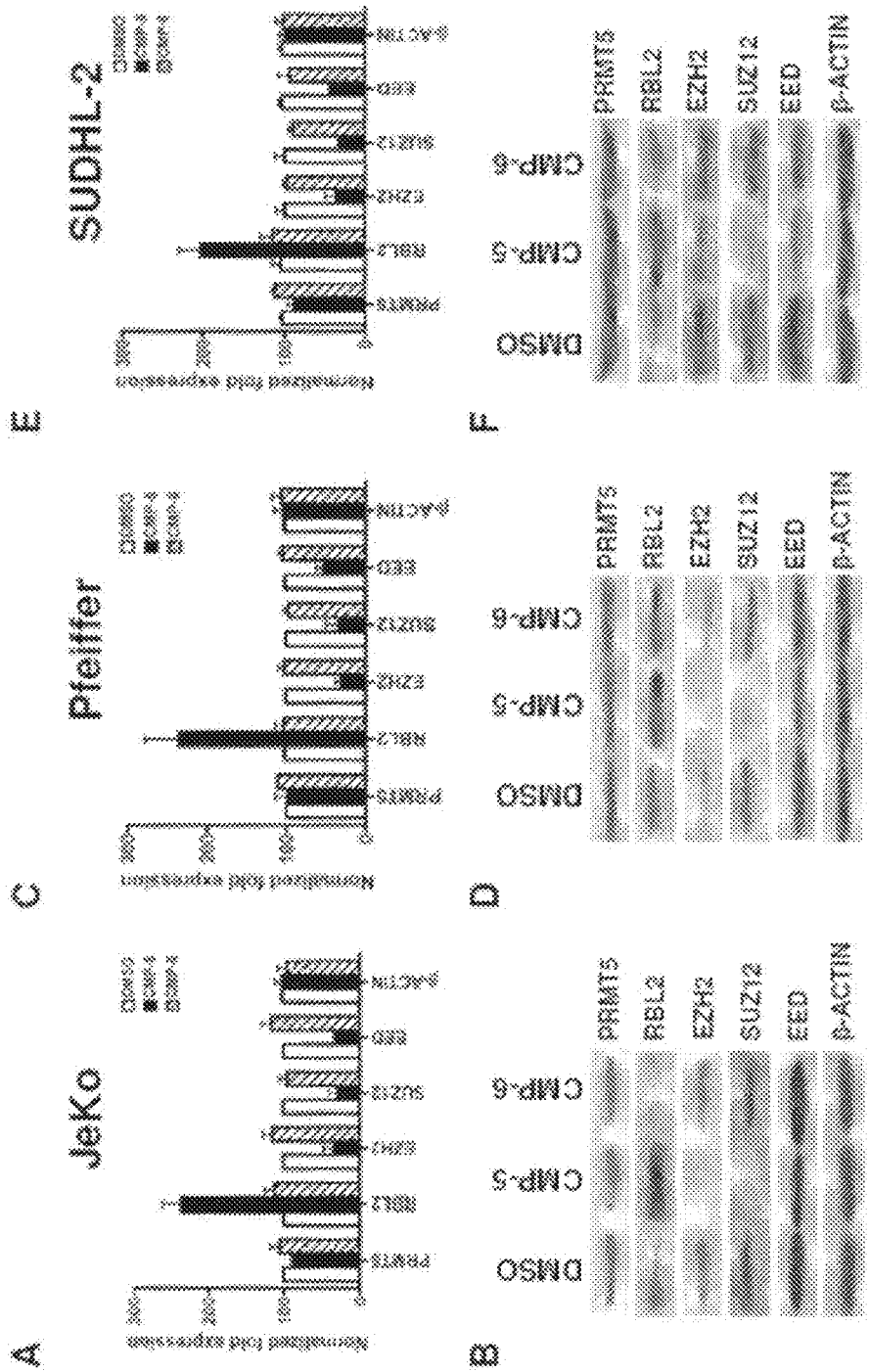
FIG. 19 shows representative data indicating that PRMT5 inhibitors reactivate RBL2 and suppress PRC2 expression. PRMT5 directly represses RBL2 and inhibition allows for transcriptional de-repression of RBL2 which can work with E2F and HDAC enzymes to silence PRC2.

PRMT5 inhibitors are capable of promoting restoration of RBL2 transcription (FIGS. 19A, 19C, and 19E) and protein expression (FIGS. 19B, 19D, and 19F). Restoration of RBL2 expression coincided with PRC2 transcriptional silencing (FIGS. 19A, 19C, and 19E) and loss of protein over expression (FIGS. 19B, 19D, and 19F). This led to the hypothesis that PRMT5-driven transcriptional silencing of RBL2 may be associated to the regulation of PRC2 genes.

Figure 20:
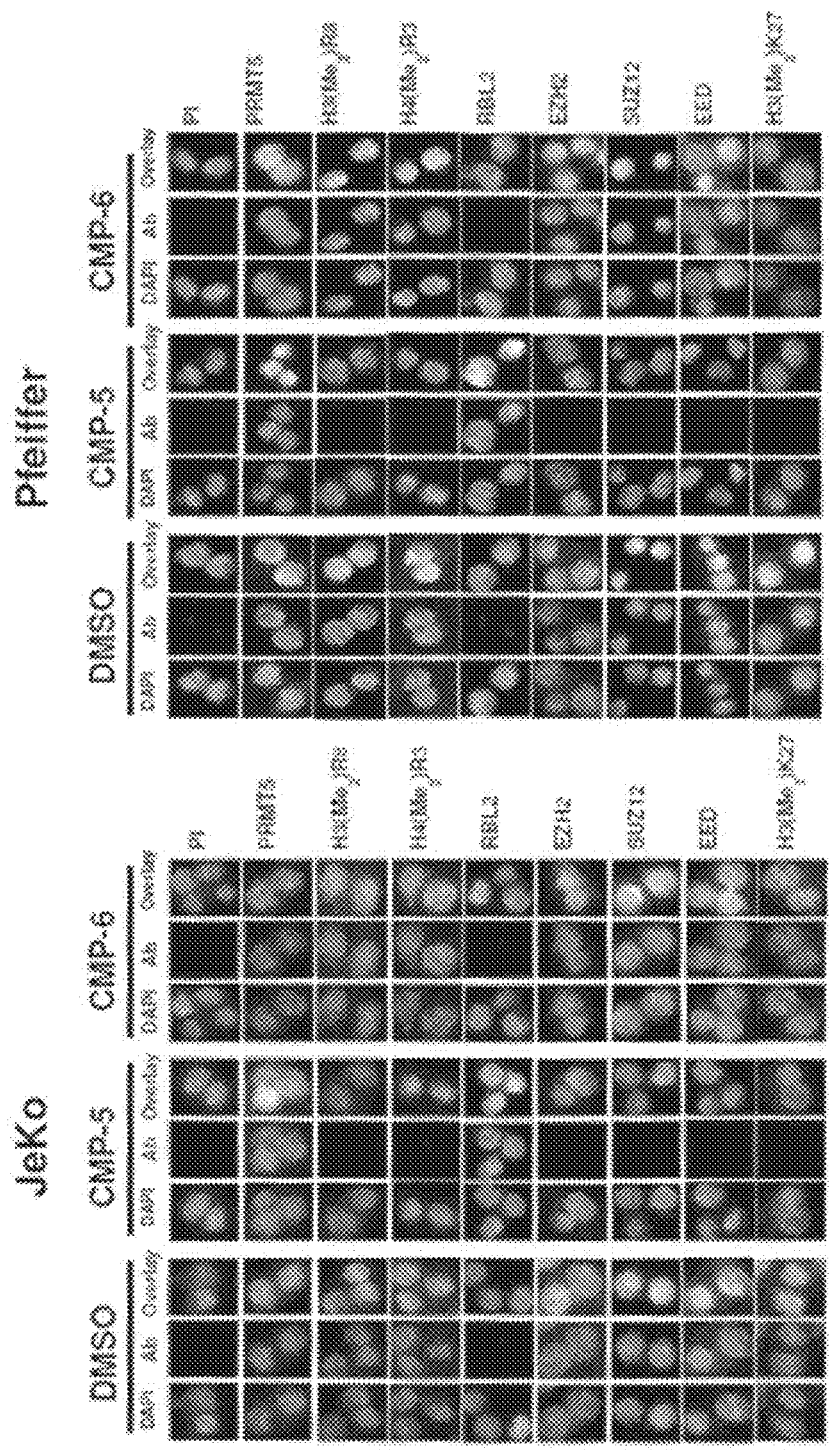
FIG. 20 shows representative data indicating that PRMT5 inhibitors reactivate RBL2 and abolish PRC2-induced H3(Me$_3$)K27 in NHL cells.
Figure 20:
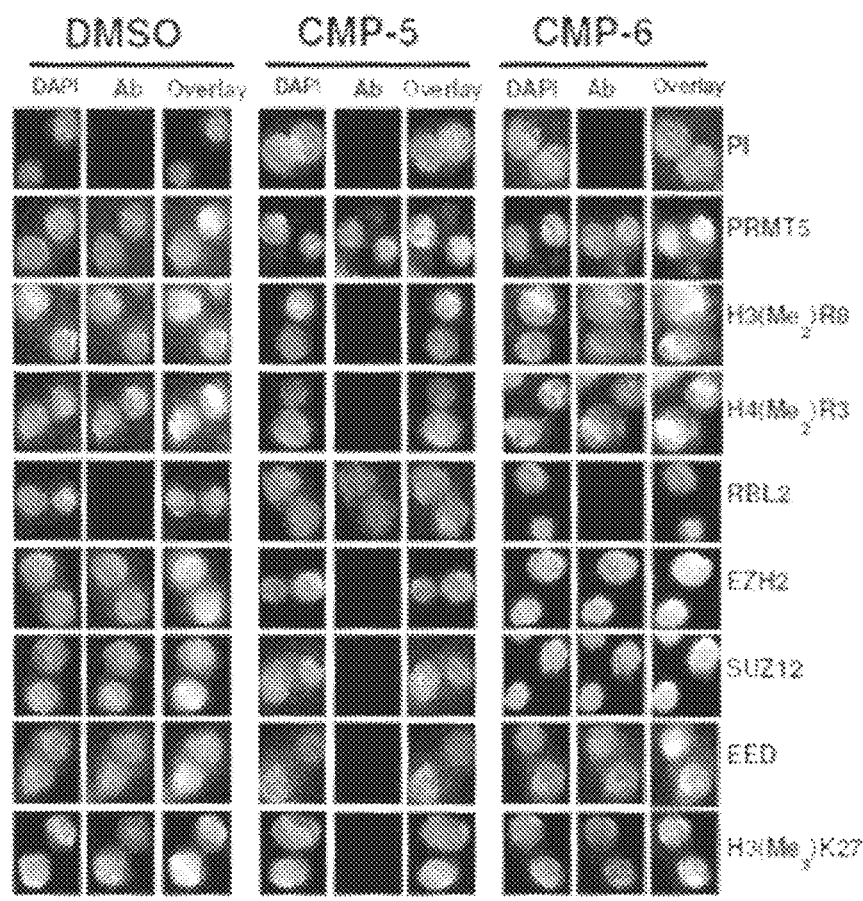

Compound HLCL-S leads to restoration of RBL2 protein expression and abolishes PRC2 induced epigenetic mark H2(Me3)K27 in NHL cell lines. The PRC2 proteins EZH2, SUZ12 and EED are over-expressed in Jeko, Pfeiffer and SUDHL DLBCL cells. This expression of each PRC2 protein and associated epigenetic mark H2(Me$_3$)K27 is silenced after PRMT5 enzyme inhibition by the selective inhibitor HLCL-5 (FIG. 20). Without wishing to be bound by theory, this data suggests that inhibition of PRMT5 may lead to changes in PRC2 protein expression and the PRC2 driven epigenetic mark lysine methylation.

b. Components of PRC2 Complex are E2F Target Genes

Figure 21:
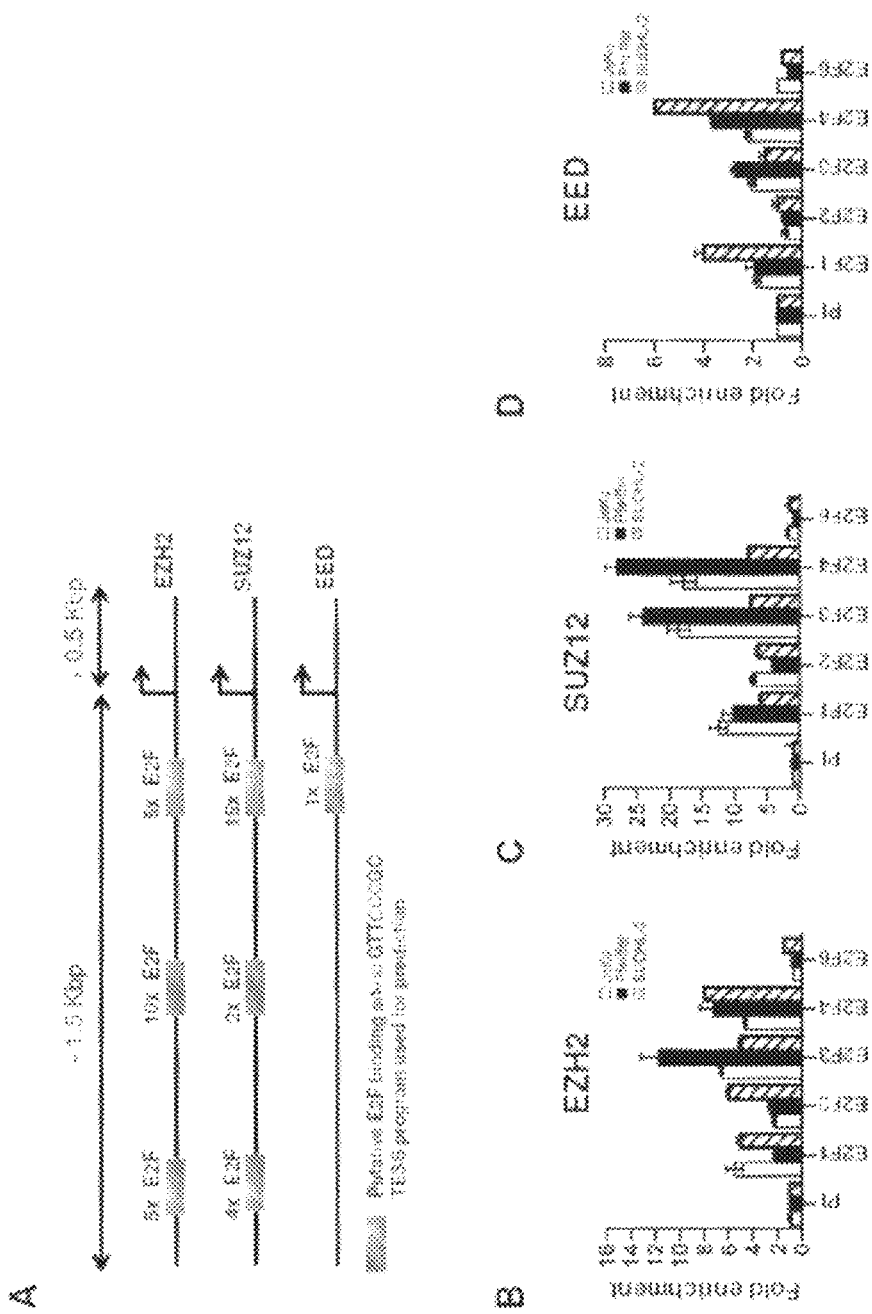
FIG. 21 shows representative data pertaining to the components of the PRC2 complex.

Search for putative E2F binding sites was performed using TESS program. FIG. 21A shows a schematic diagram of the 1.5 kb region upstream initiation of transcription site of EZH2, SUZ12 and EED genes. Chromatin immunoprecipitation (ChIP) experiments using antibodies specific for E2F1, E2F2, E2F3, E2F4 and E2F6 were used to show that E2F1, 2, 3, and 4 were enriched on all promoters in Jeko, Pfeifer and SUDHL2 cells (FIG. 21B-D). Without wishing to be bound by theory, this data suggests that inhibition of PRMT5 may lead to changes in non-PRMT5 target genes by altering the epigenome.

c. PRMT5 Inhibition Promotes RB1, RBL2 AND HDAC2 Recruitment to PRC2 Promoters.

Figure 22:
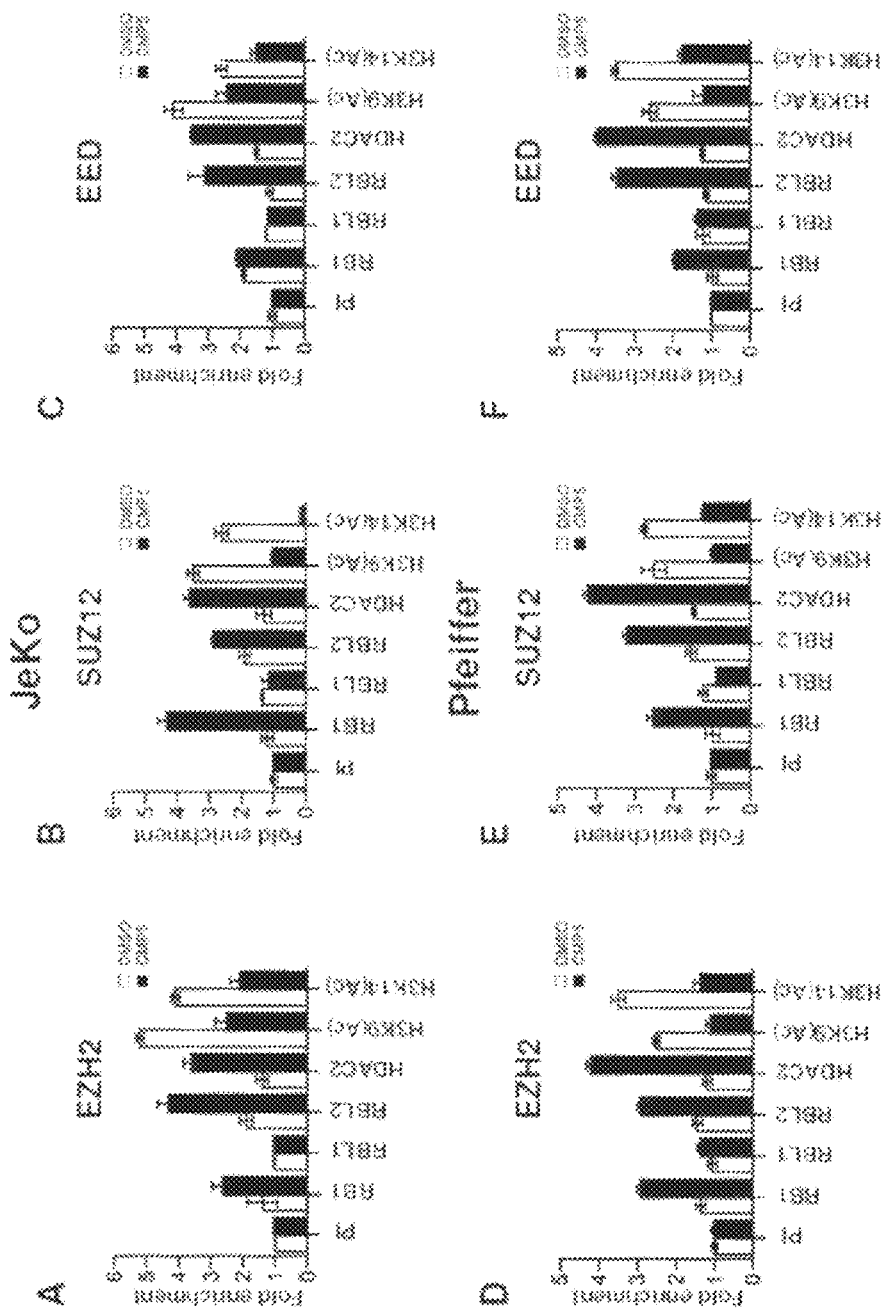
FIG. 22 shows representative data demonstrating that PRMT5 inhibition enhances RB1, RBL2, and HDAC2 recruitment to the promoter region of EZH2, SUZ12, and EED. Epigenetic marks associated with active transcription are lost with PRMT5 inhibition.

Treatment of pre CC lymphoma Jeko (MCL, FIG. 22A-C), GC lymphoma line Pfeifer (FIG. 22D-F) and post GC line SUDHL2 (FIG. 23A-C) promotes recruitment of RB1, RBL2, and HDAC2 to the promoters of PRC2 genes. This recruitment leads to loss of H3K9 acetylation and H3K14 acetylation. Without wishing to be bound by theory, this data suggests that inhibition of PRMT5 may lead to changes in lysine acetylation.

d. PRMT5 Inhibition Reactivates the RB/E2F Pathway to Silence PRC2 Target Genes in NHL Cell Lines.

Figure 23:
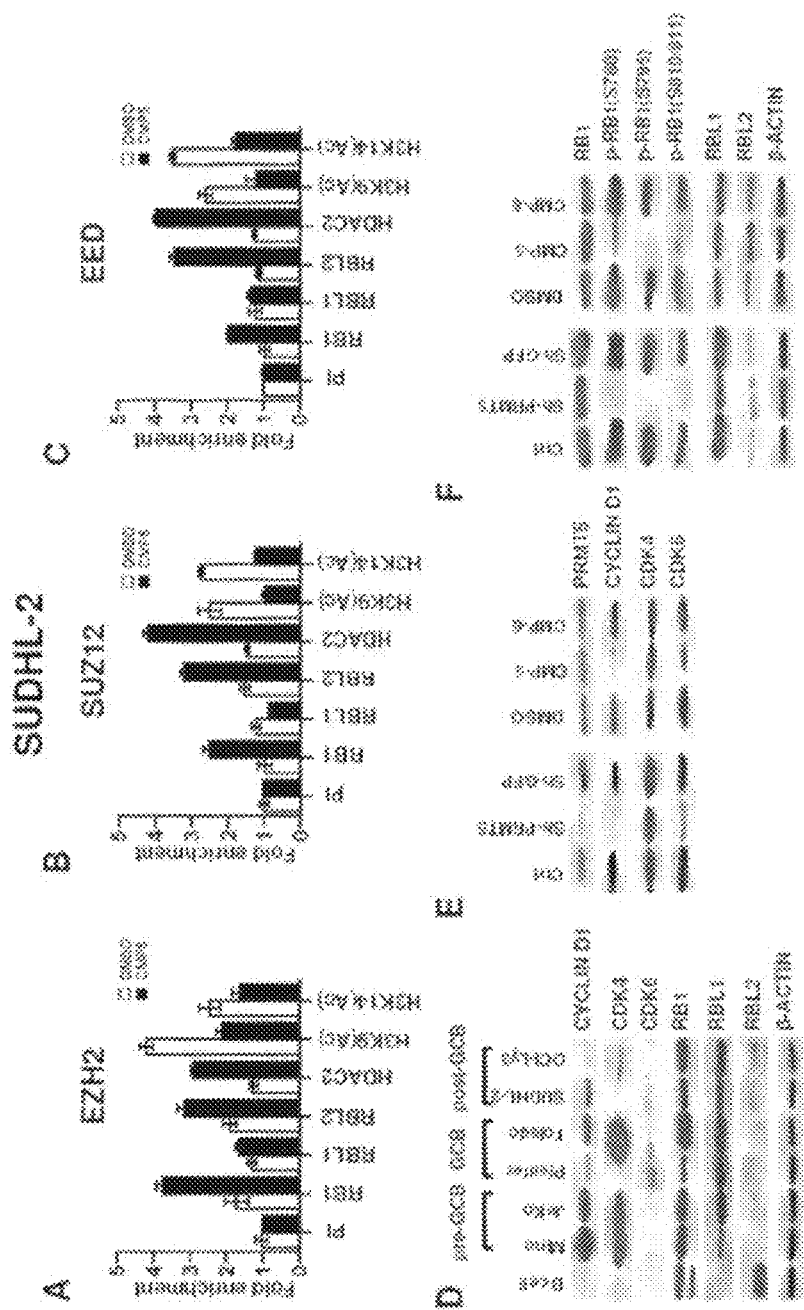
FIG. 23 shows representative data demonstrating that PRMT5 inhibition reactivates the RB/E2F pathway, which in turn silences PRC2 in NHL cells.

Referring to FIG. 23D-F, protein expression profile in pre-GC, GC and post-GC lymphoma cells are shown for the indicated proteins (FIG. 23D). PRMT5 knockdown (with shRNA) or PRMT5 inhibition with HLCL-5 results in reduced CYCLIN D1 protein levels (FIG. 23E). Depletion of CYCLIN D1 following PRMT5 inhibition leads to loss of phosphorylation of the RB1 tumor suppressor gene product and repression of the RBL2 protein (FIG. 23F). Without wishing to be bound by theory, this may indicate that PRMT5 inhibition leads to restoration of the RB pathway.

Figure 24:
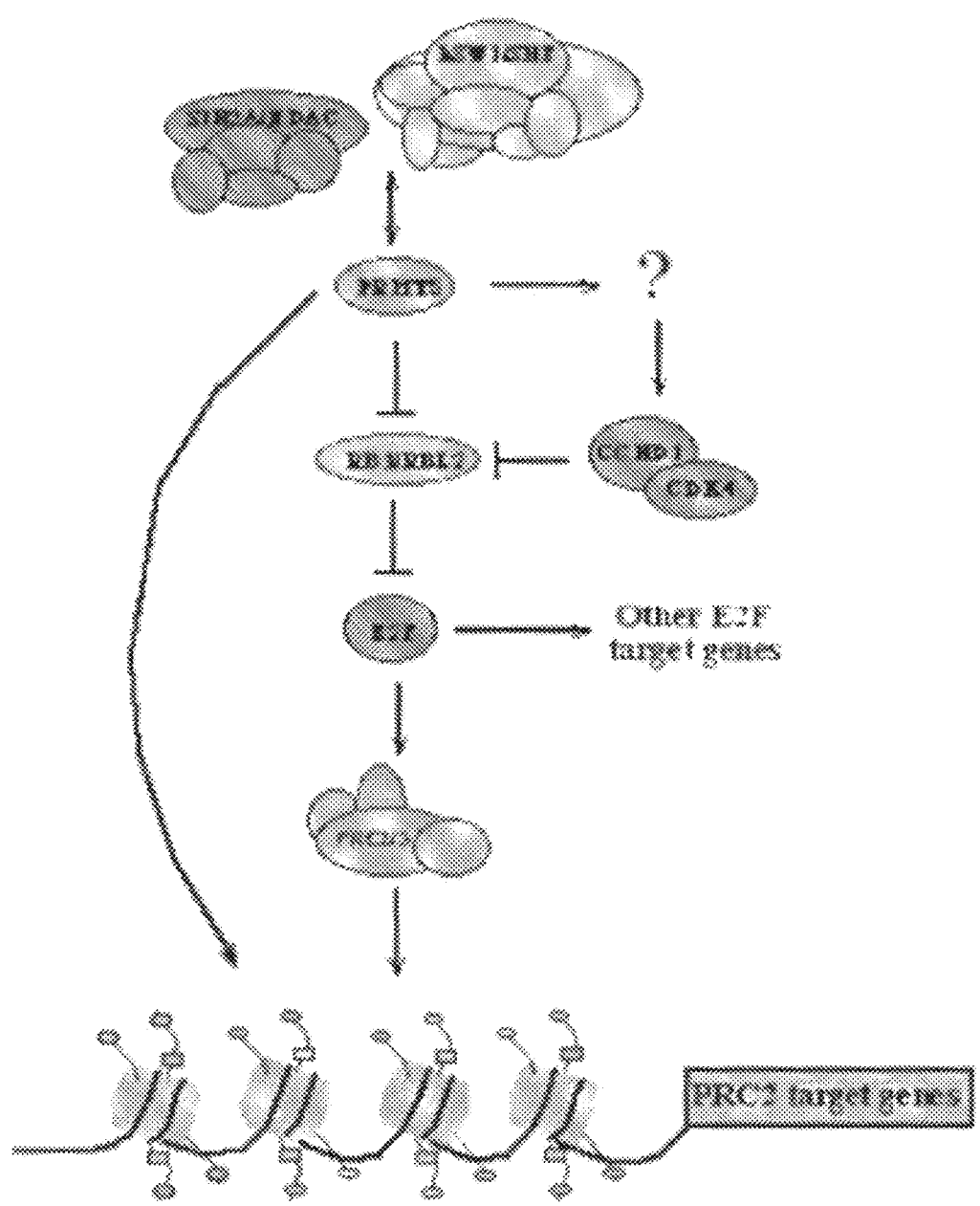
FIG. 24 shows a cartoon illustration of the role of PRMT5 in the RB/E2F pathway. By inhibiting PRMT5, both repressive epigenetic marks on arginine and lysine are affected.

PRMT5 controls PRC2 via restoration of the RB/E2F pathway. FIG. 24 shows a schematic of how PRMT5 inhibitors affect one of the most common pathways that is dysregulated in cancer.

e. Role of PRMT5 Expression in Squamous Cell Carcinoma of the Head and Neck

PRMT-5 expression in oropharynx squamous cell carcinoma patients can be predictive of overall survival and inversely related to p16 status. PRMT5 (type II) has been found to be important in cell signaling, RNA processing, gene transcription, and cellular transport. Alterations in PRMT5 activity and expression have been associated with tumorigenesis in some solid tumors. The role of PRMT5 expression in squamous cell carcinoma of the head and neck has not yet been previously investigated.

Figure 25:
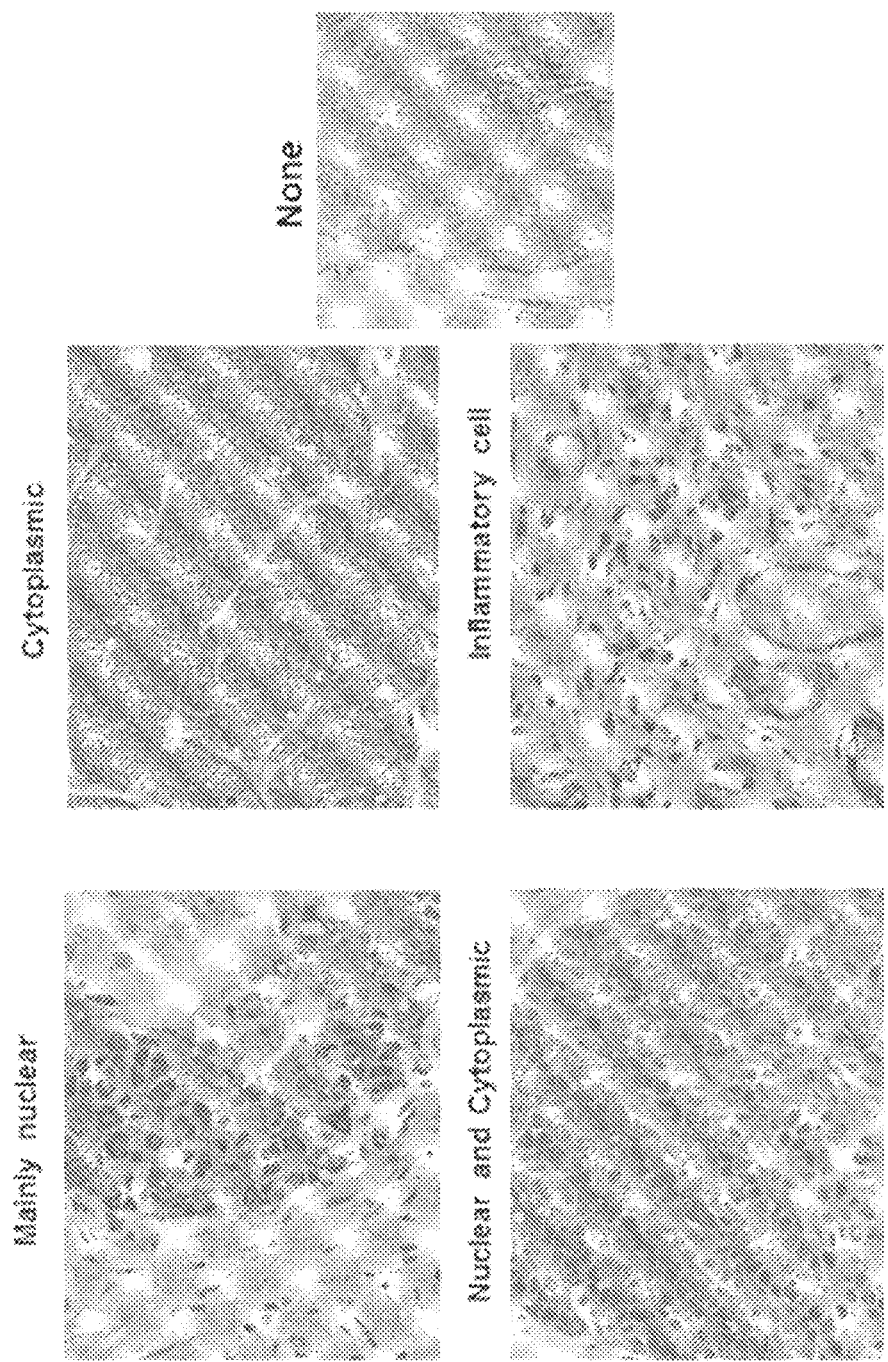
FIG. 25 shows representative data illustrating the staining patterns of PRMT5 expression for oropharynx squamous cell carcinoma patients.
Figure 26:
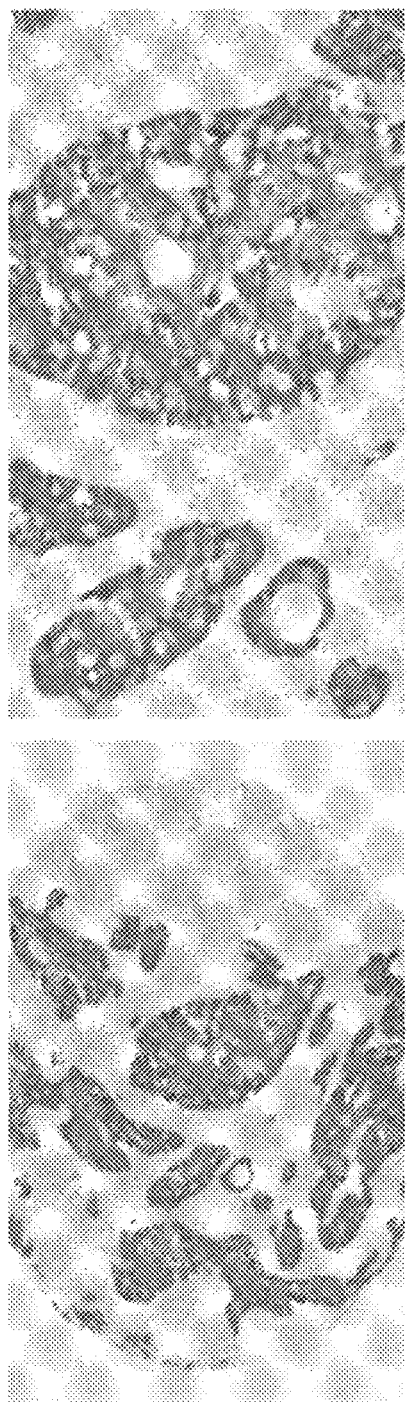
FIG. 26 shows representative data illustrating the staining patterns of PRMT5 and p16 for oropharynx squamous cell carcinoma patients.

Tissue was obtained from Tissue microarray-237 oropharyngeal cancer patients treated at Ohio State University from 2002-2008. Staining for PRMT5 was performed. PRMT5 stain intensity was scored from 0-3 (none-high) within the cell nucleus, cytoplasm and surrounding inflammatory cells. P16 staining was performed (positive or negative). Retrospective chart review was used to establish a database of the patients' clinical information. Including smoking history, TNM staging, and patient survival. Stained tissue is shown in FIG. 25. Greater intensity=improved survival (Hazard ratio: 0.681 (p=0.0412)). Patients with negative p16 staining had a significantly higher average PRMT5 nuclear stain intensity (p=0.0170), and poorer survival (FIG. 26).

With respect to PRMT5 and smoking status (Two-Sample t-test), patients with a >10 pack year smoking history had a significantly higher average nuclear PRMT5 stain intensity than those with ≤10 pack year smoking history (p=0.0129). There was not a significant difference in average cytoplasmic or inflammatory cell PRMT5 stain intensity based on smoking history of > or less than 10 pack years (p=0.2726, p=0.6413, respectively).

With respect to PRMT5 and T and N staging (Kruskal-Wallis test), there was not a significant difference in nuclear, cytoplasmic, or inflammatory cell PRMT5 stain intensity based on T or N stage of disease.

Accordingly, PRMT5 expression and function can play a role in the development and behavior of oropharyngeal squamous cell carcinoma. An inverse relationship exists between nuclear PRMT5 stain intensity and p16 status (a tumor suppressor). Nuclear PRMT5 stain intensity is higher in patients with a >10 pack year smoking history. Nuclear PRMT5 stain intensity in tumors is inversely proportional to patient survival. PRMT5 staining intensity in tumor-infiltrating lymphocytes may indicate that PRMT5 is relevant to tumor immunity. P16 negative squamous cell carcinomas are more aggressive and thus represent an ideal disease to treat with PRMT5 inhibitors.

5. Evaluation of PRMT5 Inhibitors in Acute Myeloid Leukemia (AML)

Acute myeloid leukemia (AML) is the most common type of acute leukemias in adults (Fröhling, S., et al. (2005) *J. Clin. Oncol.* 23, 6285-6295; Estey, E. & Döhner, H. (2005) *Lancet* 368, 1894-1907; McKenzie, S. B. (2005) *Clin. Lab. Sci.* 18, 28-37). Although the incidence and mortality rate associated with AML increases by age, the overall long-term survival achieved by AML patients remains as low as only ~35-40% (Estey, E. & Döhner, H. (2005) *Lancet* 368, 1894-1907; Dombret, H. (2011) *Blood* 118, 5366-5367). The major complexity in treating AML is the highly heterogeneous nature of this disease genetically, epigenetically and clinically, which further highlights the significance of using prognostic clinical, cytogenetic and molecular factors to guide the selection of the type and the intensity of treatment (Marcucci, G., et al. (2011) *J. Clin. Oncol.* 29, 475-486; Döhner, H., et al. (2010) *Blood* 115, 453-474).

Approximately 30% of AML cases carry an Internal Tandem Duplication mutation of the FMS-like tyrosine kinase 3 gene (FLT3-ITD) that results in constitutive activation of the receptor tyrosine kinase (Kindler, T., et al. (2010) *Blood* 116, 5089-5102; Weisberg, E., et al. (2010) *Oncogene* 29, 5120-5134), and is associated with worse clinical outcome by supporting leukemia cell proliferation and survival (Stirewalt, D. L and Radich, J. P. (2003) *Nat Rev. Cancer* 3, 650-665). In addition, over-expression of wild-type FLT3 also carries a negative clinical significance. Targeting of FLT3 kinase activity with small molecules has provided interesting results, but this approach remains far from being curative (Weisberg, E., et al. (2009) *Drug Resist. Updat.* 12, 81-89). In addition to a relative lack of specificity of the targeting compounds for FLT3, numerous mechanisms of resistance have been discovered (Weisberg. E., et al. (2010) *Oncogene* 29, 5120-5134). It has been previously hypothesized that interfering with mechanisms of FLT3 transcription along with the enzymatic inhibition may produce a synergistic anti-leukemia activity (Blum, W., et al. (2012) *Blood* 119, 6025-6031). However, to effectively pursue this approach, it is necessary to understand the mechanisms that regulate the expression of this gene.

The requirement for SP1 transcription factor in dynamically activating the transcription of oncogenic tyrosine kinases KIT and FLT3 has been previously demonstrated (Blum, W., et al. (2012) *Blood* 119, 6025-6031; Liu, S., et al. (2010) *Cancer Cell* 17, 333-347). Without wishing to be bound by theory, this data strongly indicates that localization of SP1 onto the promoter region of FLT3, alone or in complex with p65 subunit of NFκB, is both essential and potent in up-regulating FLT3 expression (Blum, W., et al. (2012) *Blood* 119, 6025-6031). Herein it is shown that Protein Arginine Methyltransferase 5 (PRMT5) also participates in FLT3 regulation and that inhibition of the epigenetic activity of this enzyme leads to suppression of FLT3 transcription. PRMTs catalyze transfer of one or two methyl groups to the guanidine nitrogen atoms of arginine residues of peptides (Pal, S. (2007) 306-315, doi: 10.1002/JCP; Bedford, M. T. (2007) *J. Cell Sci.* 120, 4243-4246). The PRMT family of enzymes, with 11 known members so far, is categorized as type I and type II enzymes. Type I PRMTs (e.g., PRMT1, 3, 4, 6 and 8) are responsible for asymmetric dimethylation (aDMA) of arginine residues while type II PRMTs (e.g., PRMT5, 7 and 9) catalyze symmetric dimethylation (sDMA) events. The intermediate mono-methylation (MMA) event is carried out by both types of PRMTs (Pal, S. (2007) 306-315, doi: 10.1002/JCP; Bedford, M. T. (2007) *J. Cell Sc.* 120, 4243-4246).

PRMT5, with multiple substrates like histones H3, H4 and H2A and proteins P53, MBD2 (Jansson, M., et al. (2008) *Nat. Cell Biol.* 10, 1431-1439; Guezennec, X. i.e., et al. (2006) doi: 10.1128/MCB.26.3.843) has gained attention as an emerging regulator of protein function in cancer (Bedford, M. T. and Richard, S. (2005) *Mol. Cell* 18, 263-272). The post-translational changes induced by PRMT5 have a significant impact on cell growth and proliferation (Scoumanne, A, et al. (2009) *Nucleic Acid Res.* 37, 4965-4976). Over-expression of PRMT5 has been reported in hematologic and solid malignancies (mantle cell lymphoma (Pal, S., et al. (2007) *EMBO J.* 26, 3558-3569; Wang, L, et al. (2008) *Mol. Cell Biol.* 28, 6262-6277), lung and bladder cancer (Wei, H., et al. (2013) *Proc. Natl. Acad Sci. U.S.A.* 110, 13516-13521), gastric cancer (Kim, J., et al. (2005) *Cancer Res.* 11, 473-482), and germ cell tumors (type II testicular germ cell tumors (TOC), i.e. seminomas) (Eckert, D., et al. (2008) *BMC Dev. Biol.* 8, 106), and represents a promising therapeutic target. More importantly, in context of hematologic neoplasms it was shown that mutant constitutively active tyrosine kinase, JAK2V617F can interact with PRMT5 and regulate activity of this enzyme via posttranslational phosphorylation in myeloproliferative disorders (Liu, F., et al. (2011) *Cancer Cell* 19, 283-294).

Herein it is demonstrated that PRMT5 inhibition has potent adverse effects on AML cell growth and survival. Without wishing to be bound by theory, this data suggests that PRMT5 is involved in up-regulating FLT3 pathway by interacting with key regulators of FLT3, including SP1 and miR-29b, and consequently modulating the activity of this oncogenic tyrosine kinase. In AML cells, PRMT5 up-regulates FLT3 levels by enhancing SP1 expression and activity through suppressing miR-29b which is carried out by H4R3, major PRMT5 methylation mark. Without wishing to be bound by theory, these data indicate that PRMT5 functions in up-regulating FLT3 in AML and suggest that FLT3-ITD AML patients may benefit from targeting PRMT5 especially cases with resistance to FLT3-ITD inhibitors.

a. Up-Regulated PRMT5 Contributes to Leukemia Growth

Figure 27A:
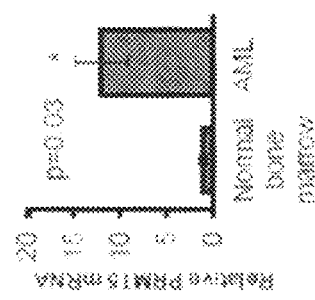
FIG. 27A-C shows representative data pertaining to the transcript levels of PRMT5 (27A) and the proliferation rate of AML cells overexpressing PRMT5 lentivirus and empty lentivector (27B and 27C).

Previous studies have demonstrated a role for PRMT5 in supporting cancer cell growth (Gu, Z., et al. (2012) *Biochem. J.* 446, 235-241; Bao, X. et al. (2013) *J. Histochem. Cytochem.* 61, 206-217; Nicholas, C., et al. (2013) *PloS One* 8, 074710). Herein, PRMT5 was found to be expressed at relatively higher levels in the AML cells (primary patients' samples; n=6 and patient-derived cell lines; n=7) compared to normal bone marrow (n=4) (P=0.03) (FIG. 27A). PRMT5 was ectopically expressed in AML cell lines; MV4-11 (FLT3-ITD) and THP-1 (FLT3-WT) using Lentivirus (Lenti-PRMT5), and compared with empty vector-transfected (Lenti-EV) negative controls. Up-regulation of PRMT5 was confirmed by Western blotting (FIG. 23B inset). PRMT5 up-regulation resulted in significantly enhanced AML cell proliferation potential as measured by the growth curve assay and colony forming assay as disclosed herein above. More than 35% increase in proliferation rate (growth curve assay, FIG. 27B) and >1.8 fold increase in AML cell survival and colony forming ability (FIGS. 28A and 28B) was documented in PRMT5-overexpressing cells. In contrast, knockdown of PRMT5 significantly hindered AML cell growth, as evaluated by the colony forming assay. To this end, MV4-11 and THP-1 cell lines and two patient samples (#1; FLT3-ITD and #2; FLT3-WT) were treated with either scrambled control (sc) or RNA interference (small interfering RNA (siRNA) or short hairpin RNA (shRNA)) against PRMT5. Significantly fewer number of colonies were formed by PRMT5-depleted cells than control samples (>1.6 fold, P=0.01) (FIG. 29A-D). Without wishing to be bound by theory, these results suggest a positive contribution of PRMT5 towards AML cell growth.

Referring to FIG. 27A, transcript levels of PRMT5 were measured by qRT-PCR analysis (* is p<0.05 and ** is p<0.005). Significance was calculated using i test and error bars indicate SEM.

Figure 27C:
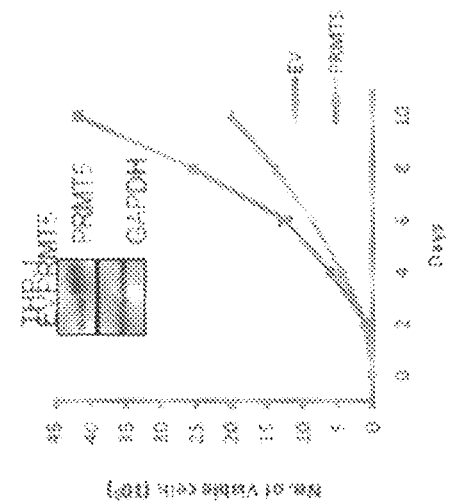
Figure 27B:
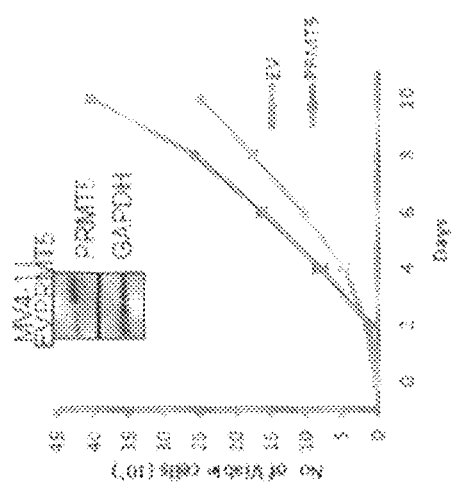

Referring to FIGS. 27B and 27C, a growth curve assay comparing proliferation rate of AML cells overexpressing PRMT5 lentivirus and empty lentivector is illustrated. Cells were counted for extended period of time (>10 days). Each treatment was set up in triplicates. Western blotting was used to confirm PRMT5 overexpression in Lenti-PRMT5 treated cells compared to Lenti-EV while GAPDH levels served as loading control.

Figure 28A:
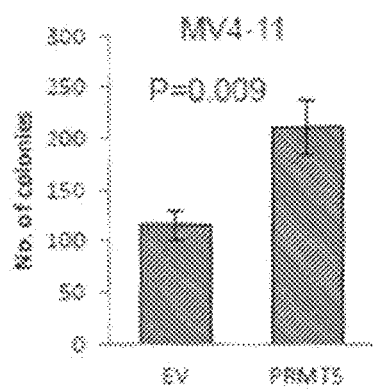
FIG. 28 shows representative data pertaining to the proliferation potential of AML cells transuded with Lenti-PRMT5 versus empty vector (EV-Lenti) control.
Figure 28B:
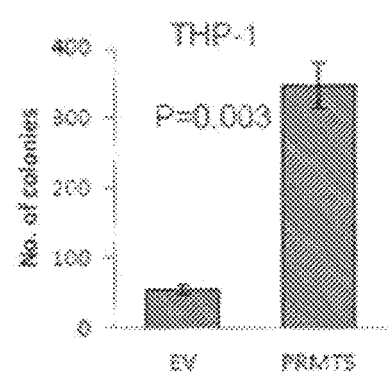

Referring to FIGS. 28A and 28B, a colony formation assay comparing proliferation potential of AML cells transuded with Lenti-PRMT5 or empty vector (EV-Lenti) control is illustrated. Colonies were counted 10-14 days after plating. Each assay was repeated in three independent experiments per treatment.

Referring to FIG. 29A-D, a colony formation assay was used to measure proliferation rate in AML cell lines and patient primary blasts transfected with either PRMT5 RNA interference (siPRMT5 or shPRMT5) or scrambled control (sc). Tranfections were carried out in triplicates and western blotting was used to confirm sufficient downregulation of PRMT5 in the presence of siPRMT5 or shPRMT5.

Figure 30:
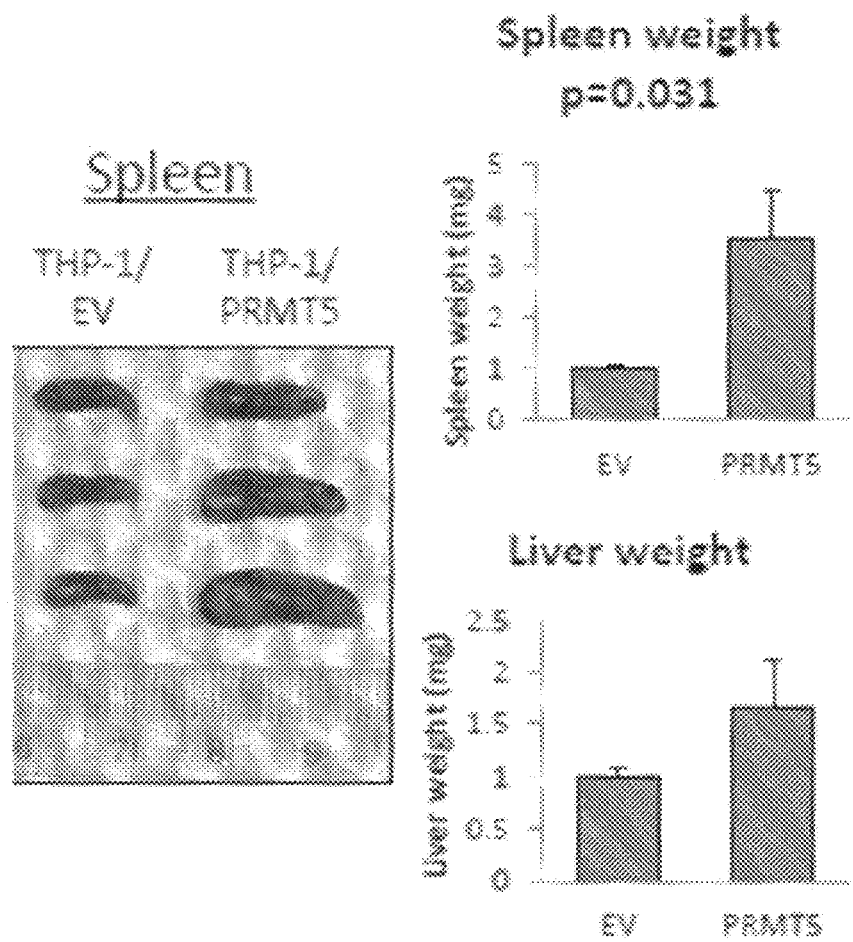
FIG. 30 shows representative data pertaining to the effect of PRMT5-over-expression on mice spleen and liver.
Figure 31A:
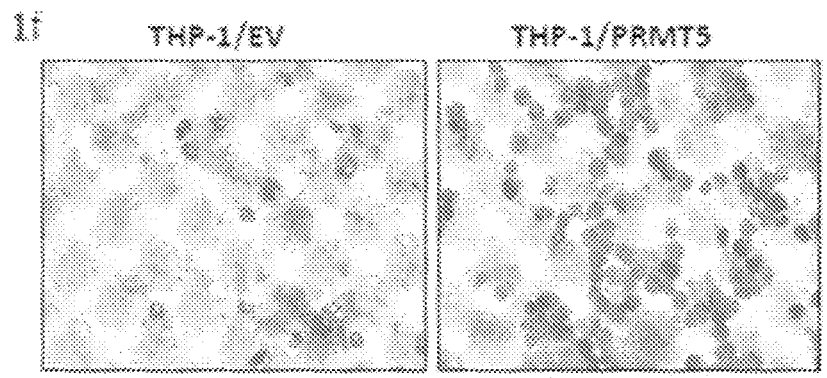
FIG. 31 shows representative Wright-Giemsa staining indicating the presence of blasts in PRMT5 over-expressing mice.
Figure 31B:
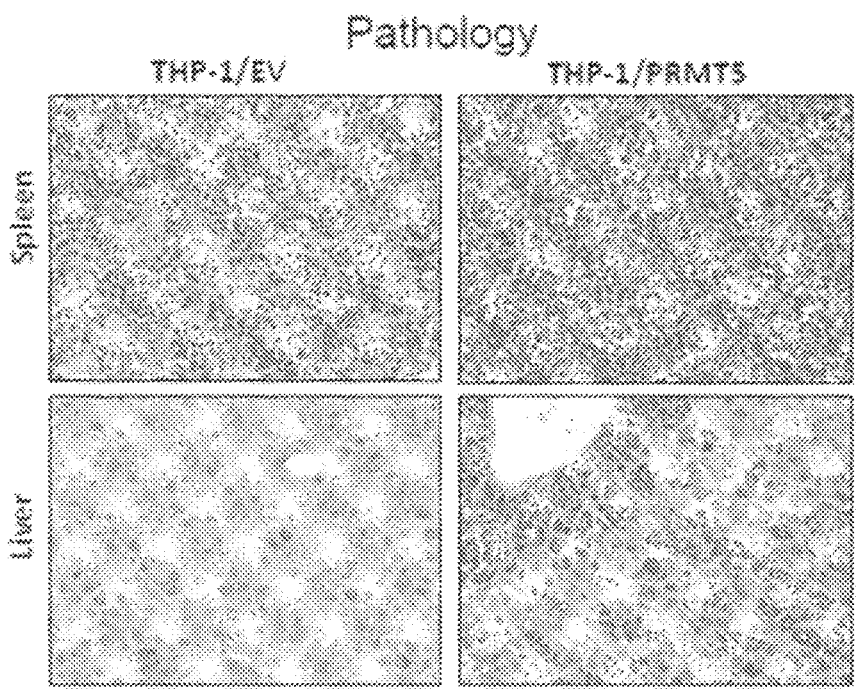
Figure 32:
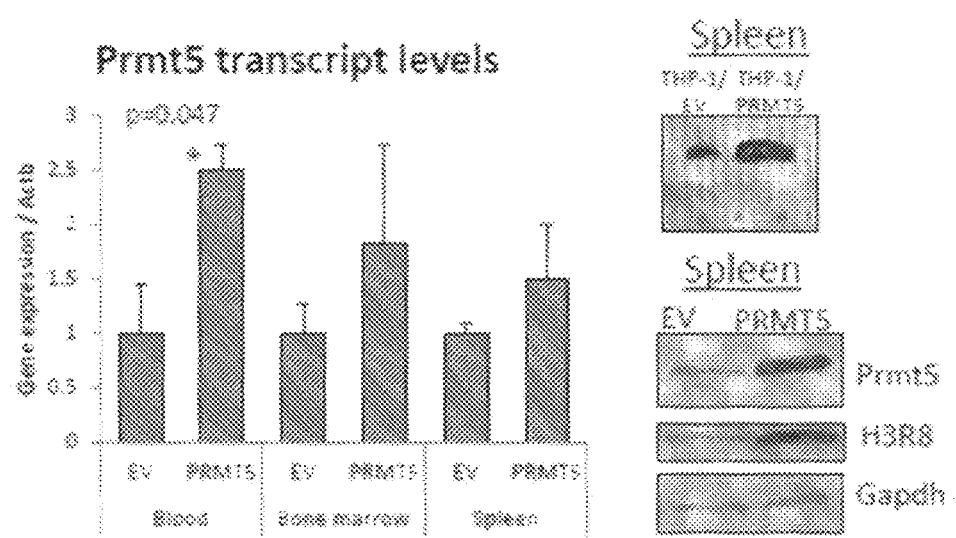
FIG. 32 shows representative data from a qRT-PCR analysis demonstrating the up-regulation of PRMT5 in representative spleen samples.

To examine the impact of PRMT5 on leukemia growth in vivo, NOD/SCID/Gamma (NSG) mice were injected, through tail vein, with THP-1 ($1 \times 10^6$) cells which were stably transduced with either Lenti-PRMT5 (THP-1/PRMT5) to overexpress PRMT5 or Lenti-EV (THP-1/EV) as negative control. Ten weeks post injection (engraftment), three mice from each group were sacrificed and samples/organs were taken for further analyses. Mice with THP-1/PRMT5 had significantly larger spleens (p=0.03) and livers (p=0.031) and a higher number of circulating blasts than THP-1/EV control mice (FIGS. 30, 31A, and 31B). Higher PRMT5 expression was confirmed in RNA from bone marrow, spleen and blood of THP-1/PRMT5 engrafted animals (FIG. 32). In addition, PRMT5 protein levels and its specific methylation mark, H3R8, were significantly higher in the THP-1/PRMT5 than control animals (FIG. 32). Additionally, preliminary data show NSG mice engrafted with THP-1/PRMT5 cells had a lower survival rate than those engrafted with THP-1/EV cells. Without wishing to be bound by theory, these data support PRMT5 involvement in enhancing leukemia growth and highlight the importance of this protein in modulating leukemia cell function.

Referring to FIG. 30, spleens were harvested from mica engrafted with THP-1/PRMT5 to over-express PRMT5 and THP-1/EV as a negative control $1 \times 10^6$ cells were injected per mouse and animals were euthanized after 10 weeks. Enlarged spleens were observed in mice over-expressing PRMT5. The bar graphs represent a significant increase in size (depicted as weight) of the spleens and livers taken from PRMT5 over-expressing animals compared to negative control mice.

Referring to FIGS. 31A and 31B, Wright-Giemsa staining of the blood sowing blast infiltration in blood of THP-1/PRMT5 engrafted mice is illustrated. Staining was carried out after red cell lysis and the presence, of normal differentiated white blood cells in normal animals; dominant presence of blasts in PRMT5 over-expressing mice is clearly distinguishable.

Referring to FIG. 32, a qRT-PCR analysis depicting PRMT5 transcript up-regulation in THP-1/PRMT5S mice vs. THP-1/EV animals is shown. The difference was statistically significant in spleen samples but, nevertheless, elevated in the PRMT5 over-expressing model. Western blotting confirmed apparent up-regulation of PRMT5 and its epigenetic mark, symmetrically dimethylated H3 (H3R5me2), in representative spleen sample from THP-1/PRMT5 mouse compared to THP-1/EV normal mouse. Immunostaining was done using anti-PRMT5 antibody followed by stripping and re-staining with anti-H3R8 antibody while Gapdh levels served as internal loading control.

b. Anti-Leukemic Activity of PRMT5 Inhibition in AML Cells

Figure 33A:
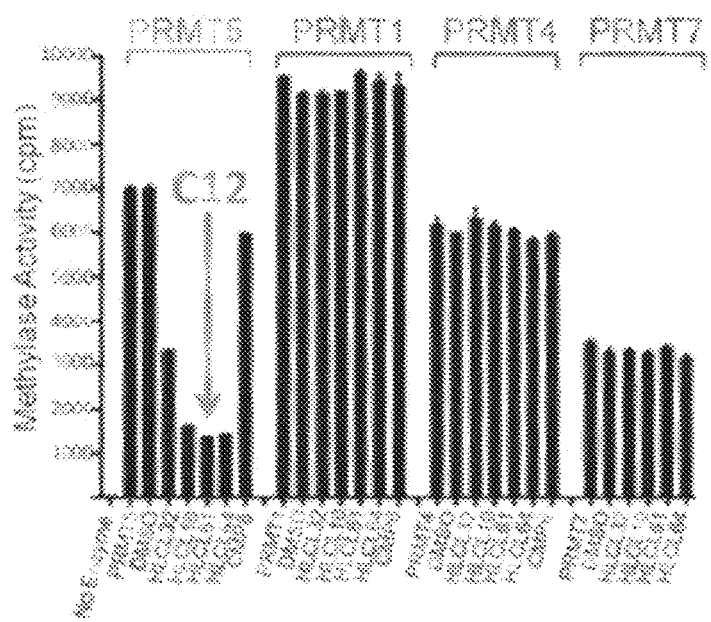
FIG. 33A shows the effect of PRMT inhibitors and different PRMT enzymes on methylase activity.
Figure 33B:
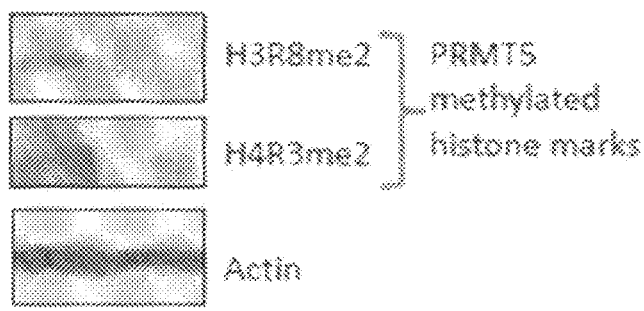
FIG. 33B shows downregulation of symmetrically di-methylated H3 (H3R8me2) and H4 (H4R3me2) in the presence of CMDP 12.

To test whether inhibition of the enzyme activity of PRMT5 may represent a viable therapeutic strategy hi AML, a first in class single molecule inhibitor of PRMT5 labeled C12 (HLCL61), which was developed at the Ohio State University by in silico screening of a model of human PRMT5 catalytic site, was used. C12 was one of the eight compounds selected for biological validation from the initial 10,000 compounds identified in the screening. This compound is designed to dock into the catalytic domain and block the interaction between the cofactor S-Adenosyl methionine (SAM) methyl-donor and arginine substrate pocket. Using an in vitro enzyme assay to measure methylase activity, C12 was determined to be the most potent of these inhibitors (FIG. 33A). Furthermore, selectivity of C12 in targeting PRMT5 was shown by its ineffectiveness on other type I PRMTs: PRMT1 and PRMT4 as well as the other type II PRMT; PRMT7 (FIG. 33A). C12 was also most effective in methylation inhibition of histones H3 and H4 in AML samples (FIG. 33B).

Figure 34B:
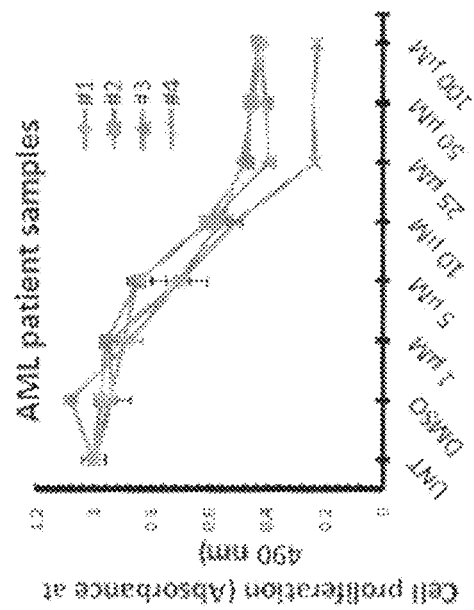
FIG. 34 shows representative data pertaining to the proliferation rate of AML cell lines and primary blasts following incubation with HLCL-61 or CMPD 12.
Figure 34A:
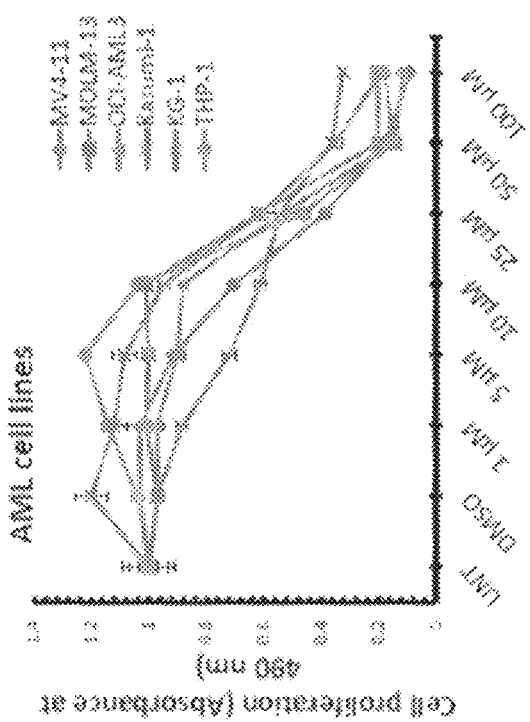
Figure 35D:
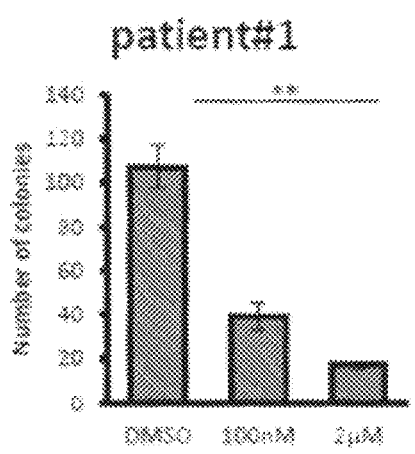
Figure 35E:
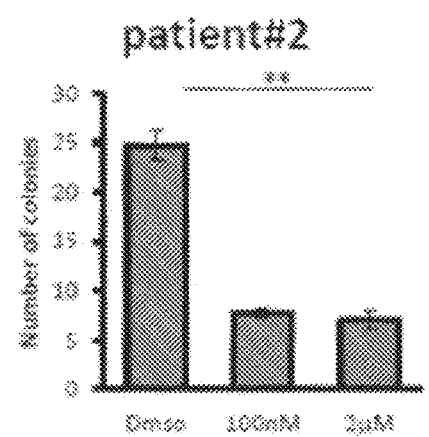
Figure 36:
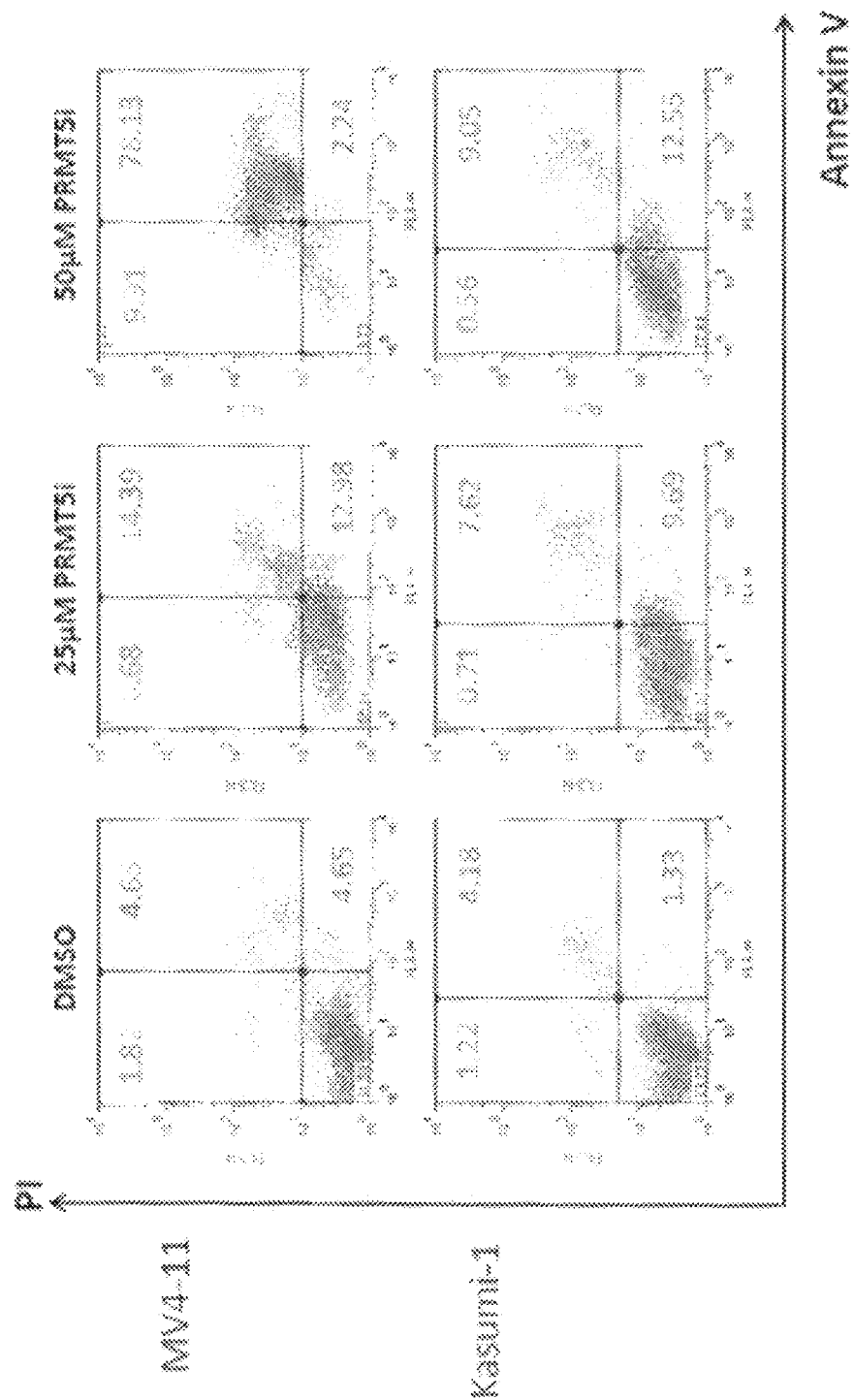
FIG. 36 shows representative data pertaining to the effect of PRMT5 inhibitors on programmed cell death.
Figure 37:
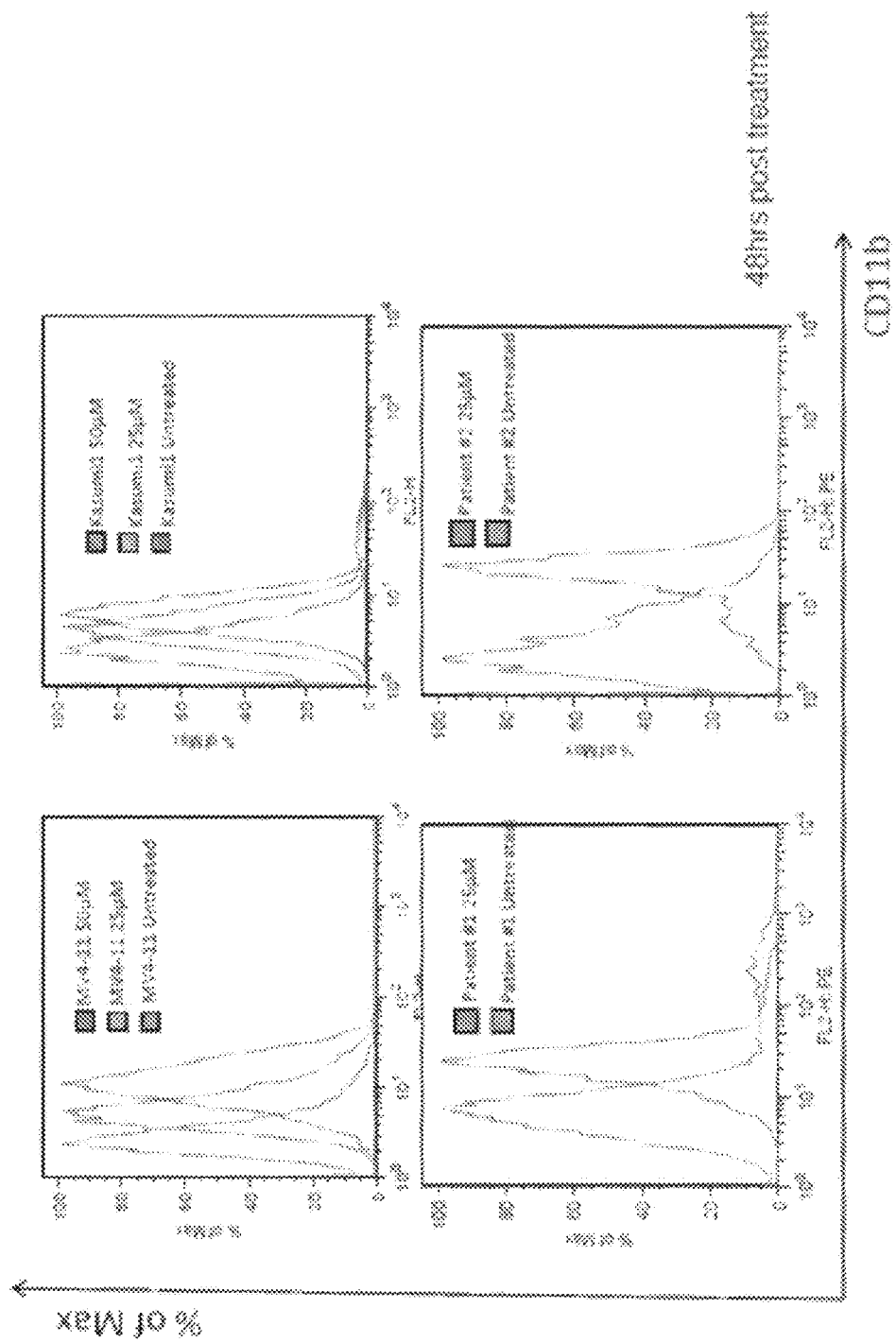
FIG. 37 shows representative data pertaining to induction of differentiation in AML cell lines and patient samples treated with CMPD 12 for 48 h.
Figure 39A:
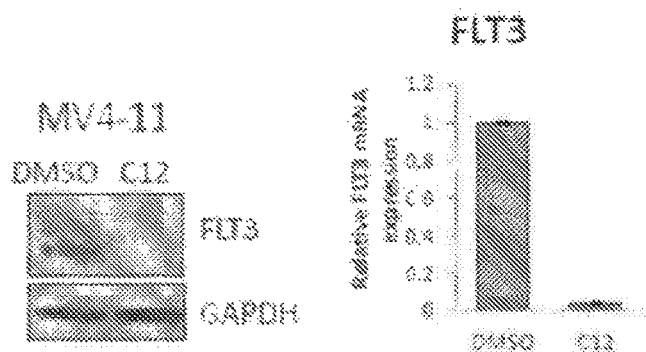
FIG. 39A-F show representative data pertaining to the inhibition of PRMT5 in various cell lines.
Figure 39B:
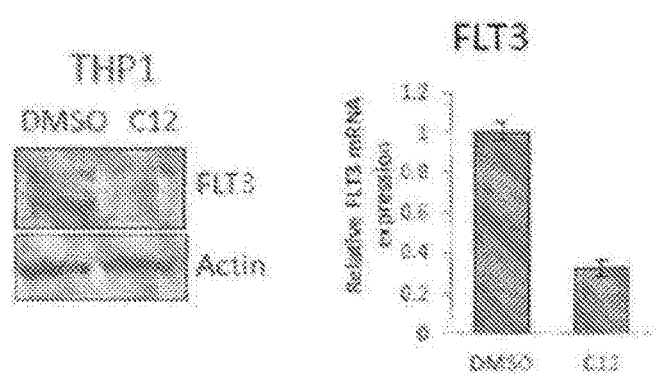
Figure 39C:
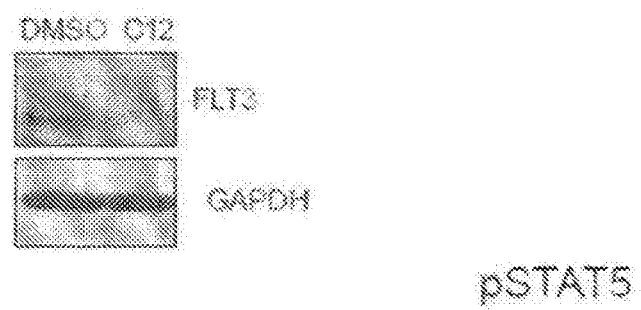
Figure 39D:
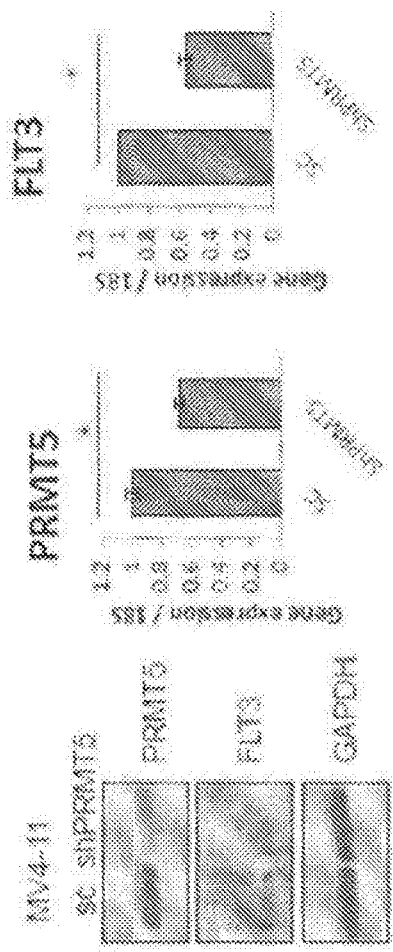
Figure 39E:
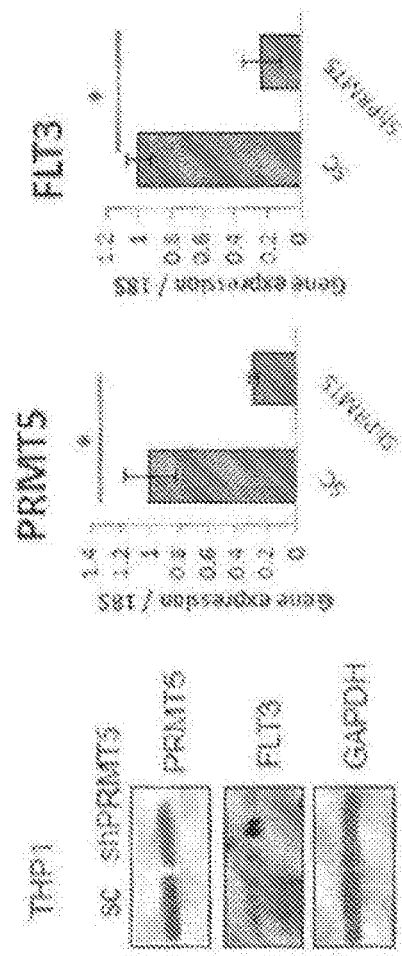
Figure 39F:
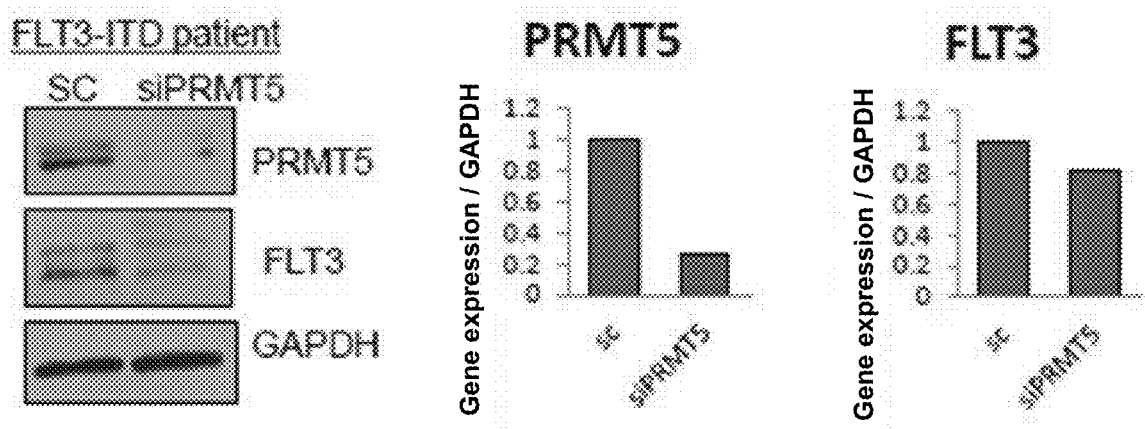

Treatment of AML cell lines and primary patients' blasts with C12 resulted in dose-dependent (1 to 100 µM) inhibition of cell proliferation, measured by MTS assay (FIGS. 34A and 34B, and Tables 5 and 6). At 48 h post treatment, IC50 values were between 21-21.46 µM for cell lines and 3.98-8.72 M for patient samples. The colony forming assay also demonstrated the growth inhibition in AML cell lines MV4-11 (FLT3-TD+), THP-1(FLT3-WT) and Kasumi-1 ($KIT^{mut}$) and AML patient samples #1 FLT3-ITD+, and #2 (FLT3-WT) in the presence of C12. Significantly fewer colonies were formed by AML dell lines and blasts when cultured in the presence of remarkably low doses of C12 (100 nM) when compared to vehicle treated control cells (FIG. 35A-E). PRMT5 inhibition by C12 was also effective in promoting apoptosis and differentiation. A dose-dependent increase in apoptosis was observed in AML cell lines (MV4-11 (FLT3-ITD) and Kasumi-1 ($KIT^{mut}$)) treated with 25 and 50 µM of C12 for 48 hours (FIG. 36). Incubation of AML cells (MV4-11 (FLT3-ITD) and Kasumi-1 ($KIT^{mut}$)) with C12 resulted in a dose-dependent up-regulation of early differentiation marker CD11b (FIG. 37). In primary AML patient samples treatment with 25 µM of C12 resulted in >4 fold Increase in expression of CD11b compared with vehicle-treated cells (FIG. 37), suggesting an additional role for PRMT5 in the differentiation process of hematopoietic cells. Without wishing to be bound theory, these data suggest that clinical inhibition of PRMT5, alone or in combination with chemotherapy, may represent a viable therapeutic target in AML treatment.

TABLE 5

| Cells | Mutation status | $IC_{50}$ µM; 24 h | $IC_{50}$ µM; 48 h | $IC_{50}$ µM; 72 h |
|---|---|---|---|---|
| MV411 | FLT3-ITD+ | 17.9 | 14.12 | 10.94 |
| MOLM-13 | FLT3-ITD+ | — | 21.46 | — |
| OCI-AML3 | NPM1+ | — | 19.06 | — |
| Kasumi-1 | KIT mutation | 6.99 | 7.21 | 5.63 |
| KG-1 | P53 mutation | — | 7.21 | — |
| THP-1 | FLT3-WT | — | 16.74 | — |

TABLE 6

| Cells | Mutation status | $IC_{50}$ µM; 48 h |
|---|---|---|
| Patient #1 | FLT3-ITD+, NPM1+ | 3.98 |
| Patient #2 | FLT3-ITD+ | 8.72 |
| Patient #3 | — | 5.99 |
| Patient #4 | NPM1− | 6.30 |

Referring to FIG. 33A, an in vitro enzyme assay measuring methylase activity in the presence of PRMT5 inhibitor compounds and different PRMT enzymes is shown. CMPD 12, shown by arrow, was most potent in inhibiting enzymatic activity of PRMT5. PRMT5 inhibitors were not effective towards PRMT1, PRMT4 and PRMT7 enzymatic activities. Referring to FIG. 33B, Western blotting in an AML cell line indicates efficient PRMT5 inhibition by showing downregulation of symmetrically dimethylated H3 (H3R8me2) and H4 (H4R3me2) in the presence of C12.

Referring to FIGS. 34A and 34B, a colorimetric MTS assay was used to measure the proliferation rate of AML cell lines and primary blasts from patients after 48 hours incubation with a PRMT5 inhibitor compound (HLCL61 or C12). The dose-dependent decrease in absorbance indirectly correlates with the number of metabolically active live cells. The $IC_{50}$ values represent the concentration of the compound at which 50% cell death was achieved.

Referring to FIG. 35A-E, a colony formation assay measured significantly reduced proliferation potentials of AML cell lines and primary tumor calls in the presence of sublethal doses of CMPD 12. Colonies were counted 10-14 days after plating and each treatment was carried out in triplicates.

Referring to FIG. 36, a flow cytometry analysis of AML cell lines treated with PRMT5 inhibitor and stained for cell surface markers AnnexinV and PI indicates a dose-dependent increase in the percentage of apoptotic and dead cells when compared to DMSO-treated cells. Induction of programmed cell death was stronger in the FLT3-ITD AML cell line MV4-11.

Referring to FIG. 37, a histogram of staining with early differentiation marker CD11b shows induction of differentiation in AML cell lines and patient samples treated with CMPD 12 for 48 hours. The increase in CD11b expression in AML cells lines followed a dose-dependent manner.

c. PRMT5 Up-Regulates FLT3 by Enhancing FLT3 Transcription

Figure 40:
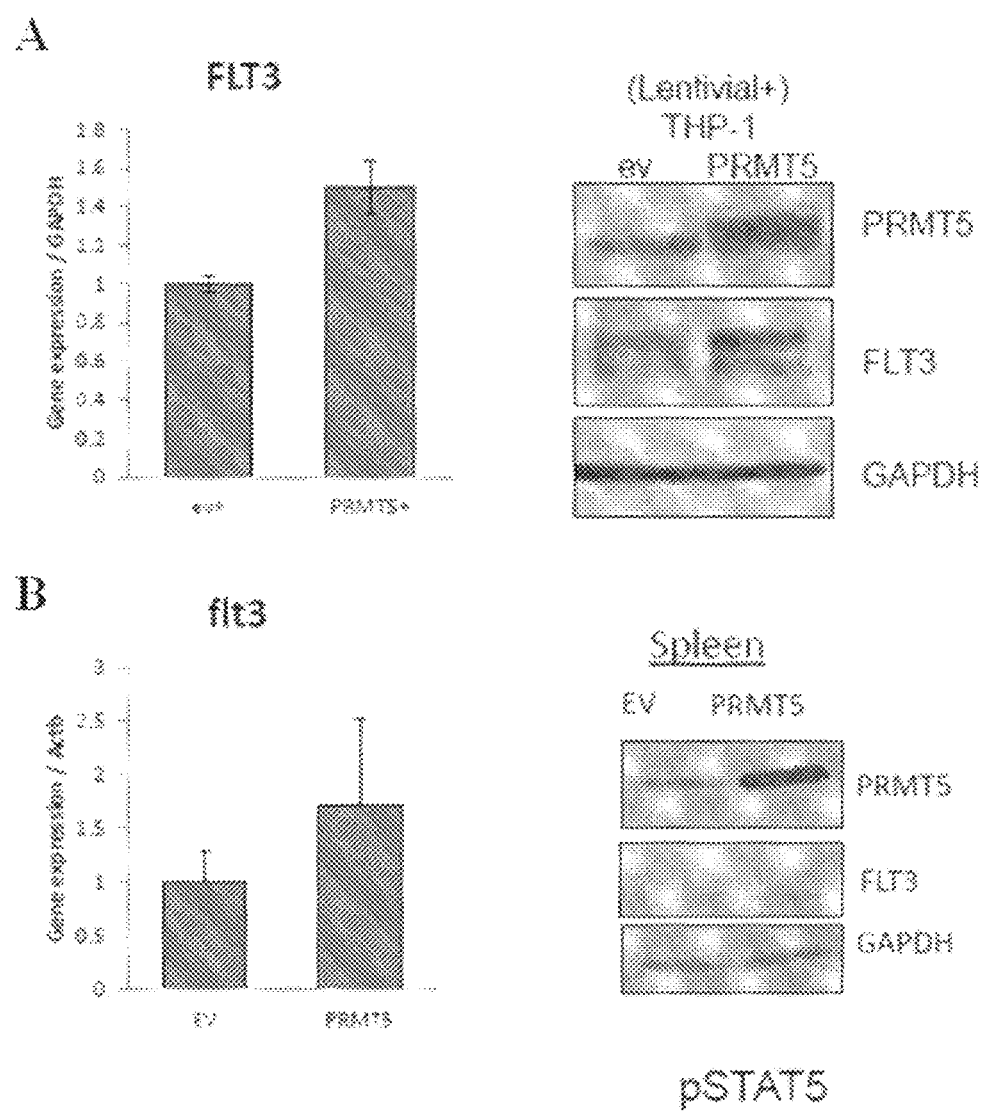
FIG. 40 shows representative data demonstrating the over-expression of PRMT5 sufficiently up-regulates FLT3 transcription and protein expression.

PRMT5 has been reported to interact with, and to be regulated via posttranslational phosphorylation by mutant constitutively active tyrosine kinase; JAK2V617F (Liu, F., et al. (2011) *Cancer Cell* 19, 283-294). In order to better understand PRMT5 mechanism of function in AML, the potential interplay between PRMT5 and oncogenic tyrosine kinase FLT3 was examined. Using Co-Immunoprecipitation (Co-IP) assay, it was found that PRMT5 did not physically interact with wild-type or mutated FLT3 (MV411, FLT3-ITD and THP-1 FLT3-WT) (FIGS. 38A and 38B). Furthermore, FLT3 inhibition by either tyrosine kinase inhibitor (TKI) PKC412 or a specific FLT3 inhibitor (CALBIOCHEM #343020) did not change PRMT5 expression and phosphorylation levels (FIG. 38C). However, inhibition of PRMT5, tested with both C12 and transient transfection with PRMT54-specific siRNA and shRNA, resulted in significant downregulation of wild-type or mutated FLT3 RNA and protein as shown in MV4-11 (FLT3-ITD) and THP-1 (FLT3-WT) cells and FLT3-ITD patient samples (FIG. 39A-F). Activated FLT3 can contribute to malignant phenotype in leukemia blasts by signaling through downstream effector STAT5 (Spiekermann, K., et al. (2003) *Clin. Cancer. Res.* 9, 2140-2150). To further confirm FLT3 downregulation following PRMT5 knockdown, kinase activity was measured by detecting phosphorylated STAT5 levels. FLT3 downregulation via PRMT5 inhibition resulted in reduced phosphorylation of STAT5 (pSTAT5) (FIG. 35A-F). Consistent with these results, overexpression of PRMT5 in THP-1 cells resulted in an evident increase in FLT3 mRNA and protein expression (FIGS. 40A and 40B). THP-1 cells carry wild type FLT3 and low basal levels of endogenous FLT3 expression and activity; these cells therefore represent an appropriate model to investigate and measure the experimentally induced up-regulation of FLT3. Similar observations were recapitulated in the spleen of mice engrafted with THP-1/PRMT5 cells where higher FLT3 levels directly correlated with overexpression of PRMT5 (FIGS. 40A and 40B). Without wishing to be bound by theory, these data suggest a role for PRMT5 in positively regulating FLT3 expression and activity.

Referring to FIGS. 38A and 38B, pulling down with anti-PRMT5 and immunostaining with both anti-PRMT5 and anti-FLT3 reveals no apparent physical association between PRMT5 and FLT3 in AML cell lines. Referring to FIG. 38C, inhibition of FLT3 kinase activity did not influence overall phosphorylated PRMT5 levels. Whole cell lysate was used to pull down phosphorylated tyrosine residues (anti-p-Tyr) in cells treated with FLT3 inhibitor. Phosphorylated ERK1/2 (p-ERK1/2) level was detected as control for p-Tyr IP and effectiveness of kinase inhibitory effects of treatment.

Referring to FIG. 39A-F, inhibition of PRMT5 in AML call lines and patient samples carried out with either C12 or siPRMT5 and shPRMT5, led to significant down-regulation of FLT3 RNA and protein expression. qRT-PCR was used to measure relative PRMT5 mRNA levels, and western blotting was used to detect protein levels of PRMT5, FLT3, and GAPDH, respectively.

Figure 43A:
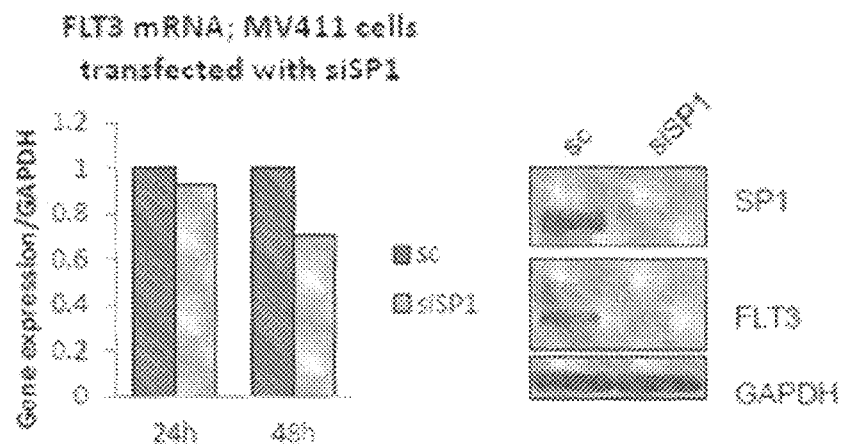
FIGS. 43A and 43B shows representative data pertaining to regulation of FLT3 expression by modulation of SP1. Specifically.
Figure 43B:
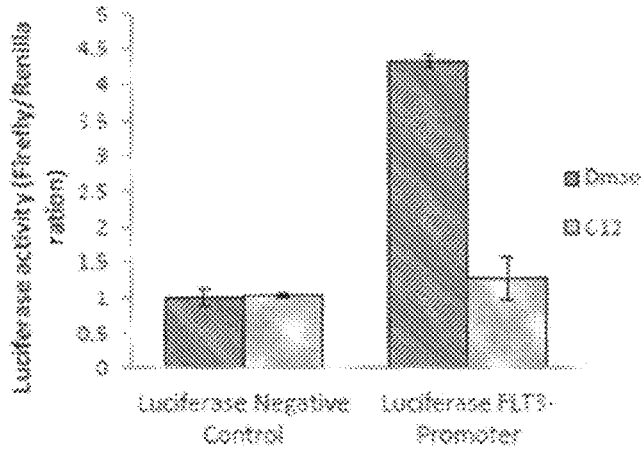

Referring to FIGS. 40A and 40B, ectopic over-expression of PRMT5 in AML cell line THP-1 with low basal levels of FLT3 using Lentivirus, sufficiently up-regulated FLT3 transcription and protein expression. qRT-PCR and protein detection in representative spleen samples comparing THP-1/PRMT5 and THP-II/EV in a mouse model of PRMT5 over-expression indicated a PRMT5-dependent up-regulation of FLT3 levels in Wyo.

d. PRMT5 Modulates Transcription of FLT3 by Regulating SP1/NFκB(P65) Transcription Complex A key regulator of FLT3 expression in AML has bee previously identified: a transactivation complex composed of transcription factors SP1 and NFκB(p65) (Liu, S., et al. (2010) *Cancer Cell* 17, 333-347; Blum, W., et al. (2012) *Blood* 119, 6025-6031). This transcriptional complex was therefore examined in relationship with PRMT5 expression and activity. Immunoprecipitation (IP) assays revealed that PRMT5 physically interacts with both SP1 and NFκB(p65) (FIG. 41), which may suggest a potential scaffolding function for PRMT5 in the assembly of this transactivation complex. The role of PRMT5 in recruitment and localization of these factors to regulatory region of FLT3 was then tested using a chromatin immunoprecipitation (ChIP) assay and antibodies specific for NFκB(p65), SP1 and primers designed to amplify predicted binding sites at the promoter region of FLT3 (Liu, S., et al. (2008) *Blood* 4, 2364-2373; Liu, S., et al. (2010) *Cancer Cell* 17, 333-347). ChIP results indicated that inhibition of PRMT5 in AML cells can lead to significant decrease in binding of SP1 transcription factor to promoter of FLT3 (FIG. 42A). PRMT5 was then overexpressed in MV4-11 and THP-1 cells, and the ChIP experiment repeated. Up-regulation of PRMT5 lead to significantly enhanced localization of SP1 onto the promoter region of FLT3 supporting the PRMT5 inhibition data (FIG. 42B). The positive regulatory effects of SP1 on FLT3 expression was validated by siRNA-mediated depletion of SP1 which, as expected, resulted in significant downregulation of FLT3 (>2.6 fold) (FIG. 43A). Additionally, supporting a functional role for PRMT5 in modulating FLT3 activity, inhibition of PRMT5 following exposure to C12 disrupted the FLT3 response element (i.e. FLT3-promoter-Luciferase reporter) activities in THP-1 cells (FIG. 43B).

Figure 41:
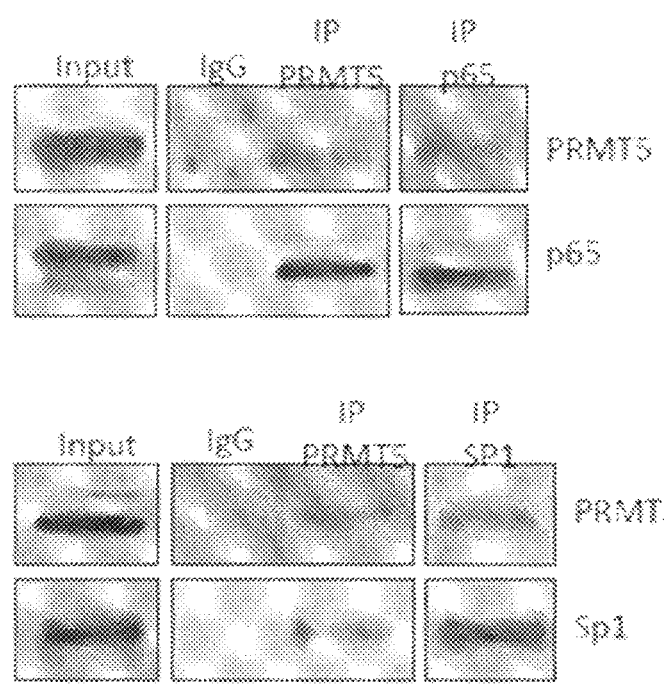
FIG. 41 shows representative data demonstrating a physical interaction between PRMT5 and transcription factors SP1 and the p65 subunit of NFκB.

Referring to FIG. 41, an immunoprecipitation (co-IP) assay revealed a physical interaction between PRMT5 and transcription factors SP1 and the p65 subunit of NF dB. Antibodies (4 μg) against PRMT5, SP1, and p65 were used to pull down each corresponding protein from whole cell lysate (minimum 500 μg) prepared from AML cell lines. Immunostaining was executed in a sequential manner, including stripping and re-staining following each antibody.

Referring to FIG. 42A, a chromatin immunoprecipitation (ChIP) assay demonstrates localization of SP to the promoter region of FLT3 as well as a significant decrease in binding of this transcription factor to the FLT3 promoter following PRMT5 inhibition; this was concomitant with significant down-regulation of FLT3 mRNA levels. Referring to FIG. 42B, a ChIP assay in cells which ectopically over-expressed PRMT5 revealed enhanced localization of SP1 to the promoter region of FLT3; this coincided with significant-up-regulation of FLT3 transcription.

Referring to FIG. 43A, transient transfection of AML cells with siRNA specific to SP1 resulted in sufficient knockdown of SP1 and, as result down-regulation of FLT3 as demonstrated by qRT-PCR assay and western blotting. Referring to FIG. 43B, a Luciferase reporter assay was used to confirm the regulatory functions of the promoter region of FLT3 for which ChIP primers were designed. The promoter site was cloned before the Luciferase gene, and THP-1 cells were transiently transfected with Luciferase-negative-control or Luciferase-FLT3-promoter construct in the presence or absence of a PRMT5 inhibitor. Luciferase activity was measured relative to Renilla and as a measure of FLT3 activity and was significantly decreased following PRMT5 inhibition.

Figure 44:
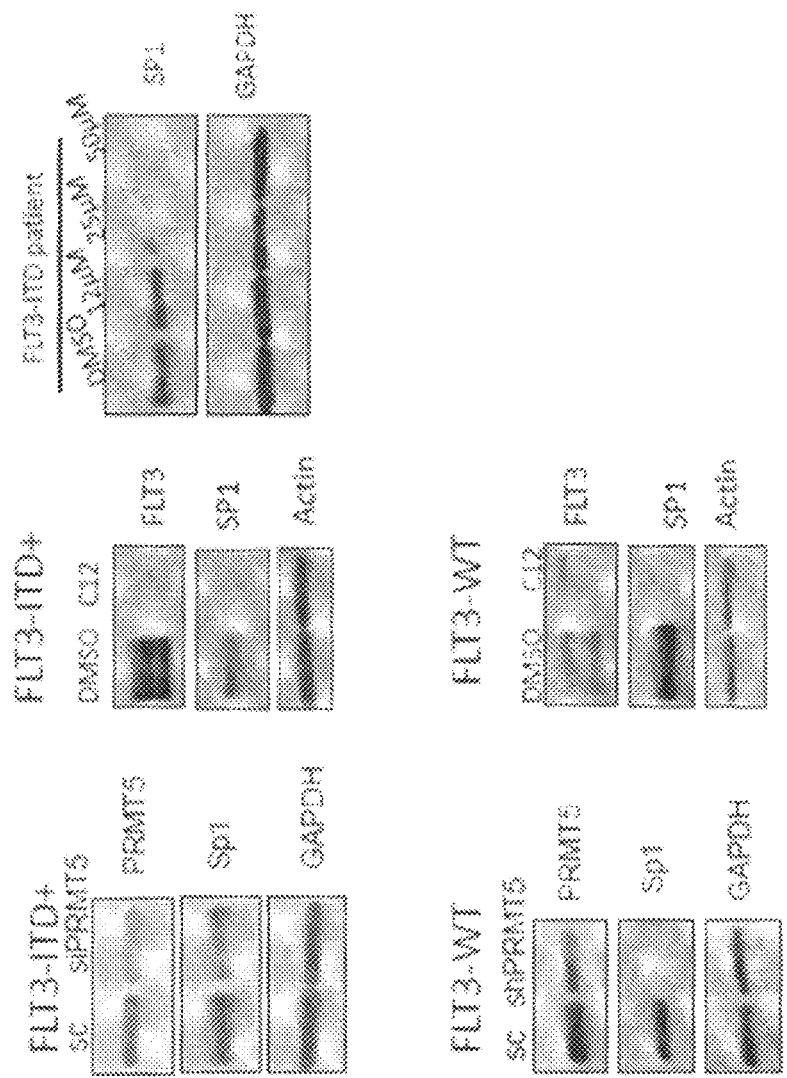
FIG. 44 shows representative data demonstrating down-regulation in protein levels of SP1 following inhibition of PRMT5.
Figure 45:
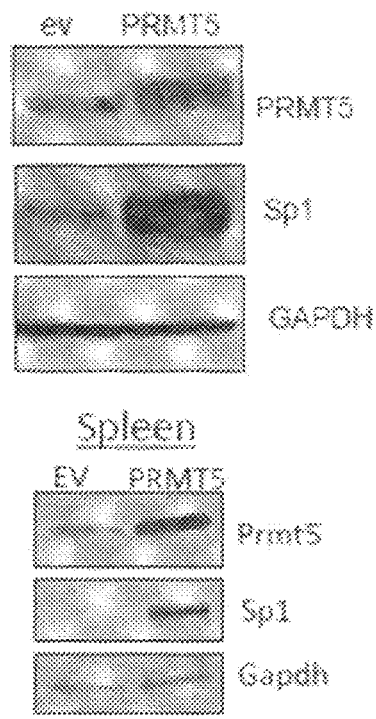
FIG. 45 shows representative data demonstrating up-regulation of SP1 and p65 proteins in Lenti-PRMT5 treated cells.

Inhibition of PRMT5 in AML cell lines (FLT3-1TD and FLT3-WT) using transient transfection and C12 treatment also resulted in significant knockdown of SP1 protein levels (FIG. 44). In contrast, overexpression of PRMT5 in THP-1 cells resulted in significant up-regulation of SP1 protein (FIG. 45). A similar trend was documented in the in vivo murine model of PRMT5 overexpression generated by THP-1/PRMT5 engraftment, as a significant increase in SP1 levels was measured when compared to THP-1/EV control mice (FIG. 45). In addition, according to qRT-PCR analysis, SP1 protein up-regulation following PRMT5 overexpression occurred without meaningful changes in SP1 mRNA levels. Without wishing to be bound by theory, these data suggest that PRMT5 contribution to SP1/NFκB(p65) transactivation activity is predominantly mediated post-translationally and via physical association with these elements. Indeed, there have been recent discoveries describing PRMT5-induced dimethylation of R30 subunit of p65 transcription factor which functionally leads to increased transcription activity of p65(NFκB) (Wei, H, et al. (2013) Proc. Natl. Acad. Sci. U.S.A. 110, 13516-13521). These data indicate that inhibition of PRMT5 can efficiently diminish the formation of the SP1/NFκB(p65) activation complex in both FLT3-WT and FLT3-ITD AML cells. Without wishing to be bound by theory, these data point to a dual function by PRMT5 in regulating the assembly of this complex by both increasing the available SP1 and facilitating the physical proximity of these regulatory elements.

Referring to FIG. 44, Western blotting was used to measure the down-regulation in protein levels of SP1 following inhibition of PRMT5 in AML cell lines PRMT5 inhibition was carried out using both small molecule inhibition and siPRMT5 or siPRMT5 alone; in both cases blockage of PRMT5 resulted in significant knockdown of Actin, or GAPDH staining was used as an internal loading control.

Referring to FIG. 45, Western blotting in AML cell lines transduced with Lenti-PRMT5 or Lenti-EV illustrated an up-regulated SP1 and, to a lesser extent, p65 proteins in Lenti-PRMT5 treated cells compared to negative control. Significant SP1 up-regulation was recapitulated in western blotting of spleen samples taken from THP-1/PRMT55 mouse when compared to normal THP-1/EV animal in vivo.

e. PRMT5 Modulates SP1 Levels by Suppressing miR-291 Expression

While these data indicate that PRMT5 increases the expression of SP1 at protein levels rather than promoting transcription of this gene, symmetric dimethylation of the PRMT5 substrate H4R3 has been shown to regulate gene transcription (both negatively and positively) (Richard, S., et al. (2005) Biochem. J. 388, 379-386; Fabbrizio, E., et al. (2002) EMBO Rep. 3, 641-645, suggesting a possible indirect mechanism of enhancing target expression. It has been previously reported that miR-29b directly targets SP1 and is aberrantly repressed in AML through epigenetic mechanisms of chromatin remodeling. Therefore, it was hypothesized that PRMT5 could participate in the repressor complex of miR-29b.

Figure 46:
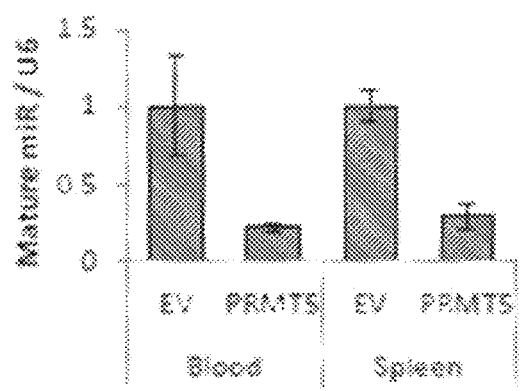
FIG. 46 shows representative data pertaining to control of miR-29b levels by PRMT5.
Figures 47A, 47B:
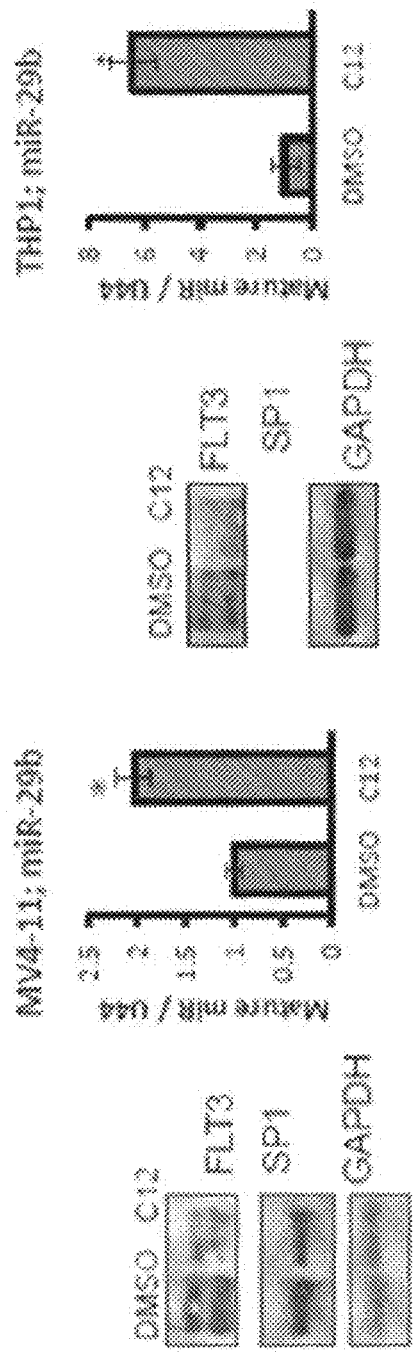
FIG. 47 shows representative data pertaining to the effect of PRMT5 inhibition on the presence of mature miR-29b.
Figure 48:
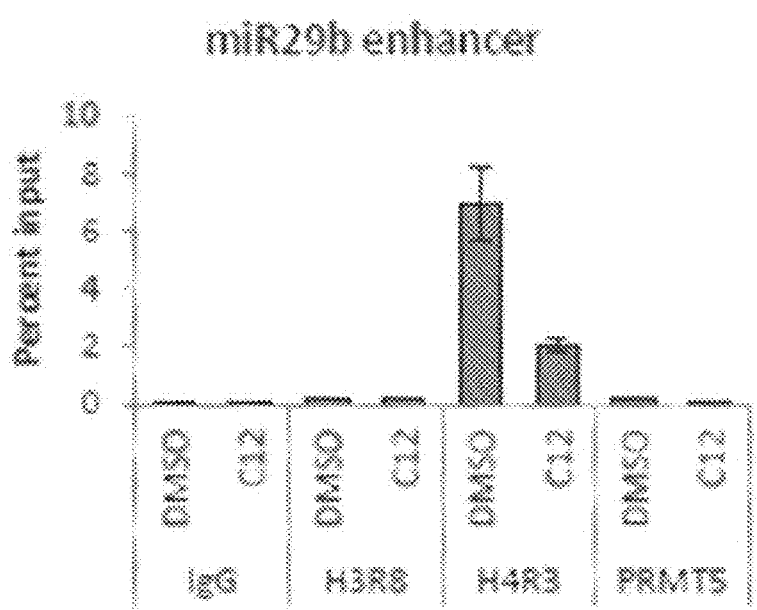
FIG. 48 shows representative data pertaining to the effect of PRMT5 inhibition on H4R3me2 localization to the miR-29b enhancer site.
Figure 50A:
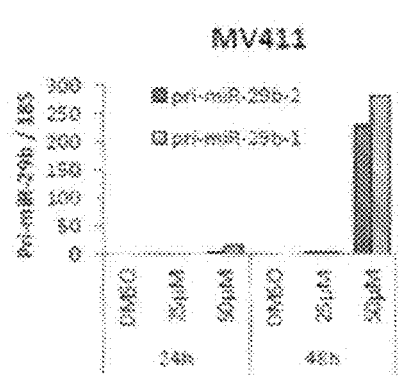
FIG. 50 shows representative data pertaining to the effect of PRMT5 inhibition on miR-29b transcription.
Figure 50B:
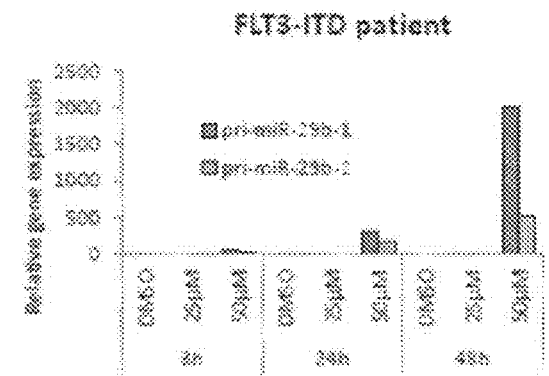
Figure 50C:
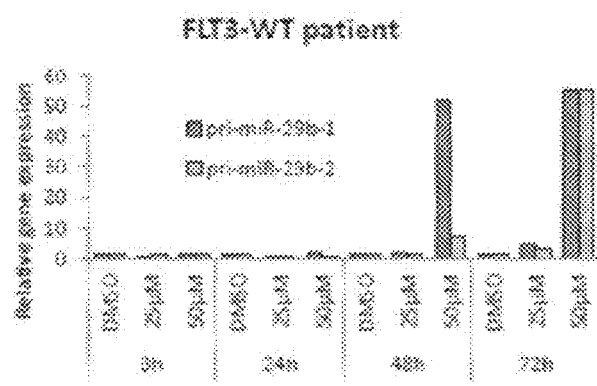
Figure 51:
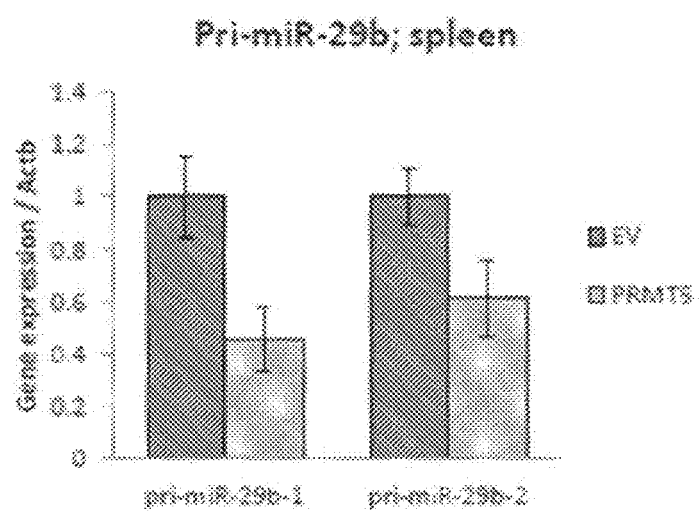
FIG. 51 shows representative data demonstrating a decrease in expression of pri-miR-29b caused by over-expression of PRMT5.

Mature miR-29b expression was significantly suppressed in blood and spleen from THP-1/PRMT5 mice compared to those from THP-1/EV controls (FIG. 46). Additionally, in MV4-1 and THP-1 cells treated with C12, PRMT5-dependent downregulation of SP1 and FLT3 coincided with a significant increase in miR-29b levels (FIGS. 47A and 47B). The regulatory region of pri-miR-29b was later checked for possible docking of PRMT5 (indirect binding) or H3R5me2 and/or H4R3me2 (direct binding) using ChIP assay with and without PRMT5 inhibition. ChIP data supported the presence of PRMT5 in the regulatory region of pri-miR-29b most likely via one of its methylation targets H4R3me2, as blocking PRMT5 with C12 resulted in significant decrease in binding of this factor to miR-29b regulatory site (FIG. 48). The efficiency of miR-29b in modulating SP1 was confirmed by miR-29b gain- and loss-of function assays in AML cells, and significant suppression of SP1 in miR-29b overexpressing cells was detected, while SP1 was re-expressed when cells were treated with miR-29b knockdown (FIGS. 49A and 49B). Furthermore, inhibition of PRMT5 using C12 led to a substantial and dose-dependent increase in pri-miR-29b transcript levels (pri-miR-29b-1 and pri-miR-29b-2) (FIG. 50A-C). In contrast, malignant overexpression of PRMT5 in THP-1/PRMT5 mice resulted in suppression of pri-miR-29b levels (FIG. 51). Without wishing to be bound by theory, these data suggest that PRMT5 potentially downregulates miR-29b levels by facilitating the localization of transcription silencer H4R3-me2 to the enhancer region of miR-29b. As a result, SP1 transcription activity may increase, for example, in response to removal of miR-29b inhibitory effects and active SP1 in turn may promote FLT3 expression.

Referring to FIG. 46, qRT-PCR analysis was used to measure reduced mature miR-29b levels in THP-1/PRMT5 mouse compared to control THP-1/EV mouse in vivo. Significance was calculated using t test and n-3 samples per group were compared.

Referring to FIGS. 47A and 47B, qRT-PCR analysis shows a significantly elevated mature miR-29b presence in AML cell lines treated with PRMT5 inhibition.

Referring to FIG. 48, a ChIP assay was used to demonstrate enrichment of H4R3me2 (methylation mark deposited by PRMT5) onto the enhancer region of miR-29b. Inhibition of PRMT5 with C12 resulted in a significant decrease of H4R3me2 localization to the miR-29b enhancer site.

Referring to FIGS. 49A, and 49B, Western blotting was used to measure changes in SP1 protein levels following transient over-expression and suppression of miR-29b in AML cell lines.

Referring to FIG. 50A-C, a qRT-PCR assay was used to measure transcript levels of pri-miR-29b (isoforms pri-miR-29b-1 and pri-miR-29b-2) in AML cell lines and patient blasts following PRMT5 inhibition. A dose-dependent increase in levels of primary miR-29b expression was evident when PRMT5 activity was inhibited.

Referring to FIG. 51, qRT-PCR analysis demonstrates a decrease in expression of pri-miR-29b in spleen samples from THP-1/PRMT5 animals compared to control mice caused by over-expression of PRMT5.

6. Evaluation of PRMT5 Inhibitors in Oropharyngeal Squamous Cell Carcinoma (OPSCC)

Figure 52:
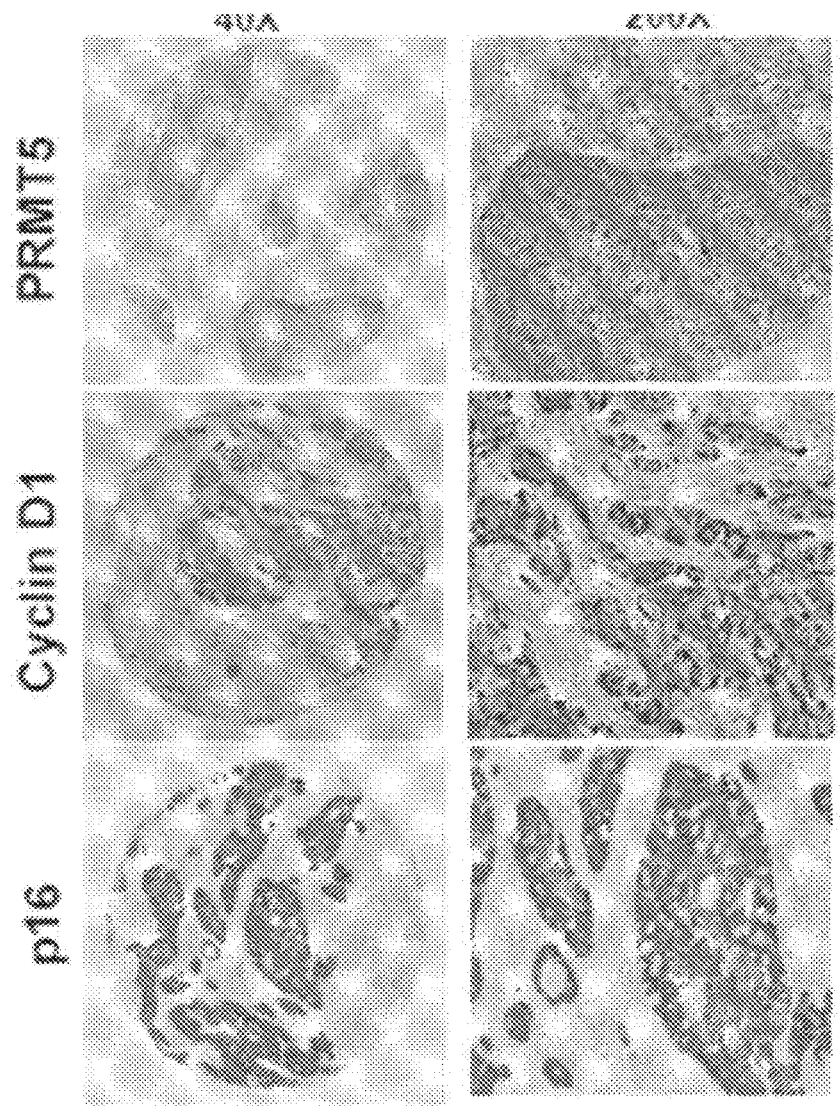
FIG. 52 shows representative images of immunohistochemical staining of PRMT5, Cyclin D1 and p16.
Figure 56:
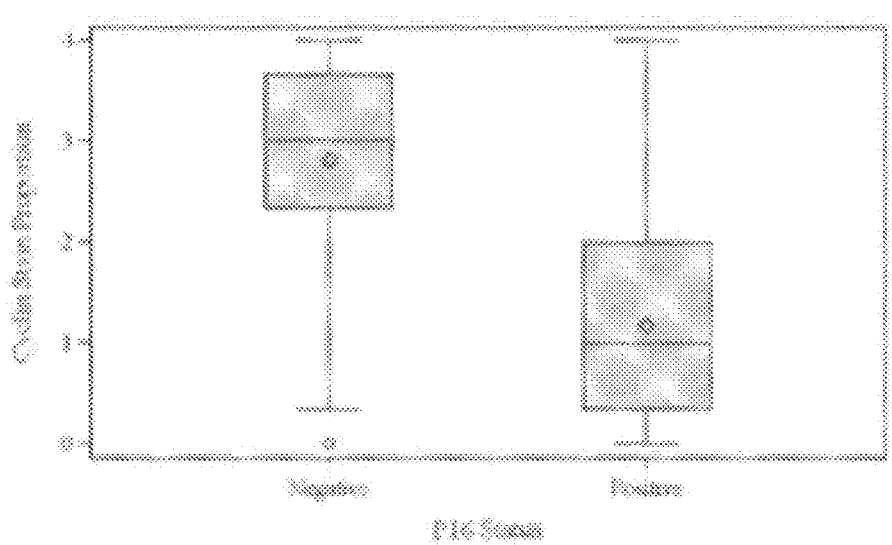
FIG. 56 shows representative data pertaining to Cyclin D expression as a function of p16 status.

Evidence from cancers such as lung, breast, lymphoma, and leukemia suggest that PRMT5 facilitates tumorigenesis by affecting cell proliferation, cell cycle progression, anchorage-independent growth and apoptosis. In addition, it has recently been shown that PMRT5 mediates cyclin-D1 induced neoplastic growth. Cyclin D1 belongs to a family of proteins called cyclins which regulate cell-cycle progression by forming complexes with cyclin-dependent kinases. Amplification of the Cyclin D1 gene and over-expression of the protein has been reported in head and neck squamous cell carcinoma (HNSCC); however, little is known about the role of PMRT5 and its association with Cyclin D1 in this disease. Referring to FIG. 52, immunohistochemical staining of PRMT5, Cyclin D1, and p16 are shown.

death increased by a factor of 2.3 (95% CI 1.5, 3.6). Cyclin D1 expression was inversely associated with p16 status (p<0.0001) (FIG. 56).

TABLE 7

| Survival Time (Years) | | | |
|---|---|---|---|
| N | Median | Min. | Max. |
| 223 | 4.00 | 0.06 | 9.82 |

TABLE 8

| Year | Survival Rates (%) |
|---|---|
| 1 | 85.65 |
| 2 | 73.99 |
| 3 | 66.25 |
| 4 | 61.73 |
| 5 | 59.25 |

Figure 57A:
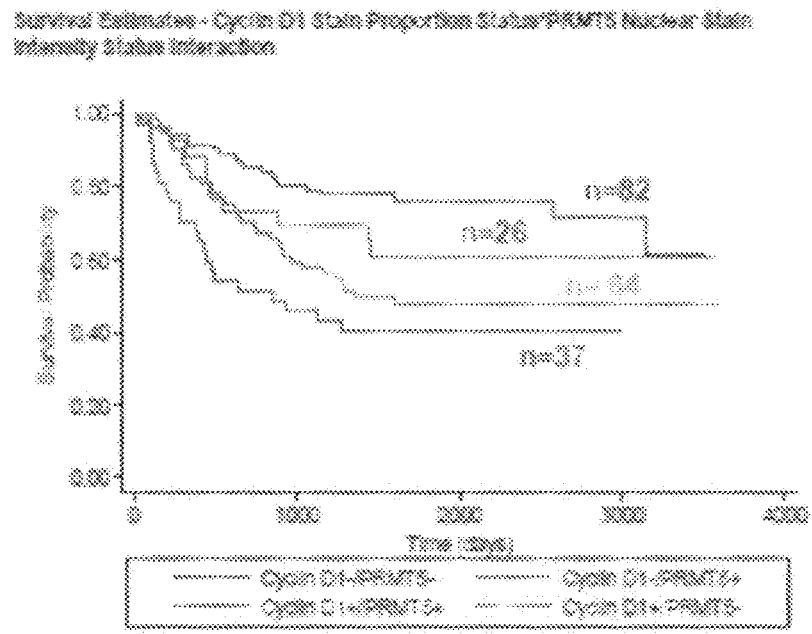
FIGS. 57A and 57B show representative data pertaining to the survival estimates of patients with PRMT5 negative tumors (57A) and patients with p16 negative tumors (57B).
Figure 57B:
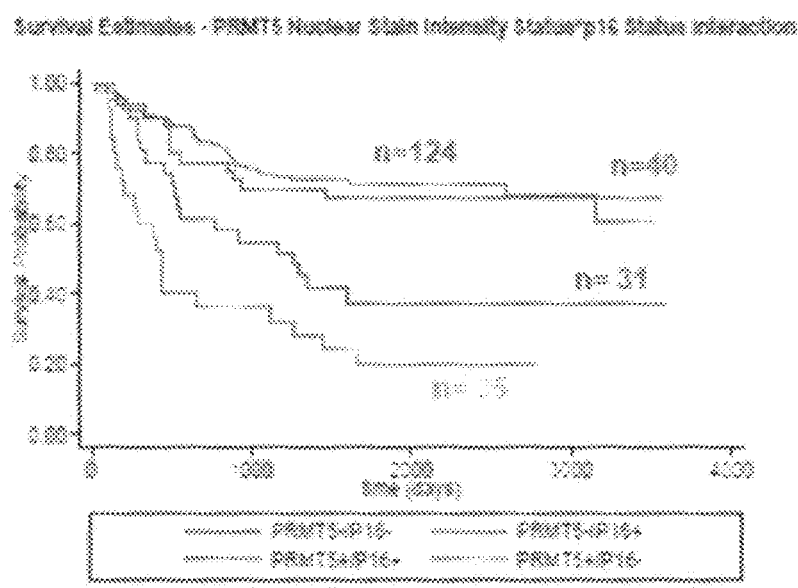

In a subgroup survival analysis comparing expression of Cyclin D1 within nuclear PRMT5− patients, those with PRMT5−/Cyclin DL− tumors had better survival compared to PRMT5−/Cyclin D1+ (p=0.0023) (FIG. 57A). In a subgroup survival analysis comparing the expression of nuclear PRMT5 within p16− patients, those with p16−/PRMT5+ tumors had worse survival compared to p164PRMT5− (p=0.0584) (FIG. 57B). In a multivariable model, after adjustment for nuclear PRMT5 and Cyclin D1 expression status, p16 was significantly associated with overall survival (p=0.0003). Patients with tumors that were p16 negative had 2.4 times the hazard of death than those that were p16 positive (95% CI 1.5, 3.9) (Table 9).

TABLE 9

Figure 53:
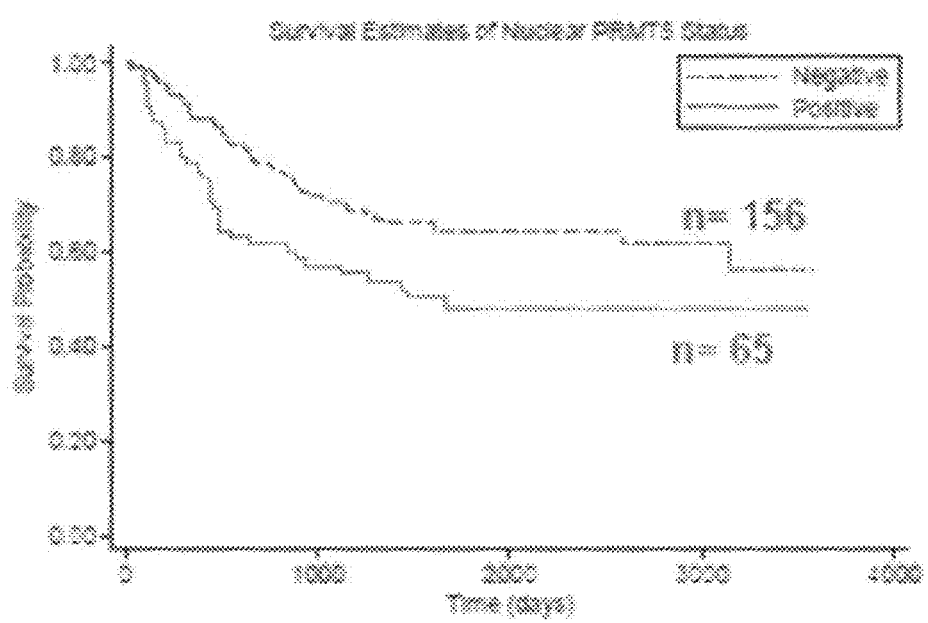
FIG. 53 shows representative data pertaining to the survival estimates of patients with tumors having nuclear PRMT5 expression (positive) compared to patients with tumors having no nuclear PRMT5 expression (negative).
Figure 54A:
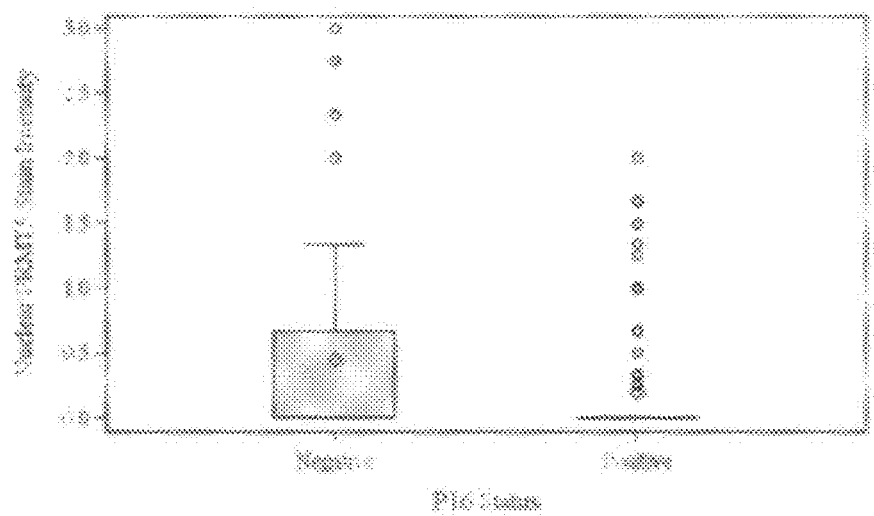
FIGS. 54A and 54B show representative data pertaining to nuclear PRMT5 expression as a function of p16 negative tumors (54A) and smoking status (54B).
Figure 54B:
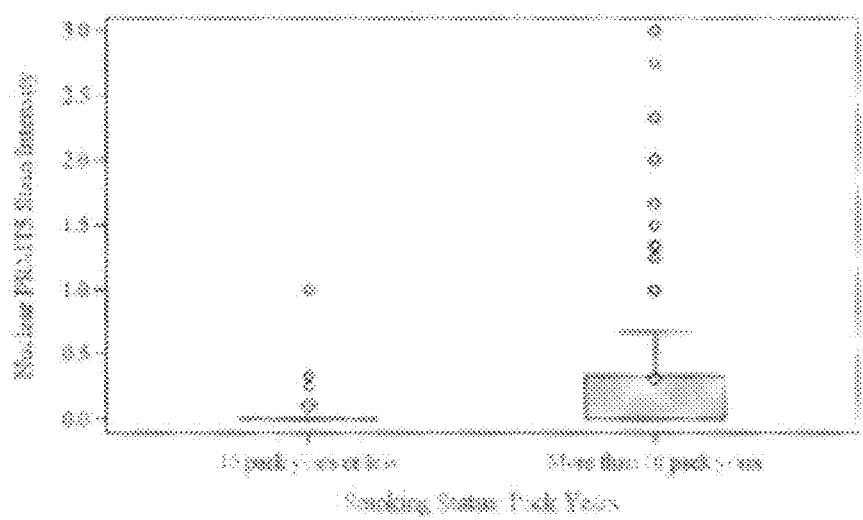
Figure 55A:
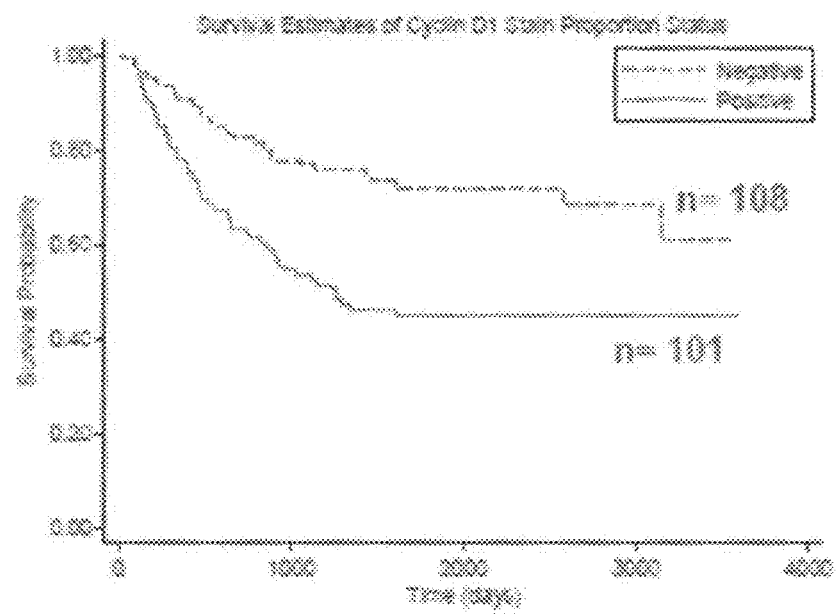
FIGS. 55A and 55B show representative data pertaining to the survival estimates of patients with tumors that overexpressed Cyclin D1 (55A) and patients with p16 negative tumors (55B).
Figure 55B:
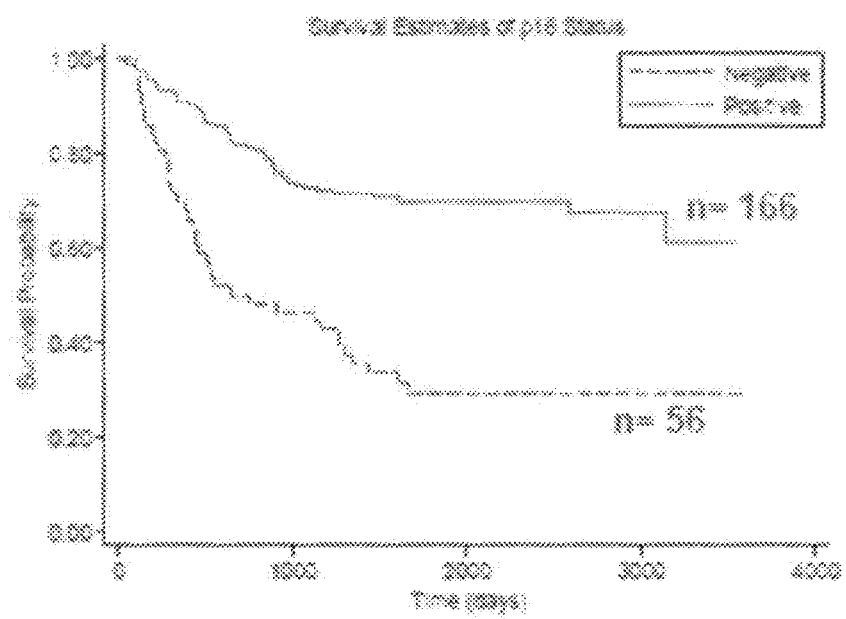
Figure 58:
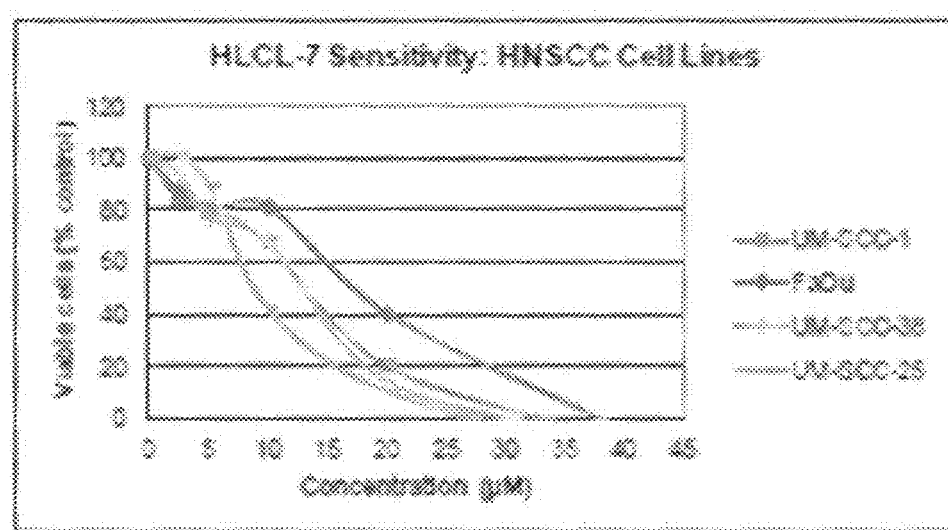
FIG. 58 shows representative data pertaining to the effect of HLCL-7 on proliferation of HNSCC tumor cells.
Figure 59A:
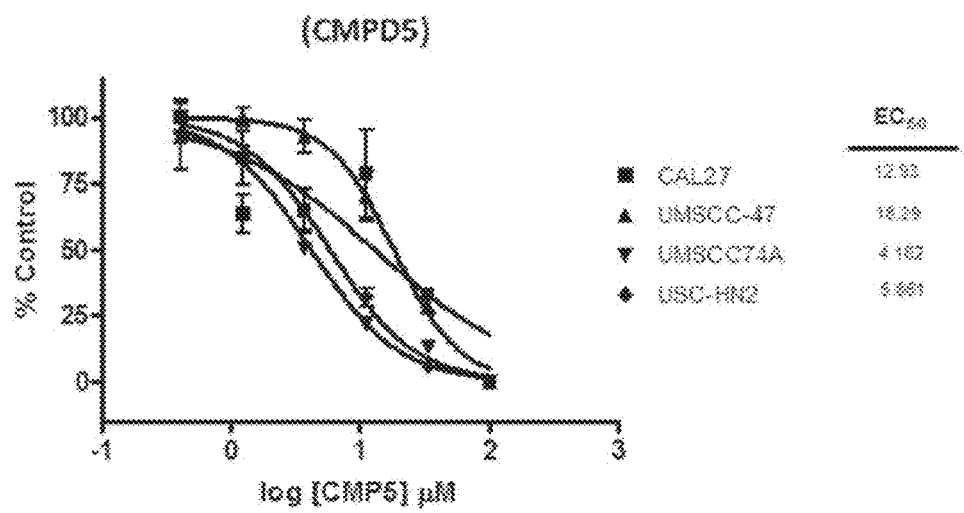
FIG. 59A-E shows representative data pertaining to proliferation of CMPD5 (59A and 59B). CMPD 7 (59C), HLCL-61/CMPD 12 (99D), and HLCL-65/CMPD 65 (59E).
Figure 59B:
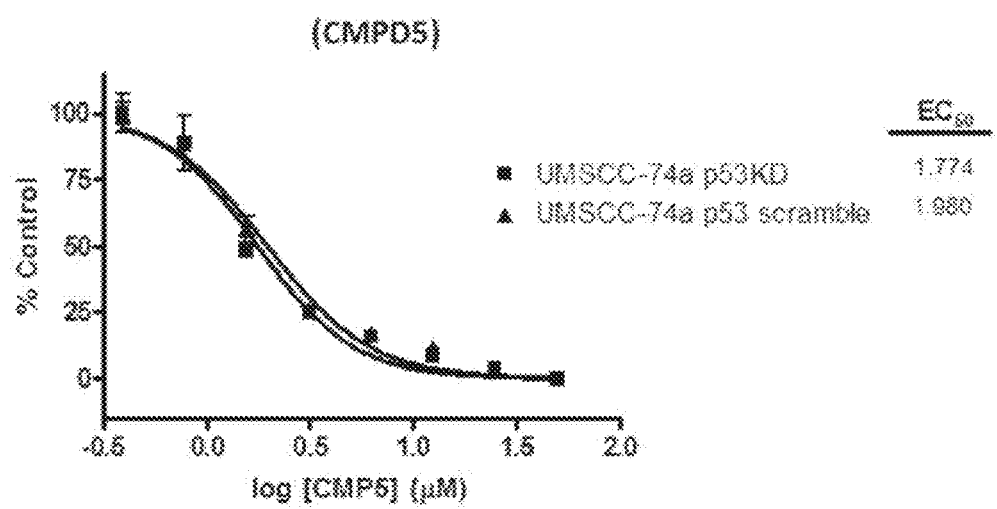
Figure 59C:
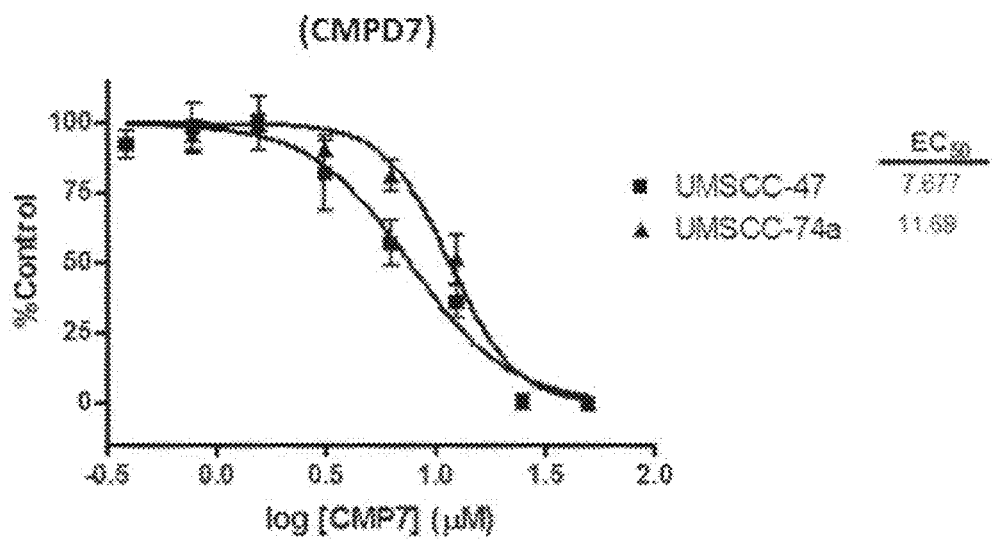
Figure 59D:
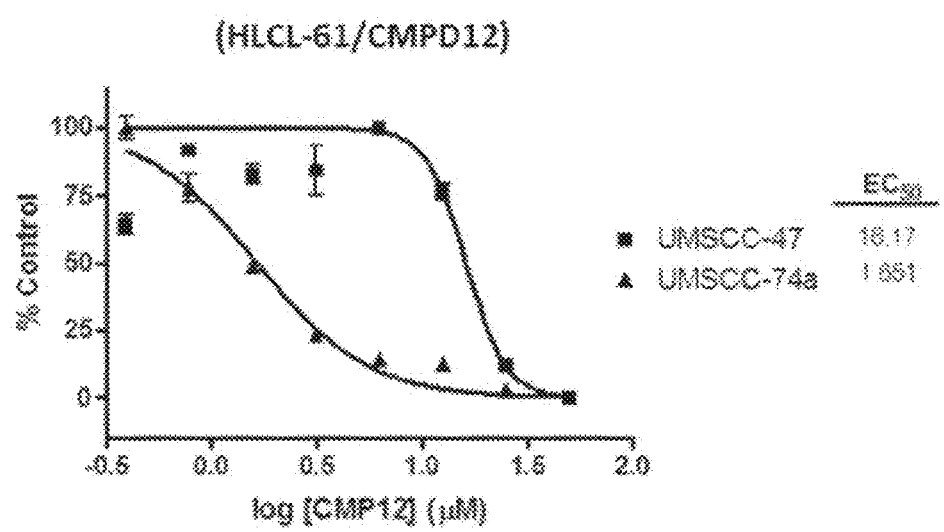
Figure 59E:
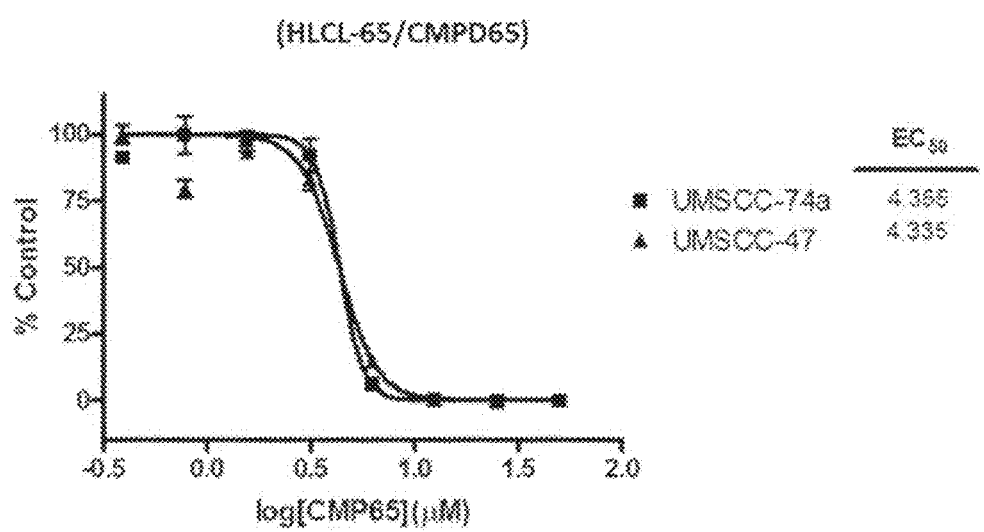

| Survival Analysis - Multivariable Model | | | | | | | | |
|---|---|---|---|---|---|---|---|---|
| Parameter | | DF | Parameter Estimate | Std. Error | Chi-Square | Pr > Chi-Sq. | Hazard Ratio | 95% Hazard Ratio Confidence Limits | |
| Nuclear PRMT5 Status | + | 1 | 0.367 | 0.225 | 2.661 | 0.1028 | 1.44 | 0.929 | 2.245 |
| Cyclin D1 Stain Proportion Status | + | 1 | 0.451 | 0.254 | 3.167 | 0.0752 | 1.57 | 0.955 | 2.581 |
| p16 Status | − | 1 | 0.885 | 0.247 | 12.832 | 0.0003 | 2.42 | 1.493 | 3.932 | a. High Expression of PRMT5 and Cyclin D1 is Associated with Poor Outcome in OPSCC Patients In univariate analyses, nuclear PRMT5 expression was associated with worse overall survival (p=0.0185) (FIG. 53 and Tables 7 and 8). For each unit increase in average nuclear stain intensity, the hazard of death increased by 1.7 (95% CI 1.1, 2.6). Nuclear PRMT5 expression was inversely associated with p16 status (p=0.0041) (FIG. 50A) and directly associated with >10 pack-years smoking history (p=0.0174) (FIG. 54B). Cyclin D1 expression was associated with worse overall survival (p=0.0002) (FIG. 55A; see FIG. 55B for survival estimates of p16 status). For each unit increase in average cyclin D1 stain proportion, the hazard of Without wishing to be bound by theory, these data suggest that Cyclin D1 and PRMT5 are promising therapeutic targets, particularly in p16 negative cancers. Indeed, HLCL-7 was evaluated to determine the effect on HNSCC tumor cells and found to inhibit proliferation in a dose-dependent manner (FIG. 58).

b. Biological Evaluation of PRMT5 Inhibitors: HLCL-61, HLCL-65, and HLCL-66

Proliferation of multiple cell lines was evaluated for CMPD 5, CMPD7, HLCL-61, HLCL-65, and HLCL-66 (FIG. 59A-E). Potencies in the low micromolar range were observed for all compounds tested.

Figure 60:
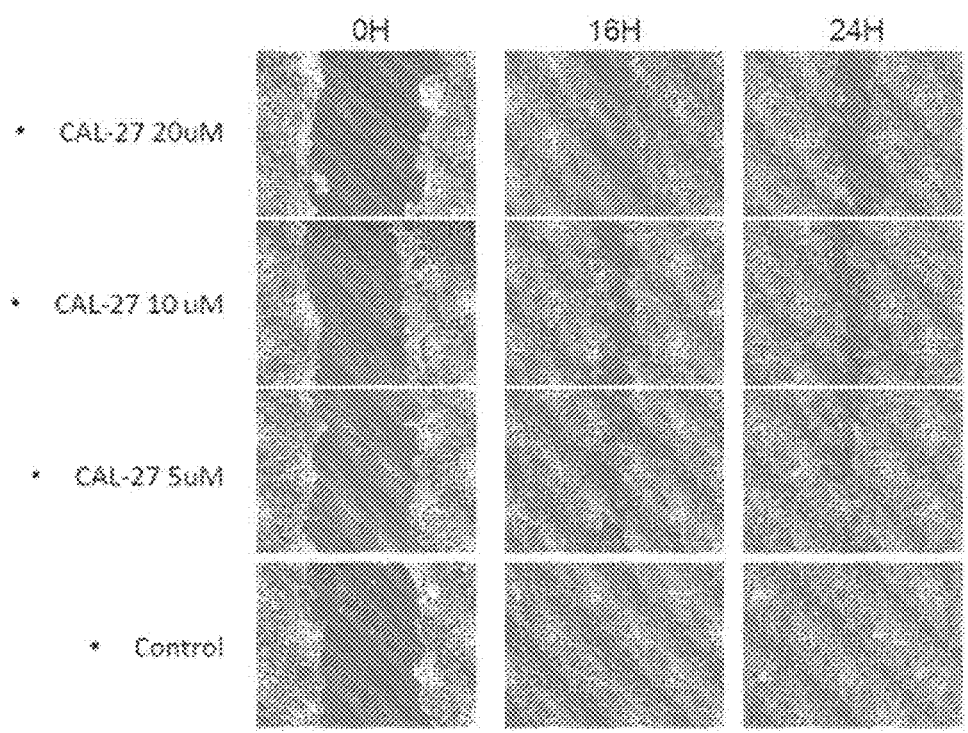
FIG. 60 shows representative data pertaining to squamous cell carcinoma migration in response to varying concentrations of HLCL-65.
Figure 61A:
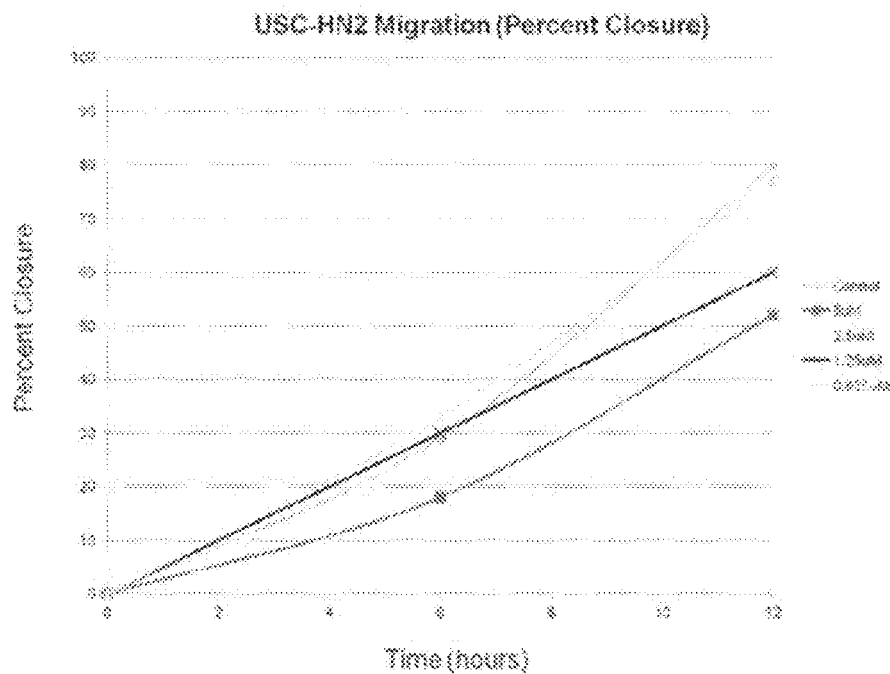
FIG. 61A-D show representative data pertaining to squamous cell carcinoma migration in several cell lines in response to HLCL-65.
Figure 61B:
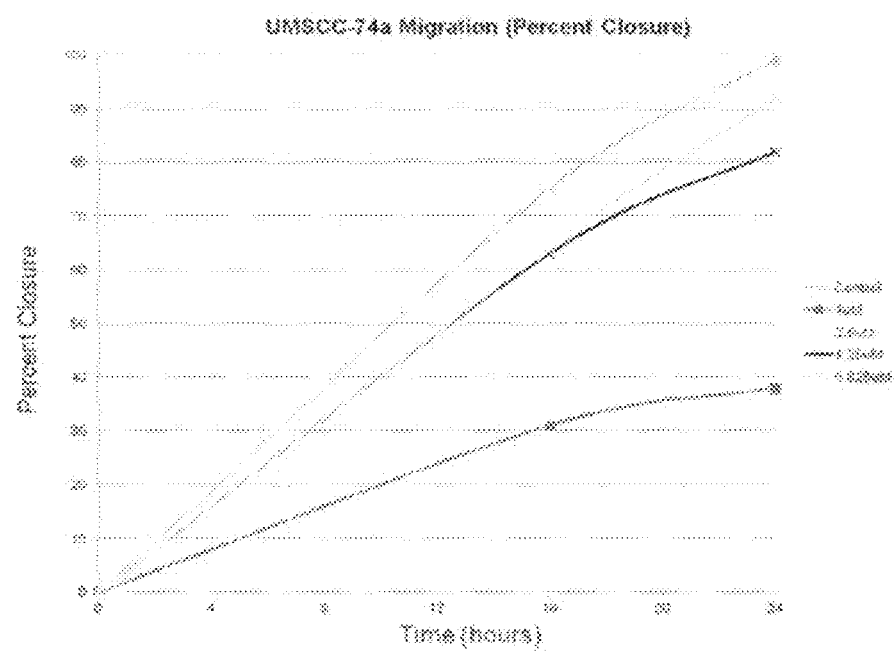
Figure 61C:
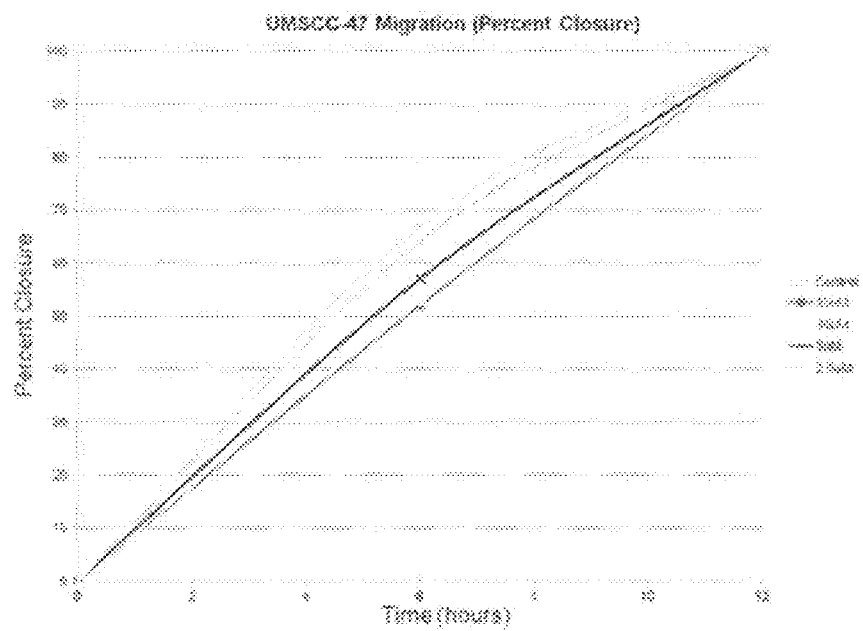
Figure 61D:
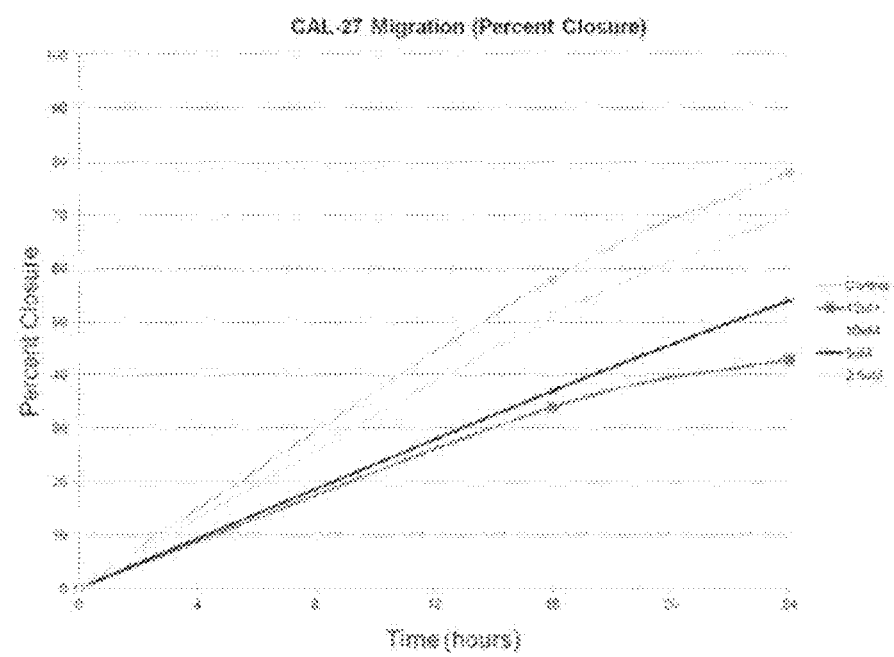

Referring to FIG. 60, PRMT5 and squamous cell carcinoma migration in response to HLCL-66 is illustrated. Migration was performed as previously described (Nowleki, M. O., et al. (2008) *Neur. Oncol.* 10, 690-699). Briefly, a migration scratch assay was performed with CAL-27 cell line treated with HLCL-66 for 0, 16, and 24 hours. Gap closure was affected in a dose-response fashion at both 16 h and 24 h time points indicating that PRMT5 inhibition leads to loss of migratory activity of squamous cell carcinoma cell lines.

Referring to FIG. 61A-D, PRMT5 and migration of different cell lines (e.g., USC-HN2, UMSCC-74a, UMSCC-47, and CAL-27, respectively) in response to HLCL-65 is illustrated. Migration was performed as described herein above.

7. Evaluation of PRMT5 Inhibitors in Mantle Cell Lymphoma (MCL)

Pharmacokinetic data of compounds HLCL-7, HLCL-61, and HLCL-66 taken from an in vive study is illustrated in Table 10. Compounds were dosed either via intravenous (IV) administration at 5 mg/kg in a Tween80 formulation or via intraperitoneal (IP) administration at 25 mg/kg in a DMSO solution.

TABLE 10

| Time (h) | Mouse plasma concentration (nM) | |
|---|---|---|
| | IV | IP |
| HLCL-7 | | |
| 0.08 | 3236.1 | 7566.3 |
| 0.17 | 3073.4 | 885.8 |
| 0.33 | 1497.0 | 7544.6 |
| 0.50 | 911.0 | 7483.5 |
| 1.00 | 601.1 | 4905.5 |
| 2.00 | 506.6 | 7682.4 |
| 4.00 | 200.2 | 4128.6 |
| 6.00 | 76.2 | 2542.8 |
| 8.00 | 77.1 | 2789.2 |
| 24.0 | 1.38 | 1.35 |
| HLCL-61 | | |
| 0.08 | 1215.3 | 3151.2 |
| 0.17 | 1614.3 | 2280.4 |
| 0.33 | 702.4 | 2039.3 |
| 0.50 | 993.5 | 1833.8 |
| 1.00 | 942.3 | 1389.7 |
| 2.00 | 525.2 | 1497.3 |
| 4.00 | 155.3 | 712.2 |
| 6.00 | 94.4 | 695.8 |
| 8.00 | 51.1 | 331.6 |
| 24.0 | 6.76 | 1.40 |
| HLCL-65 | | |
| 0.08 | 2941.5 | 6237.4 |
| 0.17 | 2053.2 | 6274.0 |
| 0.33 | 2936.1 | 5277.7 |
| 0.50 | 2391.0 | 1659.9 |
| 1.00 | 1890.3 | 1592.3 |
| 2.00 | 1932.4 | 8446.3 |
| 4.00 | 1527.8 | 4509.2 |
| 6.00 | 719.5 | 5480.4 |
| 8.00 | 512.6 | 3710.9 |
| 24.0 | 29.6 | 480.3 |

Figure 62A:
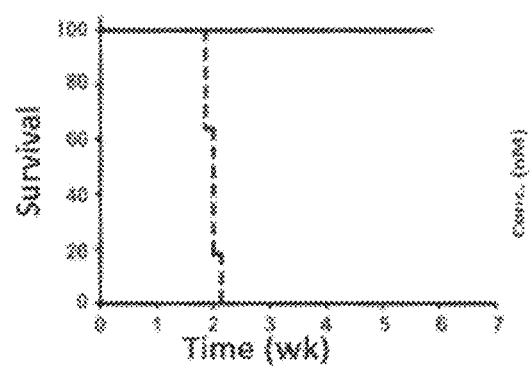
FIG. 62A-C show representative data pertaining to the effect of PRMT5 inhibition on multiple cell lymphoma survival in vivo. Specifically.
Figure 62B:
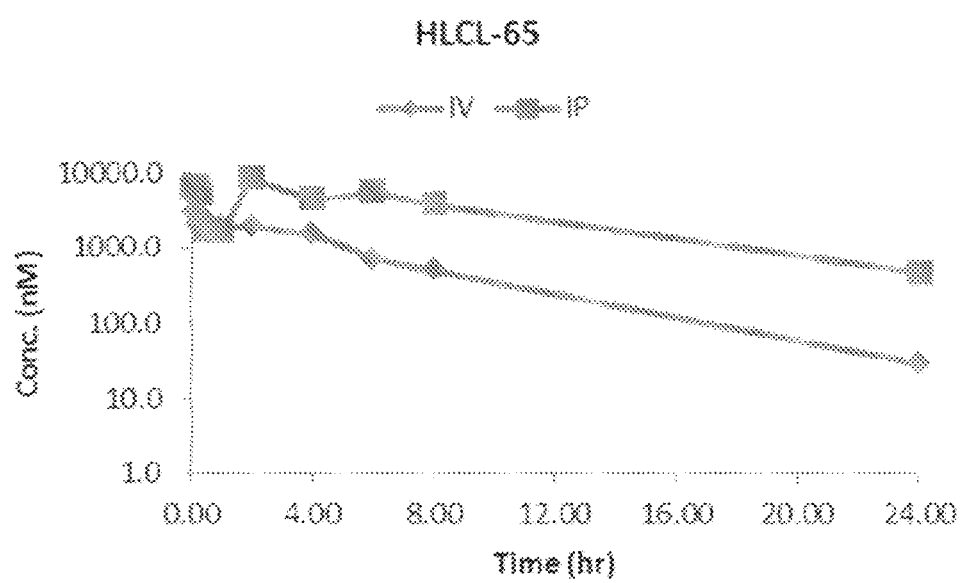
Figure 62C:
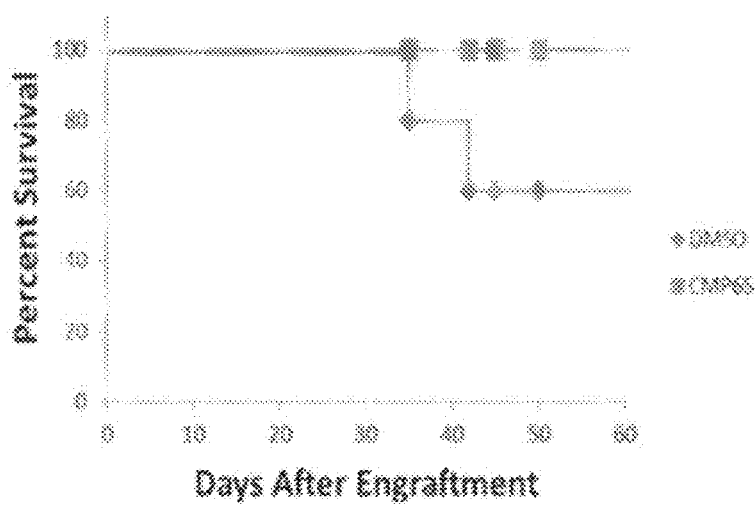
Figure 63A:
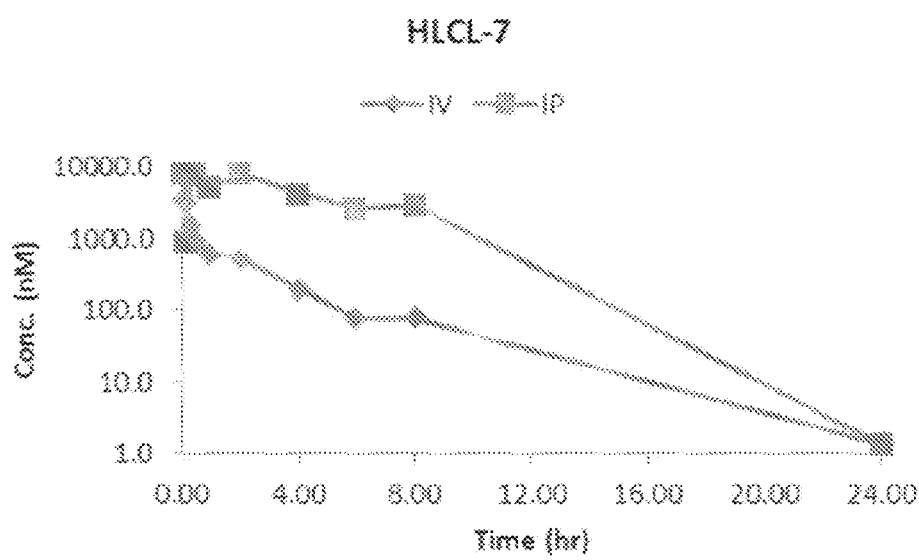
FIGS. 63A and 63B show representative data pertaining to pharmacokinetic results obtained in vivo with HLCL-7 (63A) and HLCL-61 (63B).
Figure 63B:
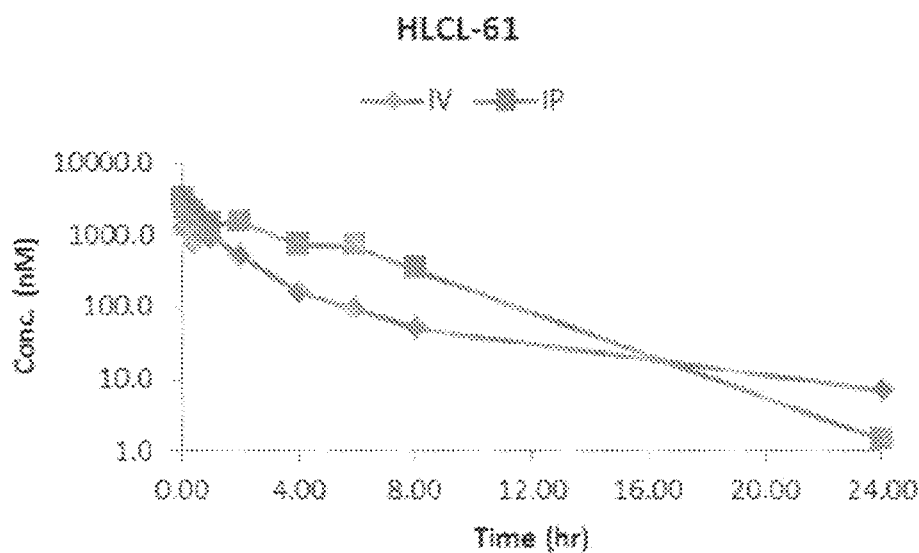

Controlled shRNA depletion was evaluated in a murine lymphoma model (Eμ-BRD2 (Chung, J., et al. (2013) *J. Biological Chemistry* 288, 35534-35547)) and human xenograft model of glioblastoma (Yan, F., at al (2014) *Cancer Research In Press*). Referring to FIG. 62A, controlled expression of a PRMT5 shRNA (solid line) but not control shRNA (dashed line) leads to 100% survival of mice engrafted primary DLBCL tumor cells. Referring to FIG. 62B, PK experiments of HLCL-65 delivered via IV and IP routes at a dose of 25 mg/kg showed peak plasma concentrations ranging from 8-20 μM (See FIGS. 63A and 63B for PK data pertaining to HLCL-7 and HLCL-61). The maximum tolerated dose (MTD, single dose) was identified at 50 mg/kg (see Table 11 below). A sub-toxic dose (25 mg/kg) was used to treat FcMCL mice. Control mice developed peripheral blood and lymph node tumor burden starting day 20 post-engraftment. A preliminary experiment indicates that treatment with HLCL-65 (25 mg/kg, IP, every other day) leads to improved survival by controlling development of lymph node tumor burden but not peripheral blood FcMCL tumor burden (FIG. 63C). Without wishing to be bound by theory, this data suggests that PRMT5 inhibition may lead to microenvironment changes that facilitate lymphomagenesis.

TABLE 11

| 24 hr Quick MTD test Route/Dose (mg/kg) | One mouse for each dose | | |
|---|---|---|---|
| | HLCL-7 | HLCL-61 | HLCL-65 |
| IP-200 | Dead within 1 hr after dosing | Dead within 30 min after dosing | Paralyzed after dosing, dead within 1 hr |
| IP-100 | Dead within 1 hr after dosing | Alive after 24 hr but still slow moving | Alive after 24 hr but paralyzed |
| IP-50 | Alive 24 hr after dosing | Alive 24 hr after dosing | Alive 24 hr after dosing |
| IV-20 | Dead instantly after dosing | Dead instantly after dosing | Dead instantly after dosing |
| IV-10 | Alive 24 hr after dosing but slow moving | Alive 24 hr after dosing but slow moving | Dead instantly after dosing |
| IV-5 | Alive 24 hr after dosing | Alive 24 hr after dosing | Alive 24 hr after dosing |

TABLE 11-continued

| | | | |
|---|---|---|---|
| IV-2.5 | Alive 24 hr after dosing | Alive 24 hr after dosing | Dead instantly After dosing |

| MTD study Route/Dose | | Four mice each dose | |
|---|---|---|---|
| (mg/kg) | HLCL-7 | HLCL-61 | HLCL-65 |
| IP-50 | Alive within 1 hr after dosing but slow moving. Alive 24 hr after dosing, 1 out 4 mice was lethargic and slow moving | Alive within 1 hr after dosing but slow moving. Alive 24 hr after dosing, 1 out 4 mice was lethargic and slow moving | Alive within 1 hr after dosing but slow moving. Alive 24 hr after dosing, 4 out 4 mice were very lethargic and slow moving |
| IP-5 | Alive 24 hr after dosing | Alive 24 hr after dosing | Alive 24 hr after dosing |

8. Prophetic Examples a. In Vivo Preclinical Models of MCL to Explore Novel Experimental Therapeutic Strategies In one prophetic example, the activity of a PRMT5 inhibitor alone and in combination with PD0332991, GS1101-equivalent PI3K$_{\alpha/\delta}$ inhibitor GDC-0032, and ibrutinib will be tested in models of preclinical mantle cell lymphoma (MCL). Without wishing to be bound by theory, results may provide a direct opportunity to investigate preclinical activity of various experimental therapeutic strategies, as well as provide insight regarding genetic programs that contribute toward resistance to specific drug therapies.

b. Preclinical Models of MCL and PRMT5-Induced Lymphomagenesis

In one prophetic example, MCL and PRMT5-induced lymphomagenesis is evaluated in a FC-muMCL1 model. The FC-muMCL1 (Smith, M. R., et al. (2013) Leukemia 27, 1592-1594) is a system that originated from CYCLIN D1 Eu model treated with the non-specific immune adjuvant, pristane. This model has several advantages including the presence of CYCLIN D1 overexpression, MCL phenotype (CD5+CD19+, CD23−), and characteristic molecular features of MCL. The Fc-MCL model, when engrafted in C57B16 mice is a syngeneic, immunocompetent model system that allows for evaluation of anti-tumor immune response as well as toxicity of tested therapeutic strategies.

In a second prophetic example, MCL and PRMT5-induced lymphomagenes is evaluated in a human MCL-derived cell line that effectively engrafts in an immune deficient mouse (NSG). This model (CCMCL1) was recently reported at the 2013 ASH meeting by Zhao et al. (Zhao, C., et al. (2013) *Blood* 122, 645a) and was developed by engrafting primary leukemic MCL cells in NSG mice. This line expresses CYCLIN D1, SOX11, PAX5 and MCL1, and has a MCL Immunophenotype.

H. References

Ghielmini M. Zucca E. How I treat mantle cell lymphoma. Blood. 2009 Aug. 20; 114(8): 1469-76.

Jares P, et al. Genetic and molecular pathogenesis of mantle cell lymphoma: perspectives for new targeted therapeutics. Nat Rev Cancer. 2007; 7(10):750-62.

Egger G, et al. Epigenetics human disease and prospects for epigenetic therapy. Nature. 2004; 429(6990):457-63.

Ganesan A, et al. Epigenetic therapy: histone acetylation, DNA methylation and anti-cancer drug discovery. Curr Cancer Drag Targets. 2009; 9(8):963-81.

Poke F S, et al. Reversing aberrant methylation patterns in cancer. Curr Med Chem. 2010; 17(13):1246-54.

Karberg S. Switching on epigenetic therapy. Cell. 2009; 139(6):1029-31.

Pal S, and Sif S. Human SWI/SNF-associated PRMT5 methylates histone H3 arginine 8 and negatively regulates expression of ST7 and NM23 tumor suppressor genes. Mol Cell Biol. 2004; 24(21):9630-45.

ZhaQ Q, Rank G, e al. PRMT5-mediated methylation of histone H4R3 recruits DNMT3A, coupling histone and DNA methylation in gene silencing. Nat Struct Mol Biol. 2009; 16(3):304-11.

Xu X, et al. Application of machine learning methods to histone methylation ChIP-Seq data reveals H4R3me2 globally represses gene expression. BMC Bioinformatics. 2010; 11(1):396.

Ancelin K, et al. Blimp1 associates with Prmt5 and directs histone arginine methylation in mouse germ cells. Nat Cell Biol 2006; 8: 623-630.

Kim C, Lim Y, Yoo B C, Won N H, Kim S, Kim G. Regulation of post-translational protein arginine methylation during HeLa cell cycle. Biochim Biophys Acts. 2010; 1800(9):977-985.

Rank G, Cerruti L, Simpson R J, Moritz R L, Jane S M, Zhao Q. Identification of a PRMT5-dependent repressor complex linked to silencing of human fetal globin gene expression. Blood. 2010 May 21. [Epub ahead of print].

Majumder S, Alinari L, Roy S, Miller T, Datta J, Sif S, Baiocchi R, Jacob S T. Methylation of histone H3 and H4 by PRMT5 regulates ribosomal RNA gene transcription. J Cell Biochem. 2010; 109(3):553-63.

Scoumanne A, Zhang J, Chen X. PRMT5 is required for cell-cycle progression and p53 tumor suppressor function. Nucleic Acids Res. Nucleic Acids Res. 2009; 37(15): 4965-76.

Jansson M. et al. Arginine methylation regulates the p53 response. Nat Cell Biol 2008; 10(12):1431-9.

Durant S T, Cho E C, La Thangue N B. p53 methylation—the Argument is clear. Cell Cycle. 2009; 8(6):801-2.

Berger S L. Out of the jaws of death PRMT55 steers p53. Nat Coil Biol. 2008; 10(12):1389-90.

Tanaka H et al. PRMT5, a novel TRAIL receptor-binding protein, inhibits TRAIL-induced apoptosis via nuclear factor-kappaB activation. Mol Cancer Res. 2009; 7(4): 557-69.

Wang L, Pal S, Sif S. PRMT5 suppresses the transcription of the RB family of tumor suppressors in leukemia and lymphoma cells. Mol Cell Biol. 2008; 28(20):6262-77

Pal S, Baiocchi R A, Byrd J C, Grever M R, Jacob S T, Sif S. 2007. Low levels of miR-92b\96 induce PRMT5 translation and H3R/H4R3 methylation in mantle cell lymphoma. EMBO. Vol. 15, no. 26: 3558-3569 2007.

Yan F. Targeting the protein arginine methyltransferase 5 enzyme in glioblastoma multiform. Abstract Number 1584. 101$^{st}$ AACR annual meeting, 2010.

Bosch F, Jares P, et al. PRAD-1/cyclin D1 gene overexpression in chronic lymphoproliferative disorders: a highly specific marker of mantle cell lymphoma. Blood. 1994; 84(8):2726-32.

Yan F, et al. Developing a novel class of drug to inhibit PRMT5 enzyme dysregulation in mantle cell lymphoma. Blood, Abstr 595, 2012.

Aggarwal P, Vaites L P, Kim J K, Mellert H, Gurung B, Nakagawa H, Herlyn M, Hua X, Rustgi A K, McMahon S B, Diehl J A (2010) Nuclear cyclin D1/CDK4 kinase regulates CUL4 expression and triggers neoplastic growth via activation of the PRMT5 methyltransferase. Cancer Cell 18(4): 329-340.

Cho E C, Zheng S, Munro S, Liu G, Carr S M, Moehlenbrink J, Lu Y C, Stimson L, Khan O, Konietzny R, McGouan J, Coutts A S, Kessler B, Kerr D J, Thangue N B Arginine methylation controls growth regulation by E2F-1. EMBO J 31(7): 1785-1797.

Deuciri R, Anupam R, Kvaatskhelia M, Green K B, Lairmore M D, Green P L Comparative host protein interactions with HTLV-1 p30 and HTLV-2 p28: insights into difference in pathobiology of human retroviruses. Retrovirology 9: 64.

Gu Z, Gao S, Zhang F, Wang Z, Ma W, Davis RE Protein arginine methyltransferase 5 is essential for growth of lung cancer cells. Biochera J 446(2): 235-241.

Gu Z, Li Y, Lee P, Liu T, Wan C, Wang Z Protein arginine methyltransferase 5 functions in opposite ways in the cytoplasm and nucleus of prostate cancer cells. PLoS One 7(8): e44033.

Jiang W, Roomer M E, Newsham I F (2005) The tumor suppressor DAL-1/4.1B modulates protein arginine N-methyltransferase 5 activity in a substrate-specific manner. Biochem Biophys Res Commun 329(2): 522-530.

Liang J J, Wang Z, Chiriboga L, Oreco M A, Shapiro E, Huang H, Yang X J, Huang J, Peng Y, Melamed J, Oarabedian M J, Lee P (2007) The expression and function of androgen receptor coactivator p44 and protein arginine methyltransferase 5 in the developing testis and testicular tumors. J Urol 177(5): 1918-1922.

Liu F, Zhao X, Pena F, Wang L, Koppikar P, Abdel-Wahab O, Harr M W, Levine R L, Xu H, Tefferi A, Deblasio A, Hatlen M, Menendez S, Nimer S D JAK2V617F-mediated phosphorylation of PRMT5 downregulates its methyltransferate activity and promotes myeloproliferation. Cancer Cell 19(2): 283-294.

Maloney A, Clarke P A, Naaby-Hansen S, Stein R, Koopman J O, Akpan A, Yang. A, Zvelebil M, Cramer R, Stimson L, Ahern W, Banerji U, Judson I, Sharp S, Powers M, deBilly E, Salmons J, Walton M, Burlingame A, Waterfield M, Workman P (2007) Gene and protein expression profiling of human ovarian cancer cells treated with the heat shock protein 90 inhibitor 17-allylamino-17-demethoxygeldanamycin. Cancer Res 67(7): 3239-3253.

Morgan M A, Mould A W, Li L, Robertson E J, Bikoff E K Alternative splicing regulates Prdm1/Blimp-1 DNA binding activities and corepressor interactions. Mol Cell Biol 32(17): 3403-3413.

Pal S, Balocchi R A, Byrd J C, Grever M R, Jacob S T, Sif S (2007) Low levels of miR-92b/96 induce PRMT5 translation and H3R8/H4R3 methylation in mantle cell lymphoma. EMBO J 26(15): 3558-3569.

Powers M A, Fay M M, Factor R E, Welm A L, Ullman K S Protein arginine methyltransferase S accelerates tumor growth by arginine methylation of the tumor suppressor programmed cell death 4. Cancer Res 71(16): 5579-5587.

Rank G, Cerruti L, Simpson R J, Moritz R L, Jane S M, Zhao Q (2010) Identification of a PRMT5-dependent repressor complex linked to silencing of human fetal globin gene expression. Blood 116(9): 1585-1592.

Reuther G W Recurring mutations in myeloproliferative neoplasms alter epigenetic regulation of gene expression. Am J Cancer Res 1(6): 752-762.

Rozan L M, El-Deiry W S (2006) Identification, and characterization of proteins interacting with Traf4, an enigmatic p53 target. Cancer Biol Ther 5(9): 1228-1235.

Tae S, Karkhanis V, Velasco K, Yaneva M, Erdjument-Bromage H, Tempst P, Sif S Bromodomain protein 7 interacts with PRMT5 and PRC2, and is involved in transcriptional repression of their target genes. Nucleic Acids Res 39(13): 5424-5438.

Wang L, Pal S, Sif S (2008) Protein arginine methyltransferase 5 suppresses the transcription of the RB family of tumor suppressors in leukemia and lymphoma cells. Mol Cell Biol 28(20): 6262-6277.

Wei T Y, Juan C C, Hisa J Y, Su L J, Lee Y C, Chou H Y, Chen J M, Wu Y C, Chiu S C, Hsu C P, Liu K L, Yu C T Protein arginine methyltransferase 5 is a potential oncoprotein that upregulates GI cyclins/cyclin-dependent kinases and the phosphoinositide 3-kinase/AKT signaling cascade. Cancer Sci 103(9): 1640-1650.

Xu Z, He Y, Ju J, Rank G, Cerruti L, Mas C, Simpson R J, Moritz R L, Jane S M, Zhao Q The role of WDR5 in silencing human fetal globin gene expression. Haematologica 97(11): 1632-1640.

Zhang S J, Abdel-Wahab O Disordered epigenetic regulation in the pathophysiology of myeloproliferative neoplasms. Curr Hematol Malig Rep 7(1): 34-42.

Fröhling, S., et al. (2005) Genetics of myeloid malignancies: pathogenetic and clinical implications. J. Clin. Oncol. 23, 6285-6295.

Estey, E. & Döhner, H. (2005) Acute myeloid leukaemia. Lancet 368, 1894-1907.

McKenzie, S. B. (2005) Advances in understanding the biology and genetics of acute myelocytic leukemia. Clin. Lab. Sci. 18, 28-37.

Dombret, H. (2011) Gene mutation and AML pathogenesis. Blood 118, 5366-5367.

Marcucci, G., et al. (2011) Molecular genetics of adult acute myeloid leukemia: prognostic and therapeutic implications. J. Clin. Oncol. 29, 475-486.

Döhner, H., et al. (2010) Diagnosis and management of acute myeloid leukemia in adults: recommendations from an international expert panel, on behalf of the European LeukemiaNet. Blood 115, 453-474.

Kindler, T., et al. (2010) FLT3 as a therapeutic target in AML: still challenging after all these years. Blood 116, 5089-5102.

Weisberg, E., et al. (2010) Drug resistance in mutant FLT3-positive AML. Oncogene 29, 5120-5134.

Stirewalt, D. L. & Radich, J. P. (2003) The role of FLT3 in haematopoietic malignancies. Nat. Rev. Cancer 3, 650-665.

Weisberg, E., et al. (2009) FLT3 inhibition and mechanisms of drug resistance in mutant FLT3-positive AML. *Drug Resist. Updat.* 12, 81-89.

Blum, W., et al. (2012) Clinical and pharmacodynamic activity of bortezomib and decitabine in acute myeloid leukemia. *Blood* 119, 6025-6031.

Liu, S., et al. (2010) Sp1/NFkappsB/HDAC/miR-29b regulatory network in KIT-driven myeloid leukemia. *Cancer Cell* 17, 333-347.

Pal, S. (2007) Interplay Between Chromatin Remodelers and Protein Arginine Methyltransferases. doi: 10.1002/JCP Bedford, M. T. (2007) Arginine methylation at a glance. *J. Cell Sci.* 120, 4243-4246.

Jansson, M., et al. (2008) Arginine methylation regulates the p53 response. *Nat. Cell Biol.* 10, 1431-1439.

Guezennec, X. Le, et al. (2006) Complexes with Different Biochemical and Functional Properties MBD2/NuRD and MBD3/NuRD, Two Distinct Complexes with Different Biochemical and Functional Properties. doi:10.1128/MCB.26.3.843

Bedford, M. T. & Richard, S. (2005) Arginine methylation an emerging regulator of protein function. Mol. Cell 18, 263-272.

Scoumanne, A., et al. (2009) PRMT5 is required for cell-cycle progression and p53 tumor suppressor function. *Nucleic Acids Res.* 37, 4965-4976.

Pal, S., et al. (2007) Low levels of miR-92bW96 induce PRMT5 translation and H3R8/H4R3 methylation in mantle cell lymphoma. *EMBO J.* 26, 3558-3569.

Wang, L., et a. (2008) Protein arginine methyltransferase 5 suppresses the transcription of the RB family of tumor suppressors in leukemia and lymphoma cells. *Mol. Cell. Biol.* 28, 6262-6277.

Wei, H., et al. (2013) PRMT5 dimethylates R30 of the p65 subunit to activate NF-κB. *Proc. Natl. Acad. Sci. U.S.A.* 110, 13516-13521.

Kim, J., et al. (2005) Identification of Gastric Cancer—Related Genes Using a cDNA Microarray Containing Novel Expressed Sequence Tags Expressed in Gastric Cancer Cells Identification of Gastric Cancer—Related Genes Using a cDNA Microarray Containing Novel Expressed Sequence. 473-482.

Eckert, D., et al. (2008) Expression of BLIMP1/PRMT5 and concurrent histone H2A/H4 arginine 3 dimethylation in fetal germ cells, CIS/IGCNU and germ cell tumors. *BMC Dev. Biol.* 8, 106.

Liu, F., et al. (2011) JAK2V617F-mediated phosphorylation of PRMT5 downregulates its methyltransferase activity and promotes myeloproliferation. *Cancer Cell* 19, 283-294.

Gu, Z., et al. (2012) Protein arginine methyltransferase 5 is essential for growth of lung cancer cells. *Biochem. J.* 446, 235-241.

Bao, X., et al. (2013) Overexpression of PRMT5 promotes tumor cell growth and is associated with poor disease prognosis in epithelial ovarian cancer. J. Hisochem. Cytochem. 61, 206-217.

Nicholas, C., et al. (2013) PRMT5 is up-regulated in malignant and metastatic melanoma and regulates expression of MITF and p27(Kip1). *PLoS One* 8, e74710.

Spiekermann. K., et al. (2003) Overexpression and Constitutive Activation of FLT3 Induces STATS Activation in Primary Acute Myeloid Leukemia Blast Cells Overexpression and Constitutive Activation of FLT3 Induces STATS Activation in Primary Acute Myeloid Leukemia Blast Cells 1. *Clin. Cancer Res.* 9, 2140-2150.

Richard, S., et al. (2005) Arginine methylation regulates IL-2 gene expression: a role for protein arginine methyltransferase 5 (PRMT5). *Biochem. J.* 388, 379-386.

Fabbrizio, E., et al. (2002) Negative regulation of transcription by the type II arginine methyltransferase PRMT5. *EMBO Rep.* 3, 641-645.

Meshinchi, S. & Appelbaum, F. R. (2009) Structural and functional alterations of FLT3 in acute myeloid leukemia. *Clin. Cancer Res.* 15, 4263-4269.

Moore, a S., et al. (2012) Selective FLT3 inhibition of FLT3-ITD+ acute myeloid leukaemia resulting in secondary D835Y mutation: a model for emerging clinical resistance patterns. *Leukemia* 26, 1462-1470.

Knapper, S., et al. (2006) The effects of lestaurtinib (CEP701) and PKC412 on primary AML blasts: the induction of cytotoxicity varies with dependence on FLT3 signaling in both FLT3-mutated and wild-type cases. *Blood* 108, 3494-503.

Mims, A., et al. (2013) Increased anti-leukemic activity of decitabine via AR-42-induced upregulation of miR-29b: a novel epigenetic-targeting approach in acute myeloid leukemia. *Leukemia* 27, 871-878.

Park, I.-K., et al. (2013) Inhibition of the receptor tyrosine kinase Axl impedes activation of the FLT3 internal tandem duplication in human acute myeloid leukemia: implications for Axl as a potential therapeutic target. Blood 121, 2064-2073.

Gkountela, S., et al. (2014) PRMT5 is Required for Human Embryonic Stein Cell Proliferation But Not Pluripotency. *Stem Cell Rev.* doi:10.1007/s12015-013-9490-z Pal, S., et al. (2004) Negatively Regulates Expression of ST7 and NM23 Tumor Suppressor Genes Human SWI/SNF-Associated PRMT5 Methylates Histone H3 Arginine 8 and Negatively Regulates Expression of ST7 and NM23 Tumor Suppressor Genes †. doi:10.1128/MCB.2421.9630

Smith, M. R., et al. (2013) Murine mnmtle cell lymphoma model cell line. *Leukemia* 27, 1592-1594.

Zhao, X., et al. (2013) Combination Of Ibrutinib With ABT-199, a BCL-2 Pathway Inhibitor. Effective Therapeutic Strategy In a Novel Mantle Cell Lymphoma Cell Line Model. *Blood* 122, 645a.

Chung, J., et al. (2013) Protein Arginine Methyltransfermse 5 (PRMT5) Inhibition Induces Lymphoma Cell Death through Reactivation of the Retinoblastoma Tumor Suppressor Pathway and Polycomb Repressor Complex 2 (PRC2) Silencing. *The Journal of biological chmistry* 288, 35534-35547.

Yan, F., et al. (2014) Genetic validation of the protein arginine methyltramnsferase PRMT5 as a candidate therapeutic target in glioblastoma. *Cancer research* In Press.

It will be apparent to those skilled in the art that various modifications and variations can be made in the present invention without departing rom the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of treating a disorder of uncontrolled cellular proliferation, comprising administering to a patient in need thereof, a compound represented by the formula:

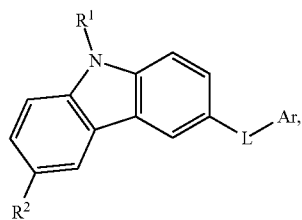

wherein, $R^1$ is $C_1$-$C_4$ alkyl;

$R^2$ is selected from the group consisting of H, F, Cl and Br;

L is selected from the group consisting of:

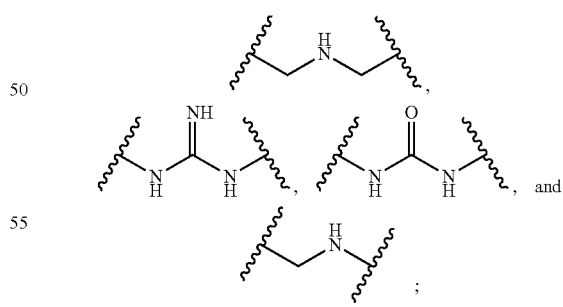

Ar is selected from:

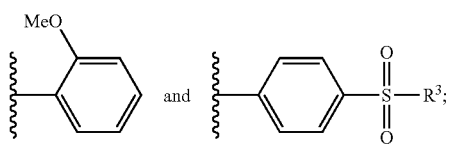

wherein R³ is selected from $C_1$-$C_4$alkyl, —$NH_2$, $NHCH_3$, and —$N(CH_3)_2$, or a pharmaceutically acceptable salt thereof, wherein the disorder of uncontrolled cellular proliferation is squamous cell carcinoma, lymphoma or leukemia.

2. The method according to claim 1, wherein the disorder of uncontrolled cellular proliferation is leukemia.

3. The method according to claim 1, wherein the disorder of uncontrolled cellular proliferation is lymphoma.

4. The method of claim 1, further comprising administering at least one additional chemotherapeutic agent to the patient.

5. The method of claim 1, wherein Ar is:

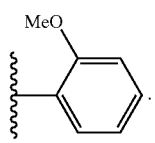 [SMILES: *c1ccccc1OC]

6. The method of claim 1, wherein L is:

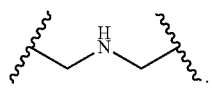

7. The method of claim 1, wherein $R^1$ is ethyl.

8. A pharmaceutical composition, comprising at least one pharmaceutically acceptable carrier, and a compound represented by the formula:

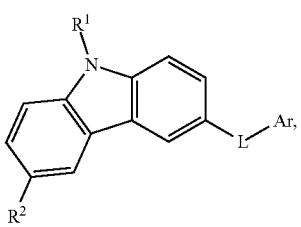

wherein,
$R^1$ is $C_1$-$C_4$ alkyl;
$R^2$ is selected from the group consisting of H, F, Cl and Br;
L is selected from the group consisting of:

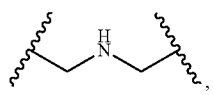

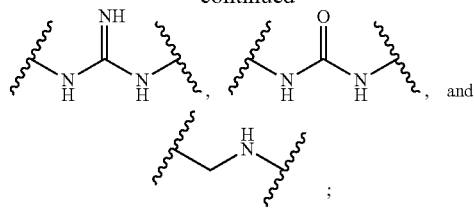

Ar is selected from:

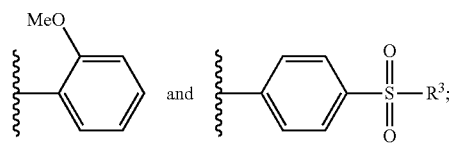

wherein $R^3$ is selected from $C_1$-$C_4$alkyl, —$NH_2$, $NHCH_3$, and —$N(CH_3)_2$, or a pharmaceutically acceptable salt thereof.

9. The composition of claim 8, wherein Ar is:

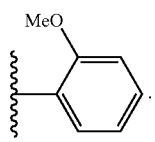

10. The composition of claim 8, wherein L is:

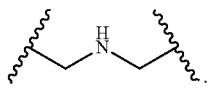

11. The composition of claim 8, wherein $R^1$ is ethyl.

12. A compound represented by the formula:

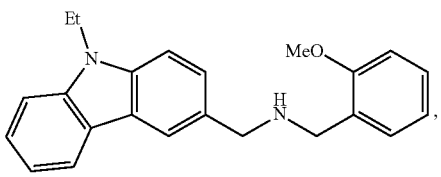 [SMILES: CCn1c2ccccc2c2cc(CNCc3ccccc3OC)ccc21]

or a pharmaceutically acceptable salt thereof.

13. The method of claim 1, wherein the disorder of uncontrolled cellular proliferation is squamous cell carcinoma.

* * * * *

SEQUENCE LISTING

<160> NUMBER OF SEQ ID NOS: 1

<210> SEQ ID NO 1
<211> LENGTH: 1086
<212> TYPE: DNA
<213> ORGANISM: Artificial Sequence
<220> FEATURE:
<223> OTHER INFORMATION: synthetic construct

<400> SEQUENCE: 1

```
cttattgcaa agaaaataat aataattttc aactcgaaaa attatgcgat gaagaacaag      60
aactattgag cggatgattc gcaacatcct ctgggatgta ttttctgtgt gttttgtttt     120
gaaggctgtt tgttaacctc cctaattgcc ttggttgaca ttgaaaccct gcctgttttt     180
cttgatcccg ccgctgactg ggtcctgagc atcctaggag atggaggcag agacaaagga     240
aatcagtcca caattaagaa tggaatggtt cttaatggaa tgctcgcctg tgcgctggcg     300
ggagttgcca gcgtgccgag cggattcagc gcctttctca gggcctcaaa gatcccagcg     360
cactaggagg gtggtttgtg gctccctgca gtccccacgc cccggatcca acgacagag      420
ttcggggact cacaggggca gcaaggcggc agagccgcgg agccagtgca acttctccgg     480
cgggaccgcg cccaatcttc cccgccgcag tcggggagcc ccggggggccg ccgagcacag    540
gctgcggacc gcgcgcgggca cgtgggctcg gctgcagcgc tgcgccaggc accggctgct    600
cggctctgcc caacctctcc gctcccgcct cggtccctgc ctctggggag agggttcctc     660
ccccccttcca ctttgcacca gtccgaggga atttgcggtc ggtgacgcgc atccttaaga   720
gagccacctg cagcgcgagg cgcgccgctc caggcggcat cgcagggctg ggccggcgcg    780
gcctggggac cccgggctcc ggaggccatg ccggcgttgg cgcgcgacgg cggccagctg    840
ccgctgctcg gtaaggcccc gctcgctcgc tcgcagcccc tcgcggtccc tcagccccca    900
ccccgcagtg tggacccggg cgcgcgcctc ctccggccca gccgcctcgc tcctccccgc    960
gctcgctcct tccattgcct cccgcgcccc tccctctttt cgcgccctcc ggactcgccc   1020
actacttgcc tgcggccccg gcgtttccca ccccgcgtcc tcttccctct tctccgaagt   1080
ctctcc                                                              1086
```